US009873883B2

(12) United States Patent
Lira et al.

(10) Patent No.: US 9,873,883 B2
(45) Date of Patent: *Jan. 23, 2018

(54) GLYPHOSATE RESISTANT PLANTS AND ASSOCIATED METHODS

(71) Applicant: Dow AgroSciences LLC, Indianapolis, IN (US)

(72) Inventors: Justin M. Lira, Zionsville, IN (US); Robert M. Cicchillo, Zionsville, IN (US); Carla N. Yerkes, Crawfordsville, IN (US); Andrew E. Robinson, Brownsburg, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 246 days.

This patent is subject to a terminal disclaimer.

(21) Appl. No.: 13/757,474

(22) Filed: Feb. 1, 2013

(65) Prior Publication Data

US 2013/0212737 A1  Aug. 15, 2013

Related U.S. Application Data

(60) Provisional application No. 61/593,555, filed on Feb. 1, 2012, provisional application No. 61/625,222, filed on Apr. 17, 2012.

(51) Int. Cl.
*C12N 15/82*   (2006.01)
*A01H 5/00*   (2006.01)
*A01H 5/10*   (2006.01)
*C07K 14/195*   (2006.01)
*C07K 14/415*   (2006.01)
*C12N 9/96*   (2006.01)
*C12N 9/10*   (2006.01)
*A01N 57/20*   (2006.01)
*C12N 9/02*   (2006.01)

(52) U.S. Cl.
CPC ........ *C12N 15/8221* (2013.01); *A01N 57/20* (2013.01); *C07K 14/415* (2013.01); *C12N 9/0069* (2013.01); *C12N 9/0071* (2013.01); *C12N 9/1085* (2013.01); *C12N 9/1092* (2013.01); *C12N 9/96* (2013.01); *C12N 15/8205* (2013.01); *C12N 15/8209* (2013.01); *C12N 15/8214* (2013.01); *C12N 15/8241* (2013.01); *C12N 15/8245* (2013.01); *C12N 15/8247* (2013.01); *C12N 15/8274* (2013.01); *C12N 15/8275* (2013.01); *C12N 15/8281* (2013.01); *C12N 15/8283* (2013.01); *C12N 15/8286* (2013.01); *C12Y 113/00* (2013.01); *C12Y 114/11* (2013.01); *C12Y 205/01019* (2013.01); *C07K 2319/08* (2013.01)

(58) Field of Classification Search
CPC .................................................... C12N 15/82
See application file for complete search history.

(56) References Cited

U.S. PATENT DOCUMENTS

| 5,627,061 | A | 5/1997 | Barry |
| 5,633,435 | A * | 5/1997 | Barry ................ C12N 9/1092 435/320.1 |
| 2007/0300326 | A1* | 12/2007 | Peters ................ C12N 9/1085 800/278 |
| 2008/0227966 | A1 | 9/2008 | Francis et al. |
| 2009/0093366 | A1* | 4/2009 | Wright ................ C12N 9/0069 504/142 |
| 2011/0195845 | A1 | 8/2011 | Lira et al. |
| 2011/0214503 | A1 | 9/2011 | Dosch et al. |
| 2011/0289620 | A1 | 11/2011 | Cui et al. |

FOREIGN PATENT DOCUMENTS

| JP | 1994501615 | 2/1994 |
| JP | 2007535327 | 12/2007 |
| WO | 199204449 | 3/2000 |
| WO | 2007064828 | 6/2007 |
| WO | 2008002962 | 1/2008 |

OTHER PUBLICATIONS

Guo et al, 2004, Proc. Natl. Acad. Sci. USA 101: 9205-9210.*
NCBI Reference Sequence NZ_AATS01000008.1.*
Klee, Harry J., et al., "Cloning of an Arabidopsis thaliana gene encoding 5-enolpyruvylshikimate-3-phosphate synthase: sequence analysis and manipulation to obtain glyphosate-tolerant plants." Molecular and General Genetics MGG 210.3 (1987): 437-442.*
Guo, Haiwei H., Juno Choe, and Lawrence A. Loeb. "Protein tolerance to random amino acid change." Proceedings of the National Academy of Sciences of the United States of America 101.25 (2004): 9205-9210.*
Jain, S. Mohan. "Tissue culture-derived variation in crop improvement." Euphytica 118.2 (2001): 153-166.*
Grefen, Christopher, et al. "A ubiquitin-10 promoter-based vector set for fluorescent protein tagging facilitates temporal stability and native protein distribution in transient and stable expression studies." The Plant Journal 64.2 (2010): 355-365.*
Funke, T., et al. 2006. Proceedings of the National Academy of Sciences 103: 13010-13015.*
NCBI Reference Sequence NZ_AATS01000008.1, available since Oct. 17, 2006.*
Grefen, C., et al. 2010, The Plant Journal 64 (2): 355-365.*
Wright, et al., "Robust crop resistance to broadleaf and grass herbicides provided by aryloxyalkanoate dioxygenase transgenes" PNAS, Sep. 23, 2010, vol. 107, No. 47, pp. 20240-20245.

(Continued)

*Primary Examiner* — Lee A Visone
*Assistant Examiner* — Weihua Fan
(74) *Attorney, Agent, or Firm* — C. Philip Poirier; Magleby Cataxinos & Greenwood

(57) ABSTRACT

Provided are plants having glyphosate resistance comprising a nucleic acid encoding a polypeptide having at least 90% identity with SEQ ID NO:1, and parts, organs, seeds, and/or cells of such plants. Also provided are methods for making and growing such a plant, and methods of controlling weeds in a field or area under cultivation containing such plants. For example, some methods comprise the application of multiple herbicides to such plants.

32 Claims, 17 Drawing Sheets

(56) References Cited

OTHER PUBLICATIONS

Green et al., "New multiple-herbicide crop resistance and formulation technology to augment the utility of glyphosate" Pest Management Science, Dec. 10, 2007, vol. 64, No. 4, pp. 332-339.
International Search Report and Written Opinion for PCT Application No. PCT/US2013/024493, dated Jun. 2, 2013.
GenBank Accession No. EAU54473, dated Sep. 15, 2006.
Geneseq Sep. 15, 2006, Emerson et al., "Mariprofundus ferroxydans PV-1" Database accession No. AATS01000008, see nucleotides 74420 to 75769.
Haghani, et al. "Comparative studies of wild typ *Escherichia coli* 5-enolpyruvylshikimate 3-phosphate synthase with three glyphosate-insensitive mutate forms: Activity, stability and structural characterization", Biochimca et biophysica acta (BBA)—Proteins & Proteomics, Sep. 1, 2008, Netherlands, vol. 1784, No. 9, pp. 1167-1175.
UniProtKB-Q0EYT4, 3-phosphoshikimate1-carboyxvinyltransferase, {online}, Last modified: Oct. 17, 2006, http://www.uniport.org.uniport/Q0EYT4.

\* cited by examiner

FIG. 1:

FIG. 2 pDAB100427 pDAB100431 pDAB100432 pDAB102787 pDAB105525

SEQUENCE LISTING

<160> NUMBER OF SEQ ID NOS: 62

<210> SEQ ID NO 1
<211> LENGTH: 449
<212> TYPE: PRT
<213> ORGANISM: Artificial Sequence
<220> FEATURE:

-continued

<223> OTHER INFORMATION: DGT-14 sequence is a modification of GENBANK
ACC NO: ZP_01452683 where the endogenous glycine was replaced with
an alanine at amino acid residue 101

<400> SEQUENCE: 1

```
Met Ser Thr Gly Gly Thr Leu Ile Ala Gly Pro Ala Ala Gly Pro Leu
1               5                   10                  15

Lys Gly Glu Leu Thr Val Pro Gly Asp Lys Ser Met Ser His Arg Ser
            20                  25                  30

Val Met Leu Ala Ala Leu Ala Asp Gly Val Thr Glu Ile His Gly Phe
        35                  40                  45

Leu Pro Gly Glu Asp Asn Ile Ala Thr Ala Arg Met Phe Ile Asp Met
50                  55                  60

Gly Val Arg Ile Glu Trp Leu Asn Asp Glu Lys Thr Ser Leu Arg Val
65                  70                  75                  80

His Gly Val Gly Leu His Gly Leu Lys Gln Pro Gln Gly Met Leu Asp
                85                  90                  95

Ala Gly Asn Ala Ala Thr Cys Val Arg Leu Met Ala Gly Ile Leu Ala
            100                 105                 110

Gly Gln His Phe Ser Ser Thr Val Thr Gly Asp Ala Ser Leu Cys Lys
        115                 120                 125

Arg Pro Met Lys Arg Val Val Asp Pro Val Arg Met Gly Ala Lys
130                 135                 140

Val Glu Gly Gly Asp Asp Gly Asn Leu Leu Pro Ile Thr Ile Ser Gly
145                 150                 155                 160

Gly Lys Leu Lys Ala Ile Asp His Val Ser Glu Val Ala Ser Ala Gln
                165                 170                 175

Val Lys Ser Cys Val Leu Leu Ala Gly Leu Tyr Ala Asp Gly Val Thr
            180                 185                 190

Ser Val Ser Glu Pro Lys Pro Thr Arg Asp His Thr Glu Arg Met Leu
        195                 200                 205

Pro Leu Phe Gly Gln Pro Val Thr Val Ala Ala Asp Gly Thr Ile Ser
210                 215                 220

Leu Asp Pro Lys Asp Arg Leu Thr Ala Pro Val Gly Val Val Asp Ile
225                 230                 235                 240

Pro Ala Asp Pro Ser Ser Ala Cys Phe Phe Ala Val Ala Ala Ser Leu
                245                 250                 255

Val Glu Gly Ser Asp Val Thr Leu Lys Ser Ile Gly Ile Asn Pro Arg
            260                 265                 270

Arg Asp Gly Trp Arg Arg Val Met Asn Gly Met Gly Ala Ala Leu Ser
        275                 280                 285

Leu Glu Asn Glu Gln Arg Val Gly Glu Glu Pro Val Ala Asp Val Arg
290                 295                 300

Ile Arg Ser Gly Gly Leu His Gly Met His Val Val Pro Asn Asp Val
305                 310                 315                 320

Pro Asp Ala Ile Asp Glu Phe Pro Val Leu Phe Ala Ala Ala Thr Leu
                325                 330                 335

Ala Asp Gly Glu Phe Val Leu Thr Asp Ala Glu Glu Leu Arg Val Lys
            340                 345                 350

Glu Ser Asp Arg Ile Ala Ala Met Ala Thr Ala Leu Arg Ser Ala Gly
        355                 360                 365

Ala Asp Ile Asp Glu Gln Pro Asp Gly Ala Val Ile Arg Gly Ile Thr
370                 375                 380

Asn Leu Arg Gly Asp Val Asp Val Asp Ala His Gly Asp His Arg Ile
```

```
                385             390              395             400
            Ala Met Ala Met Ala Val Ala Ala Gln Arg Ala Asp Gly Glu Val Arg
                                405                 410                 415

Ile His Asn Ala Ala Ala Ile Ala Thr Ser Phe Pro Asn Phe Val Gln
                        420                 425                 430

Leu Ala Gln Ser Val Gly Met Asn Val Arg Trp Ala Asp Glu Gly Glu
                    435                 440                 445

Ala

<210> SEQ ID NO 2
<211> LENGTH: 1350
<212> TYPE: DNA
<213> ORGANISM: Artificial Sequence
<220> FEATURE:
<223> OTHER INFORMATION: dicot codon optimized version of DGT-14

<400> SEQUENCE: 2
atgtcaactg gtggcactct gatagctgga ccagcagctg gaccactgaa gggagaattg      60
accgttcctg gtgacaaatc tatgtctcac agaagtgtga tgttagcagc tttggcagac     120
ggagtgacag agattcatgg attcctccct ggggaagata catcgccac tgctcgtatg      180
ttcattgata tgggagtgag aattgagtgg ttgaatgacg aaaagacaag tctgagagtt     240
catggtgtgg gattgcatgg gcttaagcaa ccacaaggca tgttggatgc tgggaacgca     300
gctacatgtg ttagactcat ggctggcatc ttggctgggc aacacttctc ctctacagtt     360
acgggagacg cctcattgtg caagagaccc atgaagaggg tggttgatcc ggtgcgtcgt     420
atgggtgcaa aggttgaggg tggggatgat ggcaatcttc ttcccataac catctctggt     480
ggcaagctca agctatcga ccacgtcagt gaagtcgcca gcgctcaagt caagagttgt      540
gtcctcttag ctggactgta tgcagatgga gttacaagtg taagcgagcc aaaacctact     600
cgtgatcata ctgaaagaat gttgccactg ttcggtcaac ccgtcaccgt cgcagcagac     660
ggaacgatta gccttgatcc taaggataga cttactgcac cagtcggagt tgttgacatt    720
ccagccgacc ctagtagcgc ttgtttcttt gcagtggcag cctccctcgt ggagggatct     780
gatgtgactc tgaagtcaat agggatcaat ccaagaagag acggttggag cgtgttatg      840
aacggaatgg gagctgcttt gtctctcgaa acgagcaga gggttggaga ggaacccgta      900
gccgatgtta gaatcagaag tggaggtctc acgggatgc acgtggtgcc caatgacgtt      960
ccggacgcta cgatgagtt ccagttttg ttcgctgctg caacattggc tgacggagag     1020
tttgtgttga cagatgcaga agaattgagg gttaaggaat cagatcgtat tgctgcaatg    1080
gccacagctt tacgtagtgc tggagctgat atcgatgaac agccagatgg tgccgtgata    1140
agagggatca ccaatctgag gggtgatgtg acgtggacg tcatggtga tcataggatt     1200
gcaatggcta tggcagtggc agctcaaaga gctgatggag aagtgagaat ccataacgct    1260
gctgctattg ccacttcatt ccctaacttc gttcaactgg ctcaatcagt cgggatgaat    1320
gtccgttggg ctgacgaggg agaggcatga                                      1350

<210> SEQ ID NO 3
<211> LENGTH: 1350
<212> TYPE: DNA
<213> ORGANISM: Artificial Sequence
<220> FEATURE:
<223> OTHER INFORMATION: monocot optimized version of dgt-14

<400> SEQUENCE: 3
```

```
atgtctacgg gaggcacact gatagctggt ccagcagctg gtccgcttaa gggtgaactc    60
actgttcctg gagacaagtc aatgagccat cgctcggtga tgctggctgc attggctgac   120
ggagtcacag agatccacgg gtttctgcct ggtgaggaca catcgcaac agcgaggatg    180 ttcatcgaca tgggagtgag gattgagtgg ctcaacgacg aaaagacgtc gcttcgcgtt   240
catggcgtgg gtctgcatgg actgaaacaa cctcaaggga tgctggatgc tgggaacgct   300
gctacttgcg tgaggcttat ggctggaatc ttggctggcc agcacttctc aagcacggtc   360
acgggtgatg ccagcctttg caaaagaccg atgaagaggg tcgttgatcc agttaggagg   420
atgggtgcca aggtcgaggg tggcgacgac gggaatcttc tgcccataac catttccgga   480
gggaaactta aggcaatcga ccacgttagc gaagtggcct ctgcccaagt caagtcgtgc   540
gttcttctcg ctggtctgta tgccgacggt gtgacatcag tttcggagcc taagcccacg   600
agggatcaca ccgagaggat gcttcccttg ttcggacagc cagtcacggt ggcagccgac   660
ggcaccatct ccctcgaccc taaggatagg ctcactgctc cagttggcgt ggtggatatc   720
ccagccgatc cgtcatctgc ttgtttcttc gcagtcgcag cgtcacttgt cgaggggtcc   780
gacgtgactc tgaaatctat tgggatcaac ccgagacgcg acggttggag aagggtcatg   840
aacgggatgg gtgctgccct ctctctcgaa acgagcaaac gcgttggcga agagccagtg   900
gcagatgtgc ggatacgctc tggtggactt catgggatgc acgtggtgcc aaacgatgtt   960
ccggatgcaa tcgatgagtt tccagtgttg ttcgcagcag ctactcttgc tgatggtgag  1020
tttgttctga ccgacgctga agaactcaga gtgaaggaga gcgaccggat cgctgcgatg  1080
gcgacagcgc tgcggtcagc tggagccgac atagatgagc aacccgacgg tgccgtcatc  1140
agagggatca ccaacttgag aggcgacgtg gatgtggatg cccacggaga tcatcgcatc  1200
gcgatggcga tggctgtcgc agcccagagg gcagatggcg aagtcagaat ccacaacgca  1260
gctgctattg ccacatcatt tccgaacttt gtgcagctgg ctcagtccgt tggcatgaat  1320
gtgcggtggg cagatgaagg agaggcgtga                                   1350
```

<210> SEQ ID NO 4
<211> LENGTH: 1380
<212> TYPE: DNA
<213> ORGANISM: Artificial Sequence
<220> FEATURE:
<223> OTHER INFORMATION: E. coli optimized version of dgt-14

<400> SEQUENCE: 4

```
atggcgcgcc catatgagca ccggtggcac cctgattgct ggtcctgcag ccggtccgct    60
gaaaggtgaa ctgaccgttc cgggtgataa aagcatgagc catcgtagcg ttatgctggc   120
agcactggca gatggtgtta ccgaaattca tggttttctg cctggcgaag ataatattgc   180
aaccgcacgc atgtttattg atatgggcgt gcgtattgaa tggctgaacg atgaaaaaac   240
cagcctgcgt gttcatggtg ttggtctgca tggtctgaaa cagccgcagg gtatgctgga   300
tgccggtaat gcagcaacct gtgttcgtct gatggcaggc attctggcag ccagcatttt   360
tagcagcacc gttactgggg atgcaagcct gtgtaaacgt ccgatgaaac gtgttgttga   420
tccggttcgt cgtatgggtg caaaagttga aggtggtgat gatggaaatc tgctgccgat   480
taccattagc ggtggtaaac tgaaagccat tgatcatgtt agcgaagttg caagcgcaca   540
ggttaaaagc tgtgttctgc tggcaggcct gtatgcagat ggtgtgacca gcgttagcga   600
accgaaaccg acccgtgatc ataccgaacg tatgctgccg ctgtttggtc agccggttac   660
cgttgcagca gatggcacca ttagcctgga tccgaaagat cgtctgaccg caccggttgg   720
```

-continued

```
tgttgttgat attccggcag atccgagcag cgcatgtttt tttgcagtgg cagcaagcct    780
ggttgaaggt tctgatgtga ccctgaaaag cattggtatt aatccgcgtc gtgatggttg    840
gcgtcgtgtt atgaatggta tgggtgcagc actgagcctg aaaatgaac agcgtgttgg     900
tgaagaaccg gttgcagatg ttcgtattcg tagcggtggc ctgcatggta tgcatgttgt    960
tccgaatgat gttccggatg ccattgatga atttccggtt ctgttttgcag cagcaaccct  1020
ggccgatggt gaatttgttc tgaccgatgc agaagaactg cgcgttaaag aaagcgaccg   1080
tattgcagca atggcaaccg cactgcgtag cgcaggcgca gatattgatg aacagccgga   1140
tggtgcagtt attcgtggta ttaccaatct gcgtggtgat gttgatgttg atgcccatgg   1200
tgatcatcgt attgcaatgg caatggcagt tgcagcccag cgtgcagatg gtgaagttcg   1260
tattcataat gcagctgcaa ttgcaaccag ctttccgaat tttgttcagc tggcacagag   1320
cgttggtatg aatgttcgtt gggcagatga aggtgaagca taataactcg agttaattaa   1380
```

<210> SEQ ID NO 5
<211> LENGTH: 441
<212> TYPE: PRT
<213> ORGANISM: Bartonella bacilliformis

<400> SEQUENCE: 5

```
Met Gln Asn Ala Ile Pro Ala Thr Ala Gln Lys Ser Thr Ala Leu Ser
1               5                  10                  15

Gly Lys Ile Lys Ile Pro Gly Asp Lys Ser Ile Ser His Arg Ser Leu
            20                  25                  30

Ile Leu Gly Gly Leu Ala Asn Gly Glu Thr His Ile His Gly Leu Leu
        35                  40                  45

Glu Ser Asp Asp Ile Leu His Thr Ala Ala Ala Met Gln Ala Met Gly
    50                  55                  60

Ala His Ile Arg Lys Glu Asn Gly Ile Trp Ile Ile Arg Gly Thr Gly
65                  70                  75                  80

Asn Gly Cys Leu Leu Gln Ala Gln Lys Pro Leu Asn Phe Gly Asn Ser
                85                  90                  95

Ala Thr Gly Ala Arg Leu Ile Met Gly Met Val Ser Ser Tyr His Met
            100                 105                 110

Lys Thr Thr Phe Thr Gly Asp Ala Ser Leu Ser Lys Arg Pro Met Glu
        115                 120                 125

Arg Ile Leu Asn Pro Leu Arg Leu Met Gly Thr Asn Ile Glu Ala Thr
    130                 135                 140

Ser Asn Asn Leu Pro Leu Thr Leu Tyr Gly Pro Lys Met Ala Asn Pro
145                 150                 155                 160

Ile Cys Tyr Arg Leu Pro Ile Ala Ser Ala Gln Val Lys Ser Ser Ile
                165                 170                 175

Leu Leu Ala Ser Leu Asn Thr Ala Gly Ile Thr Thr Val Ile Glu Pro
            180                 185                 190

Ile Leu Thr Arg Asp His Thr Glu Lys Ile Leu Glu Leu Phe Gly Ala
        195                 200                 205

Lys Leu Asp Ile Glu Thr Asn Lys Glu Gly Thr Arg Phe Ile His Met
    210                 215                 220

His Gly Gln Pro His Leu Thr Gly Gln Ser Ile Asp Ile Pro Gly Asp
225                 230                 235                 240

Pro Ser Ser Ala Ala Phe Pro Leu Ile Ala Ala Leu Leu Ile Glu Asp
                245                 250                 255
```

Ser Asp Ile Ile Ile Glu Asn Val Leu Ile Asn Ser Arg Ile Gly
            260                 265                 270

Leu Ile Gln Thr Leu Trp Glu Met Gly Ala Lys Ile Glu Phe Leu Asn
        275                 280                 285

Gln Arg Gln Gln Gly Gly Glu Asn Ile Ala Asp Leu Arg Val Arg Ser
    290                 295                 300

Ser Val Leu Lys Gly Val Thr Val Pro Lys Glu Arg Ala Pro Ser Met
305                 310                 315                 320

Ile Asp Glu Tyr Pro Ala Leu Ala Val Ala Ala Phe Ala Glu Gly
                325                 330                 335

Lys Thr Thr Met Leu Gly Ile Glu Glu Leu Arg Val Lys Glu Ser Asp
            340                 345                 350

Arg Leu Ser Thr Ile Ala Gln Gly Leu Lys Ile Asn His Val Asp Cys
        355                 360                 365

Glu Lys Gly Val Asp Phe Leu Ile Ile His Gly Gln Asn Ser Ser Lys
    370                 375                 380

Gly Leu Gly Gly Gly Cys Ile Lys Thr His Leu Asp His Arg Ile Ala
385                 390                 395                 400

Met Cys Phe Leu Val Phe Gly Leu Ala Ser Glu Lys Pro Val Thr Ile
                405                 410                 415

Asp Asp Arg Arg Val Ile Ala Thr Ser Phe Pro Ala Phe Ile Pro Leu
            420                 425                 430

Met Asn Gln Leu Gly Gly Lys Ile His
        435                 440

<210> SEQ ID NO 6
<211> LENGTH: 1323
<212> TYPE: DNA
<213> ORGANISM: Artificial Sequence
<220> FEATURE:
<223> OTHER INFORMATION: E. coli optimized version of dgt-11

<400> SEQUENCE: 6
atgcagaatg caattccggc aaccgcacag aaaagcaccg cactgagcgg caaaattaaa      60
atccctggcg ataaaagcat tagccatcgt agcctgattc tgggtggtct ggcaaatggt     120
gaaacccata ttcatggtct gctggaatct gatgatattc tgcataccgc agcagcaatg     180
caggcaatgg gtgcacatat tcgcaaagaa acggcatttg gattattcg tggcaccggt      240 aatggttgtc tgctgcaggc acagaaaccg ctgaattttg gtaatagcgc aaccggtgca     300
cgtctgatta tgggtatggt gagcagctat cacatgaaaa ccacctttac cggtgatgca     360
agcctgagca acgtccgat ggaacgtatt ctgaatccgc tgcgtctgat gggcaccaat      420
attgaagcaa ccagcaacaa tctgccgctg accctgtatg gtccgaaaat ggcaaatccg     480
atttgttatc gtctgccgat gcaagcgca caggttaaaa gcagcattct gctggcaagc     540
ctgaataccg caggcattac caccgttatt gaaccgattc tgacccgtga tcataccgaa     600
aaaattctgg aactgttcgg tgcaaaactg gatatcgaaa ccaataaaga aggcacccgc     660
tttattcaca tgcatggtca gccgcatctg acaggtcaga gcattgatat tccgggtgat     720
ccgagcagcg cagcatttcc gctgattgca gcactgctga ttgaagatag cgatatcatc     780
atcgaaaacg tgctgattaa tagcagccgt attggactga ttcagaccct gtgggaaatg     840
ggtgccaaaa tcgaatttct gaatcagcgt cagcagggtg gtgaaaatat tgcagatctg     900
cgtgttcgta caagcgttct gaaaggtgtt accgttccga aagaacgtgc accgagcatg     960
attgatgaat atccggcact ggcagttgca gcagcatttg ctgaaggtaa aaccaccatg    1020

```
ctgggtattg aagaactgcg tgtgaaagaa agcgatcgtc tgagcaccat tgcacagggt    1080
ctgaaaatta accatgtgga ttgcgaaaaa ggtgtggatt ttctgattat ccatggccag    1140
aatagcagca aaggtctggg tggtggttgt attaaaaccc atctggatca tcgtattgcc    1200
atgtgctttc tggtttttgg tctggcaagc gaaaaaccgg ttaccattga tgatcgtcgt    1260
gttattgcaa ccagctttcc ggcatttatt ccgctgatga atcagctggg tggcaaaatc    1320
cac                                                                  1323
```

<210> SEQ ID NO 7
<211> LENGTH: 448
<212> TYPE: PRT
<213> ORGANISM: Artificial Sequence
<220> FEATURE:
<223> OTHER INFORMATION: DGT-12 sequence is a modification of GENBANK
      ACC NO: ZP_01622155.1 where the endogenous glycine was replaced
      with an alanine at amino acid residue 111

<400> SEQUENCE: 7

Met Leu Thr Gly Ile Ile Glu Thr Lys Thr Ser Glu Ser Gln Gln Thr
1               5                   10                  15

Leu Ser Val Glu Pro Pro Thr Ser Gly Leu Ser Leu His Gly Ser Ile
            20                  25                  30

Glu Ile Pro Gly Asp Lys Ser Ile Ser His Arg Ala Leu Met Leu Gly
        35                  40                  45

Ala Leu Ala Thr Gly Thr Thr Ile Ile Glu Gly Leu Leu Leu Gly Ala
    50                  55                  60

Asp Pro Arg Ser Thr Ala Ser Cys Phe Ser Gln Met Gly Ala Gln Ile
65                  70                  75                  80

Ser Glu Leu Asn Glu Lys Arg Val Glu Val Arg Gly Ile Gly Leu Gly
                85                  90                  95

Gln Leu His Glu Pro Thr Ala Val Leu Asp Ala Gly Asn Ser Ala Thr
            100                 105                 110

Thr Leu Arg Leu Met Leu Gly Ile Leu Ala Ser His Pro Asp Arg Phe
        115                 120                 125

Phe Thr Val Thr Gly Asp His Ser Leu Val Arg Arg Pro Met Asp Arg
    130                 135                 140

Val Val Lys Pro Leu Gln Glu Met Gly Ala Met Ile Trp Gly Arg Glu
145                 150                 155                 160

Gly Gly Ser Phe Ala Pro Leu Ala Ile Gln Gly Gln Arg Leu Asn Pro
                165                 170                 175

Ile His Tyr Lys Ser Pro Ile Ala Ser Ala Gln Val Lys Ser Cys Val
            180                 185                 190

Leu Leu Ala Gly Leu Met Ala Glu Gly Glu Thr Thr Val Thr Glu Pro
        195                 200                 205

Ala Leu Ser Arg Asp His Ser Glu Arg Met Leu Arg Ala Phe Gly Ala
    210                 215                 220

Thr Val Thr Val Asp Pro Glu Thr His Ser Ala Thr Val Ile Gly Pro
225                 230                 235                 240

Ala Thr Leu Gln Gly Gln Pro Val Val Pro Gly Asp Ile Ser Ser
                245                 250                 255

Ala Ala Phe Trp Leu Val Ala Gly Ala Ile Ile Pro Gly Ser Glu Leu
            260                 265                 270

Leu Ile Gln Asn Val Gly Val Asn Pro Thr Arg Thr Gly Ile Leu Asp
        275                 280                 285

```
Ala Leu Glu Met Met Glu Ala Asp Ile Gln Leu Glu Asn Gln Arg Glu
         290                 295                 300

Val Ala Gly Glu Pro Val Ala Asp Leu Arg Val Lys Tyr Ser Gln Leu
305                 310                 315                 320

Lys Ala Cys Thr Leu Glu Gly Ala Leu Ile Pro Arg Leu Ile Asp Glu
                325                 330                 335

Ile Pro Ile Leu Ala Val Ala Ala Thr Ser Ala Gln Gly Thr Thr Ile
                340                 345                 350

Ile Arg Asp Ala Glu Glu Leu Arg Val Lys Glu Ser Asp Arg Ile Thr
                355                 360                 365

Val Met Ala Ala Glu Leu Asn Arg Met Gly Ala Lys Ile Ser Glu Leu
370                 375                 380

Pro Asp Gly Met Glu Ile Val Gly Gly Thr Ala Leu Thr Gly Ala Glu
385                 390                 395                 400

Val Asp Ser Tyr Thr Asp His Arg Ile Ala Met Ser Leu Ala Ile Ala
                405                 410                 415

Ala Leu Lys Ala Ser Gly Lys Thr Thr Ile Gly Arg Ala Glu Ala Ala
                420                 425                 430

Ser Ile Ser Tyr Pro Gln Phe Thr Thr Thr Leu Gln Gln Ile Cys Gly
                435                 440                 445

<210> SEQ ID NO 8
<211> LENGTH: 1344
<212> TYPE: DNA
<213> ORGANISM: Artificial Sequence
<220> FEATURE:
<223> OTHER INFORMATION: E. coli optimized version of dgt-12

<400> SEQUENCE: 8
atgctgaccg gtattatcga aaccaaaacc agcgaaagcc agcagaccct gagcgttgaa      60
ccgcctacca gcggtctgag cctgcatggt agcattgaaa ttccgggtga taaaagcatt     120
agccatcgtg cactgatgct gggtgcactg caaccggca ccaccattat gaaggtctg      180 ctgctgggtg cagatccgcg tagcaccgca agctgtttta gccagatggg tgcacagatt     240
agcgaactga tgaaaaaacg tgttgaagtg cgtggtattg gtctgggtca gctgcatgaa     300
ccgaccgcag ttctggatgc cggtaatagc gcaaccaccc tgcgtctgat gctgggcatt     360
ctggcaagcc atccggatcg ttttttttacc gttaccggtg atcatagcct ggttcgtcgt     420
ccgatggatc gtgttgttaa accgctgcaa gaaatgggtg caatgatttg gggtcgtgaa     480
ggtggttctt ttgcaccgct ggcaattcag ggtcagcgtc tgaatccgat ccattataaa     540
agcccgattg caagcgcaca ggttaaaagc tgtgttctgc tggcaggcct gatggcagaa     600
ggtgaaacca ccgttaccga accggcactg agccgtgatc atagcgaacg tatgctgcgt     660
gcatttggtg caaccgttac cgtggatccg gaaaacccata gcgcaaccgt tattggtccg     720
gcaaccctgc agggtcagcc ggttgttgtt cctggtgata ttagcagcgc agcattttgg     780
ctggttgccg gtgcaattat tccgggtagc gaactgctga ttcagaatgt tggtgttaat     840
ccgacccgta ccggtattct ggatgcactg aaatgatgg aagcagatat ccagctggaa     900
aatcagcgtg aagttgccgg tgaaccggtt gcagatctgc gtgttaaata cagccagctg     960
aaagcatgta ccctggaagg tgcactgatt ccgcgtctga ttgatgaaat tccgattctg    1020
gcagttgcag caaccagcgc acagggtaca accattattc gtgatgcaga agaactgcgc    1080
gttaaagaaa gcgatcgtat taccgttatg gcagcagaac tgaatcgtat gggtgccaaa    1140
atttctgaac tgccggatgg tatggaaatt gttggtggca ccgcactgac cggtgcagaa    1200
```

```
gttgatagct ataccgatca tcgtattgca atgagcctgg ccattgcagc actgaaagca    1260
agcggtaaaa ccaccattgg tcgtgcagaa gcagcaagca ttagctatcc gcagtttacc    1320
accaccctgc agcagatttg tggt                                           1344
```

<210> SEQ ID NO 9
<211> LENGTH: 428
<212> TYPE: PRT
<213> ORGANISM: Artificial Sequence
<220> FEATURE:
<223> OTHER INFORMATION: DGT-18 sequence is a modification of GENBANK
      ACC NO: NP_928909.1 where the endogenous glycine was replaced with
      an alanine at amino acid residue 96

<400> SEQUENCE: 9

```
Met Gln Ser Leu Met Leu Gln Pro Ile Ser Tyr Ile Asn Gly Thr Ile
1               5                   10                  15

Asn Leu Pro Gly Ser Lys Ser Val Ser Asn Arg Ala Leu Leu Leu Ala
            20                  25                  30

Ala Phe Ala Lys Gly Ala Thr Cys Leu Thr Asn Leu Leu Asp Ser Asp
        35                  40                  45

Asp Ile Arg His Met Leu Asn Ala Leu Ala Ala Leu Gly Ile Ser Tyr
    50                  55                  60

Arg Leu Ser Asp Asp Arg Thr Cys Cys Glu Val Asp Gly Ile Gly Gly
65                  70                  75                  80

Leu Ile Thr His Gln Gly Pro Ile Glu Leu Phe Leu Gly Asn Ala Ala
                85                  90                  95

Thr Ala Met Arg Pro Leu Thr Ala Ala Leu Cys Leu Gly Lys Asn Asp
            100                 105                 110

Val Val Leu Thr Gly Glu Pro Arg Met Lys Glu Arg Pro Ile Gly His
        115                 120                 125

Leu Val Asp Ala Leu Arg Gln Gly Gly Ala Glu Ile Asp Tyr Leu Glu
    130                 135                 140

Gln Glu Asn Tyr Pro Pro Leu His Val Lys Gly Gly Phe Val Gly Gly
145                 150                 155                 160

Lys Val Met Val Asp Gly Arg Val Ser Ser Gln Phe Leu Thr Ala Leu
                165                 170                 175

Leu Met Ala Ala Pro Leu Ala Glu Asn Asp Ser Glu Ile His Ile Gln
            180                 185                 190

Gly Glu Leu Val Ser Lys Pro Tyr Ile Asp Ile Thr Leu Ala Leu Met
        195                 200                 205

Lys Ser Phe Gly Ile Thr Ile Asn His Asp Gln Tyr Gln Ile Phe His
    210                 215                 220

Ile Lys Gly Arg Gln Gln Tyr Val Ser Pro Gly His Tyr Leu Val Glu
225                 230                 235                 240

Gly Asp Ala Ser Ser Ala Ser Tyr Phe Leu Ala Ala Ala Ile Lys
                245                 250                 255

Gly Gly Thr Val Arg Val Thr Gly Ile Gly Lys Asn Ser Leu Gln Gly
            260                 265                 270

Asp Thr Lys Phe Ala Asn Val Leu Glu Lys Met Gly Ala Lys Ile Arg
        275                 280                 285

Trp Gly Asp Asp Phe Val Glu Cys Glu Arg Gly Thr Leu Thr Gly Ile
    290                 295                 300

Asp Met Asp Met Asn Glu Ile Pro Asp Ala Ala Met Thr Ile Ala Thr
305                 310                 315                 320
```

```
Thr Ala Leu Phe Ala Ala Gly Glu Thr Val Ile Arg Asn Ile Tyr Asn
            325                 330                 335

Trp Arg Val Lys Glu Thr Asp Arg Leu His Ala Met Ala Thr Glu Leu
        340                 345                 350

Arg Lys Val Gly Ala Glu Val Glu Gly Val Asp Tyr Ile Arg Ile
    355                 360                 365

Thr Pro Pro Arg Leu Leu Pro Ala Glu Ile Gly Thr Tyr Asn Asp
    370                 375                 380

His Arg Met Ala Met Cys Phe Ser Leu Val Ala Leu Ser Asp Thr Pro
385                 390                 395                 400

Val Thr Ile Leu Asp Pro Gly Cys Thr Ala Lys Thr Phe Pro Asp Tyr
            405                 410                 415

Phe Asn Gln Leu Glu Arg Leu Ser Gln Arg Lys Ser
            420                 425
```

<210> SEQ ID NO 10
<211> LENGTH: 1284
<212> TYPE: DNA
<213> ORGANISM: Artificial Sequence
<220> FEATURE:
<223> OTHER INFORMATION: E. coli optimized version of dgt-18

<400> SEQUENCE: 10

```
atgcagagcc tgatgctgca gccgattagc tatattaacg gcaccattaa tctgcctggt      60
agcaaaagcg ttagcaatcg tgcactgctg ctggcagcat ttgcaaaagg tgcaacctgt     120
ctgaccaatc tgctggattc tgatgatatt cgccacatgc tgaatgcact ggcagcactg     180
ggtattagct atcgtctgtc tgatgatcgt acctgttgtg aagttgatgg tattggtggt     240
ctgattaccc atcagggtcc gattgaactg tttctgggta tgcagcaac cgcaatgcgt      300
ccgctgaccg cagcactgtg tctgggtaaa atgatgttg ttctgaccgg tgaaccgcgt      360
atgaaagaac gtccgattgg tcatctggtt gatgcactgc gtcagggtgg tgcagaaatt     420
gattacctgg aacaggaaaa ttatccgcct ctgcatgtta aggtggtttt tgtgggtggt     480
aaagtgatgg ttgatggtcg tgttagcagc cagtttctga ccgcactgct gatggctgca     540
ccgctggcag aaaatgatag cgaaatccat attcagggtg aactggttag caaaccgtat     600
attgatatta ccctggccct gatgaaaagc tttggcatca ccattaacca tgatcagtac     660
cagatctttc atattaaagg tcgccagcag tatgtttctc cgggtcatta tctggttgaa     720
ggtgatgcaa gcagcgcaag ctatttctg gcagcagcag caattaaagg tggcaccgtt      780
cgtgttaccg gtattggtaa aaatagcctg cagggcgata ccaaatttgc aaatgtgctg     840
gaaaaaatgg gtgcaaaaat tcgttggggt gatgattttg ttgaatgtga acgtggcacc     900
ctgaccggta ttgatatgga tatgaacgaa attccggatg cagcaatgac cattgcaacc     960
accgcactgt ttgcagccgg tgaaaccgtt attcgcaaca tttataattg gcgtgtgaaa    1020
gaaccgatc gtctgcatgc aatggcaacc gaactgcgta agttggtgc agaagttgaa      1080
gaaggcgttg attatatccg tattacaccg cctccgcgtc tgctgcctgc agaaattggc    1140
acctataatg atcatcgtat ggccatgtgt tttagcctgg ttgcactgag cgatacaccg    1200
gttaccattc tggatccggg ttgtaccgca aaaacctttc cggattactt taatcagctg    1260
gaacgtctga gccagcgtaa aagc                                            1284
```

<210> SEQ ID NO 11
<211> LENGTH: 426
<212> TYPE: PRT

<213> ORGANISM: Artificial Sequence
<220> FEATURE:
<223> OTHER INFORMATION: DGT-29 sequence is a modification of GENBANK
      ACC NO: YP_322772.1 where the endogenous glycine was replaced with
      an alanine at amino acid residue 96

<400> SEQUENCE: 11

Met Asp Thr Ile Ala Ile Pro Ala Leu Asn Arg Pro Val Asp Ala Thr
1               5                   10                  15

Val Glu Ile Pro Gly Ser Lys Ser Ile Thr Asn Arg Ala Leu Leu Val
            20                  25                  30

Ala Ala Leu Ala Gln Gly Asp Ser Thr Leu Glu Asn Ala Leu Phe Ser
        35                  40                  45

Glu Asp Ser Glu Tyr Phe Ala Lys Cys Val Glu Gln Leu Gly Ile Pro
    50                  55                  60

Ile Thr Leu Asn Pro His Leu Ala Gln Ile Gln Val Ser Gly Lys Gly
65                  70                  75                  80

Gly Asp Ile Pro Ala Lys Gln Ala Asp Leu Phe Val Gly Leu Ala Ala
                85                  90                  95

Thr Ala Ala Arg Phe Ile Thr Ala Leu Val Ala Leu Gly Asn Gly Glu
            100                 105                 110

Tyr Arg Leu Asp Gly Val Pro Arg Met Arg Glu Arg Pro Met Gly Asp
        115                 120                 125

Leu Val Thr Val Leu Gln Asn Ser Gly Ile Lys Ile Asn Phe Glu Gly
    130                 135                 140

Asn Ser Gly Phe Met Pro Tyr Thr Ile Tyr Gly Gln Gln Phe Ala Gly
145                 150                 155                 160

Gly His Phe Arg Leu Lys Ala Asn Gln Thr Ser Gln Leu Ser Ala
                165                 170                 175

Leu Leu Met Ile Ala Pro Tyr Ala Gln Gln Asp Thr Thr Ile Glu Val
            180                 185                 190

Glu Gly Thr Leu Val Ser Gln Ser Tyr Val Lys Met Thr Cys Arg Leu
        195                 200                 205

Met Ala Asp Phe Gly Val Asp Val Thr Gln Thr Asp Asp Asn Gln Phe
    210                 215                 220

His Ile Lys Ala Gly Gln Arg Tyr Gln Ala Arg His Tyr Thr Ile Glu
225                 230                 235                 240

Pro Asp Ala Ser Asn Ala Ser Tyr Phe Phe Ala Ala Ala Val Thr
                245                 250                 255

Gly Gly Arg Val Arg Val Asn His Leu Thr Lys Gln Ser Cys Gln Gly
            260                 265                 270

Asp Ile Leu Trp Leu Asn Val Leu Glu Gln Met Gly Cys Gln Val Leu
        275                 280                 285

Glu Gly Glu Asp Tyr Thr Glu Val Ile Gly Pro Glu Gln Leu Gln Gly
    290                 295                 300

Ile Asp Val Asp Met Asn Asp Met Ser Asp Leu Val Gln Thr Leu Gly
305                 310                 315                 320

Ala Ile Ala Pro Tyr Ala Asn Ser Pro Val Ile Ile Arg Asn Val Glu
                325                 330                 335

His Ile Arg Tyr Lys Glu Thr Asp Arg Ile Arg Ala Val Val Thr Glu
            340                 345                 350

Leu Arg Arg Leu Gly Val Lys Val Glu Glu Phe Ala Asp Gly Met Lys
        355                 360                 365

Ile Glu Pro Thr Pro Ile Asn Pro Ala Ala Ile Glu Thr Tyr His Asp
    370                 375                 380

His Arg Met Ala Met Ala Phe Ala Val Thr Gly Leu Lys Thr Pro Gly
385                 390                 395                 400

Ile Val Ile Gln Asp Pro Gly Cys Thr Ala Lys Thr Phe Pro Asp Tyr
                405                 410                 415

Phe Thr Arg Phe Phe Lys Met Ile Gly Gln
            420                 425

<210> SEQ ID NO 12
<211> LENGTH: 1278
<212> TYPE: DNA
<213> ORGANISM: Artificial Sequence
<220> FEATURE:
<223> OTHER INFORMATION: E. coli optimized version of dgt-29

<400> SEQUENCE: 12

| | | |
|---|---|---|
| atggatacca ttgcaattcc ggcactgaat cgtccggttg atgcaaccgt tgaaattccg | 60 |
| ggtagcaaaa gcattaccaa tcgtgcactg ctggttgcag cactggcaca aggtgatagc | 120 |
| accctggaaa atgcactgtt tagcgaagat agcgaatatt ttgcgaaatg tgtggaacag | 180 |
| ctgggtattc cgattaccct gaatccgcat ctggcacaga ttcaggttag cggtaaaggt | 240 |
| ggtgatattc cggcaaaaca ggcagacctg tttgttggtc tggcagcaac cgcagcacgt | 300 |
| tttattaccg cactggttgc actgggtaat ggtgaatatc gtctggatgg tgttccgcgt | 360 |
| atgcgtgaac gtccgatggg tgatctggtt accgttctgc agaatagcgg cattaaaatt | 420 |
| aactttgagg gcaacagcgg tttttatgccg tataccattt atggtcagca gtttgccggt | 480 |
| ggtcattttc gtctgaaagc aaatcagacc agccagcagc tgtctgcact gctgatgatt | 540 |
| gcaccgtatg cacagcagga taccaccatt gaagttgaag caccctggt tagccagagc | 600 |
| tatgttaaaa tgacctgtcg tctgatggca gattttggtg ttgatgttac ccagaccgat | 660 |
| gataaccagt ttcacattaa agccggtcag cgttatcagg cacgtcatta ccattgaa | 720 |
| ccggatgcca gcaatgcaag ctattttttt gcagcagcag cagttaccgg tggtcgtgtt | 780 |
| cgtgttaatc atctgaccaa acagagctgt cagggtgata ttctgtggct gaatgtgctg | 840 |
| gaacaaatgg ttgtcaggt tctggaaggt gaagattata ccgaagtgat tggtccggaa | 900 |
| cagctgcagg tattgatgt ggatatgaac gatatgagcg atctggttca gaccctgggt | 960 |
| gcaattgctc cgtatgcaaa ttctccggtg attattcgca acgtggaaca cattcgctat | 1020 |
| aaagaaaccg aacgtattcg tgcagttgtt accgaactgc gtcgtctggg tgttaaagtt | 1080 |
| gaagaattcg ccgatggcat gaaaattgaa ccgaccccga ttaatccggc agcaatcgaa | 1140 |
| acctatcatg atcatcgtat ggcaatggca tttgccgtta ccggtctgaa acaccgggt | 1200 |
| attgttattc aggatccggg ttgtaccgca aaaacctttc cggattattt tacccgcttt | 1260 |
| tttaaaatga tcggccag | 1278 |

<210> SEQ ID NO 13
<211> LENGTH: 426
<212> TYPE: PRT
<213> ORGANISM: Artificial Sequence
<220> FEATURE:
<223> OTHER INFORMATION: DGT-30 sequence is a modification of GENBANK
      ACC NO: ZP_02156189.1 where the endogenous glycine was replaced
      with an alanine at amino acid residue 96

<400> SEQUENCE: 13

Met Lys Gln Leu Arg Leu Glu Pro Ile Ser Lys Val Gln Gly Thr Ile
1               5                   10                  15

```
Asn Ile Pro Gly Ser Lys Ser Ile Ser Asn Arg Ala Leu Leu Ala
             20                  25                  30

Thr Leu Ala Lys Gly Thr Thr Leu Thr Asn Leu Leu Asp Ala Asp
             35                  40                  45

Asp Ile Arg Tyr Met Leu Ala Ser Leu Lys Gln Leu Gly Val Asn Tyr
 50                  55                  60

Arg Leu Ser Asp Asn Asn Thr Val Cys Glu Leu Glu Gly Ile Gly Ala
 65                  70                  75                  80

Pro Leu Asn Ala Lys Leu Ala Gln Thr Leu Phe Leu Gly Asn Ala Ala
             85                  90                  95

Thr Ala Met Arg Pro Leu Cys Ala Ala Leu Thr Leu Gly Gln Gly Glu
            100                 105                 110

Phe Thr Leu Thr Gly Glu Pro Arg Met Glu Glu Arg Pro Ile Gly Asp
            115                 120                 125

Leu Val Asp Ala Leu Arg Gln Leu Gly Ala Ser Val Thr Tyr Leu Lys
            130                 135                 140

Asn Glu Gly Phe Pro Pro Leu Thr Ile Lys Ala Thr Gly Leu Asn Ala
145                 150                 155                 160

Gly Asp Val Glu Ile Ala Gly Asp Leu Ser Ser Gln Phe Leu Thr Ala
            165                 170                 175

Leu Leu Met Val Ala Pro Leu Ala Lys Gly Glu Val Asn Ile Lys Ile
            180                 185                 190

Lys Gly Glu Leu Val Ser Lys Pro Tyr Ile Asp Ile Thr Ile Ala Leu
            195                 200                 205

Met Ala Gln Phe Gly Val Glu Val Ile Asn His Asp Tyr Arg Arg Phe
            210                 215                 220

Glu Ile Lys Ala Gly Gln Thr Tyr Val Ser Pro Gly Lys Val Leu Val
225                 230                 235                 240

Glu Gly Asp Ala Ser Ser Ala Ser Tyr Phe Leu Ala Ala Gly Ala Ile
            245                 250                 255

Lys Gly Gly Glu Val Lys Val Thr Gly Val Gly Arg Leu Ser Ile Gln
            260                 265                 270

Gly Asp Val Lys Phe Ala Asp Val Leu Glu Lys Met Gly Ala Asp Ile
            275                 280                 285

Glu Trp Gly Asp Asp Tyr Ile Ile Ser Arg Gly Ala Lys Leu Lys Gly
            290                 295                 300

Val Asp Leu Asp Met Asn His Ile Pro Asp Ala Ala Met Thr Ile Ala
305                 310                 315                 320

Thr Val Ala Leu Phe Ala Thr Gly Thr Thr Thr Ile Arg Asn Ile Tyr
            325                 330                 335

Asn Trp Arg Ile Lys Glu Thr Asp Arg Leu Ala Ala Met Ala Thr Glu
            340                 345                 350

Leu Arg Lys Val Gly Ala Ile Val Glu Glu Gly His Asp Tyr Ile Ser
            355                 360                 365

Ile Thr Pro Pro Ser Lys Pro His Thr Ala Glu Ile Asp Thr Tyr Asn
            370                 375                 380

Asp His Arg Met Ala Met Cys Phe Ser Met Leu Ala Phe Ala Asp Cys
385                 390                 395                 400

Gly Ile Thr Ile Asn Asp Pro Asp Cys Thr Ser Lys Thr Phe Pro Asn
            405                 410                 415

Tyr Phe Gln Gln Phe Ala Ala Leu Ala Gln
            420                 425
```

<210> SEQ ID NO 14
<211> LENGTH: 1278
<212> TYPE: DNA
<213> ORGANISM: Artificial Sequence
<220> FEATURE:
<223> OTHER INFORMATION: E. coli optimized version of dgt-30

<400> SEQUENCE: 14

| | |
|---|---|
| atgaaacagc tgcgtctgga accgattagc aaagttcagg gcaccattaa tattccgggt | 60 |
| agcaaaagca ttagcaatcg tgcactgctg ctggcaaccc tggcaaaagg caccaccacc | 120 |
| ctgaccaatc tgctggatgc agatgatatt cgttatatgc tggcctctct gaaacagctg | 180 |
| ggtgttaatt atcgtctgag cgataataat accgtttgcg aactggaagg tattggtgca | 240 |
| ccgctgaatg caaaactggc acagaccctg tttctgggta atgcagcaac cgcaatgcgc | 300 |
| ccgctgtgtg cagcactgac cctgggacaa ggtgaattta ccctgacagg tgaaccgcgt | 360 |
| atggaagaac gtccgattgg tgatctggtt gatgcattac gtcagctggg tgcaagcgtt | 420 |
| acctatctga aaaatgaagg ttttccgcct ctgaccatta agcaaccgg tctgaatgcc | 480 |
| ggtgatgttg aaattgccgg tgatctgagc agccagtttc tgaccgcact gctgatggtt | 540 |
| gcaccgctgg ctaaaggtga agtgaacatt aaaattaaag cgaactggt gagcaaaccg | 600 |
| tatattgata tcaccattgc actgatggca cagtttggtg tggaagtgat caatcatgat | 660 |
| tatcgtcgct ttgaaattaa agccggtcag acctatgttt ctccgggtaa agttctggtt | 720 |
| gaaggtgatg caagcagcgc aagctatttt ctggcagccg gtgcaattaa aggtggtgaa | 780 |
| gtgaaagtta ccggtgttgg tcgtctgagc attcagggtg atgttaaatt tgcagatgtg | 840 |
| ctggaaaaaa tgggtgcaga tatcgaatgg ggtgatgatt atattattag ccgtggtgcg | 900 |
| aaactgaaag tgttgatct ggatatgaac catattccgg atgcagcaat gaccattgca | 960 |
| accgttgcac tgtttgcaac cggtacaacc accattcgca catttataa ttggcgcatt | 1020 |
| aaagaaaccg atcgtctggc agcaatggca accgaactgc gtaaagttgg tgccattgtg | 1080 |
| gaagaaggcc acgattatat tagcattacc cctccgagca aaccgcatac cgcagaaatt | 1140 |
| gataccctata cgatcatcg tatggccatg tgttttagca tgctggcatt tgcagattgt | 1200 |
| ggcatcacca ttaatgatcc ggattgtacc agcaaaacct cccgaatta ttttcagcag | 1260 |
| tttgcagcac tggcacag | 1278 |

<210> SEQ ID NO 15
<211> LENGTH: 38
<212> TYPE: DNA
<213> ORGANISM: Artificial Sequence
<220> FEATURE:
<223> OTHER INFORMATION: Primer Sequence

<400> SEQUENCE: 15
ggatgccggt aatgcaggaa cctgtgttcg tctgatgg       38

<210> SEQ ID NO 16
<211> LENGTH: 38
<212> TYPE: DNA
<213> ORGANISM: Artificial Sequence
<220> FEATURE:
<223> OTHER INFORMATION: Primer Sequence

<400> SEQUENCE: 16
ccatcagacg aacacaggtt cctgcattac cggcatcc       38

<210> SEQ ID NO 17

<211> LENGTH: 1353
<212> TYPE: DNA
<213> ORGANISM: Artificial Sequence
<220> FEATURE:
<223> OTHER INFORMATION: E.coli optimized sequence of GENBANK ACC NO: ZP_01452683

<400> SEQUENCE: 17

| | | |
|---|---|---|
| atgagcaccg tggcaccct gattgctggt cctgcagccg gtccgctgaa aggtgaactg | 60 |
| accgttccgg gtgataaaag catgagccat cgtagcgtta tgctggcagc actggcagat | 120 |
| ggtgttaccg aaattcatgg ttttctgcct ggcgaagata atattgcaac cgcacgcatg | 180 |
| tttattgata tgggcgtgcg tattgaatgg ctgaacgatg aaaaaaccag cctgcgtgtt | 240 |
| catggtgttg gtctgcatgg tctgaaacag ccgcaggta tgctggatgc cggtaatgca | 300 |
| ggaacctgtg ttcgtctgat ggcaggcatt ctggcaggcc agcatttag cagcaccgtt | 360 |
| actggggatg caagcctgtg taaacgtccg atgaaacgtg ttgttgatcc ggttcgtcgt | 420 |
| atgggtgcaa aagttgaagg tgttgatgat ggaaatctgc tgccgattac cattagcggt | 480 |
| ggtaaactga agccattga tcatgttagc gaagttgcaa gcgcacaggt taaaagctgt | 540 |
| gttctgctgg caggcctgta tgcagatggt gtgaccagcg ttagcgaacc gaaaccgacc | 600 |
| cgtgatcata ccgaacgtat gctgccgctg tttggtcagc cggttaccgt tgcagcagat | 660 |
| ggcaccatta gcctggatcc gaaagatcgt ctgaccgcac cggttggtgt tgttgatatt | 720 |
| ccggcagatc cgagcagcgc atgttttttt gcagtggcag caagcctggt tgaaggttct | 780 |
| gatgtgaccc tgaaaagcat tggtattaat ccgcgtcgtg atggttggcg tcgtgttatg | 840 |
| aatggtatgg gtgcagcact gagcctggaa atgaacagc gttggtga agaaccggtt | 900 |
| gcagatgttc gtattcgtag cggtggcctg catggtatgc atgttgttcc gaatgatgtt | 960 |
| ccggatgcca ttgatgaatt ccggttctg tttgcagcag caaccctggc cgatggtgaa | 1020 |
| tttgttctga ccgatgcaga gaactgcgc gttaaagaaa gcgaccgtat tgcagcaatg | 1080 |
| gcaaccgcac tgcgtagcgc aggcgcagat attgatgaac agccggatgg tgcagttatt | 1140 |
| cgtggtatta ccaatctgcg tggtgatgtt gatgttgatg cccatggtga tcatcgtatt | 1200 |
| gcaatggcaa tggcagttgc agcccagcgt gcagatggtg aagttcgtat tcataatgca | 1260 |
| gctgcaattg caaccagctt tccgaatttt gttcagctgg cacagagcgt tggtatgaat | 1320 |
| gttcgttggg cagatgaagg tgaagcataa taa | 1353 |

<210> SEQ ID NO 18
<211> LENGTH: 213
<212> TYPE: DNA
<213> ORGANISM: Artificial Sequence
<220> FEATURE:
<223> OTHER INFORMATION: Artificial chloroplast transit peptide sequence of TraP4 v5

<400> SEQUENCE: 18

| | | |
|---|---|---|
| atgcttgcta gacaaggtgg aagtctgaga gcttctcaat gcaacgctgg acttgctaga | 60 |
| agagttgaag ttggtgctct tgttgttcct agacctatct ctgttaacga cgttgttcct | 120 |
| cacgtttact ctgctccact ttctgttgct agaaggtctt gctctaagtc cagcattagg | 180 |
| tccactagaa ggcttcaaac tactgtgtgc tct | 213 |

<210> SEQ ID NO 19
<211> LENGTH: 186
<212> TYPE: DNA
<213> ORGANISM: Artificial Sequence

```
<220> FEATURE:
<223> OTHER INFORMATION: Artificial chloroplast transit peptide sequence
      Trap5 v1

<400> SEQUENCE: 19
atgcagctcc tcaaccagcg tcaggccctg cgcctgggcc gctcttctgc tagcaagaac      60
cagcaggttg ctcctctggc ctctcgccct gcgtcttcct tgagcgtcag cgcctcgagc     120
gtcgcgccgg cgcctgcttg cagtgctccc gcgggcgcag gtcgccgcgc tgttgtcgtg     180
cgcgca                                                                186

<210> SEQ ID NO 20
<211> LENGTH: 186
<212> TYPE: DNA
<213> ORGANISM: Artificial Sequence
<220> FEATURE:
<223> OTHER INFORMATION: Artificial chloroplast transit peptide sequence
      Trap5 v2

<400> SEQUENCE: 20
atgcaactcc tgaatcagag gcaagccctg cgtcttggtc gttcatctgc ttcaaagaac      60
cagcaagttg ctccactggc ctctaggcct gcttcttcct tgagcgtcag cgcatccagc     120
gtcgcacctg cacctgcttg ctcagctcct gctggagctg gaaggcgtgc tgttgtcgtg     180
agagca                                                                186

<210> SEQ ID NO 21
<211> LENGTH: 198
<212> TYPE: DNA
<213> ORGANISM: Artificial Sequence
<220> FEATURE:
<223> OTHER INFORMATION: Artificial chloroplast transit peptide sequence
      of TraP8 v2

<400> SEQUENCE: 21
atggctcaat ctagcagaat ctgccacggt gtgcagaacc catgtgtgat catttccaat      60
ctctccaaat ccaaccagaa caaatctcct ttctcagtca gcctcaagac tcaccagcag     120
cagcgtcgtg cttaccagat atctagctgg ggattgaaga agtcaaacaa cgggtccgtg     180
attcgtccgg ttaaggca                                                   198

<210> SEQ ID NO 22
<211> LENGTH: 198
<212> TYPE: DNA
<213> ORGANISM: Artificial Sequence
<220> FEATURE:
<223> OTHER INFORMATION: Artificial chloroplast transit peptide sequence
      of TraP9 v2

<400> SEQUENCE: 22
atggcacaag ccagccgtat ctgccagaat ccatgtgtga tatccaatct ccccaaaagc      60
aaccaccgta gtccccttt ctctgtctca ctcaagacgc atcagcctag agcctcttca     120
tggggactta agaagtctgg caccatgctg aacggttcag tgattagacc cgtcaaggtg     180
acagcttctg tttccgca                                                   198

<210> SEQ ID NO 23
<211> LENGTH: 225
<212> TYPE: DNA
<213> ORGANISM: Artificial Sequence
<220> FEATURE:
<223> OTHER INFORMATION: Artificial chloroplast transit peptide sequence
      of TraP12 v2
```

<400> SEQUENCE: 23

| | | | | |
|---|---|---|---|---|
| atggcacaat | ctagcagaat | ctgccacggt | gtgcagaacc | catgtgtgat catttcaaat | 60 |
| ctctcaaagt | ccaatcagaa | caaatcacct | ttctccgtct | ccctcaagac acaccagcat | 120 |
| ccaagggcat | acccgataag | cagctcatgg | ggactcaaga | gagcggaat gactctgatt | 180 |
| ggctctgagc | ttcgtcctct | taaggttatg | tcctctgttt | ccgca | 225 |

<210> SEQ ID NO 24
<211> LENGTH: 207
<212> TYPE: DNA
<213> ORGANISM: Artificial Sequence
<220> FEATURE:
<223> OTHER INFORMATION: Artificial chloroplast transit peptide sequence of TraP13 v2

<400> SEQUENCE: 24

| | | | | |
|---|---|---|---|---|
| atggcacaag | ttagcagaat | ctgtaatggt | gtgcagaacc | catctcttat ctccaatctc | 60 |
| tcaaagtcca | gccaacgtaa | gtctcccctc | agcgtgtctc | tgaaaactca gcagcccaga | 120 |
| gcttcttcat | ggggtttgaa | gaaatctgga | acgatgctta | acggctcagt cattcgtccg | 180 |
| gttaaggtga | cagcctccgt | ctccgct | | | 207 |

<210> SEQ ID NO 25
<211> LENGTH: 1566
<212> TYPE: DNA
<213> ORGANISM: Artificial Sequence
<220> FEATURE:
<223> OTHER INFORMATION: In-frame fusion of TraP4 v5:dgt-14 v2

<400> SEQUENCE: 25

| | | | | |
|---|---|---|---|---|
| atgcttgcta | gacaaggtgg | aagtctgaga | gcttctcaat | gcaacgctgg acttgctaga | 60 |
| agagttgaag | ttggtgctct | tgttgttcct | agacctatct | ctgttaacga cgttgttcct | 120 |
| cacgtttact | ctgctccact | ttctgttgct | agaaggtctt | gctctaagtc cagcattagg | 180 |
| tccactagaa | ggcttcaaac | tactgtgtgc | tctgctgcat | caactggtgg cactctgata | 240 |
| gctggaccag | cagctggacc | actgaaggga | gaattgaccg | ttcctggtga caaatctatg | 300 |
| tctcacagaa | gtgtgatgtt | agcagctttg | gcagacggag | tgacagagat tcatggattc | 360 |
| ctccctgggg | aagataacat | cgccactgct | cgtatgttca | ttgatatggg agtgagaatt | 420 |
| gagtggttga | atgacgaaaa | gacaagtctg | agagttcatg | gtgtgggatt gcatgggctt | 480 |
| aagcaaccac | aaggcatgtt | ggatgctggg | aacgcagcta | catgtgttag actcatggct | 540 |
| ggcatcttgg | ctgggcaaca | cttctcctct | acagttacgg | gagacgcctc attgtgcaag | 600 |
| agacccatga | gagggtggt | tgatccggtg | cgtcgtatgg | gtgcaaaggt tgagggtggg | 660 |
| gatgatggca | atcttcttcc | cataaccatc | tctggtggca | agctcaaagc tatcgaccac | 720 |
| gtcagtgaag | tcgccagcgc | tcaagtcaag | agttgtgtcc | tcttagctgg actgtatgca | 780 |
| gatggagtta | caagtgtaag | cgagccaaaa | cctactcgtg | atcatactga agaatgttg | 840 |
| ccactgttcg | gtcaacccgt | caccgtcgca | gcagacggaa | cgattagcct tgatcctaag | 900 |
| gatagactta | ctgcaccagt | cggagttgtt | gacattccag | ccgaccctag tagcgcttgt | 960 |
| ttctttgcag | tggcagcctc | cctcgtggag | ggatctgatg | tgactctgaa gtcaataggg | 1020 |
| atcaatccaa | gaagagacgg | ttggaggcgt | gttatgaacg | gaatgggagc tgctttgtct | 1080 |
| ctcgaaaacg | agcagagggt | tggagaggaa | cccgtagccg | atgttagaat cagaagtgga | 1140 |
| ggtctccacg | ggatgcacgt | ggtgcccaat | gacgttccgg | acgctatcga tgagtttcca | 1200 |

```
gttttgttcg ctgctgcaac attggctgac ggagagtttg tgttgacaga tgcagaagaa    1260
ttgagggtta aggaatcaga tcgtattgct gcaatggcca cagctttacg tagtgctgga    1320
gctgatatcg atgaacagcc agatggtgcc gtgataagag ggatcaccaa tctgaggggt    1380
gatgtggacg tggacgctca tggtgatcat aggattgcaa tggctatggc agtggcagct    1440
caaagagctg atggagaagt gagaatccat aacgctgctg ctattgccac ttcattccct    1500
aacttcgttc aactggctca atcagtcggg atgaatgtcc gttgggctga cgagggagag    1560
gcatga                                                               1566

<210> SEQ ID NO 26
<211> LENGTH: 1551
<212> TYPE: DNA
<213> ORGANISM: Artificial Sequence
<220> FEATURE:
<223> OTHER INFORMATION: In frame fusion of TraP5 v1: dgt-14 v2

<400> SEQUENCE: 26
atgcagctcc tcaaccagcg tcaggccctg cgcctgggcc gctcttctgc tagcaagaac      60
cagcaggttg ctcctctggc ctctcgccct gcgtcttcct tgagcgtcag cgcctcgagc     120
gtcgcgccgg cgcctgcttg cagtgctccc gcgggcgcag gtcgccgcgc tgttgtcgtg     180
cgcgcagcgt catctggcgc catgtcaact ggtggcactc tgatagctgg accagcagct     240
ggaccactga agggagaatt gaccgttcct ggtgacaaat ctatgtctca gaagtgtg       300 atgttagcag cttttggcaga cggagtgaca gagattcatg gattcctccc tggggaagat    360
aacatcgcca ctgctcgtat gttcattgat atgggagtga gaattgagtg gttgaatgac    420
gaaaagacaa gtctgagagt tcatggtgtg ggattgcatg ggcttaagca accacaaggc    480
atgttggatg ctgggaacgc agctacatgt gttagactca tggctggcat cttggctggg    540
caacacttct cctctacagt tacgggagac gcctcattgt gcaagagacc catgaagagg    600
gtggttgatc cggtgcgtcg tatgggtgca aaggttgagg gtggggatga tggcaatctt    660
cttcccataa ccatctctgg tggcaagctc aaagctatcg accacgtcag tgaagtcgcc    720
agcgctcaag tcaagagttg tgtcctctta gctggactgt atgcagatgg agttacaagt    780
gtaagcgagc caaaacctac tcgtgatcat actgaaagaa tgttgccact gttcggtcaa    840
cccgtcaccg tcgcagcaga cggaacgatt agccttgatc ctaaggatag acttactgca    900
ccagtcggag ttgttgacat tccagccgac cctagtagcg cttgtttctt tgcagtggca    960
gcctccctcg tggagggatc tgatgtgact ctgaagtcaa tagggatcaa tccaagaaga   1020
gacggttgga ggcgtgttat gaacggaatg ggagctgctt tgtctctcga aaacgagcag   1080
agggttggag aggaacccgt agccgatgtt agaatcagaa gtggaggtct ccacgggatg   1140
cacgtggtgc ccaatgacgt tccggacgct atcgatgagt ttccagtttt gttcgctgct   1200
gcaacattgg ctgacggaga gtttgtgttg acagatgcag aagaattgag ggttaaggaa   1260
tcagatcgta ttgctgcaat ggccacagct ttacgtagtg ctggagctga tatcgatgaa   1320
cagccagatg gtgccgtgat aagagggatc accaatctga gggtgatgt ggacgtggac   1380 gctcatggtg atcataggat tgcaatggct atggcagtgg cagctcaaag agctgatgga   1440
gaagtgagaa tccataacgc tgctgctatt gccacttcat tccctaactt cgttcaactg   1500
gctcaatcag tcgggatgaa tgtccgttgg gctgacgagg gagaggcatg a             1551

<210> SEQ ID NO 27
```

<211> LENGTH: 1533
<212> TYPE: DNA
<213> ORGANISM: Artificial Sequence
<220> FEATURE:
<223> OTHER INFORMATION: In-frame fusion of TraP5 v2: dgt-14 v2

<400> SEQUENCE: 27

| | |
|---|---|
| atgcaactcc tgaatcagag gcaagccctg cgtcttggtc gttcatctgc ttcaaagaac | 60 |
| cagcaagttg ctccactggc ctctaggcct gcttcttcct tgagcgtcag cgcatccagc | 120 |
| gtcgcacctg cacctgcttg ctcagctcct gctggagctg aaggcgtgc tgttgtcgtg | 180 |
| agagcagcat caactggtgg cactctgata gctggaccag cagctggacc actgaaggga | 240 |
| gaattgaccg ttcctggtga caaatctatg tctcacagaa gtgtgatgtt agcagctttg | 300 |
| gcagacggag tgacagagat tcatggattc ctccctgggg aagataacat cgccactgct | 360 |
| cgtatgttca ttgatatggg agtgagaatt gagtggttga atgacgaaaa gacaagtctg | 420 |
| agagttcatg gtgtgggatt gcatgggctt aagcaaccac aaggcatgtt ggatgctggg | 480 |
| aacgcagcta catgtgttag actcatggct ggcatcttgg ctgggcaaca cttctcctct | 540 |
| acagttacgg gagacgcctc attgtgcaag agacccatga gagggtggt tgatccggtg | 600 |
| cgtcgtatgg gtgcaaaggt tgagggtggg atgatggca atcttcttcc cataaccatc | 660 |
| tctggtggca agctcaaagc tatcgaccac gtcagtgaag tcgccagcgc tcaagtcaag | 720 |
| agttgtgtcc tcttagctgg actgtatgca gatggagtta caagtgtaag cgagccaaaa | 780 |
| cctactcgtg atcatactga agaatgttg ccactgttcg gtcaacccgt caccgtcgca | 840 |
| gcagacggaa cgattagcct tgatcctaag gatagactta ctgcaccagt cggagttgtt | 900 |
| gacattccag ccgaccctag tagcgcttgt ttctttgcag tggcagcctc cctcgtggag | 960 |
| ggatctgatg tgactctgaa gtcaataggg atcaatccaa gaagagacgg ttggaggcgt | 1020 |
| gttatgaacg gaatgggagc tgctttgtct ctcgaaaacg agcagagggt tggagaggaa | 1080 |
| cccgtagccg atgttagaat cagaagtgga ggtctccacg gatgcacgt ggtgcccaat | 1140 |
| gacgttccgg acgctatcga tgagtttcca gttttgttcg ctgctgcaac attggctgac | 1200 |
| ggagagtttg tgttgacaga tgcagaagaa ttgagggtta aggaatcaga tcgtattgct | 1260 |
| gcaatggcca cagctttacg tagtgctgga gctgatatcg atgaacagcc agatggtgcc | 1320 |
| gtgataagag ggatcaccaa tctgaggggt gatgtgacg tggacgctca tggtgatcat | 1380 |
| aggattgcaa tggctatggc agtggcagct caaagagctg atggagaagt gagaatccat | 1440 |
| aacgctgctg ctattgccac ttcattccct aacttcgttc aactggctca atcagtcggg | 1500 |
| atgaatgtcc gttgggctga cgagggagag gca | 1533 |

<210> SEQ ID NO 28
<211> LENGTH: 1545
<212> TYPE: DNA
<213> ORGANISM: Artificial Sequence
<220> FEATURE:
<223> OTHER INFORMATION: In-frame fusion of TraP8 v2: dgt-14 v2

<400> SEQUENCE: 28

| | |
|---|---|
| atggctcaat ctagcagaat ctgccacggt gtgcagaacc catgtgtgat catttccaat | 60 |
| ctctccaaat ccaaccagaa caaatctcct ttctcagtca gcctcaagac tcaccagcag | 120 |
| cagcgtcgtg cttaccagat atctagctgg ggattgaaga agtcaaacaa cgggtccgtg | 180 |
| attcgtccgg ttaaggcagc atcaactggt ggcactctga tagctggacc agcagctgga | 240 |
| ccactgaagg gagaattgac cgttcctggt gacaaatcta tgtctcacag aagtgtgatg | 300 |

```
ttagcagctt tggcagacgg agtgacagag attcatggat tcctccctgg ggaagataac      360
atcgccactg ctcgtatgtt cattgatatg ggagtgagaa ttgagtggtt gaatgacgaa      420
aagacaagtc tgagagttca tggtgtggga ttgcatgggc ttaagcaacc acaaggcatg      480
ttggatgctg ggaacgcagc tacatgtgtt agactcatgg ctggcatctt ggctgggcaa      540
cacttctcct ctacagttac gggagacgcc tcattgtgca agagaccat gaagagggtg       600 gttgatccgg tgcgtcgtat gggtgcaaag gttgagggtg gggatgatgg caatcttctt      660
cccataacca tctctggtgg caagctcaaa gctatcgacc acgtcagtga agtcgccagc      720
gctcaagtca agagttgtgt cctcttagct ggactgtatg cagatggagt tacaagtgta      780
agcgagccaa aacctactcg tgatcatact gaaagaatgt tgccactgtt cggtcaaccc      840
gtcaccgtcg cagcagacgg aacgattagc cttgatccta aggatagact tactgcacca      900
gtcggagttg ttgacattcc agccgaccct agtagcgctt gtttctttgc agtggcagcc      960
tccctcgtgg agggatctga tgtgactctg aagtcaatag ggatcaatcc aagaagagac     1020
ggttggaggc gtgttatgaa cggaatggga gctgctttgt ctctcgaaaa cgagcagagg     1080 gttgagagg aacccgtagc cgatgttaga atcagaagtg aggtctcca cgggatgcac       1140 gtggtgccca atgacgttcc ggacgctatc gatgagtttc cagttttgtt cgctgctgca     1200
acattggctg acggagagtt tgtgttgaca gatgcagaag aattgagggt taaggaatca     1260
gatcgtattg ctgcaatggc cacagcttta cgtagtgctg gagctgatat cgatgaacag     1320
ccagatggtg ccgtgataag agggatcacc aatctgaggg gtgatgtgga cgtggacgct     1380
catggtgatc ataggattgc aatggctatg gcagtggcag ctcaaagagc tgatggagaa     1440
gtgagaatcc ataacgctgc tgctattgcc acttcattcc ctaacttcgt tcaactggct     1500
caatcagtcg ggatgaatgt ccgttgggct gacgagggag aggca                     1545

<210> SEQ ID NO 29
<211> LENGTH: 1545
<212> TYPE: DNA
<213> ORGANISM: Artificial Sequence
<220> FEATURE:
<223> OTHER INFORMATION: In-frame fusion of TraP9 v2: dgt-14 v2

<400> SEQUENCE: 29
atggcacaag ccagccgtat ctgccagaat ccatgtgtga tatccaatct ccccaaaagc       60
aaccaccgta agtcccctt ctctgtctca ctcaagacgc atcagcctag agcctcttca      120
tggggactta agaagtctgg caccatgctg aacggttcag tgattagacc cgtcaaggtg     180
acagcttctg tttccgcagc atcaactggt ggcactctga tagctggacc agcagctgga     240
ccactgaagg gagaattgac cgttcctggt gacaaatcta tgtctcacag aagtgtgatg     300
ttagcagctt tggcagacgg agtgacagag attcatggat tcctccctgg ggaagataac     360
atcgccactg ctcgtatgtt cattgatatg ggagtgagaa ttgagtggtt gaatgacgaa     420
aagacaagtc tgagagttca tggtgtggga ttgcatgggc ttaagcaacc acaaggcatg     480
ttggatgctg ggaacgcagc tacatgtgtt agactcatgg ctggcatctt ggctgggcaa     540
cacttctcct ctacagttac gggagacgcc tcattgtgca agagaccat gaagagggtg      600 gttgatccgg tgcgtcgtat gggtgcaaag gttgagggtg gggatgatgg caatcttctt     660
cccataacca tctctggtgg caagctcaaa gctatcgacc acgtcagtga agtcgccagc     720
gctcaagtca agagttgtgt cctcttagct ggactgtatg cagatggagt tacaagtgta     780
```

| | |
|---|---|
| agcgagccaa aacctactcg tgatcatact gaaagaatgt tgccactgtt cggtcaaccc | 840 |
| gtcaccgtcg cagcagacgg aacgattagc cttgatccta aggatagact tactgcacca | 900 |
| gtcggagttg ttgacattcc agccgaccct agtagcgctt gtttctttgc agtggcagcc | 960 |
| tccctcgtgg agggatctga tgtgactctg aagtcaatag gatcaatcc aagaagagac | 1020 |
| ggttggaggc gtgttatgaa cggaatggga gctgctttgt ctctcgaaaa cgagcagagg | 1080 |
| gttgagagg aacccgtagc cgatgttaga atcagaagtg gaggtctcca cgggatgcac | 1140 |
| gtggtgccca atgacgttcc ggacgctatc gatgagtttc cagttttgtt cgctgctgca | 1200 |
| acattggctg acggagagtt tgtgttgaca gatgcagaag aattgagggt taaggaatca | 1260 |
| gatcgtattg ctgcaatggc cacagcttta cgtagtgctg gagctgatat cgatgaacag | 1320 |
| ccagatggtg ccgtgataag agggatcacc aatctgaggg gtgatgtgga cgtggacgct | 1380 |
| catggtgatc ataggattgc aatggctatg gcagtggcag ctcaaagagc tgatggagaa | 1440 |
| gtgagaatcc ataacgctgc tgctattgcc acttcattcc ctaacttcgt tcaactggct | 1500 |
| caatcagtcg ggatgaatgt ccgttgggct gacgagggag aggca | 1545 |

<210> SEQ ID NO 30
<211> LENGTH: 1572
<212> TYPE: DNA
<213> ORGANISM: Artificial Sequence
<220> FEATURE:
<223> OTHER INFORMATION: In-frame fusion of TraP12 v2: dgt-14 v2

<400> SEQUENCE: 30

| | |
|---|---|
| atggcacaat ctagcagaat ctgccacggt gtgcagaacc catgtgtgat catttcaaat | 60 |
| ctctcaaagt ccaatcagaa caaatcacct ttctccgtct ccctcaagac acaccagcat | 120 |
| ccaagggcat acccgataag cagctcatgg ggactcaaga gagcggaat gactctgatt | 180 |
| ggctctgagc ttcgtcctct taaggttatg tcctctgttt ccgcagcatc aactggtggc | 240 |
| actctgatag ctggaccagc agctggacca ctgaagggag aattgaccgt tcctggtgac | 300 |
| aaatctatgt ctcacagaag tgtgatgtta gcagctttgg cagacggagt gacagagatt | 360 |
| catggattcc tccctgggga agataacatc gccactgctc gtatgttcat tgatatggga | 420 |
| gtgagaattg agtggttgaa tgacgaaaag acaagtctga gagttcatgg tgtgggattg | 480 |
| catgggctta gcaaccaca aggcatgttg atgctgggaa acgcagctac atgtgttaga | 540 |
| ctcatggctg gcatcttggc tgggcaacac ttctcctcta cagttacggg agacgcctca | 600 |
| ttgtgcaaga gacccatgaa gagggtggtt gatccggtgc gtcgtatggg tgcaaaggtt | 660 |
| gagggtgggg atgatggcaa tcttcttccc ataaccatct ctggtggcaa gctcaaagct | 720 |
| atcgaccacg tcagtgaagt cgccagcgct caagtcaaga gttgtgtcct cttagctgga | 780 |
| ctgtatgcag atggagttac aagtgtaagc gagccaaaac ctactcgtga tcatactgaa | 840 |
| agaatgttgc cactgttcgg tcaacccgtc accgtcgcag cagacggaac gattagcctt | 900 |
| gatcctaagg atagacttac tgcaccagtc ggagttgttg acattccagc cgaccctagt | 960 |
| agcgcttgtt tctttgcagt ggcagcctcc ctcgtggagg gatctgatgt gactctgaag | 1020 |
| tcaatagga tcaatccaag aagagacggt tggaggcgtg ttatgaacgg aatgggagct | 1080 |
| gctttgtctc tcgaaaacga gcagagggtt ggagaggaac ccgtagccga tgttagaatc | 1140 |
| agaagtggag gtctccacgg gatgcacgtg gtgcccaatg acgttccgga cgctatcgat | 1200 |
| gagtttccga ttttgttcgc tgctgcaaca ttggctgacg gagagtttgt gttgacagat | 1260 |
| gcagaagaat tgagggttaa ggaatcagat cgtattgctg caatggccac agctttacgt | 1320 |

```
agtgctggag ctgatatcga tgaacagcca gatggtgccg tgataagagg gatcaccaat    1380 ctgagggtg atgtggacgt ggacgctcat ggtgatcata ggattgcaat ggctatggca     1440
gtggcagctc aaagagctga tggagaagtg agaatccata cgctgctgc tattgccact     1500 tcattcccta acttcgttca actggctcaa tcagtcggga tgaatgtccg ttgggctgac    1560
gagggagagg ca                                                        1572
```

<210> SEQ ID NO 31
<211> LENGTH: 1554
<212> TYPE: DNA
<213> ORGANISM: Artificial Sequence
<220> FEATURE:
<223> OTHER INFORMATION: In-frame fusion of TraP13 v2: dgt-14 v2

<400> SEQUENCE: 31

```
atggcacaag ttagcagaat ctgtaatggt gtgcagaacc catctcttat ctccaatctc     60
tcaaagtcca gccaacgtaa gtctcccctc agcgtgtctc tgaaaactca gcagcccaga    120
gcttcttcat ggggtttgaa gaaatctgga cgatgctta acggctcagt cattcgtccg     180
gttaaggtga cagcctccgt ctccgctgct tcaactggtg gcactctgat agctggacca    240
gcagctggac cactgaaggg agaattgacc gttcctggtg acaaatctat gtctcacaga    300
agtgtgatgt tagcagcttt ggcagacgga gtgacagaga ttcatggatt cctccctggg    360
gaagataaca tcgccactgc tcgtatgttc attgatatgg gagtgagaat tgagtggttg    420
aatgacgaaa agacaagtct gagagttcat ggtgtgggat tgcatgggct taagcaacca    480
caaggcatgt tggatgctgg aacgcagct acatgtgtta gactcatggc tggcatcttg    540
gctgggcaac acttctcctc tacagttacg ggagacgcct cattgtgcaa gagacccatg    600
aagagggtgg ttgatccggt gcgtcgtatg ggtgcaaagg ttgagggtgg ggatgatggc    660
aatcttcttc ccataaccat ctctggtggc aagctcaaag ctatcgacca cgtcagtgaa    720
gtcgccagcg ctcaagtcaa gagttgtgtc ctcttagctg gactgtatgc agatggagtt    780
acaagtgtaa gcgagccaaa acctactcgt gatcatactg aaagaatgtt gccactgttc    840
ggtcaacccg tcaccgtcgc agcagacgga acgattagcc ttgatcctaa ggatagactt    900
actgcaccag tcggagttgt tgacattcca gccgaccta gtagcgcttg tttctttgca    960
gtggcagcct cctcgtggga gggatctgat gtgactctga agtcaatagg gatcaatcca   1020
agaagagacg gttggaggcg tgttatgaac ggaatgggag ctgctttgtc tctcgaaaac   1080
gagcagaggg ttggagagga acccgtagcc gatgttagaa tcagaagtgg aggtctccac   1140
gggatgcacg tggtgcccaa tgacgttccg gacgctatcg atgagtttcc agttttgttc   1200
gctgctgcaa cattggctga cggagagttt gtgttgacga tgcagaagaa attgagggtt   1260
aaggaatcag atcgtattgc tgcaatggcc acagctttac gtagtgctgg agctgatatc   1320
gatgaacagc cagatggtgc cgtgataaga gggatcacca atctgagggg tgatgtggac   1380
gtggacgctc atggtgatca taggattgca atggctatgg cagtggcagc tcaaagagct   1440
gatggagaag tgagaatcca taacgctgct gctattgcca cttcattccc taacttcgtt   1500
caactggctc aatcagtcgg gatgaatgtc cgttgggctg acgagggaga ggca          1554
```

<210> SEQ ID NO 32
<211> LENGTH: 19
<212> TYPE: DNA
<213> ORGANISM: Artificial Sequence
<220> FEATURE:

<223> OTHER INFORMATION: primer sequence

<400> SEQUENCE: 32
agccacatcc cagtaacga                                                19

<210> SEQ ID NO 33
<211> LENGTH: 17
<212> TYPE: DNA
<213> ORGANISM: Artificial Sequence
<220> FEATURE:
<223> OTHER INFORMATION: primer sequence

<400> SEQUENCE: 33
cctccctctt tgacgcc                                                  17

<210> SEQ ID NO 34
<211> LENGTH: 20
<212> TYPE: DNA
<213> ORGANISM: Artificial Sequence
<220> FEATURE:
<223> OTHER INFORMATION: primer sequence

<400> SEQUENCE: 34
cagcccaatg aggcatcagc                                               20

<210> SEQ ID NO 35
<211> LENGTH: 19
<212> TYPE: DNA
<213> ORGANISM: Artificial Sequence
<220> FEATURE:
<223> OTHER INFORMATION: primer sequence

<400> SEQUENCE: 35
cctcttagct ggactgtat                                                19

<210> SEQ ID NO 36
<211> LENGTH: 22
<212> TYPE: DNA
<213> ORGANISM: Artificial Sequence
<220> FEATURE:
<223> OTHER INFORMATION: primer sequence

<400> SEQUENCE: 36
cttaggatca aggctaatcg tt                                            22

<210> SEQ ID NO 37
<211> LENGTH: 25
<212> TYPE: DNA
<213> ORGANISM: Artificial Sequence
<220> FEATURE:
<223> OTHER INFORMATION: primer sequence

<400> SEQUENCE: 37
agagaagttt cgacggattt cgggc                                         25

<210> SEQ ID NO 38
<211> LENGTH: 22
<212> TYPE: DNA
<213> ORGANISM: Artificial Sequence
<220> FEATURE:
<223> OTHER INFORMATION: primer sequence

<400> SEQUENCE: 38
gaggattagg gtttcaacgg ag                                            22

```
<210> SEQ ID NO 39
<211> LENGTH: 21
<212> TYPE: DNA
<213> ORGANISM: Artificial Sequence
<220> FEATURE:
<223> OTHER INFORMATION: primer sequence

<400> SEQUENCE: 39
gagaattgag ctgagacgag g                                      21

<210> SEQ ID NO 40
<211> LENGTH: 24
<212> TYPE: DNA
<213> ORGANISM: Artificial Sequence
<220> FEATURE:
<223> OTHER INFORMATION: primer sequence

<400> SEQUENCE: 40
ctgcaggtca acggatcagg atat                                   24

<210> SEQ ID NO 41
<211> LENGTH: 24
<212> TYPE: DNA
<213> ORGANISM: Artificial Sequence
<220> FEATURE:
<223> OTHER INFORMATION: primer sequence

<400> SEQUENCE: 41
tgggctgaat tgaagacatg ctcc                                   24

<210> SEQ ID NO 42
<211> LENGTH: 20
<212> TYPE: DNA
<213> ORGANISM: Artificial Sequence
<220> FEATURE:
<223> OTHER INFORMATION: primer sequence

<400> SEQUENCE: 42
cgtccacaaa gctgaatgtg                                        20

<210> SEQ ID NO 43
<211> LENGTH: 20
<212> TYPE: DNA
<213> ORGANISM: Artificial Sequence
<220> FEATURE:
<223> OTHER INFORMATION: primer sequence

<400> SEQUENCE: 43
cgaagtcatg gaagccactt                                        20

<210> SEQ ID NO 44
<211> LENGTH: 19
<212> TYPE: DNA
<213> ORGANISM: Artificial Sequence
<220> FEATURE:
<223> OTHER INFORMATION: primer sequence

<400> SEQUENCE: 44
cctcttagct ggactgtat                                         19

<210> SEQ ID NO 45
<211> LENGTH: 22
<212> TYPE: DNA
<213> ORGANISM: Artificial Sequence
<220> FEATURE:
<223> OTHER INFORMATION: primer sequence
```

```
<400> SEQUENCE: 45
cttaggatca aggctaatcg tt                                                    22

<210> SEQ ID NO 46
<211> LENGTH: 74
<212> TYPE: PRT
<213> ORGANISM: Artificial Sequence
<220> FEATURE:
<223> OTHER INFORMATION: Amino acid fragment of DGT-14

<400> SEQUENCE: 46
```

Glu Lys Thr Ser Leu Arg Val His Gly Val Gly Leu His Gly Leu Lys
1               5                   10                  15

Gln Pro Gln Gly Met Leu Asp Ala Gly Asn Ala Ala Thr Cys Val Arg
            20                  25                  30

Leu Met Ala Gly Ile Leu Ala Gly Gln His Phe Ser Thr Val Thr
        35                  40                  45

Gly Asp Ala Ser Leu Cys Lys Arg Pro Met Lys Arg Val Val Asp Pro
    50                  55                  60

Val Arg Arg Met Gly Ala Lys Val Glu Gly
65                  70

```
<210> SEQ ID NO 47
<211> LENGTH: 73
<212> TYPE: PRT
<213> ORGANISM: Bartonella bacilliformis

<400> SEQUENCE: 47
```

Asn Gly Ile Trp Ile Ile Arg Gly Thr Gly Asn Gly Cys Leu Leu Gln
1               5                   10                  15

Ala Gln Lys Pro Leu Asn Phe Gly Asn Ser Ala Thr Gly Ala Arg Leu
            20                  25                  30

Ile Met Gly Met Val Ser Ser Tyr His Met Lys Thr Thr Phe Thr Gly
        35                  40                  45

Asp Ala Ser Leu Ser Lys Arg Pro Met Glu Arg Ile Leu Asn Pro Leu
    50                  55                  60

Arg Leu Met Gly Thr Asn Ile Glu Ala
65                  70

```
<210> SEQ ID NO 48
<211> LENGTH: 72
<212> TYPE: PRT
<213> ORGANISM: Agrobacterium tumefaciens

<400> SEQUENCE: 48
```

Asp Thr Trp Ile Ile Asp Gly Val Gly Asn Gly Gly Leu Leu Ala Pro
1               5                   10                  15

Glu Ala Pro Leu Asp Phe Gly Asn Ala Ala Thr Gly Cys Arg Leu Thr
            20                  25                  30

Met Gly Leu Val Gly Val Tyr Asp Phe Asp Ser Thr Phe Ile Gly Asp
        35                  40                  45

Ala Ser Leu Thr Lys Arg Pro Met Gly Arg Val Leu Asn Pro Leu Arg
    50                  55                  60

Glu Met Gly Val Gln Val Lys Ser
65                  70

```
<210> SEQ ID NO 49
<211> LENGTH: 74
<212> TYPE: PRT
```

```
<213> ORGANISM: Artificial Sequence
<220> FEATURE:
<223> OTHER INFORMATION: Amino acid fragment of DGT-12

<400> SEQUENCE: 49

Glu Lys Arg Val Glu Val Arg Gly Ile Gly Leu Gly Gln Leu His Glu
1               5                   10                  15

Pro Thr Ala Val Leu Asp Ala Gly Asn Ser Ala Thr Thr Leu Arg Leu
            20                  25                  30

Met Leu Gly Ile Leu Ala Ser His Pro Asp Arg Phe Phe Thr Val Thr
        35                  40                  45

Gly Asp His Ser Leu Val Arg Arg Pro Met Asp Arg Val Val Lys Pro
    50                  55                  60

Leu Gln Glu Met Gly Ala Met Ile Trp Gly
65                  70

<210> SEQ ID NO 50
<211> LENGTH: 74
<212> TYPE: PRT
<213> ORGANISM: Artificial Sequence
<220> FEATURE:
<223> OTHER INFORMATION: Amino acid fragment of DGT-18

<400> SEQUENCE: 50

Asp Arg Thr Cys Cys Glu Val Asp Gly Ile Gly Gly Leu Ile Thr His
1               5                   10                  15

Gln Gly Pro Ile Glu Leu Phe Leu Gly Asn Ala Ala Thr Ala Met Arg
            20                  25                  30

Pro Leu Thr Ala Ala Leu Cys Leu Gly Lys Asn Asp Val Val Leu Thr
        35                  40                  45

Gly Glu Pro Arg Met Lys Glu Arg Pro Ile Gly His Leu Val Asp Ala
    50                  55                  60

Leu Arg Gln Gly Gly Ala Glu Ile Asp Tyr
65                  70

<210> SEQ ID NO 51
<211> LENGTH: 74
<212> TYPE: PRT
<213> ORGANISM: Escherichia coli

<400> SEQUENCE: 51

Asp Arg Thr Arg Cys Glu Ile Ile Gly Asn Gly Gly Pro Leu His Ala
1               5                   10                  15

Asp Gly Ala Leu Glu Leu Phe Leu Gly Asn Ala Gly Thr Ala Met Arg
            20                  25                  30

Pro Leu Ala Ala Ala Leu Cys Leu Gly Ser Asn Asp Ile Val Leu Thr
        35                  40                  45

Gly Glu Pro Arg Met Lys Glu Arg Pro Ile Gly His Leu Val Asp Ala
    50                  55                  60

Leu Arg Leu Gly Gly Ala Lys Ile Thr Tyr
65                  70

<210> SEQ ID NO 52
<211> LENGTH: 74
<212> TYPE: PRT
<213> ORGANISM: Artificial Sequence
<220> FEATURE:
<223> OTHER INFORMATION: Amino acid fragment of DGT-30

<400> SEQUENCE: 52
```

```
Asn Asn Thr Val Cys Glu Leu Glu Gly Ile Gly Ala Pro Leu Asn Ala
1               5                   10                  15

Lys Leu Ala Gln Thr Leu Phe Leu Gly Asn Ala Ala Thr Ala Met Arg
            20                  25                  30

Pro Leu Cys Ala Ala Leu Thr Leu Gly Gln Gly Glu Phe Thr Leu Thr
        35                  40                  45

Gly Glu Pro Arg Met Glu Arg Pro Ile Gly Asp Leu Val Asp Ala
    50                  55                  60

Leu Arg Gln Leu Gly Ala Ser Val Thr Tyr
65                  70
```

<210> SEQ ID NO 53
<211> LENGTH: 73
<212> TYPE: PRT
<213> ORGANISM: Artificial Sequence
<220> FEATURE:
<223> OTHER INFORMATION: Amino acid fragment of DGT-29

<400> SEQUENCE: 53

```
His Leu Ala Gln Ile Gln Val Ser Gly Lys Gly Gly Asp Ile Pro Ala
1               5                   10                  15

Lys Gln Ala Asp Leu Phe Val Gly Leu Ala Ala Thr Ala Ala Arg Phe
            20                  25                  30

Ile Thr Ala Leu Val Ala Leu Gly Asn Gly Glu Tyr Arg Leu Asp Gly
        35                  40                  45

Val Pro Arg Met Arg Glu Arg Pro Met Gly Asp Leu Val Thr Val Leu
    50                  55                  60

Gln Asn Ser Gly Ile Lys Ile Asn Phe
65                  70
```

<210> SEQ ID NO 54
<211> LENGTH: 70
<212> TYPE: PRT
<213> ORGANISM: Artificial Sequence
<220> FEATURE:
<223> OTHER INFORMATION: unknown origination, described as SEQ ID NO:29
      in US PAT NO 7834249

<400> SEQUENCE: 54

```
Asp Asp Trp Val Val Glu Gly Leu Gly Gln Ala Pro Asn Leu Asp Ala
1               5                   10                  15

Asp Ile Trp Cys Glu Asp Ala Gly Thr Val Ala Arg Phe Leu Pro Pro
            20                  25                  30

Phe Val Ala Ala Gly Gln Gly Lys Phe Thr Phe Asp Gly Ser Glu Gln
        35                  40                  45

Leu Arg Arg Arg Pro Leu Arg Pro Val Val Asp Gly Ile Arg His Leu
    50                  55                  60

Gly Ala Arg Val Ser Ser
65                  70
```

<210> SEQ ID NO 55
<211> LENGTH: 80
<212> TYPE: PRT
<213> ORGANISM: Triticum aestivum

<400> SEQUENCE: 55

```
Val Ala Lys Arg Ala Val Val Val Gly Cys Gly Gly Arg Phe Pro Val
1               5                   10                  15

Glu Lys Asp Ala Gln Glu Glu Val Lys Leu Phe Leu Gly Asn Ala Gly
            20                  25                  30
```

Thr Ala Met Arg Pro Leu Thr Ala Ala Val Val Ala Ala Gly Gly Asn
          35                  40                  45

Ala Thr Tyr Val Leu Asp Gly Val Pro Arg Met Arg Glu Arg Pro Ile
    50                  55                  60

Gly Asp Leu Val Val Gly Leu Gln Gln Leu Gly Ala Asp Ala Asp Cys
65                  70                  75                  80

<210> SEQ ID NO 56
<211> LENGTH: 80
<212> TYPE: PRT
<213> ORGANISM: Glycine max

<400> SEQUENCE: 56

Thr Thr Lys Gln Ala Ile Val Glu Gly Cys Gly Gly Leu Phe Pro Thr
1               5                   10                  15

Ser Lys Glu Ser Lys Asp Glu Ile Asn Leu Phe Leu Gly Asn Ala Gly
            20                  25                  30

Thr Ala Met Arg Pro Leu Thr Ala Ala Val Val Ala Ala Gly Gly Asn
          35                  40                  45

Ala Ser Tyr Val Leu Asp Gly Val Pro Arg Met Arg Glu Arg Pro Ile
    50                  55                  60

Gly Asp Leu Val Ala Gly Leu Lys Gln Leu Gly Ala Asp Val Asp Cys
65                  70                  75                  80

<210> SEQ ID NO 57
<211> LENGTH: 80
<212> TYPE: PRT
<213> ORGANISM: Brassica napus

<400> SEQUENCE: 57

Val Asn Asn Arg Ala Val Val Glu Gly Cys Gly Gly Ile Phe Pro Ala
1               5                   10                  15

Ser Leu Asp Ser Lys Ser Asp Ile Glu Leu Tyr Leu Gly Asn Ala Gly
            20                  25                  30

Thr Ala Met Arg Pro Leu Thr Ala Ala Val Thr Ala Ala Gly Gly Asn
          35                  40                  45

Ala Ser Tyr Val Leu Asp Gly Val Pro Arg Met Arg Glu Arg Pro Ile
    50                  55                  60

Gly Asp Leu Val Val Gly Leu Lys Gln Leu Gly Ala Asp Val Glu Cys
65                  70                  75                  80

<210> SEQ ID NO 58
<211> LENGTH: 516
<212> TYPE: PRT
<213> ORGANISM: Brassica napus

<400> SEQUENCE: 58

Met Ala Gln Ser Ser Arg Ile Cys His Gly Val Gln Asn Pro Cys Val
1               5                   10                  15

Ile Ile Ser Asn Leu Ser Lys Ser Asn Gln Asn Lys Ser Pro Phe Ser
            20                  25                  30

Val Ser Leu Lys Thr His Gln Pro Arg Ala Ser Ser Trp Gly Leu Lys
          35                  40                  45

Lys Ser Gly Thr Met Leu Asn Gly Ser Val Ile Arg Pro Val Lys Val
    50                  55                  60

Thr Ala Ser Val Ser Thr Ser Glu Lys Ala Ser Glu Ile Val Leu Gln
65                  70                  75                  80

```
Pro Ile Arg Glu Ile Ser Gly Leu Ile Lys Leu Pro Gly Ser Lys Ser
                85                  90                  95

Leu Ser Asn Arg Ile Leu Leu Ala Ala Leu Ser Glu Gly Thr Thr
            100                 105                 110

Val Val Asp Asn Leu Leu Asn Ser Asp Asp Ile Asn Tyr Met Leu Asp
            115                 120                 125

Ala Leu Lys Lys Leu Gly Leu Asn Val Glu Arg Asp Ser Val Asn Asn
130                 135                 140

Arg Ala Val Val Glu Gly Cys Gly Gly Ile Phe Pro Ala Ser Leu Asp
145                 150                 155                 160

Ser Lys Ser Asp Ile Glu Leu Tyr Leu Gly Asn Ala Gly Thr Ala Met
                165                 170                 175

Arg Pro Leu Thr Ala Ala Val Thr Ala Ala Gly Gly Asn Ala Ser Tyr
            180                 185                 190

Val Leu Asp Gly Val Pro Arg Met Arg Glu Arg Pro Ile Gly Asp Leu
            195                 200                 205

Val Val Gly Leu Lys Gln Leu Gly Ala Asp Val Glu Cys Thr Leu Gly
            210                 215                 220

Thr Asn Cys Pro Pro Val Arg Val Asn Ala Asn Gly Gly Leu Pro Gly
225                 230                 235                 240

Gly Lys Val Lys Leu Ser Gly Ser Ile Ser Ser Gln Tyr Leu Thr Ala
                245                 250                 255

Leu Leu Met Ala Ala Pro Leu Ala Leu Gly Asp Val Glu Ile Glu Ile
            260                 265                 270

Ile Asp Lys Leu Ile Ser Val Pro Tyr Val Glu Met Thr Leu Lys Leu
            275                 280                 285

Met Glu Arg Phe Gly Val Ser Ala Glu His Ser Asp Ser Trp Asp Arg
            290                 295                 300

Phe Phe Val Lys Gly Gly Gln Lys Tyr Lys Ser Pro Gly Asn Ala Tyr
305                 310                 315                 320

Val Glu Gly Asp Ala Ser Ser Ala Ser Tyr Phe Leu Ala Gly Ala Ala
                325                 330                 335

Ile Thr Gly Glu Thr Val Thr Val Glu Gly Cys Gly Thr Thr Ser Leu
            340                 345                 350

Gln Gly Asp Val Lys Phe Ala Glu Val Leu Glu Lys Met Gly Cys Lys
            355                 360                 365

Val Ser Trp Thr Glu Asn Ser Val Thr Val Thr Gly Pro Ser Arg Asp
            370                 375                 380

Ala Phe Gly Met Arg His Leu Arg Ala Val Asp Val Asn Met Asn Lys
385                 390                 395                 400

Met Pro Asp Val Ala Met Thr Leu Ala Val Val Ala Leu Phe Ala Asp
                405                 410                 415

Gly Pro Thr Thr Ile Arg Asp Val Ala Ser Trp Arg Val Lys Glu Thr
            420                 425                 430

Glu Arg Met Ile Ala Ile Cys Thr Glu Leu Arg Lys Leu Gly Ala Thr
            435                 440                 445

Val Glu Glu Gly Ser Asp Tyr Cys Val Ile Thr Pro Pro Ala Lys Val
            450                 455                 460

Lys Pro Ala Glu Ile Asp Thr Tyr Asp Asp His Arg Met Ala Met Ala
465                 470                 475                 480

Phe Ser Leu Ala Ala Cys Ala Asp Val Pro Val Thr Ile Lys Asp Pro
                485                 490                 495

Gly Cys Thr Arg Lys Thr Phe Pro Asp Tyr Phe Gln Val Leu Glu Ser
```

```
                    500                 505                 510

Ile Thr Lys His
            515

<210> SEQ ID NO 59
<211> LENGTH: 455
<212> TYPE: PRT
<213> ORGANISM: Glycine max

<400> SEQUENCE: 59

Met Ala Ser Val Ala Ala Glu Lys Pro Ser Thr Ser Pro Glu Ile
1               5                   10                  15

Val Leu Glu Pro Ile Lys Asp Phe Ser Gly Thr Ile Thr Leu Pro Gly
                20                  25                  30

Ser Lys Ser Leu Ser Asn Arg Ile Leu Leu Leu Ala Ala Leu Ser Glu
                35                  40                  45

Gly Thr Thr Val Val Asp Asn Leu Leu Tyr Ser Glu Asp Ile His Tyr
            50                  55                  60

Met Leu Gly Ala Leu Arg Thr Leu Gly Leu Arg Val Glu Asp Asp Lys
65                  70                  75                  80

Thr Thr Lys Gln Ala Ile Val Glu Gly Cys Gly Gly Leu Phe Pro Thr
                85                  90                  95

Ser Lys Glu Ser Lys Asp Glu Ile Asn Leu Phe Leu Gly Asn Ala Gly
                100                 105                 110

Thr Ala Met Arg Pro Leu Thr Ala Ala Val Val Ala Ala Gly Gly Asn
            115                 120                 125

Ala Ser Tyr Val Leu Asp Gly Val Pro Arg Met Arg Glu Arg Pro Ile
            130                 135                 140

Gly Asp Leu Val Ala Gly Leu Lys Gln Leu Gly Ala Asp Val Asp Cys
145                 150                 155                 160

Phe Leu Gly Thr Asn Cys Pro Pro Val Arg Val Asn Gly Lys Gly Gly
                165                 170                 175

Leu Pro Gly Gly Lys Val Lys Leu Ser Gly Ser Val Ser Ser Gln Tyr
                180                 185                 190

Leu Thr Ala Leu Leu Met Ala Ala Pro Leu Ala Leu Gly Asp Val Glu
            195                 200                 205

Ile Glu Ile Val Asp Lys Leu Ile Ser Val Pro Tyr Val Glu Met Thr
210                 215                 220

Leu Lys Leu Met Glu Arg Phe Gly Val Ser Val Glu His Ser Gly Asn
225                 230                 235                 240

Trp Asp Arg Phe Leu Val His Gly Gly Gln Lys Tyr Lys Ser Pro Gly
                245                 250                 255

Asn Ala Phe Val Glu Gly Asp Ala Ser Ser Ala Ser Tyr Leu Leu Ala
                260                 265                 270

Gly Ala Ala Ile Thr Gly Gly Thr Ile Thr Val Asn Gly Cys Gly Thr
            275                 280                 285

Ser Ser Leu Gln Gly Asp Val Lys Phe Ala Glu Val Leu Glu Lys Met
            290                 295                 300

Gly Ala Lys Val Thr Trp Ser Glu Asn Ser Val Thr Val Ser Gly Pro
305                 310                 315                 320

Pro Arg Asp Phe Ser Gly Arg Lys Val Leu Arg Gly Ile Asp Val Asn
                325                 330                 335

Met Asn Lys Met Pro Asp Val Ala Met Thr Leu Ala Val Val Ala Leu
            340                 345                 350
```

```
Phe Ala Asn Gly Pro Thr Ala Ile Arg Asp Val Ala Ser Trp Arg Val
            355                 360                 365

Lys Glu Thr Glu Arg Met Ile Ala Ile Cys Thr Glu Leu Arg Lys Leu
370                 375                 380

Gly Ala Thr Val Glu Glu Gly Pro Asp Tyr Cys Val Ile Thr Pro Pro
385                 390                 395                 400

Glu Lys Leu Asn Val Thr Ala Ile Asp Thr Tyr Asp Asp His Arg Met
                405                 410                 415

Ala Met Ala Phe Ser Leu Ala Ala Cys Gly Asp Val Pro Val Thr Ile
            420                 425                 430

Lys Asp Pro Gly Cys Thr Arg Lys Thr Phe Pro Asp Tyr Phe Glu Val
        435                 440                 445

Leu Glu Arg Leu Thr Lys His
    450                 455

<210> SEQ ID NO 60
<211> LENGTH: 456
<212> TYPE: PRT
<213> ORGANISM: Triticum aestivum

<400> SEQUENCE: 60

Met Ala Thr Ser Val Ala Ala Pro Ala Ala Pro Ser Gly Ala Glu Glu
1               5                   10                  15

Val Val Leu Gln Pro Ile Arg Glu Ile Ser Gly Ala Val Gln Leu Pro
            20                  25                  30

Gly Ser Lys Ser Leu Ser Asn Arg Ile Leu Leu Leu Ser Ala Leu Ser
        35                  40                  45

Glu Gly Thr Thr Val Val Asp Asn Leu Leu Asn Ser Glu Asp Val His
    50                  55                  60

Tyr Met Leu Glu Ala Leu Glu Ala Leu Gly Leu Ser Val Glu Ala Asp
65                  70                  75                  80

Lys Val Ala Lys Arg Ala Val Val Gly Cys Gly Gly Arg Phe Pro
                85                  90                  95

Val Glu Lys Asp Ala Gln Glu Glu Val Lys Leu Phe Leu Gly Asn Ala
            100                 105                 110

Gly Thr Ala Met Arg Pro Leu Thr Ala Ala Val Val Ala Ala Gly Gly
        115                 120                 125

Asn Ala Thr Tyr Val Leu Asp Gly Val Pro Arg Met Arg Glu Arg Pro
    130                 135                 140

Ile Gly Asp Leu Val Val Gly Leu Gln Gln Leu Gly Ala Asp Ala Asp
145                 150                 155                 160

Cys Phe Leu Gly Thr Asn Cys Pro Pro Val Arg Ile Asn Gly Lys Gly
                165                 170                 175

Gly Leu Pro Gly Gly Lys Val Lys Leu Ser Gly Ser Ile Ser Ser Gln
            180                 185                 190

Tyr Leu Ser Ser Leu Leu Met Ala Ala Pro Leu Ala Leu Glu Asp Val
        195                 200                 205

Glu Ile Glu Ile Ile Asp Lys Leu Ile Ser Val Pro Tyr Val Glu Met
    210                 215                 220

Thr Leu Lys Leu Met Glu Arg Phe Gly Val Thr Ala Glu His Ser Asp
225                 230                 235                 240

Ser Trp Asp Arg Phe Tyr Ile Lys Gly Gly Gln Lys Tyr Lys Ser Pro
                245                 250                 255

Gly Asn Ala Tyr Val Glu Gly Asp Ala Ser Ser Ala Ser Tyr Phe Leu
            260                 265                 270
```

```
Ala Gly Ala Ala Ile Thr Gly Gly Thr Val Thr Val Glu Gly Cys Gly
            275                 280                 285

Thr Thr Ser Leu Gln Gly Asp Val Lys Phe Ala Glu Val Leu Glu Met
        290                 295                 300

Met Gly Ala Lys Val Thr Trp Thr Asp Thr Ser Val Thr Val Thr Gly
305                 310                 315                 320

Pro Pro Arg Gln Pro Phe Gly Arg Lys His Leu Lys Ala Val Asp Val
                325                 330                 335

Asn Met Asn Lys Met Pro Asp Val Ala Met Thr Leu Ala Val Val Ala
            340                 345                 350

Leu Phe Ala Asp Gly Pro Thr Ala Ile Arg Asp Val Ala Ser Trp Arg
            355                 360                 365

Val Lys Glu Thr Glu Arg Met Val Ala Ile Arg Thr Glu Leu Thr Lys
        370                 375                 380

Leu Gly Ala Thr Val Glu Glu Gly Pro Asp Tyr Cys Ile Ile Thr Pro
385                 390                 395                 400

Pro Glu Lys Leu Asn Ile Thr Ala Ile Asp Thr Tyr Asp Asp His Arg
                405                 410                 415

Met Ala Met Ala Phe Ser Leu Ala Ala Cys Ala Glu Val Pro Val Thr
            420                 425                 430

Ile Arg Asp Pro Gly Cys Thr Arg Lys Thr Phe Pro Asn Tyr Phe Asp
            435                 440                 445

Val Leu Ser Thr Phe Val Lys Asn
        450                 455

<210> SEQ ID NO 61
<211> LENGTH: 6
<212> TYPE: PRT
<213> ORGANISM: Artificial sequence
<220> FEATURE:
<223> OTHER INFORMATION: synthetic peptide

<400> SEQUENCE: 61

Leu Gly Asn Ala Ala Thr
1               5

<210> SEQ ID NO 62
<211> LENGTH: 9
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (5)..(5)
<223> OTHER INFORMATION: Xaa is Ala, Ser, or Thr

<400> SEQUENCE: 62

Ala Leu Leu Met Xaa Ala Pro Leu Thr
1               5
```

GLYPHOSATE RESISTANT PLANTS AND ASSOCIATED METHODS

CROSS-REFERENCE TO RELATED APPLICATIONS

This application claims the benefit of U.S. Provisional Patent Application Ser. No. 61/593,555 filed Feb. 1, 2012, and also to U.S. Provisional Patent Application Ser. No. 61/625,222, filed Apr. 17, 2012, the disclosure of each of which is hereby incorporated herein in its entirety by this reference.

STATEMENT ACCORDING TO 37 C.F.R. §1.821(c) or (e)—SEQUENCE LISTING SUBMITTED AS ASCII TEXT FILE

Pursuant to 37 C.F.R. §1.821(c) or (e), a file containing an ASCII text version of the Sequence Listing has been submitted concomitant with this application, the contents of which are hereby incorporated by reference.

TECHNICAL FIELD

The present disclosure relates to new and distinctive plants that comprise DGT-14 as well as associated methods. Some embodiments relate to novel polypeptides involved in metabolism of N-(phosphonomethyl)glycine, nucleic acids encoding such polypeptides, and methods for identifying the same. Particular embodiments relate to plants, plant plant parts, and plant cells that comprise a foregoing polypeptides and/or nucleic acids.

BACKGROUND

Weed species have long been a problem in cultivated fields. Although once a labor intensive operation, weed control has been made easier by the availability of efficient weed killing chemical herbicides. The wide-spread use of herbicides, along with improved crop varieties and fertilizers, has made a significant contribution to the "green revolution" in agriculture. Particularly useful herbicides are those that have a broad spectrum of herbicidal activity. Unfortunately, broad spectrum herbicides typically have a deleterious effect on crop plants exposed to the herbicide. One way to overcome this problem is to produce plants that are tolerant to certain broad spectrum herbicides.

One example of a broad spectrum herbicide is N-phosphonomethyl-glycine, also known as glyphosate. Glyphosate has been used extensively by farmers worldwide for controlling weeds prior to crop planting, for example, in no-till farming. In addition, glyphosate is an efficient means to control weeds and volunteer plants between production cycles or crop rotations. Glyphosate does not carry-over in soils after use, and it is widely considered to be one of the most environmentally safe and broadly effective chemical herbicides available for use in agriculture.

Glyphosate kills plants by inhibiting the shikimic acid pathway. This pathway leads to the biosynthesis of aromatic compounds, including amino acids, vitamins and plant hormones. Glyphosate blocks the condensation of phosphoenolpyruvic acid (PEP) and 3-phosphoshikimic acid to 5-enolpyruvyl-3-phosphoshikimic acid by binding to and inhibiting activity of the enzyme 5-enolpyruvylshikimate-3-phosphate synthase, commonly referred to as "EPSP synthase," and "EPSPS."

Unfortunately, no crop plants are known that are naturally tolerant to glyphosate and, therefore, the utility of this herbicide for weed control in cultivated crops had been limited. One method to produce glyphosate tolerant crop plants is to introduce a gene encoding a heterologous glyphosate tolerant form of an EPSPS gene into the crop plant using the techniques of genetic engineering. Using chemical mutagenesis, glyphosate tolerant forms of EPSPS have been produced in bacteria and the heterologous genes were introduced into plants to produce glyphosate tolerant plants (see, e.g., Comai et al., *Science* 221:370-71 (1983)). The heterologous EPSPS genes are usually overexpressed in the crop plants to obtain the desired level of tolerance.

The foregoing examples of the related art and limitations related therewith are intended to be illustrative and not exclusive. Other limitations of the related art will become apparent to those of skill in the art upon a reading of the specification.

BRIEF SUMMARY OF THE DISCLOSURE

In embodiments, the disclosure relates to a plant, plant part, plant organ, plant seed, and/or plant cell comprising a nucleic acid encoding a polypeptide having at least 90% identity to SEQ ID NO:1.

In further embodiments, the disclosure relates to methods of generating a plant, plant part, plant organ, plant seed, and/or plant cell resistant to glyphosate comprising: transforming a plant, plant part, plant organ, plant seed, and/or plant cell with a nucleic acid encoding a polypeptide having at least 90% identity to SEQ ID NO:1; and expressing the nucleic acid so as to produce the polypeptide having at least 90% identity to SEQ ID NO:1.

Embodiments include vectors comprising a nucleic acid encoding a polypeptide having at least 90% identity to SEQ ID NO:1.

Particular examples include vectors comprising a nucleic acid encoding a polypeptide having at least 95% identity to SEQ ID NO:1.

Other embodiments include vectors comprising a nucleic acid sequence having at least 90% identity to SEQ ID NO:2 or SEQ ID NO:3. For example, a vector may comprise a nucleic acid sequence having at least 90% identity to SEQ ID NO:2 or SEQ ID NO:3.

Embodiments include glyphosate tolerant plants and plant cells expressing a polypeptide having at least 90% identity to SEQ ID NO:1.

Additional embodiments include methods for controlling weeds in a field or area under cultivation containing glyphosate resistant plants, wherein such a method may comprise: planting a plant or a plant seed comprising a nucleic acid encoding a polypeptide having at least 90% identity to SEQ ID NO:1 in the field or area under cultivation; and applying to the field or area under cultivation a sufficient amount of glyphosate to control weeds in the field without significantly affecting the plant.

In some embodiments, the disclosure relates to regenerable cells for use in tissue culture of plants resistant to glyphosate. Such a tissue culture may be capable of regenerating plants having the physiological and morphological characteristics of the foregoing glyphosate-resistant plants, and also of regenerating plants having substantially the same genotype as the foregoing plants. Regenerable cells in such tissue cultures may be, for example, embryos, protoplasts, meristematic cells, callus, pollen, leaves, anthers, roots, root tips, flowers, seeds, pods and stems. Particular embodiments relate to plants regenerated from the tissue cultures of embodiments of the disclosure.

In some embodiments, the disclosure relates to cells that are not regenerable to produce plants, for example for use in producing plant cell lines resistant to glyphosate. In other embodiments, the disclosure relates to plants comprising in part such cells.

In certain embodiments, the present disclosure relates to the application of multiple herbicides to crops planted in an area under cultivation. An over the top application of glyphosate in addition to multiple herbicides takes advantage of the different herbicide properties, so that weed control provided with an improved combination of flexibility and economy. For example, individual herbicides have different longevities in the area under cultivation, i.e., some herbicides persist and are effective for a relatively long time after they are applied to the area, while other herbicides are quickly broken down into other and/or non-active compounds. An improved herbicide application system according to particular embodiments allows the use of glyphosate and multiple herbicides so that growers can tailor the selection of particular herbicides for use in a particular situation.

In other embodiments, the present disclosure relates to methods and compositions for making and using a plant that is tolerant to more than one herbicide or class or subclass of herbicide as described below. In particular embodiments, a plant is provided that is tolerant to both glyphosate and at least one other herbicide (or class or subclass of herbicide) or chemical (or class or subclass of another chemical) (e.g., fungicides, insecticides, plant growth regulators and the like). Such plants may find use, for example, in methods comprising treatment of crop plants with multiple herbicides. Thus, the disclosure provides herbicide resistant plants which tolerate treatment with an herbicide or combination of herbicides (including a combination of herbicides that each act through a different mode of action) or a combination of at least one herbicide and at least one other chemical, including fungicides, insecticides, plant growth regulators and the like. In this manner, the disclosure describes improved methods of growing crop plants in which weeds are selectively controlled.

In one embodiment, the herbicide resistant plants comprise a nucleic acid molecule which encodes a heterologous polypeptide that confers tolerance to glyphosate and a nucleic acid molecule encoding a polypeptide that confers tolerance to 2,4-dichlorophenoxyacetic acid (2,4-D). According to the foregoing paragraphs, plants are provided that comprise least a third nucleic acid molecule encoding a polypeptide imparting to the plant a trait selected from the group consisting of an a herbicide tolerance trait; an insect resistance trait; an agronomic trait; a disease resistance trait; a modified fatty acid trait; or a reduced phytate trait.

In another embodiment, the herbicide-resistant plants comprise a heterologous nucleic acid molecule which encodes a polypeptide that confers tolerance to glyphosate and a nucleic acid molecule encoding a polypeptide that confers tolerance to glufosinate. Some examples include an herbicide-resistant plant comprising at least a third nucleic acid molecule that encodes a polypeptide imparting to the plant a herbicide tolerance trait, an insect resistance trait, an agronomic trait, a disease resistance trait, a modified fatty acid trait, or a reduced phytate trait.

In another embodiment, the herbicide resistant plant comprises a nucleic acid molecule which encodes a polypeptide that confers tolerance to glyphosate and a nucleic acid molecule encoding a polypeptide that confers tolerance to a herbicide that inhibits acetolactate synthase (ALS) (Lee et al., 1988 *EMBO J.* 7:1241) also known as acetohydroxyacid synthase (AHAS) enzyme (Miki et al., 1990 *Theor. Appl. Genet.* 80:449). Accordingly, further provided are plants comprising at least a third nucleic acid molecule that encodes a polypeptide imparting to the plant a herbicide tolerance trait, an insect resistance trait, an agronomic trait, a disease resistance trait, a modified fatty acid trait, or a reduced phytate trait.

In another embodiment, any nucleic acid molecules can be combined or "stacked" with any other nucleic acid molecule, to provide additional resistance or tolerance to glyphosate or another herbicide, and/or to provide resistance to select insects or diseases and/or nutritional enhancements, and/or improved agronomic characteristics, and/or proteins or other products useful in feed, food, industrial, pharmaceutical or other uses. Embodiments include the stacking of two or more nucleic acid sequences of interest within a plant genome. Such a stack can be accomplished via conventional plant breeding using two or more events, transformation of a plant with a construct that contains the sequences of interest, re-transformation of a transgenic plant, or addition of new traits through targeted integration via homologous recombination. An example of such a stack is any combination of the following; a dgt-14 nucleic acid molecule, a Cry34Ab1 nucleic acid molecule, a Cry35Ab1 nucleic acid molecule, a Cry1F nucleic acid molecule, a Cry1Ac nucleic acid molecule, an aad-12 nucleic acid molecule, an aad-1 nucleic acid molecule, a pat nucleic acid molecule, and a DSM-2 nucleic acid molecule.

In addition to the exemplary aspects and embodiments described above, further aspects and embodiments will become apparent by study of the following descriptions.

BRIEF DESCRIPTION OF THE FIGURES

FIG. 1 depicts a partial sequence alignment of DGT-14 (SEQ ID NO:46), DGT-11 (SEQ ID NO:47), DGT-12 (SEQ ID NO:49), DGT-18 (SEQ ID NO:50), DGT-29 (SEQ ID NO:53), and DGT-30 (SEQ ID NO:52) to other EPSP synthase enzymes, such as; grg-23 (SEQ ID NO:54; derived from U.S. Pat. No. 7,834,249), CP4 (SEQ ID NO:48; GENBANK ACC NO: AEM75108.1) from *Agrobacterium tumefaciens*, DGT-3 (SEQ ID NO:57; GENBANK ACC NO: P17688) from *Brassica napus*, DGT-1 (SEQ ID NO:56) from *Glycine max*, DGT-7 (SEQ ID NO:55; GENBANK ACC NO: EU977181) from *Triticum aestivum*, and aroA (SEQ ID NO:51; Padgette et al., (1991); Eschenburg et al., (2002); Priestman et al., (2005); Haghani et al., (2008) from *Escherichia coli*. All six DGT enzymes (DGT-14, DGT-11, DGT-12, DGT-18, DGT-30, and DGT-29) share a conserved alanine at the aroA EPSP synthase enzyme amino acid position 96. The location of this amino acid is indicated by an asterisk, and the amino acid residue is underlined.

FIG. 2 shows an alignment of the full length enzymes of DGT-1 (SEQ ID NO: 59) from *Glycine max*, DGT-3 (SEQ ID NO: 58; GENBANK ACC NO: P17688) from *Brassica napus*, and DGT-7 (SEQ ID NO: 60; GENBANK ACC NO: EU977181) from *Triticum aestivum*. The location of the amino acid residue which was mutated from glycine to alanine is indicated by the first asterisk. The location of the amino acid residue which was mutated from threonine to isoleucine is indicated by the second asterisk. The location of the third amino acid residue which was mutated from proline to serine is indicated by the third asterisk.

DETAILED DESCRIPTION

Figure 3:
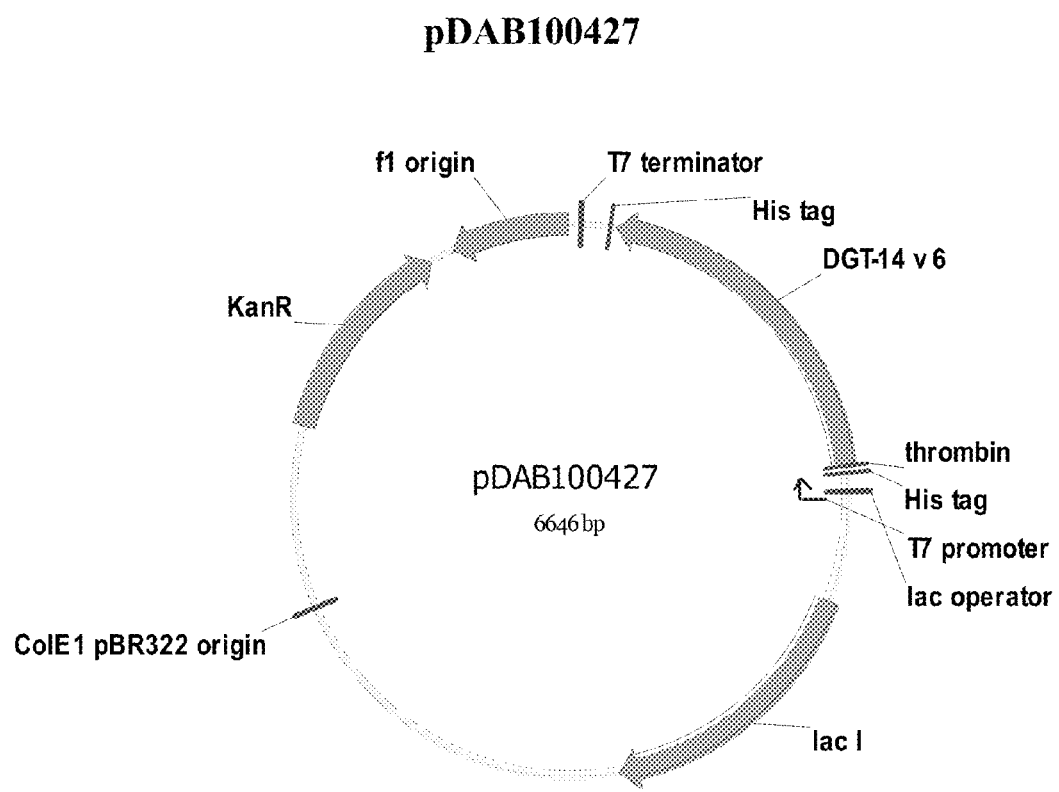
FIG. 3 depicts a plasmid map of pDAB100427.

The codon-optimized dgt-14 nucleic acid molecules disclosed herein are useful in a wide variety of applications in which glyphosate herbicide resistance can be of use in the plant.

When referring to plants that are resistant or tolerant to glyphosate, it is meant that an application of a sufficient amount of glyphosate on the plant does not significantly affect or kill the plant. A plant may be naturally tolerant to a particular herbicide, or a plant may be herbicide tolerant as a result of the hand of man such as, for example, selective breeding or the introduction of a transgene within the genome of the plant. A "glyphosate resistant plant" is a plant containing a polypeptide or nucleic acid molecule that confers herbicide tolerance on the plant or other organism expressing it (i.e., that makes a plant or other organism herbicide-tolerant). Plants that are resistant or tolerant to glyphosate may show some minimal impact from the application of glyphosate to the plant. For instance, there can be an alteration in the normal growth and development of the plant, wherein the plant may exhibit signs or symptoms that are associated with stress or disease. Such a minimal impact resulting from the application of glyphosate to plants that are resistant or tolerant to glyphosate contrasts with the adverse impact which results in the application of glyphosate to plants that are susceptible to glyphosate. The application of glyphosate to susceptible plants may significantly affect or kill the plant. Application of glyphosate to plants comprising a nucleic acid molecule that confers tolerance results in significantly less impact than application to plants not comprising a nucleic acid molecule that confers tolerance to glyphosate.

Thus, a plant is tolerant to a herbicide or other chemical if it shows damage in comparison to an appropriate control plant that is less than the damage exhibited by the control plant by at least 40%, 45%, 50%, 55%, 60%, 65%, 70%, 75%, 80%, 90%, 100%, 150%, 200%, 250%, 300%, 400%, 500%, 600%, 700%, 800%, 900%, or 1000% or more. In this manner, a plant that is tolerant to an herbicide or other chemical shows improved tolerance in comparison to an appropriate control plant. Damage resulting from herbicide or other chemical treatment is assessed by evaluating any parameter of plant growth or well-being deemed suitable by one of skill in the art. Damage can be assessed by visual inspection and/or by statistical analysis of suitable parameters of individual plants or of a group of plants. Thus, damage may be assessed by evaluating, for example, parameters such as plant height, plant weight, leaf color, leaf length, flowering, fertility, silking, yield, seed production, and the like. Damage may also be assessed by evaluating the time elapsed to a particular stage of development (e.g., silking, flowering, or pollen shed) or the time elapsed until a plant has recovered from treatment with a particular chemical and/or herbicide.

In making such assessments, particular values may be assigned to particular degrees of damage so that statistical analysis or quantitative comparisons may be made. The use of ranges of values to describe particular degrees of damage is known in the art, and any suitable range or scale may be used. For example, herbicide injury scores (also called tolerance scores) can be assigned. As indicated above, herbicide tolerance is also indicated by other ratings in this scale where an appropriate control plant exhibits a lower score on the scale, or where a group of appropriate control plants exhibits a statistically lower score in response to an herbicide treatment than a group of subject plants.

Damage caused by an herbicide or other chemical can be assessed at various times after a plant has been treated with an herbicide. Often, damage is assessed at about the time that the control plant exhibits maximum damage. Sometimes, damage is assessed after a period of time in which a control plant that was not treated with herbicide or other chemical has measurably grown and/or developed in comparison to the size or stage at which the treatment was administered. Damage can be assessed at various times, for example, at 12 hours or at 1, 2, 3, 4, 5, 6, 7, 8, 9, 10, 11, 12, 13, 14 days, or three weeks, four weeks, or longer after the test plant was treated with herbicide. Any time of assessment is suitable as long as it permits detection of a difference in response to a treatment of test and control plants.

A herbicide does not "significantly affect" a plant when it either has no effect on a plant or when it has some effect on a plant from which the plant later recovers, or when it has an effect which is detrimental but which is offset, for example, by the impact of the particular herbicide on weeds. Thus, for example, a crop plant is not "significantly affected" by a herbicide or other treatment if it exhibits less than 25%, 20%, 15%, 10%, 9%, 8%, 7%, 6%, 5%, 4%, 3%, 2%, or 1% decrease in at least one suitable parameter that is indicative of plant health and/or productivity in comparison to an appropriate control plant (e.g., an untreated crop plant). Suitable parameters that are indicative of plant health and/or productivity include, for example, plant height, plant weight, leaf length, time elapsed to a particular stage of development, flowering, yield, seed production, and the like. The evaluation of a parameter can be by visual inspection and/or by statistical analysis of any suitable parameter. Comparison may be made by visual inspection and/or by statistical analysis. Accordingly, a crop plant is not "significantly damaged by" a herbicide or other treatment if it exhibits a decrease in at least one parameter but that decrease is temporary in nature and the plant recovers fully within 1 week, 2 weeks, 3 weeks, 4 weeks, or 6 weeks.

Conversely a plant is significantly affected or damaged by a herbicide or other treatment if it exhibits more than a 50%, 60%, 70%, 80%, 90%, 100%, 110%, 120%, 150%, or 170% decrease in at least one suitable parameter that is indicative of plant health and/or productivity in comparison to an appropriate control plant (e.g., an untreated weed of the same species). Thus, a plant is significantly damaged if it exhibits a decrease in at least one parameter and the plant does not recover fully within 1 week, 2 weeks, 3 weeks, 4 weeks, or 6 weeks.

Damage resulting from an herbicide or other chemical treatment of a plant is assessed by visual inspection of other appropriate method by one of skill in the art and is evaluated by statistical analysis of suitable parameters. The plant being evaluated is referred to as the "test plant." Typically, an appropriate control plant is one that expresses the same herbicide-tolerance polypeptide(s) as the plant being evaluated for herbicide tolerance (i.e., the "test plant") but that has not been treated with herbicide.

Unless defined otherwise, all technical and scientific terms used herein have the same meaning as commonly understood by one of ordinary skill in the art to which this disclosure relates. In case of conflict, the present application including the definitions will control. Unless otherwise required by context, singular terms shall include pluralities and plural terms shall include the singular. All publications, patents and other references mentioned herein are incorporated by reference in their entireties for all purposes as if each individual publication or patent application were specifically and individually indicated to be incorporated by reference, unless only specific sections of patents or patent publications are indicated to be incorporated by reference.

In order to further clarify this disclosure, the following terms, abbreviations and definitions are provided.

As used herein, the terms "comprises," "comprising," "includes," "including," "has," "having," "contains," or "containing," or any other variation thereof, are intended to be non-exclusive or open-ended. For example, a composition, a mixture, a process, a method, an article, or an apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of an embodiment of the disclosure are intended to be nonrestrictive regarding the number of instances, i.e., occurrences of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as disclosed in the application.

A "herbicide" is a chemical that causes temporary or permanent injury to a plant. Non-limiting examples of herbicides that can be employed in the various methods and compositions of the disclosure are discussed in further detail elsewhere herein. A herbicide may be incorporated into the plant, or it may act on the plant without being incorporated into the plant or its cells. An "active ingredient" is the chemical in a herbicide formulation primarily responsible for its phytotoxicity and which is identified as the active ingredient on the product label. Product label information is available from the U.S. Environmental Protection Agency and is updated online at oaspub.epa.gov/pestlabl/ppls.own; product label information is also available online at www-.cdms.net. The term "acid equivalent" expresses the rate or quantity as the herbicidal active parent acid.

The term "plant" as used herein includes, but is not limited to, any descendant, cell, tissue, or part of a plant.

The terms "polynucleotide," "nucleic acid," and "nucleic acid molecule" are intended to encompass a singular nucleic acid as well as plural nucleic acids, a nucleic acid fragment, variant, or derivative thereof, or construct, e.g., messenger RNA (mRNA) or plasmid DNA (pDNA). A polynucleotide or nucleic acid can contain the nucleotide sequence of the full-length cDNA sequence, or a fragment thereof, including the untranslated 5' and 3' sequences and the coding sequences. A polynucleotide or nucleic acid can be composed of any polyribonucleotide or polydeoxyribonucleotide, which may be unmodified RNA or DNA or modified RNA or DNA. For example, a polynucleotide or nucleic acid can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. These terms also embrace chemically, enzymatically, or metabolically modified forms of a polynucleotide or nucleic acid.

A polynucleotide or nucleic acid sequence can be referred to as "isolated," in which it has been removed from its native environment. For example, a heterologous polynucleotide or nucleic acid encoding a polypeptide or polypeptide fragment having glyphosate tolerance activity contained in a vector is considered isolated for the purposes of the present disclosure. Further examples of an isolated polynucleotide or nucleic acid include recombinant polynucleotide maintained in heterologous host cells or a purified (partially or substantially) polynucleotide or nucleic acid in solution. An isolated polynucleotide or nucleic acid according to embodiments of the present disclosure further includes such molecules produced synthetically. An isolated polynucleotide or nucleic acid in the form of a polymer of DNA may be comprised of one or more segments of cDNA, genomic DNA or synthetic DNA.

The term "gene" refers to a nucleic acid sequence encodes functional product molecules, either RNA or protein, optionally including regulatory sequences preceding (5' non-coding sequences) and following (3' non-coding sequences) the coding sequence.

As used herein the term "coding region" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences can include promoters, translation leader sequences, introns, polyadenylation recognition sequences, RNA processing site, effector binding site and stem-loop structure.

As used herein, the term "polypeptide" is intended to encompass a singular "polypeptide" as well as plural "polypeptides" and fragments thereof, and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" can be used instead of, or interchangeably with any of these terms. A polypeptide can be derived from a natural biological source or produced by recombinant technology, but is not necessarily translated from a designated nucleic acid sequence. It can be generated in any manner, including by chemical synthesis.

By an "isolated" polypeptide or a fragment, variant, or derivative thereof is intended a polypeptide that is not in its natural milieu. No particular level of purification is required. Thus, reference to "isolated" signifies the involvement of the "hand of man" as described herein. For example, an isolated polypeptide can be removed from its native or natural environment. Recombinant polypeptides and proteins expressed in host cells are considered isolated for purposes of the disclosure, as are native or recombinant polypeptides which have been separated, fractionated, or partially or substantially purified by any suitable technique.

As used herein, "native" refers to the form of a polynucleotide, gene or polypeptide as found in nature with its own regulatory sequences, if present.

As used herein, "endogenous" refers to the native form of a polynucleotide, gene or polypeptide in its natural location in the organism or in the genome of an organism. "Endogenous polynucleotide" includes a native polynucleotide in its natural location in the genome of an organism. "Endogenous gene" includes a native gene in its natural location in the genome of an organism. "Endogenous polypeptide" includes a native polypeptide in its natural location in the organism.

As used herein, "heterologous" refers to a polynucleotide, gene or polypeptide not normally found in the host organism but that is introduced into the host organism. "Heterologous polynucleotide" includes a native coding region, or portion thereof, that is reintroduced into the source organism in a form that is different from the corresponding native polynucleotide. "Heterologous gene" includes a native coding region, or portion thereof, that is reintroduced into the source organism in a form that is different from the corresponding native gene. For example, a heterologous gene may include a native coding region that is a portion of a chimeric gene including non-native regulatory regions that is reintroduced into the native host. "Heterologous polypeptide" includes a native polypeptide that is reintroduced into the source organism in a form that is different from the corresponding native polypeptide. The subject genes and proteins can be fused to other genes and proteins to produce chimeric or fusion proteins. The genes and proteins useful in accordance with embodiments of the subject disclosure include not only the specifically exemplified full-length sequences, but also portions, segments and/or fragments (including contiguous fragments and internal and/or terminal deletions compared to the full-length molecules) of these sequences, variants, mutants, chimerics, and fusions thereof.

As used herein, the term "modification" can refer to a change in a polynucleotide disclosed herein that results in reduced, substantially eliminated or eliminated activity of a polypeptide encoded by the polynucleotide, as well as a change in a polypeptide disclosed herein that results in reduced, substantially eliminated or eliminated activity of the polypeptide. Alternatively, the term "modification" can refer to a change in a polynucleotide disclosed herein that results in increased or enhanced activity of a polypeptide encoded by the polynucleotide, as well as a change in a polypeptide disclosed herein that results in increased or enhanced activity of the polypeptide. Such changes can be made by methods well known in the art, including, but not limited to, deleting, mutating (e.g., spontaneous mutagenesis, random mutagenesis, mutagenesis caused by mutator genes, or transposon mutagenesis), substituting, inserting, down-regulating, altering the cellular location, altering the state of the polynucleotide or polypeptide (e.g., methylation, phosphorylation or ubiquitination), removing a cofactor, introduction of an antisense RNA/DNA, introduction of an interfering RNA/DNA, chemical modification, covalent modification, irradiation with UV or X-rays, homologous recombination, mitotic recombination, promoter replacement methods, and/or combinations thereof. Guidance in determining which nucleotides or amino acid residues can be modified, can be found by comparing the sequence of the particular polynucleotide or polypeptide with that of homologous polynucleotides or polypeptides, e.g., yeast or bacterial, and maximizing the number of modifications made in regions of high homology (conserved regions) or consensus sequences.

The term "derivative," as used herein, refers to a modification of a sequence set forth in the present disclosure. Illustrative of such modifications would be the substitution, insertion, and/or deletion of one or more bases relating to a nucleic acid sequence of a coding sequence disclosed herein that preserve, slightly alter, or increase the function of a coding sequence disclosed herein in crop species. Such derivatives can be readily determined by one skilled in the art, for example, using computer modeling techniques for predicting and optimizing sequence structure. The term "derivative" thus also includes nucleic acid sequences having substantial sequence identity with the disclosed coding sequences herein such that they are able to have the disclosed functionalities for use in producing DGT-14 of embodiments of the present disclosure.

As used herein, the term "variant" refers to a polypeptide differing from a specifically recited polypeptide of an embodiment of the disclosure by amino acid insertions, deletions, mutations, and substitutions, created using, e.g., recombinant DNA techniques, such as mutagenesis. Guidance in determining which amino acid residues may be replaced, added, or deleted without abolishing activities of interest, may be found by comparing the sequence of the particular polypeptide with that of homologous polypeptides and minimizing the number of amino acid sequence changes made in regions of high homology (conserved regions) or by replacing amino acids with consensus sequences. Proteins of embodiments of the subject disclosure can have substituted amino acids so long as they retain desired functional activity. "Variant" genes have nucleotide sequences that encode the same proteins or equivalent proteins having activity equivalent or similar to an exemplified protein.

The terms "variant proteins" and "equivalent proteins" refer to proteins having the same or essentially the same biological/functional activity against the target substrates and equivalent sequences as the exemplified proteins. As used herein, reference to an "equivalent" sequence refers to sequences having amino acid substitutions, deletions, additions, or insertions that improve or do not adversely affect activity to a significant extent. Fragments retaining activity are also included in this definition. Fragments and other equivalents that retain the same or similar function or activity as a corresponding fragment of an exemplified protein are within the scope of embodiments of the subject disclosure.

Variant genes can be used to produce variant proteins; recombinant hosts can be used to produce the variant proteins. Using these "gene shuffling" techniques, equivalent genes and proteins can be constructed that comprise any 5, 10, or 20 contiguous residues (amino acid or nucleotide) of any sequence exemplified herein. As one skilled in the art knows, the gene shuffling techniques, for example, can be adjusted to obtain equivalents having, for example, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, or 293 contiguous residues (amino acid or nucleotide), corresponding to a segment (of the same size) in any of the exemplified or suggested sequences (or the complements (full complements) thereof). Similarly sized segments, especially those for conserved regions, can also be used as probes and/or primers.

"Shuffling" strategies can be designed and targeted after obtaining and examining the atomic 3-D (three dimensional) coordinates and crystal structure of a protein of interest. Thus, "focused shuffling" can be directed to certain segments of a protein that are ideal for modification, such as surface-exposed segments, and preferably not internal segments that are involved with protein folding and essential 3-D structural integrity. U.S. Pat. No. 5,605,793, for example, describes methods for generating additional molecular diversity by using DNA reassembly after random or focused fragmentation. This can be referred to as gene "shuffling," which typically involves mixing fragments (of a desired size) of two or more different DNA molecules, followed by repeated rounds of renaturation. This can improve the activity of a protein encoded by a starting gene. The result is a chimeric protein having improved activity, altered substrate specificity, increased enzyme stability, altered stereospecificity, or other characteristics.

Amino acid "substitutions" can be the result of replacing one amino acid with another amino acid having similar structural and/or chemical properties, i.e., conservative amino acid replacements, or they can be the result of replacing one amino acid with an amino acid having different structural and/or chemical properties, i.e., non-conservative amino acid replacements. Amino acids can be placed in the following classes: non-polar, uncharged polar, basic, and acidic. "Conservative" amino acid substitutions can be made on the basis of similarity in polarity, charge, solubility, hydrophobicity, hydrophilicity, or the amphipathic nature of the residues involved. For example, nonpolar (hydrophobic) amino acids include glycine, alanine, leucine, isoleucine, valine, proline, phenylalanine, tryptophan, and methionine; polar neutral amino acids include serine, threonine, cysteine, tyrosine, asparagine, and glutamine; positively charged (basic) amino acids include arginine, lysine, and histidine; and negatively charged (acidic) amino acids include aspartic acid and glutamic acid.

Alternatively, "non-conservative" amino acid substitutions can be made by selecting the differences in polarity, charge, solubility, hydrophobicity, hydrophilicity, or the amphipathic nature of any of these amino acids. "Insertions" or "deletions" can be within the range of variation as structurally or functionally tolerated by the recombinant proteins. The variation allowed can be experimentally determined by systematically making insertions, deletions, or substitutions of amino acids in a polypeptide molecule using recombinant DNA techniques and assaying the resulting recombinant variants for activity.

Specific changes to the "active site" of the enzyme can be made to affect the inherent functionality with respect to activity or stereospecificity. See Muller et. al., "Structural basis for the enantiospecificities of R- and S-specific phenoxypropionate/alpha-ketoglutarate dioxygenases," *Protein Sci.* (2006). For example, the known tauD crystal structure was used as a model dioxygenase to determine active site residues while bound to its inherent substrate taurine. See Elkins et al. (2002) "X-ray crystal structure of *Escherichia coli* taurine/alpha-ketoglutarate dioxygenase complexed to ferrous iron and substrates," *Biochemistry* 41(16):5185-5192. Regarding sequence optimization and designability of enzyme active sites, see Chakrabarti et al., *PNAS* (Aug. 23, 2005), 102(34):12035-12040.

Various properties and three-dimensional features of the protein can also be changed without adversely affecting the activity/functionality of the protein. Conservative amino acid substitutions can be tolerated/made that do not adversely affect the activity and/or three-dimensional configuration of the molecule. Amino acids can be placed in the following classes: non-polar, uncharged polar, basic, and acidic. Conservative substitutions whereby an amino acid of one class is replaced with another amino acid of the same type fall within the scope of embodiments of the subject disclosure so long as the substitution is not adverse to the biological activity of the compound. Variant proteins can also be designed that differ at the sequence level but that retain the same or similar overall essential three-dimensional structure, surface charge distribution, and the like. See e.g. U.S. Pat. No. 7,058,515; Larson et al., *Protein Sci.* 2002 11: 2804-2813, "Thoroughly sampling sequence space: Large-scale protein design of structural ensembles"; Crameri et al, *Nature Biotechnology* 15, 436-438 (1997), "Molecular evolution of an arsenate detoxification pathway by DNA shuffling"; Stemmer, W. P. C. 1994. DNA shuffling by random fragmentation and reassembly: in vitro recombination for molecular evolution. *Proc. Natl. Acad. Sci. USA* 91: 10747-10751; Stemmer, W. P. C. 1994. Rapid evolution of a protein in vitro by DNA shuffling. *Nature* 370: 389-391; Stemmer, W. P. C. 1995. Searching sequence space. *Bio/Technology* 13: 549-553; Crameri, A., Cwirla, S, and Stemmer, W. P. C. 1996. Construction and evolution of antibody-phage libraries by DNA shuffling. *Nature Medicine* 2: 100-103; and Crameri, A., Whitehorn, E. A., Tate, E. and Stemmer, W. P. C. 1996. Improved green fluorescent protein by molecular evolution using DNA shuffling. *Nature Biotechnology* 14: 315-319.

Computational design of 5' or 3' UTR most suitable for DGT-14 (synthetic hairpins) can also be conducted within the scope of embodiments of the subject disclosure. Computer modeling in general, as well as gene shuffling and directed evolution, are discussed elsewhere herein. More specifically regarding computer modeling and UTRs, computer modeling techniques for use in predicting/evaluating 5' and 3' UTR derivatives in accordance with the present disclosure include, but are not limited to: MFold version 3.1 available from Genetics Corporation Group, Madison, Wis. (see Zucker et al., "Algorithms and Thermodynamics for RNA Secondary Structure Prediction: A Practical Guide," in *RNA Biochemistry and Biotechnology*, 11-43, J. Barciszewski & B. F. C. Clark, eds., NATO ASI Series, Kluwer Academic Publishers, Dordrecht, NL, (1999); Zucker et al., "Expanded Sequence Dependence of Thermodynamic Parameters Improves Prediction of RNA Secondary Structure," *J. Mol. Biol.* 288, 911-940 (1999); Zucker et al., "RNA Secondary Structure Prediction," in *Current Protocols in Nucleic Acid Chemistry*, S. Beaucage, D. E. Bergstrom, G. D. Glick, and R. A. Jones eds., John Wiley & Sons, New York, 11.2.1-11.2.10, (2000)); COVE (RNA structure analysis using covariance models (stochastic context free grammar methods)) v.2.4.2 (Eddy & Durbin, *Nucl. Acids Res.* 1994, 22: 2079-2088), which is freely distributed as source code and which can be downloaded by accessing the website genetics.wustl.edu/eddy/software/; and FOLDALIGN, also freely distributed and available for downloading at the website bioinf.au.dk. FOLDALIGN/ (see "Finding the most significant common sequence and structure motifs in a set of RNA sequences," J. Grodkin, L. J. Heyer and G. D. Stormo. *Nucleic Acids Research*, Vol. 25, no. 18 pp. 3724-3732, 1997, "Finding Common Sequence and Structure Motifs in a set of RNA Sequences," J. Gorodkin, L. J. Heyer, and G. D. Stormo. *ISMB* 5; 120-123, 1997).

Fragments of full-length genes can be made using commercially available exonucleases or endonucleases according to standard procedures. For example, enzymes such as Bbs I or site-directed mutagenesis can be used to systematically cut off nucleotides from the ends of genes. Also, partial genes that encode active fragments may be obtained using a variety of restriction enzymes. Proteases may be used to directly obtain active fragments of these proteins.

It is within the scope of embodiments of the disclosure as disclosed herein that proteins can be truncated and still retain functional activity. By "truncated protein" it is meant that a portion of a protein may be cleaved off while the remaining truncated protein retains and exhibits the desired activity after cleavage. Cleavage can be achieved by various proteases. Furthermore, effectively cleaved proteins can be produced using molecular biology techniques wherein the DNA bases encoding said protein are removed either through digestion with restriction endonucleases or other techniques available to the skilled artisan. After truncation, said proteins can be expressed in heterologous systems such as *E. coli*, baculoviruses, plant-based viral systems, yeast, and the like and then placed in herbicide tolerance bioassays as disclosed herein to determine activity. It is well-known in the art that truncated proteins can be successfully produced so that they retain functional activity while having less than the entire, full-length sequence. For example, B.t. proteins can be used in a truncated (core protein) form (see, e.g., Hofte et al. (1989), and Adang et al. (1985)). As used herein, the term "protein" can include functionally active truncations.

In some cases, especially for expression in plants, it can be advantageous to use truncated genes that express truncated proteins. Preferred truncated genes will typically encode 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the full-length protein.

The term "promoter" refers to a DNA sequence capable of controlling the expression of a coding sequence or functional RNA. In general, a coding sequence is located 3' to a promoter sequence. Promoters can be derived in their entirety from a native gene, or be composed of different elements derived from different promoters found in nature, or even comprise synthetic DNA segments. It is understood by those skilled in the art that different promoters can direct the expression of a gene in different tissues or cell types, or at different stages of development, or in response to different environmental or physiological conditions. Promoters which cause a gene to be expressed in most cell types at most times are commonly referred to as "constitutive promoters." It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of effecting the expression of that coding sequence (e.g., that the coding sequence is under the transcriptional control of the promoter). Coding sequences can be operably linked to regulatory sequences in sense or antisense orientation.

The term "expression," as used herein, refers to the transcription and stable accumulation of sense (mRNA) or antisense RNA derived from the nucleic acid fragment of embodiments of the disclosure. Expression may also refer to translation of mRNA into a polypeptide.

The term "overexpression" as used herein, refers to expression that is higher than endogenous expression of the same or related gene. A heterologous gene is overexpressed if its expression is higher than that of a comparable endogenous gene.

As used herein the term "transformation" refers to the transfer and integration of a nucleic acid or fragment into a host organism, resulting in genetically stable inheritance. Host organisms containing the transformed nucleic acid fragments are referred to as "transgenic" or "recombinant" or "transformed" organisms. Known methods of transformation include *Agrobacterium tumefaciens*- or *Agrobacterium rhizogenes*-mediated transformation, calcium phosphate transformation, polybrene transformation, protoplast fusion, electroporation, ultrasonic methods (e.g., sonoporation), liposome transformation, microinjection, naked DNA, plasmid vectors, viral vectors, biolistics (microparticle bombardment), silicon carbide WHISKERS mediated transformation, aerosol beaming, or PEG transformation as well as other possible methods.

The terms "plasmid" and "vector" as used herein, refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

As used herein the term "codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA. Such optimization includes replacing at least one, or more than one, or a significant number, of codons with one or more codons that are more frequently used in the genes of that organism.

Deviations in the nucleotide sequence that comprise the codons encoding the amino acids of any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is commonly known in the art. As a result, many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the proteins encoded by the DNA.

Many organisms display a bias for use of particular codons to code for insertion of a particular amino acid in a growing peptide chain. Codon preference, or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored or designed for optimal gene expression in a given organism based on codon optimization.

Given the large number of gene sequences available for a wide variety of animal, plant and microbial species, it is possible to calculate the relative frequencies of codon usage. Codon usage tables are readily available, for example, at the "Codon Usage Database" available at www.kazusa.or.jp/codon/ and these tables can be adapted in a number of ways. See Nakamura et al. *Nucl. Acids Res.* 28:292 (2000). By utilizing this or similar tables, one of ordinary skill in the art can apply the frequencies to any given polypeptide sequence, to design and produce a synthetic nucleic acid fragment of a codon-optimized coding region which encodes the polypeptide, but which uses codons optimal for a given species. In some embodiments, the present disclosure relates to codon optimized forms of dgt-14 and/or other accessory proteins of the disclosure, as described further herein.

To obtain high expression of heterologous genes in plants it may be preferred to design and reengineer said genes so that they are more efficiently expressed in plant cells, and in particular may be preferred where a bacterial gene is desired to be expressed in both dicotyledonous as well as monocotyledonous plant cells. The wild-type gene encoding DGT-14 has been isolated and the native nucleotide sequence coding for the predicted amino acid sequence can be found at GenBank Accession Number ZP_01452683 which is incorporated herein by reference in its entirety. The encoded protein sequence, comprising a modification wherein the glycine was modified to an alanine at amino acid residue 111 of GenBank Accession Number ZP_01452683 is disclosed as SEQ ID NO: 1.

Embodiments of the disclosure relate to a modification of dgt-14, wherein a synthetic dgt-14 gene sequence was designed for expression in plants. Design of an optimized dgt-14 gene for expression of the same DGT-14 protein in both monocotyledonous and dicotyledonous plants is shown with a reengineering of the protein coding region of this gene for optimal expression. Described herein are optimized nucleotide sequences encoding a DGT-14 polypeptide. Two such plant optimized dgt-14 nucleotide sequences are shown in SEQ ID NO:2 and SEQ ID NO:3. The modified nucleotide sequence is referred to as a dicot optimized dgt-14 for SEQ ID NO:2 or monocot optimized dgt-14 for SEQ ID NO:3 and provides tolerance to glyphosate in planta.

The dgt-14 nucleic acid molecule of SEQ ID NO: 2 was optimized to improve expression in dicotyledonous plants. The dgt-14 nucleic acid molecule of SEQ ID NO: 3 was optimized to improve expression in monocotyledonous plants. Codon usage was selected based upon preferred codon usage in that it was redesigned such that the protein is encoded by codons having a bias toward either monocot and dicot plant usage, and deleterious sequences and superfluous restriction sites were removed to increase the efficiency of transcription/translation of the DGT-14 polypeptide and to facilitate DNA manipulation steps. In doing so, expression of DGT-14 in plants will be improved and DGT-14 will provide resistance to glyphosate applications.

Likewise, the dgt-14 (v6) nucleic acid molecule of SEQ ID NO: 4 was optimized to improve expression in *Escherichia coli*. Codon usage was selected based upon preferred *E. coli* codon usage in that dgt-14 was redesigned such that the protein is encoded by codons having a bias toward *E. coli* usage. During the redesign deleterious sequences and superfluous restriction sites were removed to increase the efficiency of transcription/translation of the DGT-14 coding sequence and to facilitate DNA manipulation steps. In doing so, expression of DGT-14 in *E. coli* results in robust protein expression for enzymatic characterization of DGT-14.

The term "percent identity" (or "% identity"), as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those disclosed in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humania: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991).

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. See Russell, R., and Barton, G., "Structural Features can be Unconserved in Proteins with Similar Folds," *J. Mol. Biol.* 244, 332-350 (1994), at p. 337, which is incorporated herein by reference in its entirety.

In addition, methods to determine identity and similarity are codified in publicly available computer programs. Sequence alignments and percent identity calculations can be performed, for example, using the AlignX program of the VECTOR NTI® suite (Invitrogen, Carlsbad, Calif.) or MEGALIGN™ program of the LASERGENE bioinformatics computing suite (DNASTAR Inc., Madison, Wis.). Multiple alignment of the sequences is performed using the "Clustal method of alignment" which encompasses several varieties of the algorithm including the "Clustal V method of alignment" corresponding to the alignment method labeled Clustal V (disclosed by Higgins and Sharp, *CABIOS.* 5:151-153 (1989); Higgins, D. G. et al., *Comput. Appl. Biosci.,* 8:189-191 (1992)) and found in the MEGALIGN™ program of the LASERGENE bioinformatics computing suite (DNASTAR Inc.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program. Additionally the "Clustal W method of alignment" is available and corresponds to the alignment method labeled Clustal W (described by Higgins and Sharp, *CABIOS.* 5:151-153 (1989); Higgins, D. G. et al., *Comput. Appl. Biosci.* 8:189-191(1992)) and found in the MEGALIGN™ v6.1 program of the LASERGENE bioinformatics computing suite (DNASTAR Inc.). Default parameters for multiple alignment (GAP PENALTY=10, GAP LENGTH PENALTY=0.2, Delay Divergen Seqs (%)=30, DNA Transition Weight=0.5, Protein Weight MatrixGonnet Series, DNA Weight Matrix=IUB). After alignment of the sequences using the Clustal W program, it is possible to obtain a "percent identity" by viewing the "sequence distances" table in the same program.

It is well understood by one skilled in the art that many levels of sequence identity are useful in identifying polypeptides, from other species, wherein such polypeptides have the same or similar function or activity. Useful examples of percent identities include, but are not limited to: 55%, 60%, 65%, 70%, 75%, 80%, 85%, 90%, or 95%, or any integer percentage from 55% to 100% may be useful in describing embodiments of the present disclosure, such as 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.,* 215:403-410 (1990)); 3.) DNASTAR (DNASTAR, Inc. Madison, Wis.); 4.) Sequencher (Gene Codes Corporation, Ann Arbor, Mich.); and 5.) the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

When referring to hybridization techniques, all or part of a known nucleotide sequence can be used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, plasmid DNA fragments, cDNA fragments, RNA fragments, PCR amplified DNA fragments, oligonucleotides, or other polynucleotides, and may be labeled with a detectable group such as $^{32}P$, or any other detectable marker. Thus, for example, probes for hybridization can be made by labeling synthetic oligonucleotides based on the DNA sequences of embodiments of the disclosure. Methods for preparation of probes for hybridization and for construction of cDNA and genomic libraries are generally known in the art and are disclosed (Sambrook et al., 1989).

The nucleic acid probes and primers of embodiments of the present disclosure hybridize under stringent conditions to a target DNA sequence. Any conventional nucleic acid hybridization or amplification method can be used to identify the presence of DNA from a transgenic event in a sample. Nucleic acid molecules or fragments thereof are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if the two nucleic acid molecules exhibit complete complementarity. As used herein, molecules are said to exhibit "complete complementarity" when every nucleotide of one of the molecules is complementary to a nucleotide of the other. Molecules that exhibit complete complementarity will generally hybridize to one another with sufficient stability to permit them to remain annealed to one another under conventional "high-stringency" conditions. Conventional high-stringency conditions are described by Sambrook et al., 1989.

Two molecules are said to exhibit "minimal complementarity" if they can hybridize to one another with sufficient stability to permit them to remain annealed to one another under at least conventional "low-stringency" conditions. Conventional low-stringency conditions are described by Sambrook et al., 1989. In order for a nucleic acid molecule to serve as a primer or probe, it need only exhibit the minimal complementarity of sequence to be able to form a stable double-stranded structure under the particular solvent and salt concentrations employed.

Factors that affect the stringency of hybridization are well-known to those of skill in the art and include, but are not limited to, temperature, pH, ionic strength, and concentration of organic solvents such as, for example, formamide and dimethylsulfoxide. As is known to those of skill in the art, hybridization stringency is increased by higher temperatures, lower ionic strength and lower solvent concentrations.

The term "stringent condition" or "stringency conditions" is functionally defined with regard to the hybridization of a nucleic-acid probe to a target nucleic acid (i.e., to a particular nucleic-acid sequence of interest) by the specific hybridization procedure discussed in Sambrook et al., 1989, at 9.52-9.55. See also, Sambrook et al., 1989 at 9.47-9.52 and 9.56-9.58.

Typically, stringent conditions will be those in which the salt concentration is less than about 1.5 M Na$^+$ ion, typically about 0.01 to 1.0 M Na$^+$ ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1.0 M NaCl, 0.1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 0.1% SDS at 37° C., and a wash in 0.5× to 1×SSC at 55 to 60° C. Exemplary high stringency conditions include hybridization in 50% formamide, 1.0 M NaCl, 0.1% SDS at 37° C., and a wash in 0.1×SSC at 60 to 65° C.

Specificity is typically a function of post-hybridization washes, the critical factors being the ionic strength and temperature of the final wash solution. For DNA-DNA hybrids, the $T_m$ can be approximated from the equation $T_m$=81.5° C.+16.6 (log M)+0.41(% GC)−0.61(% form.)− 500/L, where M is the molarity of monovalent cations, % GC is the percentage of guanosine and cytosine nucleotides in the DNA, % form, is the percentage of formamide in the hybridization solution, and L is the length of the hybrid in base pairs (Meinkoth and Wahl, 1984). The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted for sequences of the desired identity to hybridize. For example, if sequences with 90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11 to 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found (1997) Ausubel et al., *Short Protocols in Molecular Biology*, pages 2-40, Third Edit. (1997) and Sambrook et al. (1989).

Standard recombinant DNA and molecular cloning techniques used here are well known in the art and are described, e.g., by Sambrook et al., *Molecular Cloning: A Laboratory Manual*, Second Edition, Cold Spring Harbor Laboratory Press, Cold Spring Harbor, N.Y. (1989); and by Silhavy et al., *Experiments with Gene Fusions*, Cold Spring Harbor Laboratory Press, Cold Spring Harbor, N.Y. (1984); and by Ausubel et al., *Current Protocols in Molecular Biology*, published by Greene Publishing Assoc. and Wiley-Interscience (1987).

The genetic manipulations of a recombinant host disclosed herein can be performed using standard genetic techniques and screening and can be made in any host cell that is suitable to genetic manipulation. In some embodiments, a recombinant host cell disclosed herein can be any organism or microorganism host useful for genetic modification and recombinant gene expression. In some embodiments, a recombinant host can be but is not limited to any higher plant, including both dicotyledonous and monocotyledonous plants, and consumable plants, including crop plants and plants used for their oils. Thus, any plant species or plant cell can be selected as described further below.

In some embodiments, plants which are genetically modified in accordance with the present disclosure (e.g., plant host cells) includes, but is not limited to, any higher plants, including both dicotyledonous and monocotyledonous plants, and particularly consumable plants, including crop plants. Such plants can include, but are not limited to, for example: alfalfa, soybeans, cotton, rapeseed (also described as canola), linseed, corn, rice, brachiaria, wheat, safflowers, sorghum, sugarbeet, sunflowers, tobacco and turf grasses. Thus, any plant species or plant cell can be selected. In embodiments, plant cells used herein, and plants grown or derived therefrom, include, but are not limited to, cells obtainable from rapeseed (*Brassica napus*); indian mustard (*Brassica juncea*); Ethiopian mustard (*Brassica carinata*); turnip (*Brassica rapa*); cabbage (*Brassica oleracea*); soybean (*Glycine max*); linseed/flax (*Linum usitatissimum*); maize (also described as corn) (*Zea mays*); safflower (*Carthamus tinctorius*); sunflower (*Helianthus annuus*); tobacco (*Nicotiana tabacum*); *Arabidopsis thaliana*; Brazil nut (*Betholettia excelsa*); castor bean (*Ricinus communis*); coconut (*Cocus nucifera*); coriander (*Coriandrum sativum*); cotton (*Gossypium* spp.); groundnut (*Arachis hypogaea*); jojoba (*Simmondsia chinensis*); oil palm (*Elaeis guineeis*); olive (*Olea eurpaea*); rice (*Oryza sativa*); squash (*Cucurbita maxima*); barley (*Hordeum vulgare*); sugarcane (*Saccharum officinarum*); rice (*Oryza sativa*); wheat (*Triticum* spp. including *Triticum durum* and *Triticum aestivum*); and duckweed (*Lemnaceae* sp.). In some embodiments, the genetic background within a plant species may vary.

"Plant parts," as used herein, include any parts of a plant, including, but not limited to, seeds (including mature seeds and immature seeds), a plant cutting, a plant cell, a plant cell culture, a plant organ, pollen, embryos, flowers, fruits, shoots, leaves, roots, stems, explants, etc. A plant cell is the structural and physiological unit of the plant, comprising a protoplast and a cell wall. A plant cell can be in the form of an isolated single cell or aggregate of cells such as a friable callus, or a cultured cell, or can be part of a higher organized unit, for example, a plant tissue, plant organ, or plant. Thus, a plant cell can be a protoplast, a gamete producing cell, or a cell or collection of cells that can regenerate into a whole plant. As such, a seed, which comprises multiple plant cells and is capable of regenerating into a whole plant, is considered a plant cell for purposes of this disclosure. A plant tissue or plant organ can be a seed, protoplast, callus, or any other groups of plant cells that is organized into a structural or functional unit. Particularly useful parts of a plant include harvestable parts and parts useful for propagation of progeny plants. A harvestable part of a plant can be any useful part of a plant, for example, flowers, pollen, seedlings, tubers, leaves, stems, fruit, seeds, roots, and the like. A part of a plant useful for propagation includes, for example, seeds, fruits, cuttings, seedlings, tubers, rootstocks, and the like. The tissue culture will preferably be capable of regenerating plants having the physiological and morphological characteristics of the foregoing inbred plant, and of regenerating plants having substantially the same genotype as the foregoing inbred plant. In contrast, some plant cells are not capable of being regenerated to produce plants. Preferably, the regenerable cells in such tissue cultures will be embryos, protoplasts, meristematic cells, callus, pollen, leaves, anthers, roots, root tips, silk, flowers, kernels, ears, cobs, husks or stalks. Still further, embodiments of the present disclosure provide plants regenerated from the tissue cultures of embodiments of the disclosure.

With regard to the production of genetically modified plants, methods for the genetic engineering of plants are well known in the art. For instance, numerous methods for plant transformation have been developed, including biological and physical transformation protocols for dicotyledenous plants as well as monocotyledenous plants (e.g., Goto-Fumiyuki et al., *Nature Biotech* 17:282-286 (1999); Miki et al., *Methods in Plant Molecular Biology and Biotechnology*, Glick, B. R. and Thompson, J. E. Eds., CRC Press, Inc., Boca Raton, pp. 67-88 (1993)). In addition, vectors and in vitro culture methods for plant cell or tissue transformation and regeneration of plants are available, for example, in Gruber et al., *Methods in Plant Molecular Biology and Biotechnology*, Glick, B. R. and Thompson, J. E. Eds., CRC Press, Inc., Boca Raton, pp. 89-119 (1993).

A large number of techniques are available for inserting DNA into a plant host cell. Those techniques include transformation with disarmed T-DNA using *Agrobacterium tumefaciens* or *Agrobacterium rhizogenes* as the transformation agent, calcium phosphate transfection, polybrene transformation, protoplast fusion, electroporation, ultrasonic methods (e.g., sonoporation), liposome transformation, microinjection, naked DNA, plasmid vectors, viral vectors, biolistics (microparticle bombardment), silicon carbide WHISKERS™ mediated transformation, aerosol beaming, or PEG as well as other possible methods.

For example, the DNA construct may be introduced directly into the genomic DNA of the plant cell using techniques such as electroporation and microinjection of plant cell protoplasts, or the DNA constructs can be introduced directly to plant tissue using biolistic methods, such as DNA particle bombardment (see, e.g., Klein et al. (1987) *Nature* 327:70-73). Additional methods for plant cell transformation include microinjection via silicon carbide WHISKERS mediated DNA uptake (Kaeppler et al. (1990) *Plant Cell Reporter* 9:415-418). Alternatively, the DNA construct can be introduced into the plant cell via nanoparticle transformation (see, e.g., U.S. patent application Ser. No. 12/245,685, which is incorporated herein by reference in its entirety).

Another known method of plant transformation is microprojectile-mediated transformation wherein DNA is carried on the surface of microprojectiles. In this method, the expression vector is introduced into plant tissues with a biolistic device that accelerates the microprojectiles to speeds sufficient to penetrate plant cell walls and membranes. Sanford et al., *Part. Sci. Technol.* 5:27 (1987), Sanford, J. C., *Trends Biotech.* 6:299 (1988), Sanford, J. C., *Physiol. Plant* 79:206 (1990), Klein et al., *Biotechnology* 10:268 (1992).

Alternatively, gene transfer and transformation methods include, but are not limited to, protoplast transformation through calcium chloride precipitation, polyethylene glycol (PEG)- or electroporation-mediated uptake of naked DNA (see Paszkowski et al. (1984) *EMBO J.* 3:2717-2722, Potrykus et al. (1985) *Molec. Gen. Genet.* 199:169-177; Fromm et al. (1985) *Proc. Nat. Acad. Sci. USA* 82:5824-5828; and Shimamoto (1989) *Nature* 338:274-276) and electroporation of plant tissues (D'Halluin et al. (1992) *Plant Cell* 4:1495-1505).

A widely utilized method for introducing an expression vector into plants is based on the natural transformation system of *Agrobacterium*. Horsch et al., *Science* 227:1229 (1985). *A. tumefaciens* and *A. rhizogenes* are plant pathogenic soil bacteria known to be useful to genetically transform plant cells. The Ti and Ri plasmids of *A. tumefaciens* and *A. rhizogenes*, respectively, carry genes responsible for genetic transformation of the plant. Kado, C. I., *Crit. Rev. Plant. Sci.* 10:1 (1991). Descriptions of *Agrobacterium* vector systems and methods for *Agrobacterium*-mediated gene transfer are also available, for example, Gruber et al., supra, Miki et al., supra, Moloney et al., *Plant Cell Reports* 8:238 (1989), and U.S. Pat. Nos. 4,940,838 and 5,464,763.

If *Agrobacterium* is used for the transformation, the DNA to be inserted should be cloned into special plasmids, namely either into an intermediate vector or into a binary vector. Intermediate vectors cannot replicate themselves in *Agrobacterium*. The intermediate vector can be transferred into *Agrobacterium tumefaciens* by means of a helper plasmid (conjugation). The Japan Tobacco Superbinary system is an example of such a system (reviewed by Komari et al., (2006) In: *Methods in Molecular Biology* (K. Wang, ed.) No. 343: *Agrobacterium* Protocols (2$^{nd}$ Edition, Vol. 1) HUMANA PRESS Inc., Totowa, N.J., pp. 15-41; and Komori et al., (2007) *Plant Physiol.* 145:1155-1160). Binary vectors can replicate themselves both in *E. coli* and in *Agrobacterium*. They comprise a selection marker gene and a linker or polylinker which are framed by the right and left T-DNA border regions. They can be transformed directly into *Agrobacterium* (Holsters, 1978). The *Agrobacterium* used as host cell is to comprise a plasmid carrying a vir region. The Ti or Ri plasmid also comprises the vir region necessary for the transfer of the T-DNA. The vir region is necessary for the transfer of the T-DNA into the plant cell. Additional T-DNA may be contained.

The virulence functions of the *Agrobacterium tumefaciens* host will direct the insertion of a T-strand containing the construct and adjacent marker into the plant cell DNA when the cell is infected by the bacteria using a binary T DNA vector (Bevan (1984) *Nuc. Acid Res.* 12:8711-8721) or the co-cultivation procedure (Horsch et al. (1985) *Science* 227:1229-1231). Generally, the *Agrobacterium* transformation system is used to engineer dicotyledonous plants (Bevan et al. (1982) *Ann. Rev. Genet.* 16:357-384; Rogers et al. (1986) *Methods Enzymol.* 118:627-641). The *Agrobacterium* transformation system may also be used to transform, as well as transfer, DNA to monocotyledonous plants and plant cells. See U.S. Pat. No. 5,591,616; Hernalsteen et al. (1984) *EMBO J.* 3:3039-3041; Hooykass-Van Slogteren et al. (1984) *Nature* 311:763-764; Grimsley et al. (1987) *Nature* 325:1677-179; Boulton et al. (1989) *Plant Mol. Biol.* 12:31-40; and Gould et al. (1991) *Plant Physiol.* 95:426-434. Following the introduction of the genetic construct into plant cells, plant cells can be grown and upon emergence of differentiating tissue such as shoots and roots, mature plants can be generated. In some embodiments, a plurality of plants can be generated. Methodologies for regenerating plants are known to those of ordinary skill in the art and can be found, for example, in: *Plant Cell and Tissue Culture*, 1994, Vasil and Thorpe Eds. Kluwer Academic Publishers and in: *Plant Cell Culture Protocols* (*Methods in Molecular Biology* 111, 1999 Hall Eds Humana Press). The genetically modified plant described herein can be cultured in a fermentation medium or grown in a suitable medium such as soil. In some embodiments, a suitable growth medium for higher plants can include any growth medium for plants, including, but not limited to, soil, sand, any other particulate media that support root growth (e.g., vermiculite, perlite, etc.) or hydroponic culture, as well as suitable light, water and nutritional supplements which optimize the growth of the higher plant.

Transformed plant cells which are produced by any of the above transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans, et al., "Protoplasts Isolation and Culture" in *Handbook of Plant Cell Culture*, pp. 124-176, Macmillian Publishing Company, New York, 1983; and Binding, *Regeneration of Plants, Plant Protoplasts*, pp. 21-73, CRC Press, Boca Raton, 1985. Regeneration can also be obtained from plant callus, explants, organs, pollens, embryos or parts thereof. Such regeneration techniques are described generally in Klee et al. (1987) *Ann. Rev. of Plant Phys.* 38:467-486.

In other embodiments, the plant cells which are transformed are not capable of regeneration to produce a plant. Such cells may be employed, for example, in developing a plant cell line having the relevant phenotype, for example, herbicide resistance.

Nucleic acids introduced into a plant cell can be used to confer desired traits on essentially any plant. A wide variety of plants and plant cell systems may be engineered for the desired physiological and agronomic characteristics described herein using the nucleic acid constructs of the present disclosure and the various transformation methods mentioned above. In preferred embodiments, target plants and plant cells for engineering include, but are not limited to, those monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); flowering plants (e.g., petunia, rose, chrysanthemum), conifers and pine trees (e.g., pine fir, spruce); plants used in phytoremediation (e.g., heavy metal accumulating plants); oil crops (e.g., sunflower, rape seed) and plants used for experimental purposes (e.g., *Arabidopsis*). Thus, the disclosed methods and compositions have use over a broad range of plants, including, but not limited to, species from the genera *Asparagus, Avena, Brassica, Citrus, Citrullus, Capsicum, Cucurbita, Daucus, Erigeron, Glycine, Gossypium, Hordeum, Lactuca, Lolium, Lycopersicon, Malus, Manihot, Nicotiana, Orychophragmus, Oryza, Persea, Phaseolus, Pisum, Pyrus, Prunus, Raphanus, Secale, Solanum, Sorghum, Triticum, Vitis, Vigna,* and *Zea mays.*

A transformed plant cell, callus, tissue or plant may be identified and isolated by selecting or screening the engineered plant material for traits encoded by the marker genes present on the transforming DNA. For instance, selection can be performed by growing the engineered plant material on media containing an inhibitory amount of the antibiotic or herbicide to which the transforming gene construct confers resistance. Further, transformed plants and plant cells can also be identified by screening for the activities of any visible marker genes (e.g., the β-glucuronidase, luciferase, or gfp genes) that may be present on the recombinant nucleic acid constructs. Such selection and screening methodologies are well known to those skilled in the art.

The term introduced in the context of inserting a nucleic acid into a cell, includes transformation into the cell, as well as crossing a plant having the sequence with another plant, so that the second plant contains the heterologous sequence, as in conventional plant breeding techniques. Such breeding techniques are well known to one skilled in the art. For a discussion of plant breeding techniques, see Poehlman (1995) *Breeding Field Crops*, AVI Publication Co., Westport Conn., 4$^{th}$ Edit. Backcrossing methods may be used to introduce a gene into the plants. This technique has been used for decades to introduce traits into a plant. An example of a description of this and other plant breeding methodologies that are well known can be found in references such as Poehlman, supra, and *Plant Breeding Methodology*, edit. Neal Jensen, John Wiley & Sons, Inc. (1988). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a plant is obtained wherein essentially all of the desired morphological and physiological characteristics of the recurrent parent are recovered in the converted plant, in addition to the single transferred gene from the nonrecurrent parent.

Certain embodiments relate to processes of making crosses using a plant of an embodiment of this disclosure as at least one parent. For example, particular embodiments relate to an $F_1$ hybrid plant having as one or both parents any of the plants exemplified herein. Other embodiments relate to seed produced by such $F_1$ hybrids. Still other embodiments relate to a method for producing an $F_1$ hybrid seed by crossing an exemplified plant with a different (e.g. inbred parent) plant and harvesting the resultant hybrid seed. Other embodiments relate to an exemplified plant that is either a female parent or a male parent. Characteristics of the resulting plants may be improved by careful consideration of the parent plants.

A transgenic plant containing a dgt-14 polynucleotide of an embodiment of the subject disclosure can be bred by first sexually crossing a first parental plant consisting of a plant grown from seed of any one of the lines referred to herein, and a second parental plant, thereby producing a plurality of first progeny plants; then selecting a first progeny plant that is resistant to glyphosate; selfing the first progeny plant, thereby producing a plurality of second progeny plants; and then selecting from the second progeny plants a plant that is resistant to glyphosate. These steps can further include the back-crossing of the first progeny plant or the second progeny plant to the second parental plant or a third parental plant. A crop comprising seeds of particular embodiments, or progeny thereof, can then be planted.

It is also to be understood that two different transgenic plants can also be mated to produce offspring that contain two independently segregating, added, exogenous genes. Selfing of appropriate progeny can produce plants that are homozygous for both added, exogenous genes. Back-crossing to a parental plant and out-crossing with a non-transgenic plant are also contemplated, as is vegetative propagation. Other breeding methods commonly used for different traits and crops are known in the art. Backcross breeding has been used to transfer genes for a simply inherited, highly heritable trait into a desirable homozygous cultivar or inbred line, which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting parent is expected to have the attributes of the recurrent parent (e.g., cultivar) and the desirable trait transferred from the donor parent.

A nucleic acid encoding the dgt-14 nucleotide sequence as described herein can be cloned into a vector for transformation into prokaryotic or eukaryotic cells for replication and/or expression. Vectors can be prokaryotic vectors, e.g., plasmids, or shuttle vectors, insect vectors, or eukaryotic vectors. A nucleic acid encoding a dgt-14 polynucleotide can also be cloned into an expression vector, for administration to a plant cell. At times, it may be preferable to have vectors that are functional in *E. coli* (e.g., production of protein for raising antibodies, DNA sequence analysis, construction of inserts, obtaining quantities of nucleic acids).

To express the DGT-14 protein, nucleotide sequences encoding the dgt-14 sequence are typically subcloned into an expression vector that contains a promoter to direct transcription. Suitable bacterial and eukaryotic promoters are well known in the art and described, e.g., in Sambrook et al., *Molecular Cloning, A Laboratory Manual* (2nd ed. 1989; 3$^{rd}$ ed., 2001); Kriegler, *Gene Transfer and Expression: A Laboratory Manual* (1990); and *Current Protocols in Molecular Biology* (Ausubel et al., supra.). Bacterial expression systems for expressing the dgt-14 sequence are available in, e.g., *E. coli, Bacillus* sp., and *Salmonella* (Palva et al., *Gene* 22:229-235 (1983)). Kits for such expression systems are commercially available. Eukaryotic expression systems for mammalian cells, yeast, and insect cells are well known by those of skill in the art and are also commercially available.

The particular expression vector used to transport the genetic information into the cell is selected with regard to the intended use of the DGT-14 protein, e.g., expression in plants, animals, bacteria, fungus, protozoa, etc. Standard bacterial and animal expression vectors are known in the art and are described in detail, for example, U.S. Patent Publication 20050064474A1 and International Patent Publications WO 05/084190, WO05/014791 and WO03/080809. Standard transfection methods can be used to produce bacterial cell lines that express large quantities of protein, which can then be purified using standard techniques.

The promoter used to direct expression of a dgt-14 encoding nucleic acid depends on the particular application.

For example, a strong constitutive promoter suited to the host cell is typically used for expression and purification of DGT-14 proteins. Non-limiting examples of preferred plant promoters include promoter sequences derived from *A. thaliana* ubiquitin-10 (ubi-10) (Callis, et al., 1990, *J. Biol. Chem.*, 265:12486-12493); *A. tumefaciens* mannopine synthase (Δmas) (Petolino et al., U.S. Pat. No. 6,730,824); and/or Cassava Vein Mosaic Virus (CsVMV) (Verdaguer et al., 1996, *Plant Molecular Biology* 31:1129-1139).

In methods disclosed herein, a number of promoters that direct expression of a gene in a plant can be employed. Such promoters can be selected from constitutive, chemically-regulated, inducible, tissue-specific, and seed-preferred promoters.

Constitutive promoters include, for example, the core Cauliflower Mosaic Virus 35S promoter (Odell et al. (1985) *Nature* 313:810-812); Rice Actin promoter (McElroy et al. (1990) *Plant Cell* 2:163-171); Maize Ubiquitin promoter (U.S. Pat. No. 5,510,474; Christensen et al. (1989) *Plant Mol. Biol.* 12:619-632 and Christensen et al. (1992) *Plant Mol. Biol.* 18:675-689); pEMU promoter (Last et al. (1991) *Theor. Appl. Genet.* 81:581-588); ALS promoter (U.S. Pat. No. 5,659,026); Maize Histone promoter (Chabouté et al. *Plant Molecular Biology*, 8:179-191 (1987)); and the like.

The range of available plant compatible promoters includes tissue specific and inducible promoters. An inducible regulatory element is one that is capable of directly or indirectly activating transcription of one or more DNA sequences or genes in response to an inducer. In the absence of an inducer the DNA sequences or genes will not be transcribed. Typically the protein factor that binds specifically to an inducible regulatory element to activate transcription is present in an inactive form which is then directly or indirectly converted to the active form by the inducer. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. Typically the protein factor that binds specifically to an inducible regulatory element to activate transcription is present in an inactive form which is then directly or indirectly converted to the active form by the inducer. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. A plant cell containing an inducible regulatory element may be exposed to an inducer by externally applying the inducer to the cell or plant such as by spraying, watering, heating or similar methods.

Any inducible promoter can be used in embodiments of the instant disclosure. See Ward et al. *Plant Mol. Biol.* 22: 361-366 (1993). Exemplary inducible promoters include ecdysone receptor promoters (U.S. Pat. No. 6,504,082); promoters from the ACE1 system which respond to copper (Mett et al. *PNAS* 90: 4567-4571 (1993)); In2-1 and In2-2 gene from maize which respond to benzenesulfonamide herbicide safeners (U.S. Pat. No. 5,364,780; Hershey et al., *Mol. Gen. Genetics* 227: 229-237 (1991) and Gatz et al., *Mol. Gen. Genetics* 243: 32-38 (1994)); Tet repressor from Tn10 (Gatz et al., *Mol. Gen. Genet.* 227: 229-237 (1991); or promoters from a steroid hormone gene, the transcriptional activity of which is induced by a glucocorticosteroid hormone, Schena et al., *Proc. Natl. Acad. Sci. U.S.A.* 88: 10421 (1991) and McNellis et al., (1998) *Plant J.* 14(2):247-257; the maize GST promoter, which is activated by hydrophobic electrophilic compounds that are used as pre-emergent herbicides (see U.S. Pat. No. 5,965,387 and International Patent Application, Publication No. WO 93/001294); and the tobacco PR-1a promoter, which is activated by salicylic acid (see Ono S, Kusama M, Ogura R, Hiratsuka K., "Evaluation of the Use of the Tobacco PR-1a Promoter to Monitor Defense Gene Expression by the Luciferase Bioluminescence Reporter System," *Biosci Biotechnol Biochem.* 2011 Sep. 23; 75(9):1796-800). Other chemical-regulated promoters of interest include tetracycline-inducible and tetracycline-repressible promoters (see, for example, Gatz et al., (1991) *Mol. Gen. Genet.* 227:229-237, and U.S. Pat. Nos. 5,814,618 and 5,789,156).

Other regulatable promoters of interest include a cold responsive regulatory element or a heat shock regulatory element, the transcription of which can be effected in response to exposure to cold or heat, respectively (Takahashi et al., *Plant Physiol.* 99:383-390, 1992); the promoter of the alcohol dehydrogenase gene (Gerlach et al., *PNAS USA* 79:2981-2985 (1982); Walker et al., *PNAS* 84(19):6624-6628 (1987)), inducible by anaerobic conditions; and the light-inducible promoter derived from the pea rbcS gene or pea psaDb gene (Yamamoto et al. (1997) *Plant J.* 12(2): 255-265); a light-inducible regulatory element (Feinbaum et al., *Mol. Gen. Genet.* 226:449, 1991; Lam and Chua, *Science* 248:471, 1990; Matsuoka et al. (1993) *Proc. Natl. Acad. Sci. USA* 90(20):9586-9590; Orozco et al. (1993) *Plant Mol. Bio.* 23(6):1129-1138), a plant hormone inducible regulatory element (Yamaguchi-Shinozaki et al., *Plant Mol. Biol.* 15:905, 1990; Kares et al., *Plant Mol. Biol.* 15:225, 1990), and the like. An inducible regulatory element also can be the promoter of the maize In2-1 or In2-2 gene, which responds to benzenesulfonamide herbicide safeners (Hershey et al., *Mol. Gen. Genet.* 227:229-237, 1991; Gatz et al., *Mol. Gen. Genet.* 243:32-38, 1994), and the Tet repressor of transposon Tn10 (Gatz et al., *Mol. Gen. Genet.* 227:229-237, 1991). Stress inducible promoters include salt/water stress-inducible promoters such as P5CS (Zang et al. (1997) *Plant Sciences* 129:81-89); cold-inducible promoters, such as, cor15a (Hajela et al. (1990) *Plant Physiol.* 93:1246-1252), cor15b (Wilhelm et al. (1993) *Plant Mol. Biol.* 23:1073-1077), wsc120 (Ouellet et al. (1998) *FEBS Lett.* 423-324-328), ci7 (Kirch et al. (1997) *Plant Mol. Biol.* 33:897-909), ci21A (Schneider et al. (1997) *Plant Physiol.* 113:335-45); drought-inducible promoters, such as Trg-31 (Chaudhary et al (1996) *Plant Mol. Biol.* 30:1247-57), rd29 (Kasuga et al. (1999) *Nature Biotechnology* 18:287-291); osmotic inducible promoters, such as Rab17 (Vilardell et al. (1991) *Plant Mol. Biol.* 17:985-93) and osmotin (Raghothama et al. (1993) *Plant Mol. Biol.* 23:1117-28); and heat inducible promoters, such as heat shock proteins (Barros et al. (1992) *Plant Mol.* 19:665-75; Marrs et al. (1993) *Dev. Genet.* 14:27-41), smHSP (Waters et al. (1996) *J. Experimental Botany* 47:325-338), and the heat-shock inducible element from the parsley ubiquitin promoter (WO 03/102198). Other stress-inducible promoters include rip2 (U.S. Pat. No. 5,332, 808 and U.S. Publication No. 2003/0217393) and rd29a (Yamaguchi-Shinozaki et al. (1993) *Mol. Gen. Genetics* 236:331-340). Certain promoters are inducible by wounding, including the *Agrobacterium* pMAS promoter (Guevara-Garcia et al. (1993) *Plant J.* 4(3):495-505) and the *Agrobacterium* ORF13 promoter (Hansen et al., (1997) *Mol. Gen. Genet.* 254(3):337-343).

Tissue-preferred promoters can be utilized to target enhanced transcription and/or expression within a particular plant tissue. When referring to preferential expression, what is meant is expression at a higher level in the particular plant tissue than in other plant tissue. Examples of these types of promoters include seed preferred expression such as that provided by the phaseolin promoter (Bustos et al. 1989. *The Plant Cell* Vol. 1, 839-853), and the maize globulin-1 gene, Belanger, et al. 1991 *Genetics* 129:863-972. For dicots, seed-preferred promoters include, but are not limited to, bean β-phaseolin, napin, β-conglycinin, soybean lectin, cruciferin, and the like. For monocots, seed-preferred promoters include, but are not limited to, maize 15 kDa zein, 22 kDa zein, 27 kDa zein, γ-zein, waxy, shrunken 1, shrunken 2, globulin 1, etc. Seed-preferred promoters also include those promoters that direct gene expression predominantly to specific tissues within the seed such as, for example, the endosperm-preferred promoter of γ-zein, the cryptic promoter from tobacco (Fobert et al. 1994. T-DNA tagging of a seed coat-specific cryptic promoter in tobacco. *Plant J.* 4: 567-577), the P-gene promoter from corn (Chopra et al. 1996. Alleles of the maize P gene with distinct tissue specificities encode Myb-homologous proteins with C-terminal replacements. *Plant Cell* 7:1149-1158, Erratum in *Plant Cell* 1997, 1:109), the globulin-1 promoter from corn (Belenger and Kriz. 1991. Molecular basis for Allelic Polymorphism of the maize Globulin-1 gene. *Genetics* 129: 863-972), and promoters that direct expression to the seed coat or hull of corn kernels, for example the pericarp-specific glutamine synthetase promoter (Muhitch et al., 2002. Isolation of a Promoter Sequence From the Glutamine Synthetase$_{1-2}$ Gene Capable of Conferring Tissue-Specific Gene Expression in Transgenic Maize. *Plant Science* 163: 865-872).

In addition to the promoter, the expression vector typically contains a transcription unit or expression cassette that contains all the additional elements required for the expression of the nucleic acid in host cells, either prokaryotic or eukaryotic. A typical expression cassette thus contains a promoter operably linked, e.g., to a nucleic acid sequence encoding the protein, and signals required, e.g., for efficient polyadenylation of the transcript, transcriptional termination, ribosome binding sites, or translation termination. Additional elements of the cassette may include, e.g., enhancers and heterologous splicing signals.

Other components of the vector may be included, also depending upon intended use of the gene. Examples include selectable markers, targeting or regulatory sequences, transit peptide sequences such as the optimized transit peptide sequence (see U.S. Pat. No. 5,510,471) stabilizing sequences such as RB7 MAR (see Thompson and Myatt, (1997) *Plant Mol. Biol.*, 34: 687-692 and WO9727207) or leader sequences, introns etc. General descriptions and examples of plant expression vectors and reporter genes can be found in Gruber, et al., "Vectors for Plant Transformation" in *Methods in Plant Molecular Biology and Biotechnology*, Glick et al eds; CRC Press pp. 89-119 (1993). The selection of an appropriate expression vector will depend upon the host and the method of introducing the expression vector into the host. The expression cassette will also include at the 3' terminus of the heterologous nucleotide sequence of interest, a transcriptional and translational termination region functional in plants. The termination region can be native with the promoter nucleotide sequence of embodiments of the present disclosure, can be native with the DNA sequence of interest, or can be derived from another source. Convenient termination regions are available from the Ti-plasmid of *A. tumefaciens*, such as the octopine synthase and nopaline synthase (nos) termination regions (Depicker et al., *Mol. and Appl. Genet.* 1:561-573 (1982) and Shaw et al. (1984) *Nucleic Acids Research vol.* 12, No. 20 pp 7831-7846(nos));

see also Guerineau et al. *Mol. Gen. Genet.* 262:141-144 (1991); Proudfoot, *Cell* 64:671-674 (1991); Sanfacon et al. *Genes Dev.* 5:141-149 (1991); Mogen et al. *Plant Cell* 2:1261-1272 (1990); Munroe et al. *Gene* 91:151-158 (1990); Ballas et al. *Nucleic Acids Res.* 17:7891-7903 (1989); Joshi et al. *Nucleic Acid Res.* 15:9627-9639 (1987).

The expression cassettes can additionally contain 5' leader sequences. Such leader sequences can act to enhance translation. Translation leaders are known in the art and include by way of example, picornavirus leaders, EMCV leader (Encephalomyocarditis 5' noncoding region), Elroy-Stein et al. *Proc. Nat. Acad. Sci. USA* 86:6126-6130 (1989); potyvirus leaders, for example, TEV leader (Tobacco Etch Virus) Carrington and Freed *Journal of Virology,* 64:1590-1597 (1990), MDMV leader (Maize Dwarf Mosaic Virus), Allison et al., *Virology* 154:9-20 (1986); human immunoglobulin heavy-chain binding protein (BiP), Macejak et al. *Nature* 353:90-94 (1991); untranslated leader from the coat protein mRNA of alfalfa mosaic virus (AMV RNA 4), Jobling et al. *Nature* 325:622-625 (1987); Tobacco mosaic virus leader (TMV), Gallie et al. (1989) *Molecular Biology of RNA,* pages 237-256; and maize chlorotic mottle virus leader (MCMV) Lommel et al. *Virology* 81:382-385 (1991). See also Della-Cioppa et al. *Plant Physiology* 84:965-968 (1987).

The construct can also contain sequences that enhance translation and/or mRNA stability such as introns. An example of one such intron is the first intron of gene II of the histone H3.III variant of *Arabidopsis thaliana.* Chaubet et al. *Journal of Molecular Biology,* 225:569-574 (1992).

In those instances where it is desirable to have the expressed product of the heterologous nucleotide sequence directed to a particular organelle, particularly the plastid, amyloplast, or to the endoplasmic reticulum, or secreted at the cell's surface or extracellularly, the expression cassette can further comprise a coding sequence for a transit peptide. Such transit peptides are well known in the art and include, but are not limited to, the transit peptide for the acyl carrier protein, the small subunit of RUBISCO, plant EPSP synthase and *Helianthus annuus* (see Lebrun et al. U.S. Pat. No. 5,510,417), Zea mays Brittle-1 chloroplast transit peptide (Nelson et al. *Plant Physiol* 117(4):1235-1252 (1998); Sullivan et al. *Plant Cell* 3(12):1337-48; Sullivan et al., *Planta* (1995) 196(3):477-84; Sullivan et al., *J. Biol. Chem.* (1992) 267(26):18999-9004) and the like. In addition, chimeric chloroplast transit peptides are known in the art, such as the Optimized Transit Peptide (see, U.S. Pat. No. 5,510,471). Additional chloroplast transit peptides have been described previously in U.S. Pat. Nos. 5,717,084; 5,728,925. One skilled in the art will readily appreciate the many options available in expressing a product to a particular organelle. For example, the barley alpha amylase sequence is often used to direct expression to the endoplasmic reticulum (Rogers, *J. Biol. Chem.* 260:3731-3738 (1985)).

It will be appreciated by one skilled in the art that use of recombinant DNA technologies can improve control of expression of transfected nucleic acid molecules by manipulating, for example, the number of copies of the nucleic acid molecules within the host cell, the efficiency with which those nucleic acid molecules are transcribed, the efficiency with which the resultant transcripts are translated, and the efficiency of post-translational modifications. Additionally, the promoter sequence might be genetically engineered to improve the level of expression as compared to the native promoter. Recombinant techniques useful for controlling the expression of nucleic acid molecules include, but are not limited to, stable integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno or Kozak sequences), modification of nucleic acid molecules to correspond to the codon usage of the host cell, and deletion of sequences that destabilize transcripts.

Reporter or marker genes for selection of transformed cells or tissues or plant parts or plants can be included in the transformation vectors. Examples of selectable markers include those that confer resistance to anti-metabolites such as herbicides or antibiotics, for example, dihydrofolate reductase, which confers resistance to methotrexate (Reiss, *Plant Physiol.* (Life Sci. Adv.) 13:143-149, 1994; see also Herrera Estrella et al., *Nature* 303:209-213, 1983; Meijer et al., *Plant Mol. Biol.* 16:807-820, 1991); neomycin phosphotransferase, which confers resistance to the aminoglycosides neomycin, kanamycin and paromycin (Herrera-Estrella, *EMBO J.* 2:987-995, 1983 and Fraley et al. *Proc. Natl. Acad. Sci. USA* 80:4803 (1983)) and hygromycin phosphotransferase, which confers resistance to hygromycin (Marsh, *Gene* 32:481-485, 1984; see also Waldron et al., *Plant Mol. Biol.* 5:103-108, 1985; Zhijian et al., *Plant Science* 108:219-227, 1995); trpB, which allows cells to utilize indole in place of tryptophan; hisD, which allows cells to utilize histinol in place of histidine (Hartman, *Proc. Natl. Acad. Sci., USA* 85:8047, 1988); mannose-6-phosphate isomerase which allows cells to utilize mannose (WO 94/20627); ornithine decarboxylase, which confers resistance to the ornithine decarboxylase inhibitor, 2-(difluoromethyl)-DL-ornithine (DFMO; McConlogue, 1987, In: *Current Communications in Molecular Biology,* Cold Spring Harbor Laboratory ed.); and deaminase from *Aspergillus terreus,* which confers resistance to Blasticidin S (Tamura, *Biosci. Biotechnol. Biochem.* 59:2336-2338, 1995).

Additional selectable markers include, for example, a mutant acetolactate synthase, which confers imidazolinone or sulfonylurea resistance (Lee et al., *EMBO J.* 7:1241-1248, 1988), a mutant psbA, which confers resistance to atrazine (Smeda et al., *Plant Physiol.* 103:911-917, 1993), or a mutant protoporphyrinogen oxidase (see U.S. Pat. No. 5,767,373), or other markers conferring resistance to an herbicide such as glufosinate. Examples of suitable selectable marker genes include, but are not limited to, genes encoding resistance to chloramphenicol (Herrera Estrella et al., *EMBO J.* 2:987-992, 1983); streptomycin (Jones et al., *Mol. Gen. Genet.* 210:86-91, 1987); spectinomycin (Bretagne-Sagnard et al., *Transgenic Res.* 5:131-137, 1996); bleomycin (Hille et al., *Plant Mol. Biol.* 7:171-176, 1990); sulfonamide (Guerineau et al., *Plant Mol. Biol.* 15:127-136, 1990); bromoxynil (Stalker et al., *Science* 242:419-423, 1988); glyphosate (Shaw et al., *Science* 233:478-481, 1986); phosphinothricin (DeBlock et al., *EMBO J.* 6:2513-2518, 1987), and the like.

One option for use of a selective gene is a glufosinate-resistance encoding DNA and in one embodiment can be the phosphinothricin acetyl transferase (pat), maize optimized pat gene or bar gene under the control of the Cassava Vein Mosaic Virus promoter. These genes confer resistance to bialaphos. See, (see, Wohlleben et al., (1988) *Gene* 70: 25-37); Gordon-Kamm et al., *Plant Cell* 2:603; 1990; Uchimiya et al., *BioTechnology* 11:835, 1993; White et al., *Nucl. Acids Res.* 18:1062, 1990; Spencer et al., *Theor. Appl. Genet.* 79:625-631, 1990; and Anzai et al., *Mol. Gen. Gen.* 219:492, 1989). A version of the pat gene is the maize optimized pat gene, described in U.S. Pat. No. 6,096,947.

In addition, markers that facilitate identification of a plant cell containing the polynucleotide encoding the marker may be employed. Scorable or screenable markers are useful, where presence of the sequence produces a measurable product and can produce the product without destruction of the plant cell. Examples include a β-glucuronidase, or uidA gene (GUS), which encodes an enzyme for which various chromogenic substrates are known (for example, U.S. Pat. Nos. 5,268,463 and 5,599,670); chloramphenicol acetyl transferase (Jefferson et al. *The EMBO Journal* vol. 6 No. 13 pp. 3901-3907); and alkaline phosphatase. In a preferred embodiment, the marker used is beta-carotene or provitamin A (Ye et al., *Science* 287:303-305-(2000)). The gene has been used to enhance the nutrition of rice, but in this instance it is employed instead as a screenable marker, and the presence of the gene linked to a gene of interest is detected by the golden color provided. Unlike the situation where the gene is used for its nutritional contribution to the plant, a smaller amount of the protein suffices for marking purposes. Other screenable markers include the anthocyanin/flavonoid genes in general (See discussion at Taylor and Briggs, *The Plant Cell* (1990)2:115-127) including, for example, a R-locus gene, which encodes a product that regulates the production of anthocyanin pigments (red color) in plant tissues (Dellaporta et al., in *Chromosome Structure and Function*, Kluwer Academic Publishers, Appels and Gustafson eds., pp. 263-282 (1988)); the genes which control biosynthesis of flavonoid pigments, such as the maize C1 gene (Kao et al., *Plant Cell* (1996) 8: 1171-1179; Scheffler et al. *Mol. Gen. Genet.* (1994) 242:40-48) and maize C2 (Wienand et al., *Mol. Gen. Genet.* (1986) 203:202-207); the B gene (Chandler et al., *Plant Cell* (1989) 1:1175-1183), the p1 gene (Grotewold et al., *Proc. Natl. Acad. Sci. USA* (1991) 88:4587-4591; Grotewold et al., *Cell* (1994) 76:543-553; Sidorenko et al., *Plant Mol. Biol.* (1999)39:11-19); the bronze locus genes (Ralston et al., *Genetics* (1988) 119:185-197; Nash et al., *Plant Cell* (1990) 2(11): 1039-1049), among others.

Further examples of suitable markers include the cyan fluorescent protein (CYP) gene (Bolte et al. (2004) *J. Cell Science* 117: 943-54 and Kato et al. (2002) *Plant Physiol.* 129: 913-42), the yellow fluorescent protein gene (PHI-YFP™ from Evrogen; see Bolte et al. (2004) *J. Cell Science* 117: 943-54); a lux gene, which encodes a luciferase, the presence of which may be detected using, for example, X-ray film, scintillation counting, fluorescent spectrophotometry, low-light video cameras, photon counting cameras or multiwell luminometry (Teeri et al. (1989) *EMBO J.* 8:343); a green fluorescent protein (GFP) gene (Sheen et al., *Plant J.* (1995) 8(5):777-84); and DsRed2 where plant cells transformed with the marker gene are red in color, and thus visually selectable (Dietrich et al. (2002) *Biotechniques* 2(2):286-293). Additional examples include a β-lactamase gene (Sutcliffe, *Proc. Natl. Acad. Sci. U.S.A.* (1978) 75:3737), which encodes an enzyme for which various chromogenic substrates are known (e.g., PADAC, a chromogenic cephalosporin); a xylE gene (Zukowsky et al., *Proc. Natl. Acad. Sci. U.S.A.* (1983) 80:1101), which encodes a catechol dioxygenase that can convert chromogenic catechols; an α-amylase gene (Ikuta et al., *Biotech.* (1990) 8:241); and a tyrosinase gene (Katz et al., *J. Gen. Microbiol.* (1983) 129:2703), which encodes an enzyme capable of oxidizing tyrosine to DOPA and dopaquinone, which in turn condenses to form the easily detectable compound melanin. Clearly, many such markers are available and known to one skilled in the art.

In certain embodiments, the nucleotide sequence can be optionally combined with another nucleotide sequence of interest. The term "nucleotide sequence of interest" refers to a nucleic acid molecule (which may also be referred to as a polynucleotide) which can be a transcribed RNA molecule as well as DNA molecule, that encodes for a desired polypeptide or protein, but also may refer to nucleic acid molecules that do not constitute an entire gene, and which do not necessarily encode a polypeptide or protein (e.g., a promoter). For example, in certain embodiments the nucleic acid molecule can be combined or "stacked" with another that provides additional resistance or tolerance to glyphosate or another herbicide, and/or provides resistance to select insects or diseases and/or nutritional enhancements, and/or improved agronomic characteristics, and/or proteins or other products useful in feed, food, industrial, pharmaceutical or other uses. The "stacking" of two or more nucleic acid sequences of interest within a plant genome can be accomplished, for example, via conventional plant breeding using two or more events, transformation of a plant with a construct which contains the sequences of interest, re-transformation of a transgenic plant, or addition of new traits through targeted integration via homologous recombination.

Such nucleotide sequences of interest include, but are not limited to, those examples provided below:

1. Genes or Coding Sequence (e.g. iRNA) that Confer Resistance to Pests or Disease (A) Plant Disease Resistance Genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. Examples of such genes include, the tomato Cf-9 gene for resistance to *Cladosporium fulvum* (Jones et al., 1994 *Science* 266:789), tomato Pto gene, which encodes a protein kinase, for resistance to *Pseudomonas syringae* pv. tomato (Martin et al., 1993 *Science* 262:1432), and *Arabidopsis* RSSP2 gene for resistance to *Pseudomonas syringae* (Mindrinos et al., 1994 *Cell* 78:1089).

(B) A *Bacillus thuringiensis* protein, a derivative thereof or a synthetic polypeptide modeled thereon, such as, a nucleotide sequence of a Bt δ-endotoxin gene (Geiser et al., 1986 *Gene* 48:109), and a vegetative insecticidal (VIP) gene (see, e.g., Estruch et al. (1996) *Proc. Natl. Acad. Sci.* 93:5389-94). Moreover, DNA molecules encoding δ-endotoxin genes can be purchased from American Type Culture Collection (Rockville, Md.), under ATCC accession numbers 40098, 67136, 31995 and 31998.

(C) A lectin, such as, nucleotide sequences of several *Clivia miniata* mannose-binding lectin genes (Van Damme et al., 1994 *Plant Molec. Biol.* 24:825).

(D) A vitamin binding protein, such as avidin and avidin homologs which are useful as larvicides against insect pests. See U.S. Pat. No. 5,659,026.

(E) An enzyme inhibitor, e.g., a protease inhibitor or an amylase inhibitor. Examples of such genes include a rice cysteine proteinase inhibitor (Abe et al., 1987 *J. Biol. Chem.* 262:16793), a tobacco proteinase inhibitor I (Huub et al., 1993 *Plant Molec. Biol.* 21:985), and an α-amylase inhibitor (Sumitani et al., 1993 *Biosci. Biotech. Biochem.* 57:1243).

(F) An insect-specific hormone or pheromone such as an ecdysteroid and juvenile hormone a variant thereof, a mimetic based thereon, or an antagonist or agonist thereof, such as baculovirus expression of cloned juvenile hormone esterase, an inactivator of juvenile hormone (Hammock et al., 1990 *Nature* 344:458).

(G) An insect-specific peptide or neuropeptide which, upon expression, disrupts the physiology of the affected pest (*J. Biol. Chem.* 269:9). Examples of such genes include an insect diuretic hormone receptor (Regan, 1994), an allostatin identified in *Diploptera punctata* (Pratt, 1989), and insect-specific, paralytic neurotoxins (U.S. Pat. No. 5,266,361).

(H) An insect-specific venom produced in nature by a snake, a wasp, etc., such as a scorpion insectotoxic peptide (Pang, 1992 *Gene* 116:165).

(I) An enzyme responsible for a hyperaccumulation of monoterpene, a sesquiterpene, a steroid, hydroxamic acid, a phenylpropanoid derivative or another non-protein molecule with insecticidal activity.

(J) An enzyme involved in the modification, including the post-translational modification, of a biologically active molecule; for example, glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. Examples of such genes include, a callas gene (PCT published application WO93/02197), chitinase-encoding sequences (which can be obtained, for example, from the ATCC under accession numbers 3999637 and 67152), tobacco hookworm chitinase (Kramer et al., 1993 *Insect Molec. Biol.* 23:691), and parsley ubi4-2 polyubiquitin gene (Kawalleck et al., 1993 *Plant Molec. Biol.* 21:673).

(K) A molecule that stimulates signal transduction. Examples of such molecules include nucleotide sequences for mung bean calmodulin cDNA clones (Botella et al., 1994 *Plant Molec. Biol.* 24:757) and a nucleotide sequence of a maize calmodulin cDNA clone (Griess et al., 1994 *Plant Physiol.* 104:1467).

(L) A hydrophobic moment peptide. See U.S. Pat. Nos. 5,659,026 and 5,607,914; the latter teaches synthetic antimicrobial peptides that confer disease resistance.

(M) A membrane permease, a channel former or a channel blocker, such as a cecropin-β lytic peptide analog (Jaynes et al., 1993 *Plant Sci.* 89:43) which renders transgenic tobacco plants resistant to *Pseudomonas solanacearum*.

(N) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. See, for example, Beachy et al. (1990) *Ann. Rev. Phytopathol.* 28:451.

(O) An insect-specific antibody or an immunotoxin derived therefrom. Thus, an antibody targeted to a critical metabolic function in the insect gut would inactivate an affected enzyme, killing the insect. For example, Taylor et al. (1994) Abstract #497, Seventh Intl. Symposium on Molecular Plant-Microbe Interactions shows enzymatic inactivation in transgenic tobacco via production of single-chain antibody fragments.

(P) A virus-specific antibody. See, for example, Tavladoraki et al. (1993) *Nature* 266:469, which shows that transgenic plants expressing recombinant antibody genes are protected from virus attack.

(Q) A developmental-arrestive protein produced in nature by a pathogen or a parasite. Thus, fungal endo α-1,4-D-polygalacturonases facilitate fungal colonization and plant nutrient release by solubilizing plant cell wall homo-α-1,4-D-galacturonase (Lamb et al., 1992) *Bio/Technology* 10:1436. The cloning and characterization of a gene which encodes a bean endopolygalacturonase-inhibiting protein is described by Toubart et al. (1992 *Plant J.* 2:367).

(R) A developmental-arrestive protein produced in nature by a plant, such as the barley ribosome-inactivating gene that provides an increased resistance to fungal disease (Longemann et al., 1992). *Bio/Technology* 10:3305.

(S) RNA interference, in which an RNA molecule is used to inhibit expression of a target gene. An RNA molecule in one example is partially or fully double stranded, which triggers a silencing response, resulting in cleavage of dsRNA into small interfering RNAs, which are then incorporated into a targeting complex that destroys homologous mRNAs. See, e.g., Fire et al., U.S. Pat. No. 6,506,559; Graham et al. U.S. Pat. No. 6,573,099.

2. Genes that Confer Resistance to a Herbicide (A) Genes encoding resistance or tolerance to a herbicide that inhibits the growing point or meristem, such as an imidazalinone, sulfonanilide or sulfonylurea herbicide. Exemplary genes in this category code for a mutant ALS enzyme (Lee et al., 1988 *EMBO J.* 7:1241), which is also known as AHAS enzyme (Miki et al., 1990 *Theor. Appl. Genet.* 80:449).

(B) One or more additional genes encoding resistance or tolerance to glyphosate imparted by mutant EPSP synthase and aroA genes, or through metabolic inactivation by genes such as GAT (glyphosate acetyltransferase) or GOX (glyphosate oxidase) and other phosphono compounds such as glufosinate (pat and bar genes; DSM-2), and aryloxyphenoxypropionic acids and cyclohexanediones (ACCase inhibitor encoding genes). See, for example, U.S. Pat. No. 4,940,835, which discloses the nucleotide sequence of a form of EPSP which can confer glyphosate resistance. A DNA molecule encoding a mutant aroA gene can be obtained under ATCC Accession Number 39256, and the nucleotide sequence of the mutant gene is disclosed in U.S. Pat. No. 4,769,061. European patent application No. 0 333 033 and U.S. Pat. No. 4,975,374 disclose nucleotide sequences of glutamine synthetase genes which confer resistance to herbicides such as L-phosphinothricin. The nucleotide sequence of a phosphinothricinacetyl-transferase gene is provided in European application No. 0 242 246. De Greef et al. (1989) *Bio/Technology* 7:61 describes the production of transgenic plants that express chimeric bar genes coding for phosphinothricin acetyl transferase activity. Exemplary of genes conferring resistance to aryloxyphenoxypropionic acids and cyclohexanediones, such as sethoxydim and haloxyfop, are the Accl-S1, Accl-S2 and Accl-S3 genes described by Marshall et al. (1992) *Theor. Appl. Genet.* 83:435.

(C) Genes encoding resistance or tolerance to a herbicide that inhibits photosynthesis, such as a triazine (psbA and gs+ genes) and a benzonitrile (nitrilase gene). Przibilla et al. (1991) *Plant Cell* 3:169 describe the use of plasmids encoding mutant psbA genes to transform *Chlamydomonas*. Nucleotide sequences for nitrilase genes are disclosed in U.S. Pat. No. 4,810,648, and DNA molecules containing these genes are available under ATCC accession numbers 53435, 67441 and 67442. Cloning and expression of DNA coding for a glutathione S-transferase is described by Hayes et al. (1992) *Biochem. J.* 285:173.

(D) Genes encoding resistance or tolerance to a herbicide that bind to hydroxyphenylpyruvate dioxygenases (HPPD), enzymes which catalyze the reaction in which para-hydroxyphenylpyruvate (HPP) is transformed into homogentisate. This includes herbicides such as isoxazoles (EP418175, EP470856, EP487352, EP527036, EP560482, EP682659, U.S. Pat. No. 5,424,276), in particular isoxaflutole, which is a selective herbicide for maize, diketonitriles (EP496630, EP496631), in particular 2-cyano-3-cyclopropyl-1-(2-SO2CH3-4-CF3 phenyl)propane-1,3-dione and 2-cyano-3-cyclopropyl-1-(2-SO2CH3-4-2,3Cl2-phenyl)propane-1,3-dione, triketones (EP625505, EP625508, U.S. Pat. No. 5,506,195), in particular sulcotrione, and pyrazolinates. A gene that produces an overabundance of HPPD in plants can provide tolerance or resistance to such herbicides, including, for example, genes described in U.S. Pat. Nos. 6,268,549 and 6,245,968 and U.S. Patent Application, Publication No. 20030066102.

(E) Genes encoding resistance or tolerance to phenoxy auxin herbicides, such as 2,4-dichlorophenoxyacetic acid (2,4-D) and which may also confer resistance or tolerance to aryloxyphenoxypropionate (AOPP) herbicides. Examples of such genes include the α-ketoglutarate-dependent dioxygenase enzyme (aad-1) gene, described in U.S. Pat. No. 7,838,733.

(F) Genes encoding resistance or tolerance to phenoxy auxin herbicides, such as 2,4-dichlorophenoxyacetic acid (2,4-D) and which may also confer resistance or tolerance to pyridyloxy auxin herbicides, such as fluoroxypyr or triclopyr. Examples of such genes include the α-ketoglutarate-dependent dioxygenase enzyme gene (aad-12), described in WO 2007/053482 A2.

(G) Genes encoding resistance or tolerance to dicamba (see, e.g., U.S. Patent Publication No. 20030135879).

(H) Genes providing resistance or tolerance to herbicides that inhibit protoporphyrinogen oxidase (PPO) (see U.S. Pat. No. 5,767,373).

(I) Genes providing resistance or tolerance to triazine herbicides (such as atrazine) and urea derivatives (such as diuron) herbicides which bind to core proteins of photosystem II reaction centers (PS II) (See Brussian et al., (1989) *EMBO J.* 1989, 8(4): 1237-1245.

3. Genes that Confer or Contribute to a Value-Added Trait (A) Modified fatty acid metabolism, for example, by transforming maize or *Brassica* with an antisense gene or stearoyl-ACP desaturase to increase stearic acid content of the plant (Knultzon et al., 1992) *Proc. Nat. Acad. Sci. USA* 89:2624.

(B) Decreased Phytate Content (1) Introduction of a phytase-encoding gene, such as the *Aspergillus niger* phytase gene (Van Hartingsveldt et al., 1993 *Gene* 127:87), enhances breakdown of phytate, adding more free phosphate to the transformed plant.

(2) A gene could be introduced that reduces phytate content. In maize, this, for example, could be accomplished by cloning and then reintroducing DNA associated with the single allele which is responsible for maize mutants characterized by low levels of phytic acid (Raboy et al., 1990 *Maydica* 35:383).

(C) Modified carbohydrate composition effected, for example, by transforming plants with a gene coding for an enzyme that alters the branching pattern of starch. Examples of such enzymes include, *Streptococcus mucus* fructosyltransferase gene (Shiroza et al., 1988) *J. Bacteriol.* 170:810, *Bacillus subtilis* levansucrase gene (Steinmetz et al., 1985 *Mol. Gen. Genet.* 200:220), *Bacillus licheniformis* α-amylase (Pen et al., 1992 *Bio/Technology* 10:292), tomato invertase genes (Elliot et al., 1993), barley amylase gene (Sogaard et al., 1993 *J. Biol. Chem.* 268:22480), and maize endosperm starch branching enzyme II (Fisher et al., 1993 *Plant Physiol.* 102:10450).

The sequence of interest can also be a nucleotide sequence introduced into a predetermined area of the plant genome through homologous recombination. Methods to stably integrate a polynucleotide sequence within a specific chromosomal site of a plant cell via homologous recombination have been described within the art. For instance, site specific integration as described in US Patent Application Publication No. 2009/0111188 A1 involves the use of recombinases or integrases to mediate the introduction of a donor polynucleotide sequence into a chromosomal target. In addition, International Patent Application No. WO 2008/021207, describes zinc finger mediated-homologous recombination to stably integrate one or more donor polynucleotide sequences within specific locations of the genome. The use of recombinases such as FLP/FRT as described in U.S. Pat. No. 6,720,475, or CRE/LOX as described in U.S. Pat. No. 5,658,772, can be utilized to stably integrate a polynucleotide sequence into a specific chromosomal site. Finally, the use of meganucleases for targeting donor polynucleotides into a specific chromosomal location was described in Puchta et al., *PNAS USA* 93 (1996) pp. 5055-5060).

Other various methods for site specific integration within plant cells are generally known and applicable (Kumar et al., *Trends in Plant Sci.* 6(4) (2001) pp. 155-159). Furthermore, site-specific recombination systems that have been identified in several prokaryotic and lower eukaryotic organisms may be applied for use in plants. Examples of such systems include, but are not limited too; the R/RS recombinase system from the pSRi plasmid of the yeast *Zygosaccharomyces rouxii* (Araki et al. (1985) *J. Mol. Biol.* 182: 191-203), and the Gin/gix system of phage Mu (Maeser and Kahlmann (1991) *Mol. Gen. Genet.* 230: 170-176).

Various assays can be employed in connection with the nucleic acid molecule of certain embodiments of the disclosure. The following techniques are useful in a variety of situations, and in one embodiment, are useful in detecting the presence of the nucleic acid molecule and/or the polypeptide encoded in a plant cell. For example, the presence of the molecule can be determined in a variety of ways, including using a primer or probe of the sequence, ELISA assay to detect the encoded protein, a Western blot to detect the protein, or a Northern or Southern blot to detect RNA or DNA. Enzymatic assays for detecting enzyme DGT-14 can be employed. Further, an antibody which can detect the presence of the DGT-14 protein can be generated using art recognized procedures. Additional techniques, such as in situ hybridization, enzyme staining, and immunostaining, also may be used to detect the presence or expression of the recombinant construct in specific plant organs and tissues. The transgene may be selectively expressed in some tissues of the plant or at some developmental stages, or the transgene may be expressed in substantially all plant tissues, substantially along its entire life cycle. However, any combinatorial expression mode is also applicable.

Southern analysis is a commonly used detection method, wherein DNA is cut with restriction endonucleases and fractionated on an agarose gel to separate the DNA by molecular weight and then transferring to nylon membranes. It is then hybridized with the probe fragment which was radioactively labeled with $^{32}P$ (or other probe labels) and washed in an SDS solution.

Likewise, Northern analysis deploys a similar protocol, wherein RNA is cut with restriction endonucleases and fractionated on an agarose gel to separate the RNA by molecular weight and then transferring to nylon membranes. It is then hybridized with the probe fragment which was radioactively labeled with $^{32}$P (or other probe labels) and washed in an SDS solution. Analysis of the RNA (e.g., mRNA) isolated from the tissues of interest can indicate relative expression levels. Typically, if the mRNA is present or the amount of mRNA has increased, it can be assumed that the corresponding transgene is being expressed. Northern analysis, or other mRNA analytical protocols, can be used to determine expression levels of an introduced transgene or native gene.

In the Western analysis, instead of isolating DNA/RNA, the protein of interest is extracted and placed on an acrylamide gel. The protein is then blotted onto a membrane and contacted with a labeling substance. See e.g., Hood et al., "Commercial Production of Avidin from Transgenic Maize; Characterization of Transformants, Production, Processing, Extraction and Purification" *Molecular Breeding* 3:291-306 (1997); Towbin et al, (1979) "Electrophoretic transfer of proteins from polyacrylamide gels to nitrocellulose sheets: procedure and some applications" *Proc Natl Acad Sci USA* 76(9): 4350-4354; Renart et al. "Transfer of proteins from gels to diazobenzyloxymethyl-paper and detection with antisera: a method for studying antibody specificity and antigen structure" *Proc Natl Acad Sci USA* 76(7): 3116-3120.

The nucleic acid molecule of embodiments of the disclosure, or segments thereof, can be used as primers for PCR amplification. In performing PCR amplification, a certain degree of mismatch can be tolerated between primer and template. Therefore, mutations, deletions, and insertions (especially additions of nucleotides to the 5' end) of the exemplified primers fall within the scope of the subject disclosure. Mutations, insertions, and deletions can be produced in a given primer by methods known to an ordinarily skilled artisan.

Another example of method detection is the pyrosequencing technique as described by Winge (*Innov. Pharma. Tech.* 00:18-24, 2000). In this method an oligonucleotide is designed that overlaps the adjacent genomic DNA and insert DNA junction. The oligonucleotide is hybridized to single-stranded PCR product from the region of interest (one primer in the inserted sequence and one in the flanking genomic sequence) and incubated in the presence of a DNA polymerase, ATP, sulfurylase, luciferase, apyrase, adenosine 5' phosphosulfate and luciferin. DNTPs are added individually and the incorporation results in a light signal that is measured. A light signal indicates the presence of the transgene insert/flanking sequence due to successful amplification, hybridization, and single or multi-base extension. (This technique is used for initial sequencing, not for detection of a specific gene when it is known.)

Molecular Beacons have been described for use in sequence detection. Briefly, a FRET oligonucleotide probe is designed that overlaps the flanking genomic and insert DNA junction. The unique structure of the FRET probe results in it containing a secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Following successful PCR amplification, hybridization of the FRET probe(s) to the target sequence results in the removal of the probe secondary structure and spatial separation of the fluorescent and quenching moieties. A fluorescent signal indicates the presence of the flanking genomic/transgene insert sequence due to successful amplification and hybridization.

Hydrolysis probe assay, otherwise known as TAQMAN® (Life Technologies, Foster City, Calif.), is a method of detecting and quantifying the presence of a DNA sequence. Briefly, a FRET oligonucleotide probe is designed with one oligo within the transgene and one in the flanking genomic sequence for event-specific detection. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization.

The ELISA or enzyme linked immunoassay has been known since 1971. In general, antigens solubilised in a buffer are coated on a plastic surface. When serum is added, antibodies can attach to the antigen on the solid phase. The presence or absence of these antibodies can be demonstrated when conjugated to an enzyme. Adding the appropriate substrate will detect the amount of bound conjugate which can be quantified. A common ELISA assay is one which uses biotinylated anti-(protein) polyclonal antibodies and an alkaline phosphatase conjugate. For example, an ELISA used for quantitative determination of laccase levels can be an antibody sandwich assay, which utilizes polyclonal rabbit antibodies obtained commercially. The antibody is conjugated to alkaline phosphatases for detection. In another example, an ELISA assay to detect trypsin or trypsinogen uses biotinylated anti-trypsin or anti-trypsinogen polyclonal antibodies and a streptavidin-alkaline phosphatase conjugate.

Glyphosate, a composition comprising N-(phosphonomethyl)glycine, is a widely used component in herbicides. Glyphosate is typically formulated as a salt in an aqueous liquid concentrate, a solid concentrate, an emulsion or a microemulsion. Suitable salt forms of glyphosate which may be used in accordance with any of the formulations include, for example, alkali metal salts, for example sodium and potassium salts, ammonium salts, di-ammonium salts such as dimethylammonium, alkylamine salts, for example dimethylamine and isopropylamine salts, alkanolamine salts, for example ethanolamine salts, alkylsulfonium salts, for example trimethylsulfonium salts, sulfoxonium salts, and mixtures or combinations thereof. Examples of commercial formulations of glyphosate include, without restriction: GLYPHOMAX®, GLYPHOMAX® XRT, GLYPHOMAX® PLUS, DURANGO®, ROUNDUP ULTRA®, ROUNDUP ULTRAMAX®, ROUNDUP® CT, ROUNDUP® EXTRA, ROUNDUP® BIOACTIVE, ROUNDUP® BIOFORCE, RODEO®, POLARIS®, SPARK®, ACCORD® SP, ACCORD® XRT, and ACCORD® CONCENTRATE, all of which contain glyphosate as its isopropylammonium salt (IPA); ROUNDUP® DRY and RIVAL™ which contain glyphosate as its ammonium salt; ROUNDUP® GEOFORCE, a sodium glyphosate formulation; TOUCHDOWN™, a glyphosate trimesium salt formulation, TOUCHDOWN IQ™, a glyphosate diammonium salt formulation, TOUCHDOWN TOTAL IQ™, a potassium glyphosate formulation, and ROUNDUP WEATHERMAX®, a potassium glyphosate formulation. Glyphosate formulations may include safening agents, surfactants, and adjuvants. Providing a plant or plant cell that is resistant to glyphosate herbicide formulations can be useful in a variety of applications, where those plant cells having such resistance can tolerate exposure to sufficient amounts of glyphosate which is used to control weeds in an area under cultivation. Modification of the native bacterial dgt-14 nucleotide sequence can provide improved resistance to the herbicide glyphosate when expressed in a plant cell.

Glyphosate can be applied over-the-top of plants from emergence throughout the various stages of plant development. Glyphosate tolerant plant varieties used in combination with glyphosate herbicidal formulations have become the standard program for weed management in crop production in the United States and throughout the world. The primary advantage to growers in using a glyphosate tolerance trait (e.g., dgt-14) is that it allows simple and convenient application of glyphosate, a broad spectrum, post-emergence herbicide, to control unwanted plants and grasses (i.e. "weeds") with excellent crop safety and less dependence on pre-plant herbicide applications. Other benefits include a better fit into no-till and reduced tillage systems. Glyphosate tolerant crops have expanded the options for weed management and made the practice of weed control much easier, less expensive and more flexible. Growers have reported making fewer trips across fields to apply herbicides as well as making fewer cultivation trips, which conserves fuel and reduces soil erosion. Glyphosate-tolerant crops, therefore, decreases the environmental risks posed by herbicides while at the same time increasing the efficacy of necessary chemical weed control.

Accordingly, in various embodiments, methods are provided for selectively controlling weeds in an area under cultivation containing a glyphosate resistant plant. The methods comprise applying a sufficient amount of a herbicidal glyphosate to the crop foliage and weeds to control growth of the weeds.

The relative amount of glyphosate present in a contemplated herbicidal composition (i.e., a particulate solid concentrate, or liquid concentrate, or alternatively a ready-to-use, or tank-mix, composition) may vary depending upon many factors, including for example the weed species to be controlled and the method of application. Generally speaking, however, the concentration of glyphosate, and optionally a surfactant and/or some other adjuvant or additive (as described elsewhere herein), used in the herbicidal composition is sufficient to control weeds within an area under cultivation.

Additionally, the concentration of glyphosate, and optionally a surfactant and/or some other adjuvant or additive (as described elsewhere herein), used in the herbicidal composition is sufficient to provide control of weed regrowth within an area under cultivation.

Accordingly, liquid concentrate compositions are formulated to include glyphosate in a concentration of at least about 50 grams, at least about 75 grams, or at least about 100, 125, 150, 175, 200, 225, 250, 275, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690 or 700 grams (acid equivalent or a.e.) per liter, or more. The glyphosate concentration ranges, for example, from about 50 to about 680 grams (a.e.) per liter, from about 100 to about 600 grams (a.e.) per liter (gpl), from about 250 to about 600 grams (a.e.) per liter, or from about 360 to about 540 grams (a.e.) per liter. When expressed as a weight percentage based on the total weight of the glyphosate concentrate, a liquid concentrate comprises at least about 10 wt. % glyphosate (acid equivalent or a.e.), at least about 15 wt. %, or at least about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 62, 63, 64, 65, 66, 67, or 68 wt. % a.e., or more. The glyphosate concentration ranges, for example, from about 10 wt. % to about 70 wt. % a.e., from about 20 wt. % to about 68 wt. % a.e., or from about 25 wt. % to about 45 wt. % a.e. If the concentrate is applied as a ready-to-use composition, the glyphosate concentration is typically from about 1 wt. % to about 3 wt. % a.e., and from about 1 wt. % to about 2 wt. % a.e.

When expressed as a weight percentage based on the total weight of the glyphosate concentrate, solid concentrate compositions are formulated to include glyphosate in a concentration of at least about 5 wt. % glyphosate (acid equivalent or a.e.), at least about 20 wt. % a.e., or at least about 25, 30, 35, 40, 45, 50, 55, 60, 65, 70, 75, 80, 85, 90, or 95 wt. % a.e., or more. The glyphosate concentration ranges, for example, from about 5 wt. % to about 97 wt. % a.e., from about 30 wt. % to about 85 wt. % a.e., or from about 50 wt. % to about 75 wt. % a.e.

Spray compositions are formulated for application of at least about 1 gallon of spray composition per acre, at least about 2, 3, 4, 5, 6, 7, 8, 9, 10, 11, 12, 13, 14, 15, 16, 17, 18, 19, or 20 gallons per acre, or more. The spray volume of the spray composition ranges, for example, from about 1 gallon to about 100 gallons per acre, from about 2 gallons to about 40 gallons per acre, and from about 2 gallons to about 5 gallons per acre for an aerial application and from about 5 gallons to about 20 gallons per acre for a ground application.

Alternatively, the glyphosate herbicidal compositions may be provided to the end-user already formulated, either at the desired dilution for application (i.e., "ready-to-use" compositions) or requiring dilution, dispersion, or dissolution in water by the end-user (i.e., "concentrate" compositions). Such pre-formulated concentrates can be liquids or particulate solids.

Liquid concentrate formulations having an aqueous phase wherein glyphosate is present predominantly in the form of a salt, and a non-aqueous phase optionally containing a second herbicidal active ingredient that is relatively water-insoluble, can be employed. Such formulations illustratively include emulsions (including macro- and microemulsions, water-in-oil, oil-in-water and water-in-oil-in-water types), suspensions and suspoemulsions. The non-aqueous phase can optionally comprise a microencapsulated component, for example a microencapsulated herbicide. In formulations having a nonaqueous phase, the concentration of glyphosate a.e. in the composition as a whole is nonetheless within the ranges recited herein for aqueous concentrate formulations.

It is to be noted that the herbicidal spray compositions are applied as aqueous solutions or dispersions, whether they are manufactured ready for application or result from the further dilution of a liquid glyphosate concentrate or the addition of water to a particulate solid glyphosate concentrate. However, the term "aqueous," as used herein, is not intended to exclude the presence of some small amount of non-aqueous solvent, so long as the predominant solvent present, is water.

An embodiment of the disclosure is directed to a method of killing or controlling weeds or unwanted vegetation in an area under cultivation containing a crop (e.g., of transgenic glyphosate resistant plants). In one embodiment, the method comprises applying glyphosate as a tank mix, and applying a herbicidally sufficient amount of the tank mix to foliage of plants genetically transformed to tolerate glyphosate, and simultaneously to foliage of weeds growing in close proximity to such plants. This method of use results in control of the weeds or unwanted vegetation while leaving the herbicide tolerant plants substantially unharmed.

In an embodiment of the disclosure, an aqueous glyphosate composition can be applied to the foliar tissues of plants to kill or control the growth of a wide variety of unwanted plants, including annual and perennial grass and broadleaf weed species, by applying to the foliar tissues of the plants aqueous glyphosate compositions. Such plants can include, but are not limited to, for example: alfalfa, soybeans, cotton, rapeseed, linseed, corn, rice, brachiaria, wheat, safflowers, sorghum, sugarbeet, sunflowers, tobacco and turf grasses. Thus, any plant species or plant cell can be selected. In embodiments, plant cells used herein, and plants grown or derived therefrom, include, but are not limited to, cells obtainable from rapeseed (*Brassica napus*); indian mustard (*Brassica juncea*); Ethiopian mustard (*Brassica carinata*); turnip (*Brassica rapa*); cabbage (*Brassica oleracea*); soybean (*Glycine max*); linseed/flax (*Linum usitatissimum*); maize (also described as corn) (*Zea mays*); safflower (*Carthamus tinctorius*); sunflower (*Helianthus annuus*); tobacco (*Nicotiana tabacum*); *Arabidopsis thaliana*, Brazil nut (*Betholettia excelsa*); castor bean (*Ricinus communis*); coconut (*Cocus nucifera*); coriander (*Coriandrum sativum*); cotton (*Gossypium* spp.); groundnut (*Arachis hypogaea*); jojoba (*Simmondsia chinensis*); oil palm (*Elaeis guineeis*); olive (*Olea eurpaea*); rice (*Oryza sativa*); squash (*Cucurbita maxima*); barley (*Hordeum vulgare*); sugarcane (*Saccharum officinarum*); rice (*Oryza sativa*); wheat (*Triticum* spp. including *Triticum durum* in addition to *Triticum aestivum*); and duckweed (*Lemnaceae* sp.). In some embodiments, the genetic background within a plant species may vary.

The herbicidal composition is applied to plants at a rate sufficient to give the desired biological results: control of weed growth without significantly affecting glyphosate tolerant crop plants. These application rates are usually expressed as amount of glyphosate per unit area treated, e.g. grams per hectare (g/ha). What constitutes a "significant effect" varies according to the standards and practice of those who investigate, develop, market and use compositions and the selection of application rates that are significantly effective for a composition is within the skill of those skilled in the art. Typically, the amount of the composition applied per unit area to give 85% control of a weed species as measured by growth reduction or mortality is often used to define a commercial rate.

The selection of a number of glyphosate herbicide application rates sufficient to control weeds in an area under cultivation is within the skill of the ordinary agricultural scientist. Those of skill in the art will likewise recognize that individual plant conditions, weather and growing conditions, as well as the specific active ingredients and their weight ratio in the composition, will influence the degree of herbicidal effectiveness achieved in practicing the methods disclosed herein.

The herbicidal spray compositions can be applied to the foliage of the plants to be treated through any of the appropriate methods that are well known to those having skill in the art, including aerial application and ground application techniques (e.g., a ground boom, a hand sprayer, rope-wick, etc.).

If desired, the user can mix one or more adjuvants with a composition of the disclosure and the water of dilution when preparing the application composition. Such adjuvants can include additional surfactant and/or an inorganic salt such as ammonium sulfate with the aim of further enhancing herbicidal efficacy.

Further improvements also include use with appropriate safeners to further protect plants and/or to add cross resistance to more herbicides. Safeners typically act to increase the plant's immune system by activating/expressing cP450. Safeners are chemical agents that reduce the phytotoxicity of herbicides to crop plants by a physiological or molecular mechanism, without compromising weed control efficacy.

Herbicide safeners include benoxacor, cloquintocet, cyometrinil, dichlormid, dicyclonon, dietholate, fenchlorazole, fenclorim, flurazole, fluxofenim, furilazole, isoxadifen, mefenpyr, mephenate, naphthalic anhydride, and oxabetrinil. Plant activators (a new class of compounds that protect plants by activating their defense mechanisms) can also be used in embodiments of the subject disclosure. These include acibenzolar and probenazole.

Commercialized safeners can be used for the protection of large-seeded grass crops, such as corn, grain sorghum, and wet-sown rice, against preplant-incorporated or preemergence-applied herbicides of the thiocarbamate and chloroacetanilide families. Safeners also have been developed to protect winter cereal crops such as wheat against postemergence applications of aryloxyphenoxypropionate and sulfonylurea herbicides. The use of safeners for the protection of corn and rice against sulfonylurea, imidazolinone, cyclohexanedione, isoxazole, and triketone herbicides is also well-established. A safener-induced enhancement of herbicide detoxification in safened plants is widely accepted as the major mechanism involved in safener action. Safeners induce cofactors such as glutathione and herbicide-detoxifying enzymes such as glutathione S-transferases, cytochrome P450 monooxygenases, and glucosyl transferases. Hatzios K K, Burgos N (2004) "Metabolism-based herbicide resistance: regulation by safeners," *Weed Science*: Vol. 52, No. 3 pp. 454-467. All publications and published patent documents cited in this specification are incorporated herein by reference to the same extent as if each individual publication or patent application was specifically and individually indicated to be incorporated by reference.

Embodiments of the present disclosure are further defined in the following Examples. It should be understood that these Examples are given by way of illustration only. From the above discussion and these Examples, one skilled in the art can ascertain the essential characteristics of the disclosure, and without departing from the spirit and scope thereof, can make various changes and modifications of the embodiments of the disclosure to adapt it to various usages and conditions. Thus, various modifications of the embodiments of the disclosure, in addition to those shown and described herein, will be apparent to those skilled in the art from the foregoing description. Such modifications are also intended to fall within the scope of the appended claims. The following is provided by way of illustration and not intended to limit the scope of the disclosure.

EXAMPLES

Example 1: Mutant EPSP Synthases

A single amino acid mutation (G96A) in the *Escherichia coli* 5-enolpyruvylshikimate 3-phosphate synthase enzyme (EPSP synthase) can result in glyphosate insensitivity (Padgette et al., (1991); Eschenburg et al., (2002); Priestman et al., (2005); Haghani et al., (2008)). While this mutation confers tolerance to glyphosate it is also known to adversely affect binding of EPSP synthase with its natural substrate, phosphoenolpyruvate (PEP). The resulting change in substrate binding efficiency can render a mutated enzyme unsuitable for providing in planta tolerance to glyphosate.

The NCBI Genbank database was screened in silico for EPSP synthase protein and polynucleotide sequences that naturally contain an alanine at an analogous position within the EPSP synthase enzyme as that of the G96A mutation which was introduced into the *E. coli* version of the enzyme (Padgette et al., (1991); Eschenburg et al., (2002); Priestman et al., (2005); Haghani et al., (2008)), or for EPSP synthase protein and polynucleotide sequences that could be altered by introducing an alanine for glycine at an analogous G96A location.

One enzyme that was identified was DGT-14 (GEN-BANK ACC NO: ZP_01452683) from *Manprofundus ferrooxydans*. Further in silico data mining revealed five other unique enzymes with homology to DGT-14; labeled as DGT-11 (GENBANK ACC NO: YP_989551.1), DGT-12 (GENBANK ACC NO: ZP_01622155.1), DGT-18 (GENBANK ACC NO: NP_928909.1), DGT-29 (GENBANK ACC NO: YP_322772.1), and DGT-30 (GENBANK ACC NO: ZP_02156189.1). One of these enzymes, DGT-11 (SEQ ID NO:5), contains a natural alanine at an analogous position within the EPSP synthase enzyme as that of the G96A mutation which was introduced into the *E. coli* version of the enzyme. Because EPSP synthase proteins from different organisms are of different lengths, the numbering of the mutation for the *E. coli* version of the EPSP synthase enzyme does not necessarily correspond with the numbering of the mutation for the EPSP synthase enzymes from the other organisms. These identified EPSP synthase enzymes, native or mutated with an alanine introduced at the glycine amino acid residue, were not previously characterized in regard to glyphosate tolerance or PEP substrate affinity.

The novel DGT-14, DGT-12, DGT-18, DGT-29 and DGT-30 enzymes were obtained and the glycine to alanine mutation was introduced into the EPSP synthase enzymes at a location analogous to the G96A location described for the *E. coli* version of the EPSP synthase enzyme. The DGT-14 protein sequence was modified by introducing an alanine to replace the endogenous glycine of GENBANK ACC NO: ZP_01452683 at amino acid residue 101, thereby resulting in SEQ ID NO:1. The DGT-12 protein sequence was modified by introducing an alanine to replace the endogenous glycine of GENBANK ACC NO: ZP_01622155.1 at amino acid residue 111, thereby resulting in SEQ ID NO:7. The DGT-18 protein sequence was modified by introducing an alanine to replace the endogenous glycine of GENBANK ACC NO: NP_928909.1 at amino acid residue 96, thereby resulting in SEQ ID NO:9. The DGT-29 protein sequence was modified by introducing an alanine to replace the endogenous glycine of GENBANK ACC NO: YP_322772.1 at amino acid residue 96, thereby resulting in SEQ ID NO:11. The DGT-30 protein sequence was modified by introducing an alanine to replace the endogenous glycine of GENBANK ACC NO: ZP_02156189.1 at amino acid residue 96, thereby resulting in SEQ ID NO:13.

The modified EPSP synthase enzymes, and native DGT-11 EPSP synthase enzyme were characterized for glyphosate tolerance and PEP substrate affinity by comparison to Class I EPSP synthase enzymes. The following Class I enzymes: DGT-1 from *Glycine max*, DGT-3 from *Brassica napus* (GENBANK ACC NO: P17688), and DGT-7 from *Triticum aestivum* (GENBANK ACC NO: EU977181) were used as a comparison. The Class I EPSP synthase enzymes and mutant variants thereof were synthesized and evaluated. A mutation introduced into the plant EPSP synthase enzymes consisted of the Glycine to Alanine mutation made within the EPSP synthase enzyme at a similar location as that of the G96A mutation from the *E. coli* version of the enzyme. In addition, Threonine to Isoleucine and Proline to Serine mutations were introduced within these Class I EPSP synthase enzymes at analogous positions as that of amino acid 97 (T to I) and amino acid 101 (P to S) in the EPSP synthase of *E. coli* as described in Funke et al., (2009).

Figure 1:
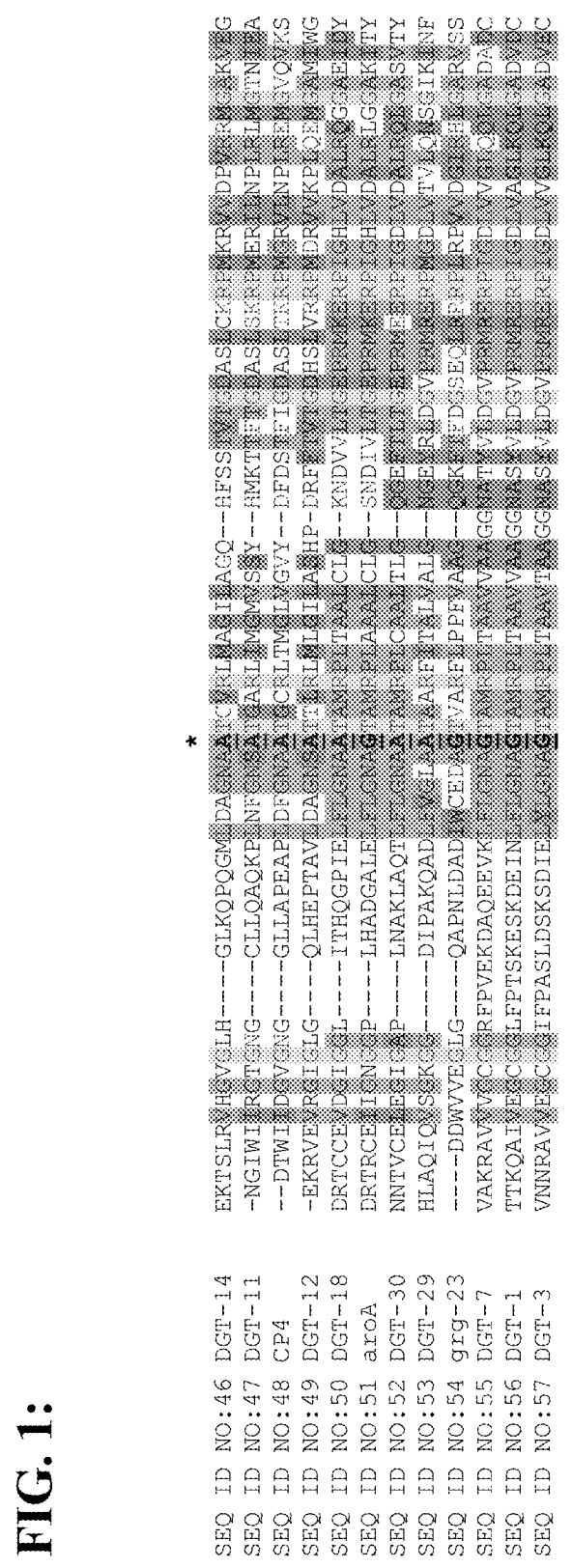

FIG. 1 depicts a partial sequence alignment of DGT-14, DGT-11, DGT-12, DGT-18, DGT-29 and DGT-30 to other EPSP synthase enzymes. As a result of the modification of the alanine for glycine for DGT-14, DGT-12, DGT-18, DGT-29 and DGT-30 these DGT enzymes share a conserved alanine at the aroA EPSP synthase enzyme amino acid position 96. The location of this amino acid is indicated by an asterisk, and the amino acid residue is underlined.

Figure 2:
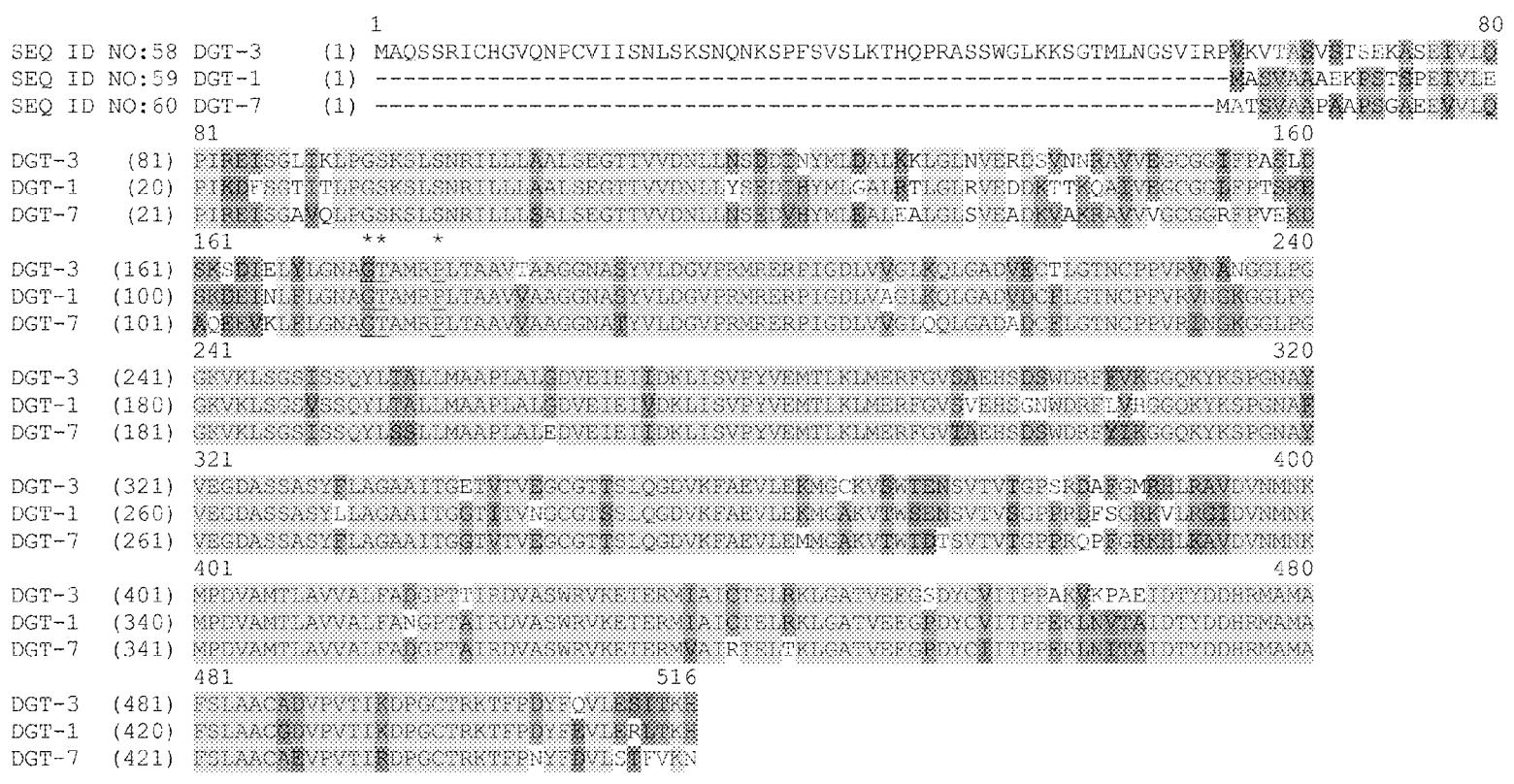

FIG. 2 shows an alignment of the DGT-1, DGT-3, and DGT-7 enzymes. The location of the amino acid residue which was mutated from glycine to alanine is indicated by the first asterisk. The location of the amino acid residue which was mutated from threonine to isoleucine is indicated by the second asterisk. The location of the third amino acid residue which was mutated from proline to serine is indicated by the third asterisk. These mutations were introduced into different versions of DGT-1, DGT-3, and DGT-7. The different versions of the genes which contain the mutations are described in more detail below.

Example 2: Optimization of Sequence for Expression in Plants and Bacteria

Analysis of the DGT-14 coding sequence from *Mariprofundus ferrooxydans* revealed the presence of several sequence motifs that were believed to be detrimental to optimal plant expression, as well as a non-optimal codon composition for expression in dicotyledonous and monocotyledonous plants. Embodiments of the present disclosure provide a design of a plant optimized gene encoding DGT-14 to generate a DNA sequence that can be expressed optimally in dicotyledonous or monocotyledonous plants, and in which the sequence modifications do not hinder translation or transcription.

Due to the plasticity afforded by the redundancy/degeneracy of the genetic code (i.e., some amino acids are specified by more than one codon), evolution of the genomes in different organisms or classes of organisms has resulted in differential usage of synonymous codons. This "codon bias" is reflected in the mean base composition of protein coding regions. For example, organisms having genomes with relatively low G+C contents utilize more codons having A or T in the third position of synonymous codons, whereas those having higher G+C contents utilize more codons having G or C in the third position. Further, it is thought that the presence of "minor" codons within an mRNA may reduce the absolute translation rate of that mRNA, especially when the relative abundance of the charged tRNA corresponding to the minor codon is low. An extension of this reasoning is that the diminution of translation rate by individual minor codons would be at least additive for multiple minor codons. Therefore, mRNAs having high relative contents of minor codons would have correspondingly low translation rates. This rate could be reflected by correspondingly low levels of the encoded protein.

In engineering a gene encoding DGT-14 for expression in dicotyledonous or monocotyledonous plants (such as cotton, canola, tobacco, corn, soybean, wheat and rice), the codon bias of the prospective host plant(s) can be determined, for example, through use of publicly available DNA sequence databases to find information about the codon distribution of plant genomes or the protein coding regions of various plant genes. The codon bias is the statistical distribution of codons that the plant uses for coding the amino acids of its proteins. The preferred codon usages for dicots or monocots (maize) are shown in Table 1.

TABLE 1

Synonymous codon representation from coding regions of monocotyledonous (maize %) and dicotyledonous (dicot %) plant genes are shown in Columns D, E, I, and J. Values for a balanced-biased codon representation set for a plant-optimized synthetic gene design are in Columns C and H.

| A<br>Amino<br>Acid | B<br>Codon | C<br>Weighted<br>Average | D<br>Maize<br>% | E<br>Dicot<br>% | F<br>Amino<br>Acid | G<br>Codon | H<br>Weighted<br>Average | I<br>Maize<br>% | J<br>Dicot<br>% |
|---|---|---|---|---|---|---|---|---|---|
| ALA (A) | GCA | 25.5 | 18 | 25 | LEU (L) | CTA | DNU | 8 | 8 |
| 100 | GCC | 35.6 | 34 | 27 | 100 | CTC | 34.3 | 26 | 19 |
|  | GCG | DNU | 24 | 6 |  | CTG | DNU | 29 | 9 |
|  | GCT | 39.0 | 24 | 42 |  | CTT | 34.3 | 17 | 28 |
| ARG (R) | AGA | 27.4 | 15 | 30 |  | TTA | DNU | 5 | 10 |
| 100 | AGG | 31.5 | 26 | 25 |  | TTG | 31.4 | 15 | 26 |
|  | CGA | DNU | 9 | 8 | LYS (K) | AAA | 30.6 | 22 | 39 |
|  | CGC | 21.7 | 24 | 11 | 100 | AAG | 69.4 | 78 | 61 |
|  | CGG | DNU | 15 | 4 | MET (M) | ATG | 100 | 100 | 100 |
|  | CGT | 19.4 | 11 | 21 | PHE (F) | TTC | 63.2 | 71 | 55 |
| ASN (N) | AAC | 61.4 | 68 | 55 | 100 | TTT | 36.8 | 29 | 45 |
| 100 | AAT | 38.6 | 32 | 45 | PRO (P) | CCA | 41.4 | 26 | 42 |
| ASP (D) | GAC | 52.6 | 63 | 42 | 100 | CCC | 25.3 | 24 | 17 |
| 100 | GAT | 47.4 | 37 | 58 |  | CCG | DNU | 28 | 9 |
| CYS (C) | TGC | 61.8 | 68 | 56 |  | CCT | 33.3 | 22 | 32 |
| 100 | TGT | 38.2 | 32 | 44 | SER (S) | AGC | 26.0 | 23 | 18 |
| END | TAA |  | 20 | 48 | 100 | AGT | DNU | 9 | 14 |
| 100 | TAG |  | 21 | 19 |  | TCA | 22.4 | 16 | 19 |
|  | TGA |  | 59 | 33 |  | TCC | 26.3 | 23 | 18 |
| GLN (Q) | CAA | 48.4 | 38 | 59 |  | TCG | DNU | 14 | 6 |
| 100 | CAG | 51.6 | 62 | 41 |  | TCT | 25.4 | 15 | 25 |
| GLU (E) | GAA | 38.8 | 29 | 49 | THR (T) | ACA | 28.0 | 21 | 27 |
| 100 | GAG | 61.2 | 71 | 51 | 100 | ACC | 39.5 | 37 | 30 |
| GLY (G) | GGA | 28.5 | 19 | 38 |  | ACG | DNU | 22 | 8 |
| 101 | GGC | 29.0 | 42 | 16 |  | ACT | 32.5 | 20 | 35 |
|  | GGG | 16.0 | 20 | 12 | TRP (W) | TGG | 100 | 100 | 100 |
|  | GGT | 26.6 | 20 | 33 | TYR (Y) | TAC | 65.0 | 73 | 57 |
| HIS (H) | CAC | 54.1 | 62 | 46 | 100 | TAT | 35.0 | 27 | 43 |
| 100 | CAT | 45.9 | 38 | 54 | VAL (V) | GTA | DNU | 8 | 12 |
| ILE (I) | ATA | 15.9 | 14 | 18 | 100 | GTC | 28.7 | 32 | 20 |
| 100 | ATC | 47.9 | 58 | 37 |  | GTG | 38.0 | 39 | 29 |
|  | ATT | 36.4 | 28 | 45 |  | GTT | 33.3 | 21 | 39 |

*DNU = Do Not Use

The codon bias can be calculated as the frequency at which a single codon is used relative to the codons for all amino acids. Alternatively, the codon bias may be calculated as the frequency at which a single codon is used to encode a particular amino acid, relative to all the other codons for that amino acid (synonymous codons). In designing coding regions for plant expression, the primary ("first choice") codons preferred by the plant should be determined, as well as the second, third, fourth etc. choices of preferred codons when multiple choices exist. A new DNA sequence can then be designed which encodes the amino acid sequence of the same DGT-14 peptide, but the new DNA sequence differs from the original DNA sequence by the substitution of plant (first preferred, second preferred, third preferred, or fourth preferred, etc.) codons to specify the amino acid at each position within the amino acid sequence. The new sequence is then analyzed for restriction enzyme sites that might have been created by the modifications. The identified sites are further modified by replacing the codons with first, second, third, or fourth choice preferred codons. Other sites in the sequence which could affect transcription or translation of the gene of interest are the stem loop structures, exon:intron junctions (5' or 3'), poly A addition signals, or RNA polymerase termination signals; these sites are removed by the substitution of plant codons. The sequence is further analyzed and modified to reduce the frequency of TA or CG doublets. In addition to the doublets, G or C sequence blocks that have more than about six residues that are the same can affect transcription or translation of the sequence. Therefore, these blocks can be advantageously modified by replacing the codons of first or second choice, etc. with the next preferred codon of choice.

Thus, a variety of methods can be used to produce a gene as described herein. An example of one such approach is further illustrated in PCT App. WO 97/13402. Thus, synthetic genes that are functionally equivalent to the dgt-14 gene of the subject disclosure can be used to transform hosts, including plants. Additional guidance regarding the production of synthetic genes can be found in, for example, U.S. Pat. No. 5,380,831.

To engineer a plant-optimized gene encoding a dgt-14, a DNA sequence was designed to encode the amino acid sequences utilizing a redundant genetic code established from a codon bias table compiled from the protein coding sequences for the particular host plants. In Table 1, Columns D and I present the distributions (in % of usage for all codons for that amino acid) of synonymous codons for each amino acid, as found in the coding regions of monocotyledonous (maize) plants. Columns E and J present the distributions (in % of usage for all codons for that amino acid) of synonymous codons for each amino acid, as found in the coding regions of dicotyledonous plants. Some synonymous codons for some amino acids are found only rarely in plant genes (e.g. CGG). Usually, a codon was considered to be rarely used if it is represented at about 10% or less of the time to encode the relevant amino acid in genes of either plant type (indicated by DNU in Columns C and H of Table 1). To balance the distribution of the remaining codon choices for an amino acid, a Weighted Average representation for each codon was calculated, using the formula:

Weighted Average % of $C1=1/(\% C1+\% C2+\% C3+\text{etc.})\times\% C1\times 100$ where C1 is the codon in question and % C2, % C3, etc. represent the averages of the % values for dicot of remaining synonymous codons (average % values for the relevant codons are taken from Columns C and H) of Table 1.

The Weighted Average % value for each codon is given in Columns C and H of Table 1.

A new DNA sequence which encodes essentially the amino acid sequence of the DGT-14 protein was designed for optimal expression in dicotyledonous plants, using a balanced codon distribution of frequently used codons found in dicotyledonous plant genes. A second DNA sequence which encodes essentially the amino acid sequence of the DGT-14 protein was designed for optimal expression in monocotyledonous plants, using a balanced codon distribution of frequently used codons found in monocotyledonous plant genes. The two novel DNA sequences differ from the original DNA sequence encoding dgt-14 by the substitution of plant (first preferred, second preferred, third preferred, or fourth preferred) codons to specify the appropriate amino acid at each position within the protein amino acid sequence. Design of the plant-optimized DNA sequence was initiated by reverse-translation of the protein sequence of the DGT-14 protein sequence (GENBANK ACC NO: ZP_01452683) which had been modified by introducing an alanine to the replace the endogenous glycine at amino acid residue 101. SEQ ID NO:1 was reverse-translated using a dicot codon bias table constructed from Table 1, Columns E and J. A second reverse-translation of SEQ ID NO:1 was completed using a monocot codon bias table constructed from Table 1 Columns D and I. The initial sequence was then modified by compensating codon changes (while retaining overall weighted average codon representation) to remove or add restriction enzyme recognition sites, remove highly stable intrastrand secondary structures, and remove other sequences that might be detrimental to cloning manipulations or expression of the engineered gene in plants. The DNA sequence was then re-analyzed for restriction enzyme recognition sites that might have been created by the modifications. The identified sites were further modified by replacing the relevant codons with first, second, third, or fourth choice preferred codons. Other sites in the sequences that could affect transcription or translation of the gene of interest include the exon:intron junctions (5' or 3'), poly A addition signals, or RNA polymerase termination signals. The modified sequences were further analyzed and further modified to reduce the frequency of TA or CG doublets, and to increase the frequency of TG or CT doublets. In addition to these doublets, sequence blocks that have more than about six consecutive residues of [G+C] or [A+T] can affect transcription or translation of the sequence. Therefore, these sequence blocks were also modified by replacing the codons of first or second choice, etc. with other preferred codons of choice. Rarely used codons are not included to a substantial extent in the gene design, being used only when necessary to accommodate a different design criterion than codon composition per se (e.g. addition or deletion of restriction enzyme recognition sites).

The newly designed, dicotyledonous plant optimized dgt-14 v2 polynucleotide sequence is listed in SEQ ID NO:2. The newly designed, monocotyledonous plant optimized dgt-14 v5 polynucleotide sequence is listed in SEQ ID NO:3. The resulting DNA sequences have a higher degree of codon diversity, a desirable base composition, contain strategically placed restriction enzyme recognition sites, and lack sequences that might interfere with transcription of the gene, or translation of the product mRNA.

Once a plant-optimized DNA sequence has been designed on paper or in silico, actual DNA molecules can be synthesized in the laboratory to correspond in sequence precisely to the designed sequence. Such synthetic nucleic acid molecules can be cloned and otherwise manipulated exactly as if they were derived from natural or native sources. Synthesis of a DNA fragment comprising SEQ ID NO:2 or SEQ ID NO:3 containing additional sequences such as 6-frame stops (stop codons located in all six reading frames which are added to the 3' end of the coding sequence), and a 5' restriction site for cloning were performed by commercial suppliers (DNA2.0, Menlo Park, Calif.). The synthetic nucleic acid molecule was then cloned into expression vectors and transformed into plants or bacteria as described in the Examples below.

Optimization for Expression in Bacteria

A new DNA sequence that encodes the DGT-14 protein of SEQ ID NO:1 which is optimized for expression in *Escherichia coli* cells was designed. Design of the *E. coli* optimized DNA sequence was initiated by reverse translation of the protein sequence of SEQ ID NO:1 using a proprietary codon optimization protocol from GeneArt (Regensburg, Germany). The initial sequence was modified by compensating codon changes (while retaining overall weighted average representation) to remove or add restriction enzyme recognition sites, remove highly stable intrastrand secondary structures, and other sequences that might be detrimental to cloning manipulations or expression of the engineered gene. An example of such detrimental sequence to avoid within a coding region is a 16S ribosomal RNA binding sequence ("Shine-Dalgarno sequence") such as AGGAGG, which could encode, for example, two consecutive arginine amino acids, but which might also serve as an intragenic (and therefore undesirable) translation initiation signal. The *E. coli* biased dgt-14 v6 DNA sequence that encodes the protein of SEQ ID NO:1 is given as SEQ ID NO:4.

To facilitate cloning and to ensure efficient translation initiation, a 5' terminal NdeI restriction enzyme recognition sequence was placed upstream of the ATG translation start codon. Also to facilitate cloning, and to ensure proper translation termination, bases encoding two TAA translation stop codons and an XhoI restriction enzyme recognition site were included at the 3' end of the coding region. Synthesis of a DNA fragment comprising SEQ ID NO: 4 was performed by the commercial supplier, GeneArt.

Similar *Escherichia coli* codon optimization strategies were used to design dgt-11 v6, dgt-12 v6, dgt-18 v6, dgt-29 v6, and dgt-30 v6. The *Escherichia coli* codon optimized version of these genes are listed as SEQ ID NO:6, SEQ ID NO:8, SEQ ID NO:10, SEQ ID NO:12, and SEQ ID NO:14, respectively.

Example 3: Construction of Vectors for Bacterial Expression of Genes which Impart Tolerance to Glyphosate Construction of pET Expression Vector, Dgt-14 for *E. coli* Expression For in vitro testing, the dgt-14 v6 *E. coli* optimized gene sequence (SEQ ID NO:3) was outsourced to GeneArt for synthesis and cloning. The synthesized dgt-14 v6 gene sequence was cloned into the pET28 expression vector via added Nde I and Xho I restriction sites. The resulting construction introduced an N-terminal 6×His tag and thrombin binding motif. The resulting construct was labeled as pDAB100427 (FIG. 3).

Figure 4:
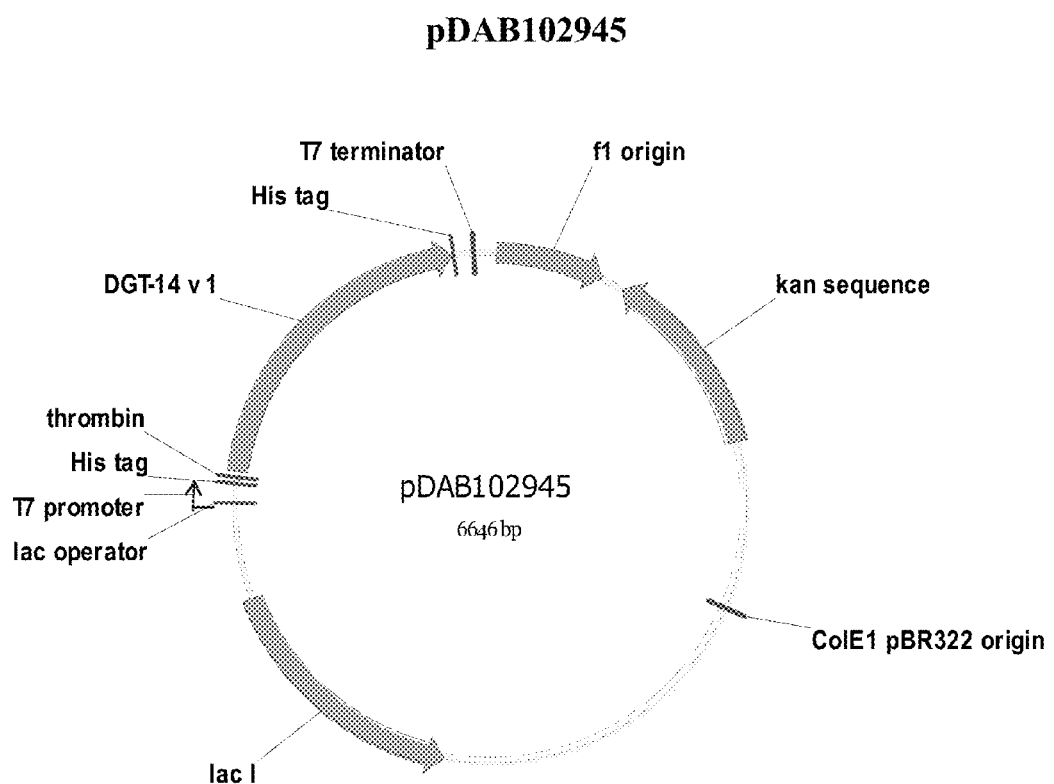
FIG. 4 depicts a plasmid map of pDAB102946.

Site directed mutagenesis was carried out on the synthetic dgt-14 v6 to confirm the role of the alanine that was introduced at the glycine residue of amino acid residue 101. THE QUICK CHANGE II® kit from Stratagene (Santa Clara, Calif.) was used to perform the mutagenesis. The following primers were designed to make the amino acid switch. DGT14 MutF: (SEQ ID NO:15 5' ggATgCCgg-TAATgCAggAACCTgTgTTCgTCTgATgg), DGT14 MutR: (SEQ ID NO:16 5' CCATCAgACgAACACAggT-TCCTgCATTACCggCATCC). PCR reactions were set up according to the QuickChange protocol using pDAB100427 (dgt-14 v6) as template DNA. The construct containing the reverted dgt-14 v1 wildtype sequence (SEQ ID NO:17) was designated pDAB102945 (FIG. 4) and confirmed via DNA sequencing.

Additional Constructions, pET Expression Vector for *E. coli* Expression

Figure 5:
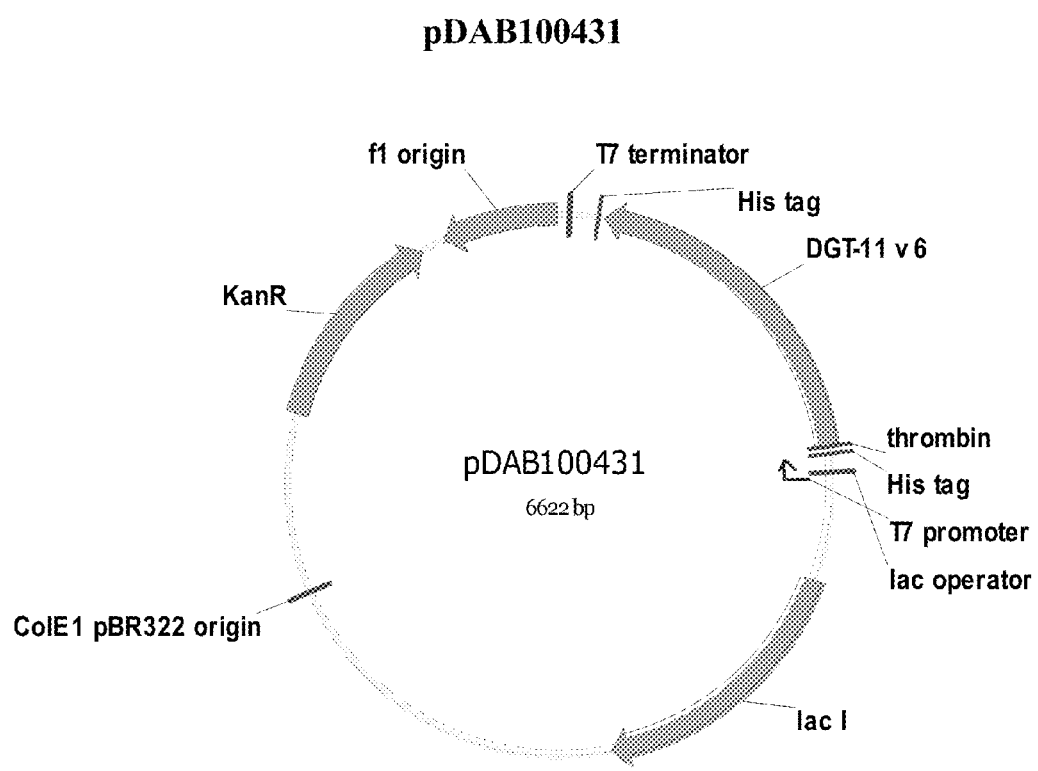
FIG. 5 depicts a plasmid map of pDAB100431.
Figure 6:
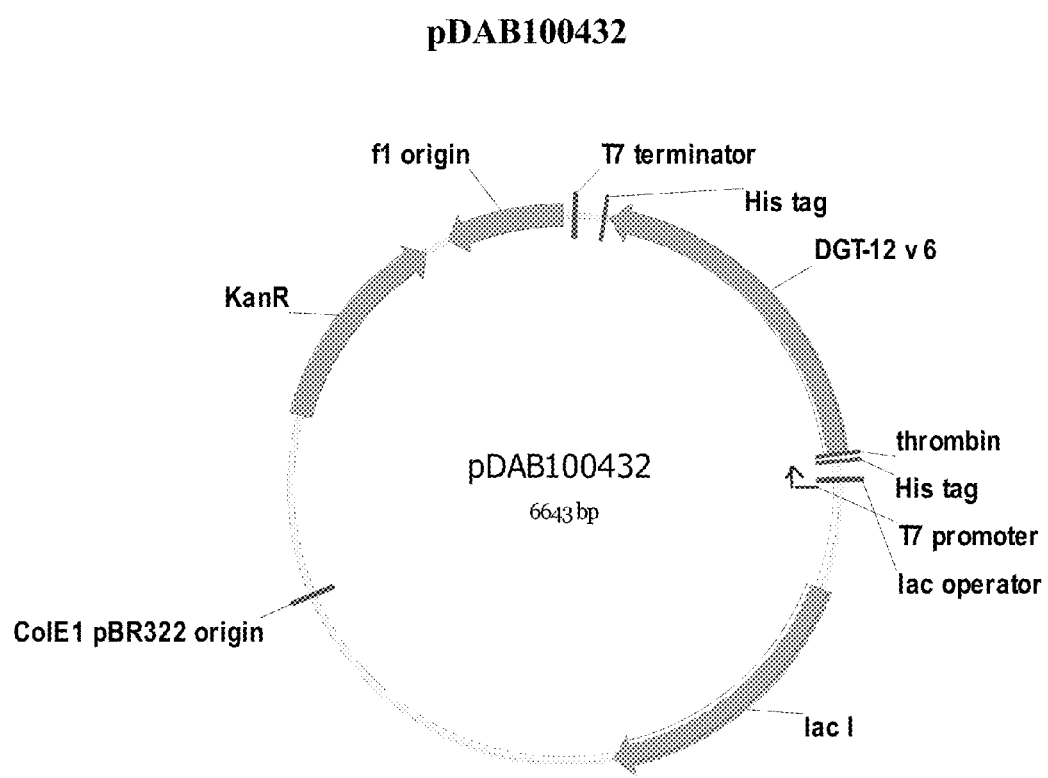
FIG. 6 depicts a plasmid map of pDAB100432.
Figure 7:
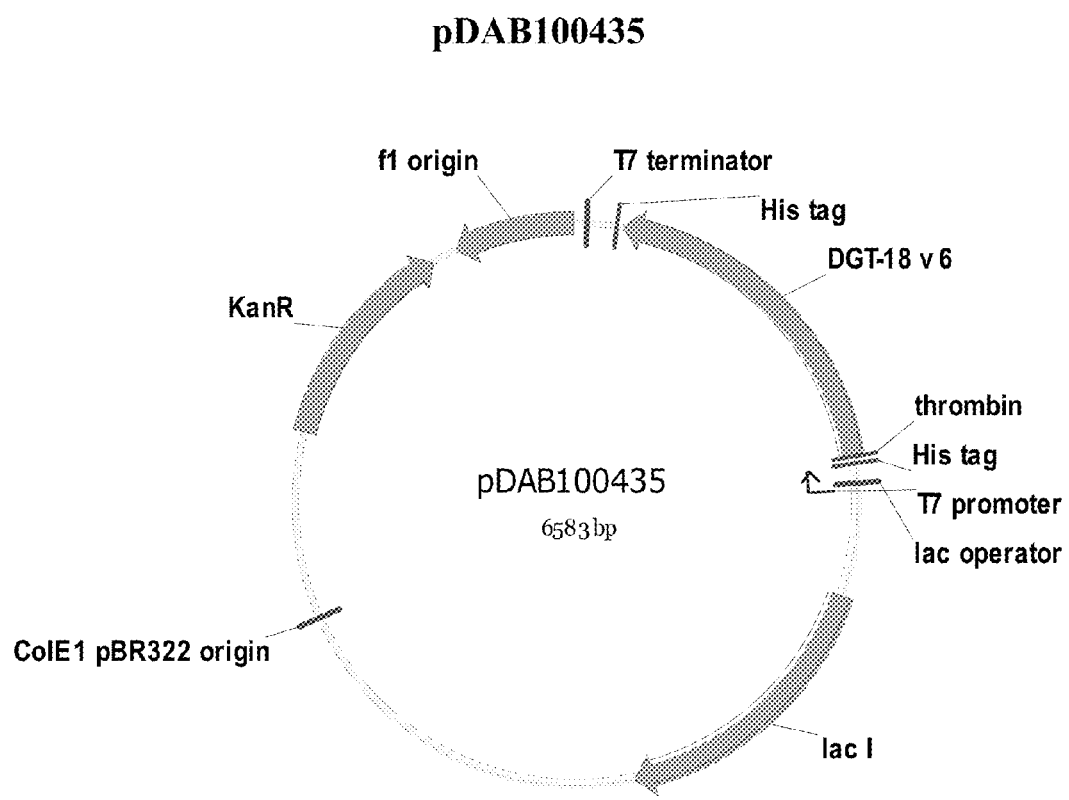
FIG. 7 depicts a plasmid map of pDAB100435.
Figure 8:
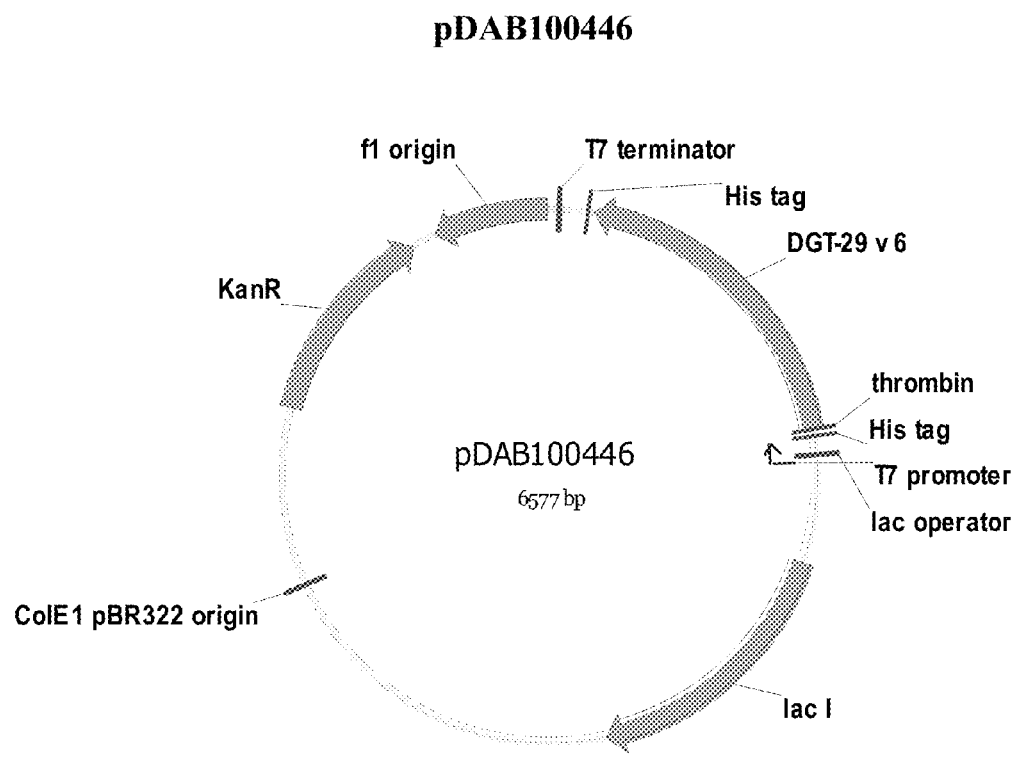
FIG. 8 depicts a plasmid map of pDAB100446.
Figure 9:
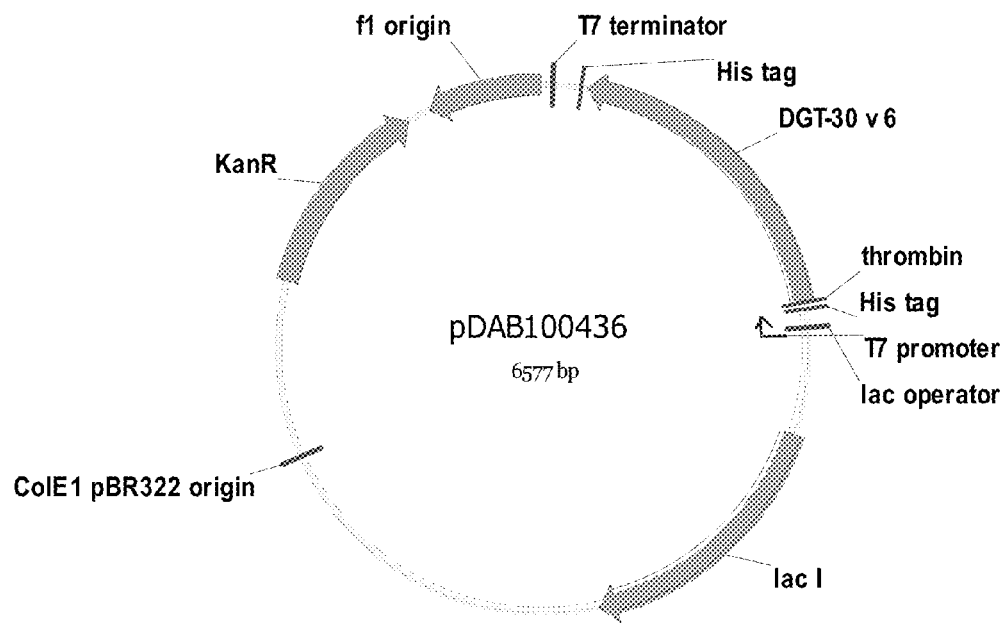
FIG. 9 depicts a plasmid map of pDAB100436.

For in vitro testing the dgt-11v6, dgt-12 v6, dgt-18 v6, dgt-29 v6, and dgt-30 v6 gene sequences were outsourced to GeneArt for synthesis and cloning. The synthesized genes were cloned into the pET28 expression vector. The resulting constructions were labeled as pDAB100431 (FIG. 5) containing dgt-11 v6, pDAB100432 (FIG. 6) containing dgt-11 v6, pDAB100435 (FIG. 7) containing dgt-18 v6, pDAB100446 (FIG. 8) containing dgt-29 v6, and pDAB100436 (FIG. 9) containing dgt-30 v6.

Additional constructs containing the dgt-1, dgt-3 and dgt-7 were synthesized. These constructs were used for in vitro testing of the dgt-1 v5, dgt-1 v6, dgt-1 v7, dgt-1 v8, dgt-3 v6, dgt-3 v7, dgt-3 v8, dgt-7 v5, dgt-7 v6, dgt-7 v7, and dgt-7 v8 gene sequences were outsourced to GeneArt for synthesis and cloning. The synthesized genes were cloned into the pET28 expression vector. The resulting constructions were labeled as pDAB102028 containing dgt-1 v5, pDAB102029 containing dgt-1 v6, pDAB102032 containing dgt-1 v7, pDAB102034 containing dgt-1 v8, pDAB100429 containing dgt-3 v6, pDAB100442 containing dgt-3 v7, pDAB100430 containing dgt-3 v8, pDAB102036 containing dgt-7 v5, pDAB102038 containing dgt-7 v6, pDAB102040 containing dgt-7 v7, and pDAB102042 containing dgt-7 v8. These constructs and the DGT protein sequences which were expressed are described in U.S. patent Ser. No. 11/975,658, incorporated herein by reference in its entirety.

Example 4: In-Vitro Biochemical Enzymatic Kinetic Assay

Overexpression and Purification of Recombinant DGT Enzymes

Recombinant DGT proteins were overexpressed in Rosetta2™ (DE3) cells (Novagen, Madison, Wis.) from the constructs described above. A single colony was used to inoculate 50 mL starter cultures of LB containing chloramphenicol (25 µg/mL) and kanamycin (50 µg/mL) which were cultivated overnight at 37° C. The overnight cultures were used to inoculate 1 L of LB containing chloramphenicol (25 µg/mL) and kanamycin (50 µg/mL). The cultures were grown at 37° C. to an $O.D._{600}=0.6$ then placed in an ice water bath for 10 minutes. Expression of the target proteins was achieved by addition of IPTG to a final concentration of 500 µM. Induction was allowed to proceed overnight at 20° C. followed by harvesting via centrifugation at 8,000 rpm for 20 minutes. The cell pellets were stored at −80° C. until required for purification. All purification steps were carried out at 4° C.

Cell pellets from 1 L cultures were resuspended in 20-30 mL Buffer A (50 mM HEPES pH 7.5, 150 mM KCl, 2 mM DTT, 1 mM EDTA, 20 mM imidazole, and 5% glycerol). COMPLETE™ protease inhibitor cocktail (1 tablet/50 mL, Roche, Indianapolis, Ind.) and lysozyme (1 mg/mL, Sigma-Aldrich, St. Louis, Mo.) were then added and the suspension was stirred for 20 minutes. Cell lysis was performed using a Branson Sonifier 250 (3×60 second bursts) followed by removal of the cell debris by centrifugation at 16,000 rpm for 45 minutes. DGT enzymes were purified to homogeneity in one step via immobilized metal affinity chromatography (IMAC) using a 5 mL HisTrap FF crude column. The column was equilibrated in Buffer A and the sample was loaded in the same buffer. The column was then washed with 10 column volumes of Buffer A followed by elution in a 0-100% Buffer B (50 mM HEPES pH 7.5, 200 mM KCl, 2 mM DTT, 1 mM EDTA, 500 mM imidazole, and 5% glycerol) linear gradient over 25 column volumes. Fractions containing target protein, as judged by SDS-PAGE analysis, were concentrated to 2.5 mL using a Millipore ultracentrifugation device equipped with a 10 kDa molecular weight cut-off (MWCO). The purified DGT enzymes were buffer exchanged using PD-10 columns (GE Healthcare) into 50 mM HEPES pH 7.5, 150 mM KCl, 2 mM DTT, and 5% glycerol and subsequently concentrated ~1 mL. Samples were typically diluted 1:50 and the UV-visible spectrum was recorded from 240-700 nm on a Cary50 Bio UV-visible spectrophotometer. A theoretical extinction coefficient was then used to calculate the protein concentration based on the absorbance at 280 nm (ExPASy, Geneva, Switzerland).

In Vitro Kinetic Characterization of Plant and Bacterial DGT Enzymes

The enzyme activities of wild-type (WT) and mutant DGTs were measured by inorganic phosphate ($P_i$) production in a modified procedure described by Lanzetta et al., (1979). Lanzetta P., Alvarez L., Reinach P., and Candia O., (1979) *Anal Bioch.*, 100:95-97. Assays were performed in 96-well plate format in a total of 50 µL on a Spectra-Max 190 plate reader (Molecular Devices, Sunnyvale, Calif.). Typical assays contained 50 mM HEPES pH 7.5, 150 mM KCl, 2 mM DTT, and 1 mM S3P. PEP and glyphosate concentrations were varied as indicated. Glyphosate was obtained from Sigma as the free acid and was resuspended in ddH$_2$O. Glyphosate was solubilized by addition of KOH until the mixture was at a neutral pH. Assays were initiated by addition of the DGT enzyme at concentrations that varied between 0.01-1 µM. Reactions were terminated by the addition of 235 µL of a 3:1 mixture of malachite green: ammonium molybdate solution. After complete color development (~1 minute), the absorbance change at 660 nm was recorded and the amount of $P_i$ formed was calculated from a standard curve. Control reactions lacking enzyme were used to correct for background absorbance. High concentrations of PEP (>2 mM) and glyphosate (>30 mM) contribute a significant amount of background absorbance using this detection method. The data were fitted to the Michaelis-Menten equation which allowed for the determination of $K_m$ and $V_{max}$ (Equation 1) while $IC_{50}$ was determined from Equation 2, where y is the relative activity and s is the Hill coefficient. Data were analyzed using GraFit version 5™ software (Erithacus Software Limited, Horley, U.K.).

$$v = \frac{V_{max} \cdot [S]}{K_m + [S]} \quad \text{Equation 1}$$

$$y = \frac{100\%}{1 + \left(\frac{x}{IC_{50}}\right)^s} \quad \text{Equation 2}$$

The $IC_{50}$ value for a competitive inhibitor will change dependent on the concentration of substrate, therefore the $IC_{50}$ values in Table 2 were obtained at 1 mM PEP and at 60 μM PEP (an estimate of the intracellular PEP concentrations in plants). Only $IC_{50}$ values measured at the same concentration of PEP should be compared. Additionally, $IC_{50}$ values of highly tolerant enzymes could not accurately be determined by the method of Lanzetta and were therefore estimated based on relative activity.

Figure 10:
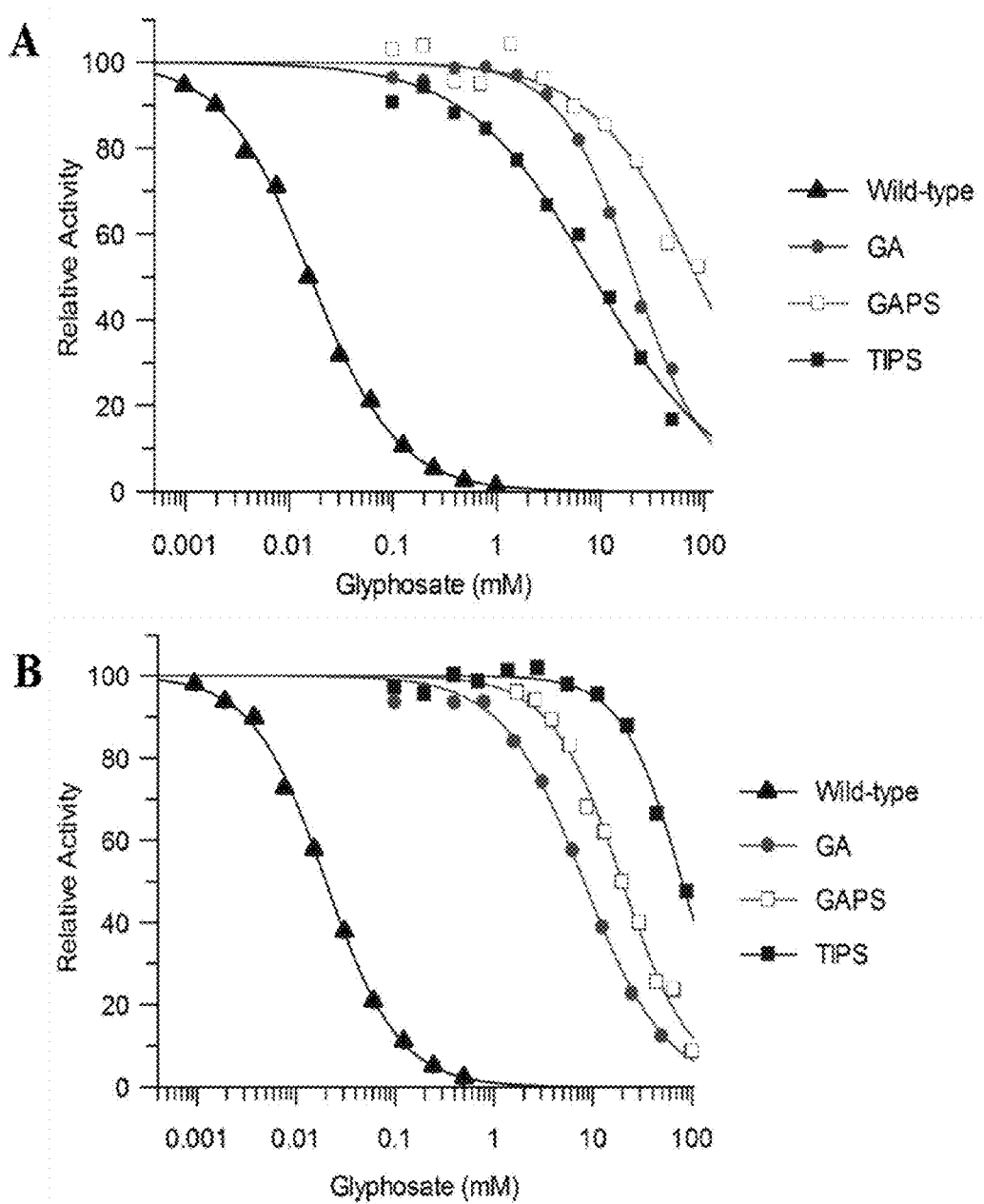
FIG. 10 depicts $IC_{50}$ values obtained after introduction of various mutations within DGT-1 (A) and DGT-7 (B) using 1 mM PEP. For both A and B $IC_{50}$ curves closed triangles represent wild-type, closed circles represent GA mutants, open squares represent GAPS mutants, and closed squares represent TIPS mutants.
Figure 11:
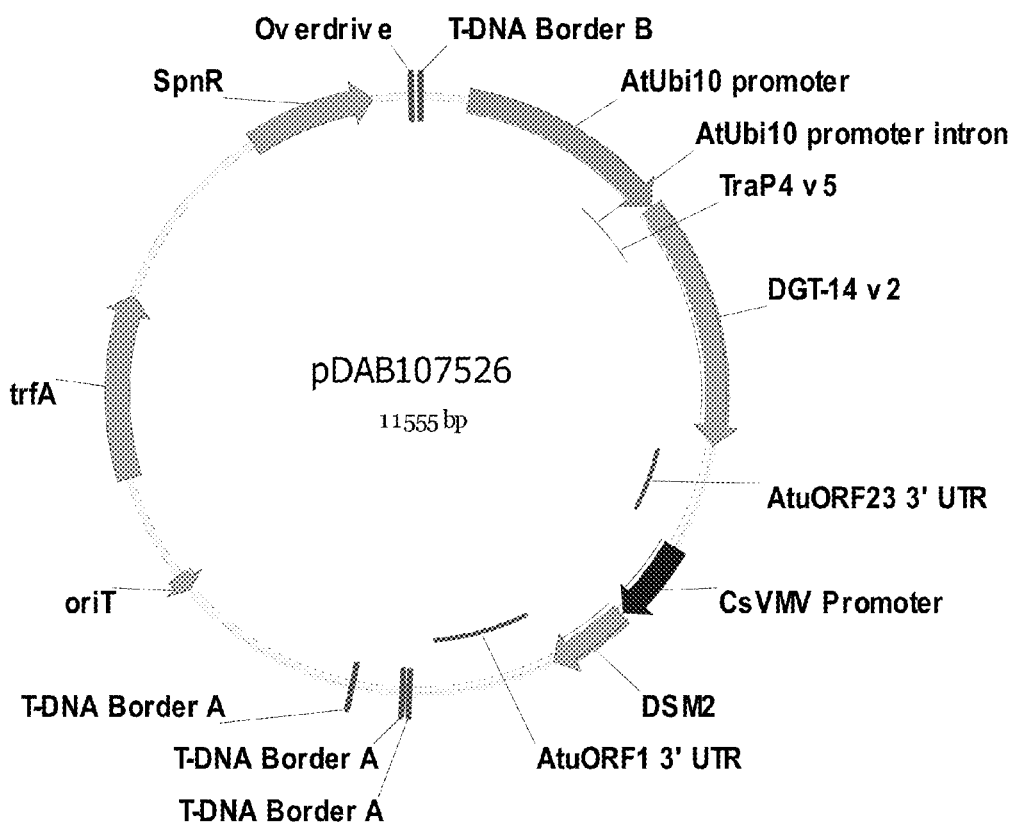
FIG. 11 depicts a plasmid map of pDAB107526.
Figure 12:
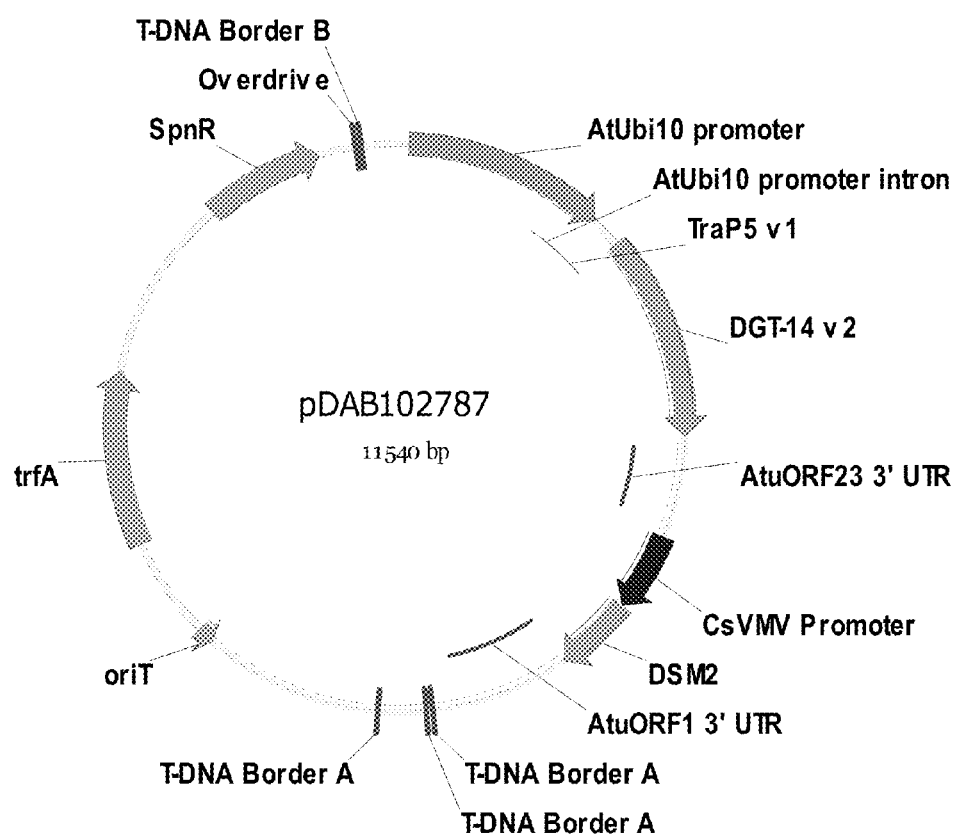
FIG. 12 depicts a plasmid map of pDAB102787.
Figure 13:
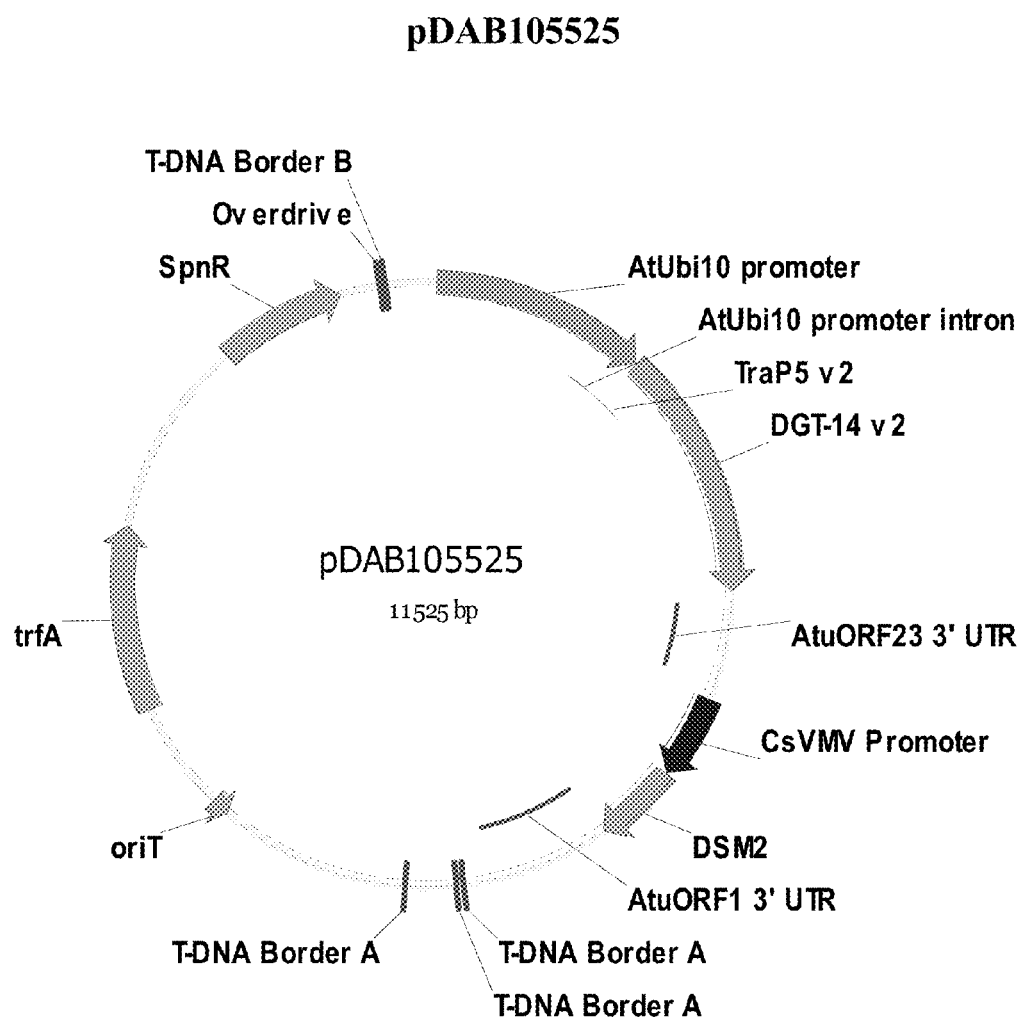
FIG. 13 depicts a plasmid map of pDAB105525.
Figure 14:
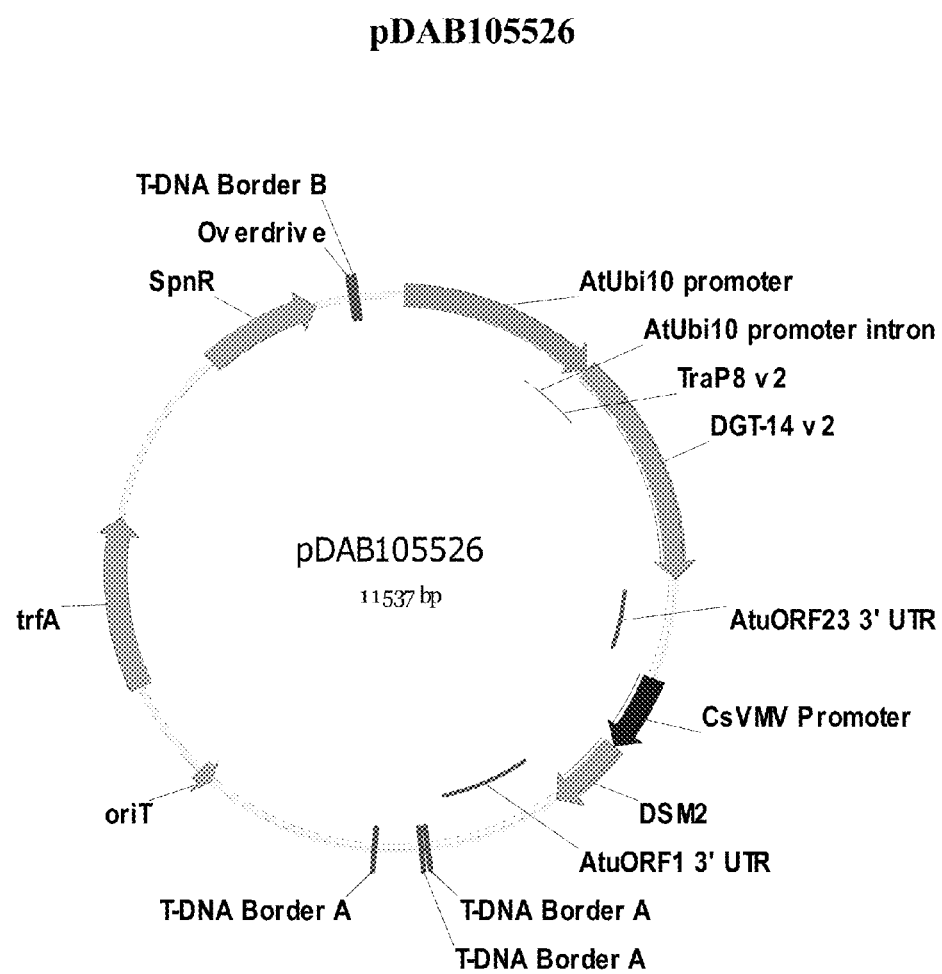
FIG. 14 depicts a plasmid map of pDAB105526.
Figure 15:
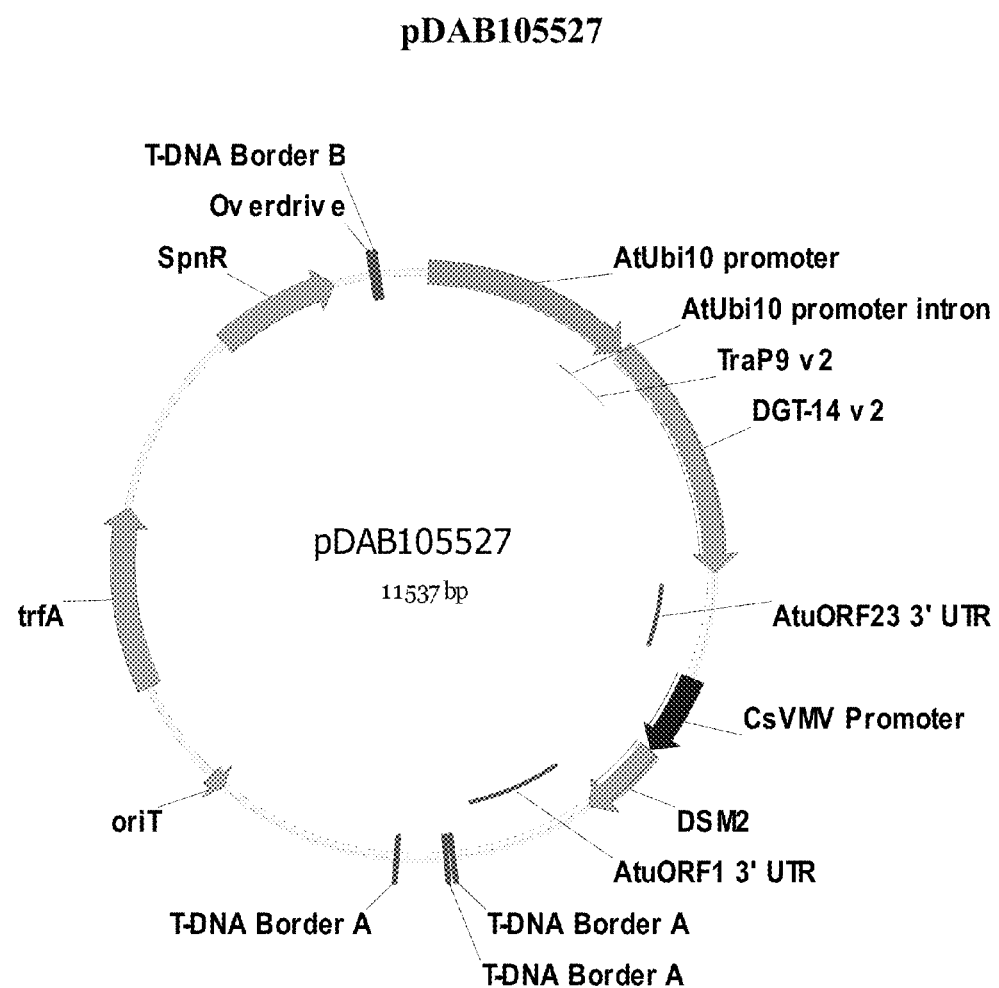
FIG. 15 depicts a plasmid map of pDAB105527.
Figure 16:
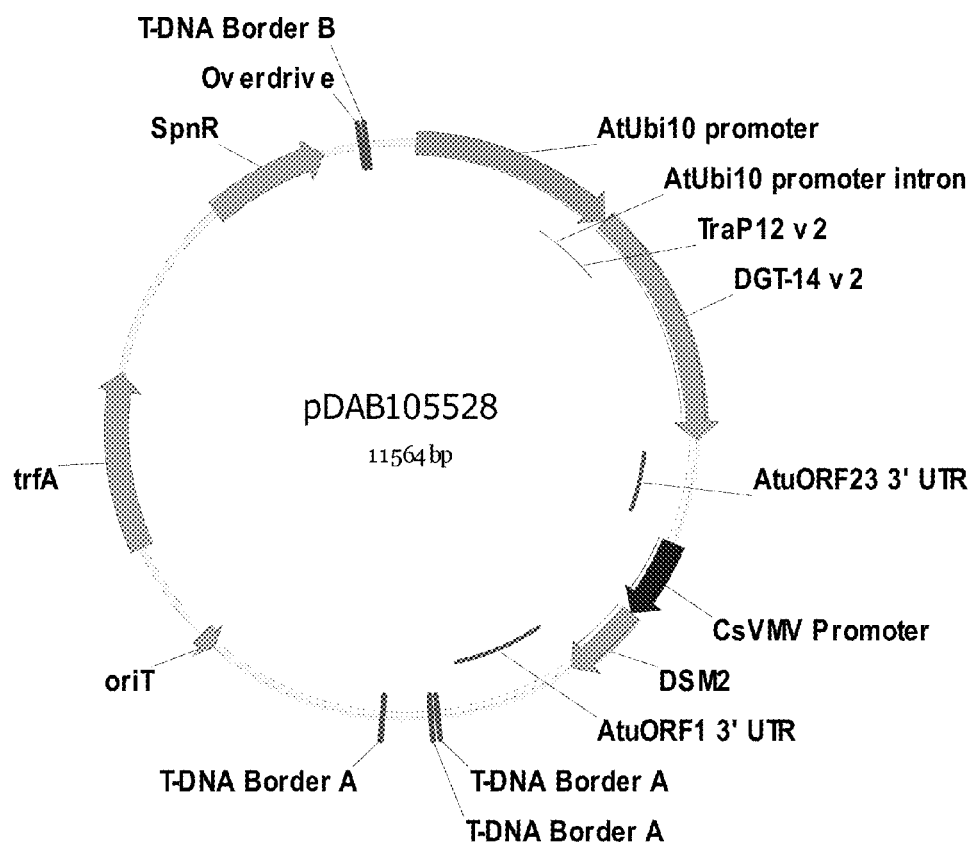
FIG. 16 depicts a plasmid map of pDAB105528.
Figure 17:
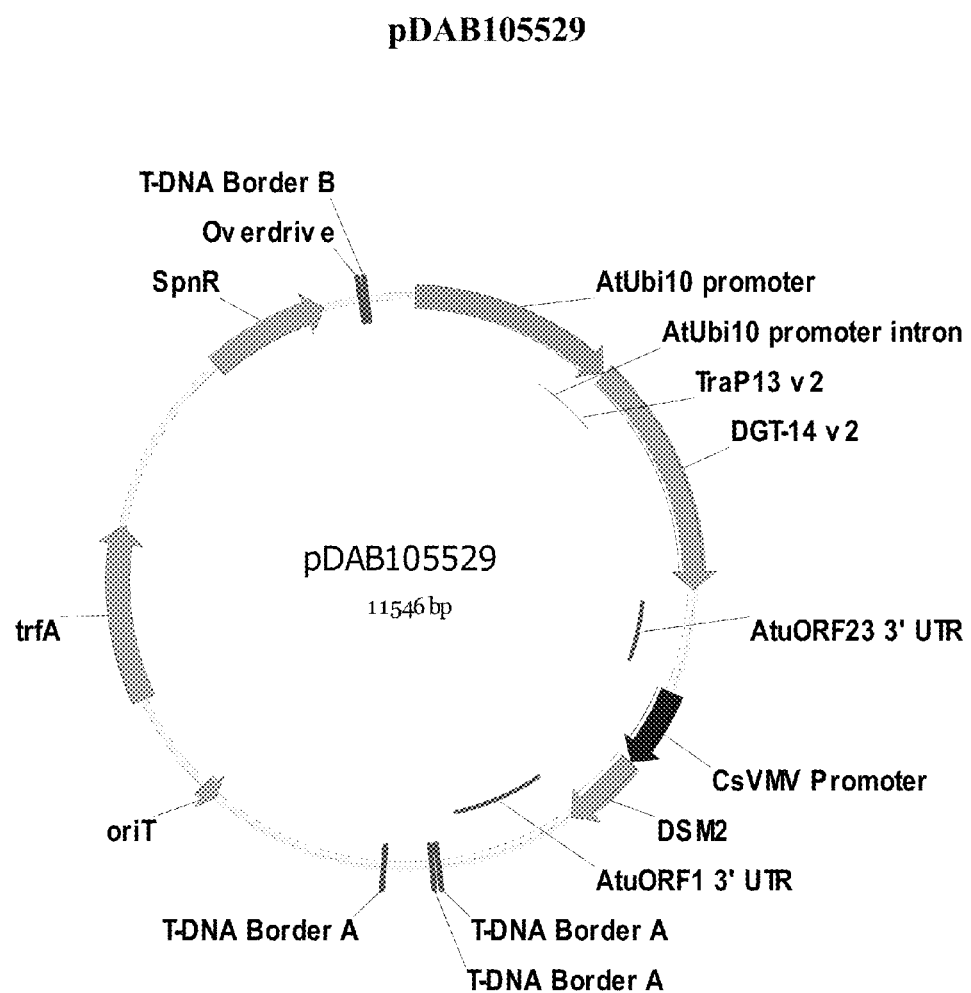
FIG. 17 depicts a plasmid map of pDAB105529.

(GAPS), for all plant derived DGTs (DGT-1 v7, DGT-3 v7, and DGT-7 v7), also enhanced glyphosate tolerance but once again resulted in a considerable elevation in the PEP $K_m$ (Table 2). The TIPS mutants (DGT-1 v8, DGT-3 v8, and DGT-7 v8) were tolerant to modest concentrations of glyphosate (3-6 mM) but in contrast to the GA and GAPS mutants, the $K_M$ levels remained close to the wild-type proteins between 60-200 μM. FIG. 10 demonstrates the shifts in glyphosate tolerance for DGT-1 (A) and DGT-7 (B) upon introduction of the specified mutations. The PEP concentration was held at 1 mM for the experiments resulting in the data shown in FIG. 10, which likely led to the elevated $IC_{50}$ (>80 mM) for DGT-7 v8. Further procedures were carried out to determine if lower levels of PEP altered the relative tolerance to glyphosate. Physiologically relevant levels of PEP range from 5-60 μM. With 60 μM PEP, the $IC_{50}$ value decreased significantly (3.6 mM), suggesting the initial determination was influenced by excess PEP, as expected from Michaelis-Menten kinetics and noted in Table 2.

FIG. 10 shows $IC_{50}$ values obtained after introduction of various mutations within DGT-1 (A) and DGT-7 (B) using 1 mM PEP. For both A and B $IC_{50}$ curves closed triangles represent wild-type, closed circles represent GA mutants, open squares represent GAPS mutants, and closed squares represent TIPS mutants.

TABLE 2

Steady-state kinetic parameters for DGT enzymes. $IC_{50}$ values greater than 50 are estimates due to limitations of the method used. *$IC_{50}$ for glyphosate was determined at 100 μM PEP.
IC50 (mM Glyphosate)

|  |  | Protein | Sequence Version | $IC_{50}$ (mM) at 1 mM PEP | $IC_{50}$ (mM) at 60 μM PEP | $K_M^{PEP}$ (μM) | $k_{cat}/K_m$ (M$^{-1}$ s$^{-1}$) |
|---|---|---|---|---|---|---|---|
| Plant Enzymes | Soybean | DGT-1 v5 | Native | 0.0 | 0.0 | 73.0 | 7.41E+04 |
|  |  | DGT-1 v6 | G→A | 21.1 | 17.3 | 608.2 | 1.34E+04 |
|  |  | DGT-1 v7 | G→A, P→S | >80.00 | >80.00 | 1291.2 | 6.67E+03 |
|  |  | DGT-1 v8 | T→I, P→S | 13.3 | 5.9 | 151.4 | 1.23E+04 |
|  | Canola | DGT-3 v6 | G→A | 15.8 | 8.7 | 1073.4 | 1.39E+04 |
|  |  | DGT-3 v7 | G→A, P→S | 50.5 | 42.0 | 2728.3 | 2.28E+03 |
|  |  | DGT-3 v8 | T→I, P→S | 13.3 | 4.8 | 196.8 | 3.29E+04 |
|  | Wheat | DGT-7 v5 | Native | 0.0 | 0.0 | 75.6 | 2.15E+05 |
|  |  | DGT-7 v6 | G→A | 8.1 | 15.1 | 538.2 | 1.61E+04 |
|  |  | DGT-7 v7 | G→A, P→S | 19.7 | 15.4 | 1103.2 | 1.46E+04 |
|  |  | DGT-7 v8 | T→I, P→S | >80.0 | 3.6 | 60.5 | 1.36E+04 |
| Bacterial Enzymes |  | DGT-14 v1 | Native | >20.16 | 0.44 | 208.6 | 5E+04 |
|  |  | DGT-14 v6 | G→A | >80.00 | >80.00 | 352.5 | 3E+04 |
|  |  | DGT-11 v6 | Native | 9.98 | — | 1576.6 | 5E+01 |
|  |  | DGT-12 v6 | G→A | 4.00 | — | 128.0 | 7E+02 |
|  |  | DGT-18 v6 | G→A | 33.25 | 9.24 | 375.9 | 4E+04 |
|  |  | DGT-29 v6 | G→A | >80.00 | >80.00* | 1502.2 | 4E+03 |
|  |  | DGT-30 v6 | G→A | 15.5 | 7.86 | 414.9 | 3E+04 |

*$K_M$ determined at 100 μM PEP

Kinetics of Plant DGTs

Two enzymes with un-mutated native sequences, DGT-1 v5 and DGT-7 v5, were tested first to establish baseline parameters for glyphosate sensitivity. Both proteins displayed low $K_m$ values for PEP (~70 μM) and were sensitive to glyphosate with $IC_{50}$ values of ~20 μM (Table 2) at 1 mM PEP. As observed for DGT-1 v6, DGT-3 v6, and DGT-7 v6, a single point mutation from G to A significantly improved tolerance to glyphosate ($IC_{50}$ values of 8-21 mM) but also increased the $K_m$ for PEP by ~8-fold. The double mutation Kinetics of Bacterial DGTs The mutated DGT-14 v6 (G101A mutation) enzyme possessed the most favorable overall kinetic parameters and tolerance to glyphosate ($k_{cat}/K_m$ and elevated $IC_{50}$). The enzyme was tolerant to glyphosate at concentrations >80 mM and displayed a catalytic efficiency of $3\times10^4$ M$^{-1}$ s$^{-1}$. As expected, wild-type DGT-14 v1 enzyme displayed a significantly lower $IC_{50}$ of 0.44 mM (at 60 μM PEP) a $K_m$ for PEP of 208.6 μM. The native or wild-type enzyme also displayed a high catalytic efficiency ($5.3\times10^4$ M$^{-1}$ s$^{-1}$). The data demonstrates that even though DGT-14 v1 is more sensitive to glyphosate when compared to DGT-14 v6, it retains some innate level of tolerance that is greater than those of the native plant enzymes. As a result of the introduction of the alanine residue for glycine at amino acid residued 101, the $IC_{50}$ shifted from ~20.16 mM to >80.00 mM at 1 mM PEP, and 0.44 mM to >0.80 mM at 60 uM PEP. Physiologically relevant levels of PEP range from 5-60 µM. Likewise, the introduction of the alanine residue for glycine at amino acid 101 resulted in an increase of $K_m$ for PEP from 208.6 µM to 352.5 µM. The introduction of the G101A mutation resulted in improved glyphosate tolerance for DGT-14 v6.

Additionally, five other bacterial enzymes were also evaluated for their tolerance to glyphosate. All were glycine to alanine mutated variants except for DGT-11v6 which comprises the wild-type protein sequence and possesses a natural alanine amino acid residue. The kinetic parameters and $IC_{50}$ values are described in Table 2. The DGT-11v6, DGT-12 v6, DGT-18 v6, DGT-29 v6, and DGT-30 v6 enzymes were tolerant to glyphosate at concentrations 9.98 mM, 4.00 mM, 33.25 mM, 80 mM, and 15.55 mM, respectively, at 1 mM PEP. The kinetic parameters and tolerance for the enzymes which possess the alanine amino acid residue are higher than the native or wild-type plant enzymes (DGT-1v5 and DGT-7v5) which possess a glycine amino acid residue. DGT-11v6, DGT-12 v6, DGT-18 v6, DGT-29 v6, and DGT-30 v6 possessed kinetic parameters which indicate that the enzymes are tolerant to glyphosate.

Example 5: Cloning of Plant Transformation Vectors

Plant Binary Vector Construction

Standard cloning methods were used in the construction of entry vectors containing a chloroplast transit peptide polynucleotide sequence joined to dgt-14 as an in-frame fusion. The entry vectors containing a chloroplast transit peptide (TraP) fused to dgt-14 were assembled using the IN-FUSION™ Advantage Technology (Clontech, Mountain View, Calif.). Transit peptides TraP4 v5 (SEQ ID NO:18), TraP5 v1 (SEQ ID NO:19), TraP5 v2 (SEQ ID NO:20), TraP8 v2 (SEQ ID NO:21), TraP9 v2 (SEQ ID NO:22), TraP12 v2 (SEQ ID NO:23), and TraP13 v2 (SEQ ID NO:24) were each synthesized by DNA2.0 (Menlo Park, Calif.) and fused to the 5' end fragment of dgt-14 up to and including a unique AccI restriction endonuclease recognition site.

Binary plasmids which contained the various TraP and dgt-14 expression cassettes were driven by the *Arabidopsis thaliana* Ubiquitin 10 promoter (AtUbi10; Callis, et al., (1990) *J. Biol. Chem.*, 265: 12486-12493) and flanked by the *Agrobacterium tumefaciens* open reading frame twenty-three 3' untranslated region (AtuORF23 3' UTR; U.S. Pat. No. 5,428,147).

The assembled TraP and dgt-14 expression cassettes were engineered using GATEWAY® Technology (Invitrogen, Carlsbad, Calif.) and transformed into plants via *Agrobacterium*-mediated plant transformation. Restriction endonucleases were obtained from New England BioLabs (NEB; Ipswich, Mass.) and T4 DNA Ligase (Invitrogen) was used for DNA ligation. Gateway reactions were performed using GATEWAY® LR CLONASE® enzyme mix (Invitrogen) for assembling one entry vector into a single destination vector which contained the selectable marker cassette Cassava Vein Mosaic Virus promoter (CsVMV; Verdaguer et al., (1996) *Plant Mol. Biol.*, 31: 1129-1139)—*DSM*-2 (U.S. Pat. App. No. 2007/086813)—*Agrobacterium tumefaciens* open reading frame one 3' untranslated region (AtuORF1 3' UTR; Huang et al., (1990) *J. Bacteria* 172:1814-1822). Plasmid preparations were performed using NUCLEOSPIN® Plasmid Kit (Macherey-Nagel Inc., Bethlehem, Pa.) or the Plasmid Midi Kit™ (Qiagen) following the instructions of the suppliers. DNA fragments were isolated using QIAquick Gel Extraction Kit™ (Qiagen) after agarose Tris-acetate gel electrophoresis.

Colonies of all assembled plasmids were initially screened by restriction digestion of miniprep DNA. Plasmid DNA of selected clones was sequenced by a commercial sequencing vendor (Eurofins MWG Operon, Huntsville, Ala.). Sequence data were assembled and analyzed using the SEQUENCHER™ software (Gene Codes Corp., Ann Arbor, Mich.).

The following binary constructs express the various TraP: dgt-14 fusion gene sequences: pDAB107526 (FIG. 11) contains TraP4 v5:dgt-14 v2 (SEQ ID NO:25); pDAB102787 (FIG. 12) contains TraP5 v1: dgt-14 v2 (SEQ ID NO:26); pDAB105525 (FIG. 13) contains TraP5 v2: dgt-14 v2 (SEQ ID NO:27); pDAB105526 (FIG. 14) contains TraP8 v2: dgt-14 v2 (SEQ ID NO:28); pDAB105527 (FIG. 15) contains TraP9 v2: dgt-14 v2 (SEQ ID NO:29); and, pDAB105528 (FIG. 16) contains TraP12 v2: dgt-14 v2 (SEQ ID NO:30); and, pDAB105529 (FIG. 17) contains TraP13 v2: dgt-14 v2 (SEQ ID NO:31).

A minor modification was made to the initial methionine residue of the dgt-14 coding sequence when the in-frame fusions were constructed. For instance, the methionine was changed to alanine in the dgt-14 coding sequences in pDAB105529, pDAB017526, pDAB105525, pDAB105526, pDAB105527, and pDAB105528. The methionine was left unchanged in pDAB102787. The modifications were introduced to facilitate cloning of the dgt-14 coding sequence behind the chloroplast transit peptides, and the sequence listings described above contain the modified amino acid residue.

Example 6: Transformation into *Arabidopsis* and Selection

*Arabidopsis thaliana* Transformation

*Arabidopsis* was transformed using the floral dip method from Clough and Bent (1998). A selected *Agrobacterium* colony containing one of the binary plasmids described above was used to inoculate one or more 100 mL pre-cultures of YEP broth containing spectinomycin (100 mg/L) and kanamycin (50 mg/L). The culture was incubated overnight at 28° C. with constant agitation at 225 rpm. The cells were pelleted at approximately 5000×g for 10 minutes at room temperature, and the resulting supernatant discarded. The cell pellet was gently resuspended in 400 mL dunking media containing: 5% (w/v) sucrose, 10 μg/L 6-benzylaminopurine, and 0.04% Silwet L-77. Plants approximately 1 month old were dipped into the media for 5-10 minutes with gentle agitation. The plants were laid down on their sides and covered with transparent or opaque plastic bags for 2-3 hours, and then placed upright. The plants were grown at 22° C., with a 16-hour light/8-hour dark photoperiod. Approximately 4 weeks after dipping, the seeds were harvested.

Selection of Transformed Plants

Freshly harvested $T_1$ seed [containing the dgt-14 and DSM-2 expression cassettes] was allowed to dry for 7 days at room temperature. $T_1$ seed was sown in 26.5×51-cm germination trays, each receiving a 200 mg aliquot of stratified $T_1$ seed (~10,000 seed) that had previously been suspended in 40 mL of 0.1% agarose solution and stored at 4° C. for 2 days to complete dormancy requirements and ensure synchronous seed germination.

Sunshine Mix LP5 was covered with fine vermiculite and subirrigated with Hoagland's solution until wet, then allowed to gravity drain. Each 40 mL aliquot of stratified seed was sown evenly onto the vermiculite with a pipette and covered with humidity domes for 4-5 days. Domes were removed 1 day prior to initial transformant selection using glufosinate postemergence spray (selecting for the co-transformed DSM-2 gene).

Seven days after planting (DAP) and again 11 DAP, $T_1$ plants (cotyledon and 2-4-1f stage, respectively) were sprayed with a 0.2% solution of Liberty herbicide (200 g ai/L glufosinate, Bayer Crop Sciences, Kansas City, Mo.) at a spray volume of 10 ml/tray (703 L/ha) using a DeVilbiss compressed air spray tip to deliver an effective rate of 280 g ai/ha glufosinate per application. Survivors (plants actively growing) were identified 4-7 days after the final spraying and transplanted individually into 3-inch pots prepared with potting media (Metro Mix 360). Transplanted plants were covered with humidity domes for 3-4 days and placed in a 22° C. growth chamber as before or moved to directly to the greenhouse. Domes were subsequently removed and plants reared in the greenhouse (22±5° C., 50±30% RH, 14 h light:10 dark, minimum 500 µE/m2 s1 natural+supplemental light). Molecular confirmation analysis was completed on the surviving $T_1$ plants to confirm that the glyphosate tolerance gene had stably integrated into the genome of the plants.

Molecular Confirmation

The presence of the dgt-14 and DSM-2 transgenes within the genome of *Arabidopsis* plants that were transformed with pDAB105525, pDAB105526, pDAB105527, pDAB105528, pDAB105529, pDAB102787 was confirmed. The presence of these polynucleotide sequences within the $T_1$ *Arabidopsis* plants were initially screened via a hydrolysis probe assay, analogous to TAQMAN™, to confirm the presence of the DSM-2 and dgt-14 transgenes. Events were screened via gene expression cassette PCR to determine whether the dgt-14 expression cassette completely integrated into the plant genomes without rearrangement. The data generated from these studies were used to determine the transgene copy number and identify select *Arabidopsis* events for self fertilization and advancement to the $T_2$ generation. The advanced $T_2$ *Arabidopsis* plants were also screened via hydrolysis probe assays to confirm the presence and to estimate the copy number of the DSM-2 and dgt-14 genes within the plant chromosome. Next, a Southern blot assay was used to confirm the estimated copy number on a subset of the $T_1$ *Arabidopsis* plants. Finally, a Western blot assay validated that the events expressed the DGT-14 protein.

Hydrolysis Probe Assay

Copy number was determined in the $T_1$ and $T_2$ *Arabidopsis* plants using the hydrolysis probe assay described below. Plants with varying numbers of transgenes were identified and advanced for subsequent glyphosate tolerance studies.

Tissue samples were collected in 96-well plates and lyophilized for 2 days. Tissue maceration was performed with a KLECO™ tissue pulverizer and tungsten beads (Environ Metal Inc., Sweet Home, Oreg.). Following tissue maceration, the genomic DNA was isolated in high-throughput format using the BIOSPRINT 96 PLANT KIT® (Qiagen, Germantown, Md.) according to the manufacturer's suggested protocol. Genomic DNA was quantified by QUANT IT PICO GREEN DNA ASSAY KIT™ (Molecular Probes, Invitrogen, Carlsbad, Calif.). Quantified genomic DNA was adjusted to around 2 ng/µL for the hydrolysis probe assay using a BIOROBOT3000™ automated liquid handler (Qiagen, Germantown, Md.). Transgene copy number determination by hydrolysis probe assay was performed by real-time PCR using the LIGHTCYCLER®480 system (Roche Applied Science, Indianapolis, Ind.). Assays were designed for DSM-2, dgt-14 and the internal reference gene, TAFII15 (Genbank ID: NC003075; Duarte et al., (201) BMC Evol. Biol., 10:61).

For amplification, LIGHTCYCLER®480 Probes Master mix (Roche Applied Science, Indianapolis, Ind.) was prepared at a 1× final concentration in a 10 µL volume multiplex reaction containing 0.1 µM of each primer for DSM-2 and dgt-14, 0.4 µM of each primer for TAFII15 and 0.2 µM of each probe (Table 3). A two-step amplification reaction was performed with an extension at 60° C. for 40 seconds with fluorescence acquisition. All samples were run and the averaged Cycle threshold (Ct) values were used for analysis of each sample. Analysis of real time PCR data was performed using LIGHTCYCLER® software release 1.5 using the relative quant module and is based on the ΔΔCt method. For this, a sample of genomic DNA from a single copy calibrator and known 2 copy check were included in each run. The copy number results of the hydrolysis probe screen were determined for the $T_1$ and $T_2$ transgenic *Arabidopsis* plants.

TABLE 3

Primer and probe Information for hydrolysis probe assay of DSM-2, dgt-14 and internal reference gene (TAFII15).

| Primer Name | Sequence |
| --- | --- |
| DSM2A (SEQ ID NO: 32) | 5' AGCCACATCCCAGTAACGA 3' |
| DSM2S (SEQ ID NO: 33) | 5' CCTCCCTCTTTGACGCC 3' |
| DSM2 Cy5 probe (SEQ ID NO: 34) | 5' CAGCCCAATGAGGCATCAGC 3' |
| DGT14F (SEQ ID NO: 35) | 5' CCTCTTAGCTGGACTGTAT 3' |
| DGT14R (SEQ ID NO: 36) | 5' CTTAGGATCAAGGCTAATCGTT 3' |
| UPL145 probe | Cat# 04694317001 (Roche, Indianapolis, IN) |

TABLE 3-continued

Primer and probe Information for hydrolysis probe assay of DSM-2, dgt-14 and internal reference gene (TAFII15).

| Primer Name | Sequence |
|---|---|
| TAFFY-HEX probe (SEQ ID NO: 37) | 5' AGAGAAGTTTCGACGGATTTCGGGC 3' |
| TAFII15-F (SEQ ID NO: 38) | 5' GAGGATTAGGGTTTCAACGGAG 3' |
| TAFII15-R (SEQ ID NO: 39) | 5' GAGAATTGAGCTGAGACGAGG 3' |

Dgt-14 Integration Confirmation Via Southern Blot Analysis.

Southern blot analysis was used to establish the integration pattern of the inserted T-strand DNA fragment and identify events which contained dgt-14. Data were generated to demonstrate the integration and integrity of the transgene inserts within the *Arabidopsis* genome. Southern blot data were used to identify simple integration of an intact copy of the T-strand DNA. Detailed Southern blot analysis was conducted using a PCR amplified probe specific to the dgt-14 gene expression cassette. The hybridization of the probe with genomic DNA that had been digested with specific restriction enzymes identified genomic DNA fragments of specific molecular weights, the patterns of which were used to identify full length, simple insertion $T_1$ transgenic events for advancement to the next generation.

Tissue samples were collected in 2 mL conical tubes (Eppendorf) and lyophilized for 2 days. Tissue maceration was performed with a KLECKO™ tissue pulverizer and tungsten beads. Following tissue maceration, the genomic DNA was isolated using a CTAB isolation procedure. The genomic DNA was further purified using the Qiagen Genomic Tips kit. Genomic DNA was quantified by Quant-IT Pico Green DNA™ assay kit (Molecular Probes, Invitrogen, Carlsbad, Calif.). Quantified genomic DNA was adjusted to 4 µg for a consistent concentration.

For each sample, 4 µg of genomic DNA was thoroughly digested with the restriction enzyme SwaI (New England Biolabs, Beverley, Mass.) and incubated at 25° C. overnight, then NsiI was added to the reaction and incubated at 37° C. for 6 hours. The digested DNA was concentrated by precipitation with Quick Precipitation Solution™ (Edge Biosystems, Gaithersburg, Md.) according to the manufacturer's suggested protocol. The genomic DNA was then resuspended in 25 µL of water at 65° C. for 1 hour. Resuspended samples were loaded onto a 0.8% agarose gel prepared in 1×TAE and electrophoresed overnight at 1.1 V/cm in 1×TAE buffer. The gel was sequentially subjected to denaturation (0.2 M NaOH/0.6 M NaCl) for 30 minutes, and neutralization (0.5 M Tris-HCl (pH 7.5)/1.5 M NaCl) for 30 minutes.

Transfer of DNA fragments to nylon membranes was performed by passively wicking 20×SSC solution overnight through the gel onto treated IMMOBILON™ NY+ transfer membrane (Millipore, Billerica, Mass.) by using a chromatography paper wick and paper towels. Following transfer, the membrane was briefly washed with 2×SSC, cross-linked with the STRATALINKER™ 1800 (Stratagene, LaJolla, Calif.), and vacuum baked at 80° C. for 3 hours.

Blots were incubated with pre-hybridization solution (Perfect Hyb plus, Sigma, St. Louis, Mo.) for 1 hour at 65° C. in glass roller bottles using a model 400 hybridization incubator (Robbins Scientific, Sunnyvale, Calif.). Probes were prepared from a PCR fragment containing the entire coding sequence. The PCR amplicon was purified using QIAEX II gel extraction Kit™ and labeled with α32P-dCTP via the Random RT Prime IT™ labeling kit (Stratagene, La Jolla, Calif.). Blots were hybridized overnight at 65° C. with denatured probe added directly to hybridization buffer to approximately 2 million counts per blot per mL. Following hybridization, blots were sequentially washed at 65° C. with 0.1×SSC/0.1% SDS for 40 minutes. Finally, the blots were exposed to storage phosphor imaging screens and imaged using a Molecular Dynamics Storm 860™ imaging system.

The Southern blot analyses completed in this study were used to determine the copy number and confirm that selected events contained the dgt-14 transgene within the genome of *Arabidopsis*.

Dgt-14 Gene Expression Cassette Confirmation Via PCR Analysis

The presence of the dgt-14 gene expression cassette contained in the $T_1$ plant events was detected by an end point PCR reaction. Primers (see Table 4) specific to the AtUbi10 promoter v2 and AtuORF23 3'UTR v1 regions of the dgt-14 gene expression cassette were used for detection.

TABLE 4

Oligonucleotide primers used for dgt-14 gene expression cassette confirmation.

| Primer Name | Sequence |
|---|---|
| Forward oligo (SEQ ID NO: 40) | 5' CTGCAGGTCAACGGATCAGGATAT 3' |
| Reverse oligo (SEQ ID NO: 41) | 5' TGGGCTGAATTGAAGACATGCTCC 3' |

The PCR reactions required a standard three step PCR cycling protocol to amplify the gene expression cassette. All of the PCR reactions were completed using the following PCR conditions: 94° C. for three minutes followed by 35 cycles of 94° C. for thirty seconds, 60° C. for thirty seconds, and 72° C. for three minutes. The reactions were completed using the EX-TAQ PCR™ kit (TaKaRa Biotechnology Inc. Otsu, Shiga, Japan) per manufacturer's instructions. Following the final cycle, the reaction was incubated at 72° C. for 10 minutes. TAE agarose gel electrophoresis was used to determine the PCR amplicon size. PCR amplicons of an expected size indicated the presence of a full length gene expression cassette was present in the genome of the transgenic *Arabidopsis* events.

Dgt-14 Relative Transcription Confirmation Via Quantitative Reverse Transcription PCR Analysis Tissue samples of dgt-14 transgenic plants were collected in 96-well plates and frozen at 80° C. Tissue maceration was performed with a KLECO™ tissue pulverizer and tungsten beads (Environ Metal INC., Sweet Home, Oreg.). Following tissue maceration, the Total RNA was isolated in high-throughput format using the Qiagen Rneasy 96™ kit (Qiagen, Germantown, Md.) according to the manufacturer's suggested protocol which included the optional DnaseI treatment on the column. This step was subsequently followed by an additional DnaseI (Ambion, Austin, Tex.) treatment of the eluted total RNA. cDNA synthesis was carried out using the total RNA as template with the High Capacity cDNA Reverse Transcription™ kit (Applied Biosystems, Austin, Tex.) following the manufacturer's suggested procedure with the addition of the oligonucleotide, TVN. Quantification of expression was completed by hydrolysis probe assay and was performed by real-time PCR using the LIGHTCYCLER®480 system (Roche Applied Science, Indianapolis, Ind.). Assays were designed for dgt-14 and the internal reference gene "unknown protein" (Genbank Accession Number: AT4G24610) using the LIGHTCYCLER® Probe Design Software 2.0. For amplification, LIGHTCYCLER®480 Probes Master mix (Roche Applied Science, Indianapolis, Ind.) was prepared at 1× final concentration in a 10 µL volume singleplex reaction containing 0.4 µM of each primer, and 0.2 µM of each probe (Table 5).

A two-step amplification reaction was performed with an extension at 60° C. for 40 seconds with fluorescence acquisition. All samples were run in triplicate and the averaged Cycle threshold (Ct) values were used for analysis of each sample. A minus reverse transcription reaction was run for each sample to ensure that no gDNA contamination was present. Analysis of real time PCR data was performed based on the ΔΔCt method. This assay was used to determine the relative expression of dgt-14 in transgenic *Arabidopsis* events which were determined to be hemizygous and homozygous. The relative transcription levels of the dgt-14 mRNA ranged from 25.3 fold to 313.7 fold higher than the internal control. These data indicate that dgt-14 transgenic plants contained a functional dgt-14 gene expression cassette, and the plants were capable of transcribing the dgt-14 transgene.

TABLE 5

PCR primers used for quantitative reverse transcription PCR analysis of dgt-14

| Primer Name | Sequence |
| --- | --- |
| T26410LP (SEQ ID NO: 42) | 5' cgtccacaaagctgaatgtg 3' |
| T26410RP (SEQ ID NO: 43) | 5' cgaagtcatggaagccactt 3' |
| PL146 | Cat# 04694325001 (Roche, Indianapolis, IN) |
| GT14F (SEQ ID NO: 44) | 5' CCTCTTAGCTGGACTGTAT 3' |
| GT14R (SEQ ID NO: 45) | 5' CTTAGGATCAAGGCTAATCGTT 3' |
| PL145 probe | Cat# 04694317001 (Roche, Indianapolis, IN) |

Western Blotting Analysis

DGT-14 was detected in leaf samples obtained from transgenic *Arabidopsis thaliana* plants. Plant extracts from dgt-14 transgenic plants and DGT-14 protein standards were incubated with 8M urea denaturing sample buffer at 90° C. for 5 minutes and electrophoretically separated in an acrylamide precast gel. Proteins were then electro-transferred onto nitrocellulose membrane using the manufacturer's protocol. After blocking with the WESTERNBREEZE®Blocking Mix (Invitrogen) the DGT-14 protein was detected by anti-DGT-14 antiserum followed by goat anti-rabbit phosphatase. The detected protein was visualized by chemiluminescence substrate BCIP/NBT Western Analysis Reagent (KPL, Gaithersburg, Md.). Production of an intact DGT-14 protein via Western blot indicated that the dgt-14 transgenic plants which were assayed expressed the DGT-14 protein.

Example 7: Glyphosate Tolerance

Transgenic $T_1$ *Arabidopsis* plants containing the dgt-14 transgene were sprayed with differing rates of glyphosate. A distribution of varying concentrations of glyphosate rates, including elevated rates, were applied in this study to determine the relative levels of resistance (105, 420, 1,680 or 3,360 g ae/ha). The typical 1× field usage rate of glyphosate is 1,120 g ae/ha. The $T_1$ *Arabidopsis* plants that were used in this study were variable in copy number for the dgt-14 transgene. The low copy dgt-14 $T_1$ *Arabidopsis* plants were identified using the molecular confirmation assays described above, and self-pollinated and used to produce $T_2$ plants. Table 6 shows the resistance for dgt-14 transgenic plants, as compared to control plants comprising a glyphosate herbicide resistance gene, dgt-1 (as described in U.S. patent Ser. No. 12/558,351, incorporated herein by reference in its entirety), and wildtype controls.

Results of Glyphosate Selection of Transformed Dgt-14 *Arabidopsis* Plants

The *Arabidopsis* $T_1$ transformants were first selected from the background of untransformed seed using a glufosinate selection scheme. Three flats or 30,000 seed were analyzed for each $T_1$ construct. The $T_1$ plants selected above were molecularly characterized and the plants were subsequently transplanted to individual pots and sprayed with various rates of commercial glyphosate as previously described. The dose response of these plants is presented in terms of % visual injury 2 weeks after treatment (WAT). Data are presented in a table which shows individual plants exhibiting little or no injury (<20%), moderate injury (20-40%), or severe injury (>40%). An arithmetic mean and standard deviation is presented for each construct used for *Arabidopsis* transformation. The range in individual response is also indicated in the last column for each rate and transformation. Wildtype, non-transformed *Arabidopsis* (c.v. Columbia) served as a glyphosate sensitive control.

The level of plant response varied in the $T_1$ *Arabidopsis* plants. This variance can be attributed to the fact each plant represents an independent transformation event and thus the copy number of the gene of interest varies from plant to plant. An overall population injury average by rate is presented in Table 6 to demonstrate the tolerance provided by each of the dgt-14 constructs linked with a chloroplast transit peptide versus the dgt-1 and non-transformed wildtype controls for varying rates of glyphosate. The events contained dgt-14 linked with TraP8 v2 (pDAB105526), TraP9 v2 (pDAB105527), TraP12 v2 (pDAB105528) and TraP13 v2 (pDAB105529). Data from the glyphosate selection of $T_1$ plants demonstrated that when dgt-14 was linked with these chloroplast transit peptides, robust tolerance to high levels of glyphosate was provided. Comparatively, dgt-14 linked with TraP4 v5 (pDAB107526), TraP5 v2 (pDAB105525), and TraP5 v1 (pDAB102787) did not provide tolerance to the treatment of high concentrations of glyphosate, but these constructs were more tolerant than the non-transformed (or wild-type) controls which were treated with the same rates of glyphosate. In addition, there were instances when events that were shown to contain three or more copies of dgt-14 were more susceptible to elevated rates of glyphosate. These instances are demonstrated within the percent visual injury range shown in Table 6. It is likely that the presence of high copy numbers of the transgenes within the *Arabidopsis* plants result in transgene silencing or other epigenetic effects which resulted in sensitivity to glyphosate, despite the presence of the dgt-14 transgene.

TABLE 6 dgt-14 transformed $T_1$ *Arabidopsis* response to a range of glyphosate rates applied postemergence, compared to a dgt-1 ($T_2$) segregating population, and a non-transformed control. Visual % injury 2 weeks after application.

| Application Rate | % Injury Range (No. Replicates) | | | % Injury Analysis | | |
|---|---|---|---|---|---|---|
| | <20% | 20-40% | >40% | Ave | Std dev | Range (%) |
| TraP4 v5::dgt-14 (pDAB107526) | | | | | | |
| 0 g ae/ha glyphosate | 4 | 0 | 0 | 0.0 | 0.0 | 0 |
| 105 g ae/ha glyphosate | 0 | 0 | 4 | 85.8 | 4.3 | 80-90 |
| 420 g ae/ha glyphosate | 0 | 0 | 4 | 91.0 | 7.1 | 85-99 |
| 1680 g ae/ha glyphosate | 0 | 0 | 4 | 96.5 | 1.7 | 95-98 |
| 3360 g ae/ha glyphosate | 0 | 0 | 4 | 95.8 | 1.5 | 95-98 |
| TraP5 v1::dgt-14 (pDAB102787) | | | | | | |
| 0 g ae/ha glyphosate | 6 | 0 | 0 | 0.0 | 0.0 | 0 |
| 105 g ae/ha glyphosate | 0 | 0 | 6 | 64.0 | 13.0 | 50-80 |
| 420 g ae/ha glyphosate | 0 | 0 | 6 | 99.0 | 2.0 | 95-100 |
| 1680 g ae/ha glyphosate | 0 | 0 | 6 | 100.0 | 0.0 | 100 |
| 3360 g ae/ha glyphosate | | NT | | | NT | |
| TraP5 v2::dgt-14 (pDAB105525) | | | | | | |
| 0 g ae/ha glyphosate | 5 | 0 | 0 | 0.0 | 0.0 | 0 |
| 105 g ae/ha glyphosate | 0 | 0 | 5 | 93.0 | 2.7 | 90-95 |
| 420 g ae/ha glyphosate | 0 | 0 | 5 | 98.6 | 2.2 | 95-100 |
| 1680 g ae/ha glyphosate | 0 | 0 | 5 | 98.0 | 1.9 | 95-100 |
| 3360 g ae/ha glyphosate | 0 | 0 | 5 | 96.0 | 2.2 | 95-100 |
| TraP8 v2::dgt-14 (pDAB105526) | | | | | | |
| 0 g ae/ha glyphosate | 4 | 0 | 0 | 0.0 | 0.0 | 0 |
| 105 g ae/ha glyphosate | 0 | 2 | 2 | 40.0 | 14.1 | 20-50 |
| 420 g ae/ha glyphosate | 3 | 0 | 1 | 23.8 | 31.5 | 0-70 |
| 1680 g ae/ha glyphosate | 0 | 1 | 3 | 66.3 | 28.4 | 25-85 |
| 3360 g ae/ha glyphosate | 3 | 0 | 1 | 26.5 | 42.5 | 0-90 |
| TraP9 v2::dgt-14 (pDAB105527) | | | | | | |
| 0 g ae/ha glyphosate | 4 | 0 | 0 | 0.0 | 0.0 | 0 |
| 105 g ae/ha glyphosate | 2 | 1 | 1 | 23.0 | 25.7 | 0-50 |
| 420 g ae/ha glyphosate | 2 | 0 | 2 | 37.5 | 37.7 | 0-70 |
| 1680 g ae/ha glyphosate | 2 | 0 | 2 | 48.8 | 39.0 | 15-85 |
| 3360 g ae/ha glyphosate | 1 | 0 | 3 | 63.8 | 39.2 | 5-85 |
| TraP12 v2::dgt-14 (pDAB105528) | | | | | | |
| 0 g ae/ha glyphosate | 5 | 0 | 0 | 0.0 | 0.0 | 0 |
| 105 g ae/ha glyphosate | 5 | 0 | 0 | 6.0 | 6.5 | 0-15 |
| 420 g ae/ha glyphosate | 4 | 1 | 0 | 11.0 | 5.5 | 5-20 |
| 1680 g ae/ha glyphosate | 3 | 1 | 1 | 20.4 | 14.3 | 10-45 |
| 3360 g ae/ha glyphosate | 2 | 3 | 0 | 19.0 | 4.2 | 15-25 |
| TraP13 v2::dgt-14 (pDAB105529) | | | | | | |
| 0 g ae/ha glyphosate | 4 | 0 | 0 | 0.0 | 0.0 | 0 |
| 105 g ae/ha glyphosate | 2 | 0 | 2 | 34.5 | 32.4 | 5-65 |
| 420 g ae/ha glyphosate | 2 | 1 | 0 | 21.3 | 27.2 | 0-60 |
| 1680 g ae/ha glyphosate | 3 | 0 | 1 | 27.0 | 35.6 | 5-80 |
| 3360 g ae/ha glyphosate | 3 | 1 | 0 | 32.8 | 31.5 | 15-80 |

TABLE 6-continued dgt-14 transformed $T_1$ *Arabidopsis* response to a range of glyphosate rates applied postemergence, compared to a dgt-1 ($T_2$) segregating population, and a non-transformed control. Visual % injury 2 weeks after application.

| Application Rate | % Injury Range (No. Replicates) | | | % Injury Analysis | | |
|---|---|---|---|---|---|---|
| | <20% | 20-40% | >40% | Ave | Std dev | Range (%) |
| dgt-1 (pDAB3759) | | | | | | |
| 0 g ae/ha glyphosate | 4 | 0 | 0 | 0.0 | 0.0 | 0 |
| 105 g ae/ha glyphosate | 0 | 3 | 1 | 40.0 | 14.1 | 30-60 |
| 420 g ae/ha glyphosate | 0 | 4 | 0 | 30.0 | 0.0 | 30 |
| 1680 g ae/ha glyphosate | 0 | 3 | 1 | 55.0 | 30.0 | 40-100 |
| 3360 g ae/ha glyphosate | 0 | 0 | 4 | 57.5 | 8.7 | 45-65 |
| Non-transformed control | | | | | | |
| 0 g ae/ha glyphosate | 4 | 0 | 0 | 0.0 | 0.0 | 0 |
| 105 g ae/ha glyphosate | 0 | 0 | 4 | 100.0 | 0.0 | 100 |
| 420 g ae/ha glyphosate | 0 | 0 | 4 | 100.0 | 0.0 | 100 |
| 1680 g ae/ha glyphosate | 0 | 0 | 4 | 100.0 | 0.0 | 100 |
| 3360 g ae/ha glyphosate | 0 | 0 | 4 | 100.0 | 0.0 | 100 |

Selected $T_1$ *Arabidopsis* plants which were identified to contain low-copy numbers of transgene insertions (1-3 copies) were self-fertilized to produce a second generation for additional assessment of glyphosate tolerance. The second generation *Arabidopsis* plants ($T_2$) which contained 1-3 copies of the dgt-14 transgene were further characterized for glyphosate tolerance and glufosinate tolerance (glufosinate resistance indicated that the PAT expression cassette was intact and did not undergo rearrangements during the selfing of the $T_1$ plants). In the $T_2$ generation hemizygous and homozygous plants were available for testing for each event and therefore were included for each rate of glyphosate tested. Hemizygous plants contain two different alleles at a locus as compared to homozygous plants which contain the same two alleles at a locus. The copy number and ploidy levels of the $T_2$ plants were confirmed using the molecular analysis protocols previously described. Likewise, glyphosate was applied using the methods and rates as previously described. The dose response of the plants is presented in terms of % visual injury 2 weeks after treatment (WAT). Data are presented as a histogram of individuals exhibiting little or no injury (<20%), moderate injury (20-40%), or severe injury (>40%). An arithmetic mean and standard deviation are presented for each construct used for *Arabidopsis* transformation. The range in individual response is also indicated in the last column for each rate and transformation. Wildtype, non-transformed *Arabidopsis* (cv. Columbia) served as a glyphosate sensitive control. In addition, plants comprising a glyphosate herbicide resistance gene, dgt-1 (as described in U.S. patent Ser. No. 12/558,351, incorporated herein by reference in its entirety) were included as a positive control.

In the $T_2$ generation both single copy and low-copy (two or three copy) dgt-14 events were characterized for glyphosate tolerance. An overall population injury average by rate is presented in Table 7 to demonstrate the tolerance provided by each of the dgt-14 constructs linked with a chloroplast transit peptide versus the dgt-1 and non-transformed wild-type controls for varying rates of glyphosate. The $T_2$ generation events contained dgt-14 linked with TraP8 v2 (pDAB105526), TraP9 v2 (pDAB105527), TraP12 v2 (pDAB105528) and TraP13 v2 (pDAB105529). All of these Events are highly resistant to glyphosate. The results indicated that the injury range for the $T_2$ *Arabidopsis* plants was less than 20% for all concentrations of glyphosate that were tested. $T_2$ Arabidopsis Events containing dgt-14 linked with TraP4 v5 (pDAB107526), TraP5 v2 (pDAB105525), and TraP5 v1 (pDAB102787) did not provide robust tolerance to glyphosate as compared to the other dgt-14 constructs which contained other TraP transit peptides. However, the dgt-14 constructs linked with TraP4 v5 (pDAB107526), TraP5 v2 (pDAB105525), and TraP5 v1 (pDAB102787) did provide a low level of glyphosate tolerance that was significantly higher as compared to the non-transformed control. Overall, the results showed that plants containing and expressing DGT-14 yielded commercial level resistance to glyphosate at levels of up to 3 times the field rate (1120 g ae/ha).

TABLE 7 dgt-14 transformed $T_2$ Arabidopsis response to a range of glyphosate rates applied postemergence, compared to a dgt-1 ($T_2$) segregating population, and a non-transformed control. Visual % injury 2 weeks after application. Data represents a selected single copy line from each construct that segregated as a single locus in the heritability screen.

| Application Rate | % Injury Range (No. Replicates) | | | % Injury Analysis | | |
|---|---|---|---|---|---|---|
| | <20% | 20-40% | >40% | Ave | Std dev | Range (%) |
| TraP4 v5::dgt-14 (pDAB107526) | | | | | | |
| 0 g ae/ha glyphosate | 4 | 0 | 0 | 0.0 | 0.0 | 0 |
| 420 g ae/ha glyphosate | 0 | 0 | 4 | 85.0 | 0.0 | 85 |
| 840 g ae/ha glyphosate | 0 | 0 | 4 | 87.5 | 3.5 | 85-90 |
| 1680 g ae/ha glyphosate | 0 | 0 | 4 | 92.5 | 3.5 | 90-95 |
| 3360 g ae/ha glyphosate | 0 | 0 | 4 | 95.0 | 0.0 | 95 |
| TraP5 v1::dgt-14 (pDAB102787) | | | | | | |
| 0 g ae/ha glyphosate | 4 | 0 | 0 | 0.0 | 0.0 | 0 |
| 420 g ae/ha glyphosate | 0 | 0 | 4 | 90.0 | 0.0 | 90 |
| 840 g ae/ha glyphosate | 0 | 0 | 4 | 90.0 | 0.0 | 90 |
| 1680 g ae/ha glyphosate | 0 | 0 | 4 | 88.8 | 2.5 | 85-90 |
| 3360 g ae/ha glyphosate | 0 | 0 | 4 | 94.5 | 3.3 | 90-98 |
| TraP5 v2::dgt-14 (pDAB105525) | | | | | | |
| 0 g ae/ha glyphosate | 4 | 0 | 0 | 0.0 | 0.0 | 0 |
| 420 g ae/ha glyphosate | 0 | 0 | 4 | 86.3 | 2.5 | 85-90 |
| 840 g ae/ha glyphosate | 0 | 0 | 4 | 90.0 | 4.1 | 85-95 |
| 1680 g ae/ha glyphosate | 0 | 0 | 4 | 90.0 | 7.1 | 85-100 |
| 3360 g ae/ha glyphosate | 0 | 0 | 4 | 97.0 | 2.4 | 95-100 |
| TraP8 v2::dgt-14 (pDAB105526) | | | | | | |
| 0 g ae/ha glyphosate | 4 | 0 | 0 | 0.0 | 0.0 | 0 |
| 420 g ae/ha glyphosate | 4 | 0 | 0 | 0.5 | 1.0 | 0-2 |
| 840 g ae/ha glyphosate | 4 | 0 | 0 | 0.0 | 0.0 | 0 |
| 1680 g ae/ha glyphosate | 4 | 0 | 0 | 2.5 | 2.9 | 0-5 |
| 3360 g ae/ha glyphosate | 4 | 0 | 0 | 5.0 | 4.8 | 0-10 |
| TraP9 v2::dgt-14 (pDAB105527) | | | | | | |
| 0 g ae/ha glyphosate | 4 | 0 | 0 | 0.0 | 0.0 | 0 |
| 420 g ae/ha glyphosate | 4 | 0 | 0 | 0.0 | 0.0 | 0 |
| 840 g ae/ha glyphosate | 4 | 0 | 0 | 0.0 | 0.0 | 0 |
| 1680 g ae/ha glyphosate | 4 | 0 | 0 | 1.8 | 2.4 | 0-5 |
| 3360 g ae/ha glyphosate | 2 | 2 | 0 | 17.5 | 17.6 | 0-35 |
| TraP12 v2::dgt-14 (pDAB105528) | | | | | | |
| 0 g ae/ha glyphosate | 4 | 0 | 0 | 0.0 | 0.0 | 0 |
| 420 g ae/ha glyphosate | 4 | 0 | 0 | 1.8 | 2.4 | 0-5 |
| 840 g ae/ha glyphosate | 4 | 0 | 0 | 2.5 | 2.9 | 0-5 |
| 1680 g ae/ha glyphosate | 4 | 0 | 0 | 2.0 | 4.0 | 0-8 |
| 3360 g ae/ha glyphosate | 4 | 0 | 0 | 3.8 | 4.8 | 0-10 |

TABLE 7-continued dgt-14 transformed $T_2$ Arabidopsis response to a range of glyphosate rates applied postemergence, compared to a dgt-1 ($T_2$) segregating population, and a non-transformed control. Visual % injury 2 weeks after application. Data represents a selected single copy line from each construct that segregated as a single locus in the heritability screen.

| Application Rate | % Injury Range (No. Replicates) | | | % Injury Analysis | | |
|---|---|---|---|---|---|---|
| | <20% | 20-40% | >40% | Ave | Std dev | Range (%) |
| TraP13 v2::dgt-14 (pDAB105529) | | | | | | |
| 0 g ae/ha glyphosate | 4 | 0 | 0 | 0 | 0 | 0 |
| 420 g ae/ha glyphosate | 4 | 0 | 0 | 0 | 0 | 0 |
| 840 g ae/ha glyphosate | 4 | 0 | 0 | 1.3 | 2.5 | 0-5 |
| 1680 g ae/ha glyphosate | 4 | 0 | 0 | 1.8 | 2.4 | 0-5 |
| 3360 g ae/ha glyphosate | 4 | 0 | 0 | 3.8 | 4.8 | 0-10 |
| dgt-1 (pDAB3759) | | | | | | |
| 0 g ae/ha glyphosate | 4 | 0 | 0 | 0.0 | 0.0 | 0 |
| 420 g ae/ha glyphosate | 2 | 0 | 2 | 40.0 | 40.4 | 5-75 |
| 840 g ae/ha glyphosate | 0 | 2 | 2 | 47.5 | 31.8 | 20-75 |
| 1680 g ae/ha glyphosate | 0 | 2 | 2 | 41.3 | 23.9 | 20-70 |
| 3360 g ae/ha glyphosate | 0 | 4 | 0 | 35.0 | 0.0 | 35 |
| Non-transformed control | | | | | | |
| 0 g ae/ha glyphosate | 4 | 0 | 0 | 0.0 | 0.0 | 0 |
| 420 g ae/ha glyphosate | 0 | 0 | 4 | 100.0 | 0.0 | 100 |
| 840 g ae/ha glyphosate | 0 | 0 | 4 | 100.0 | 0.0 | 100 |
| 1680 g ae/ha glyphosate | 0 | 0 | 4 | 100.0 | 0.0 | 100 |
| 3360 g ae/ha glyphosate | 0 | 0 | 4 | 100.0 | 0.0 | 100 |

Randomly selected $T_2$ Arabidopsis plants which were identified to contain low-copy numbers of transgene insertions (1-3 copies) were self-fertilized to produce a third generation for additional assessment of glyphosate tolerance. Arabidopsis seed from the third generation ($T_3$) were planted and evaluated for glyphosate tolerance using the same protocols as previously described. The Events tested in the $T_3$ generation contained replicates from each line that were homozygous (as determined by using a glufosinate resistance screen to identify if any of the advanced plants showed segregation of the transgenes). These Events were assayed via LC-MS-MS to confirm that the plants expressed the DGT-14 protein. The results of the $T_3$ generation for overall population injury average by rate of glyphosate is presented in Table 8 which shows the tolerance to glyphosate provided by each of the dgt-14 constructs for varying rates of glyphosate. Exemplary resistant $T_3$ Events comprised dgt-14 linked with TraP8 v2 (pDAB105526), TraP9 v2 (pDAB105527), TraP12 v2 (pDAB105528) and TraP13 v2 (pDAB105529). All of these Events are highly resistant to glyphosate. The results indicated that the injury range for the $T_3$ Arabidopsis plants was less than 20% for all concentrations of glyphosate that were tested. $T_3$ Arabidopsis Events containing dgt-14 linked with TraP5 v2 (pDAB105525), and TraP5 v1 (pDAB102787) did not provide robust tolerance to glyphosate as compared to the other dgt-14 constructs which contained different TraP transit peptides. However, the dgt-14 constructs linked with TraP5 v2 (pDAB105525), and TraP5 v1 (pDAB102787) did provide a low level of glyphosate tolerance that was significantly higher as compared to the non-transformed control. Overall, the results showed that plants containing and expressing DGT-14 yielded commercial level resistance to glyphosate at levels of up to 3 times the field rate (1120 g ae/ha).

TABLE 8 dgt-14 transformed T$_3$ Arabidopsis response to a range of glyphosate rates applied postemergence, compared to a dgt-1 (T$_2$) segregating population, and a non-transformed control. Visual % injury 2 weeks after application. Data represents a selected single copy population from each construct that segregated as a single locus in the T$_2$ heritability screen.

| Application Rate | % Injury Range (No. Replicates) | | | % Injury Analysis | | |
|---|---|---|---|---|---|---|
| | <20% | 20-40% | >40% | Ave | Std dev | Range (%) |
| TraP5 v1::dgt-14 (pDAB102787) | | | | | | |
| 0 g ae/ha glyphosate | 4 | 0 | 0 | 0.0 | 0.0 | 0 |
| 420 g ae/ha glyphosate | 0 | 0 | 4 | 85.0 | 4.1 | 80-90 |
| 840 g ae/ha glyphosate | 0 | 0 | 4 | 86.3 | 2.5 | 85-90 |
| 1680 g ae/ha glyphosate | 0 | 0 | 4 | 93.7 | 4.8 | 90-100 |
| 3360 g ae/ha glyphosate | 0 | 0 | 4 | 93.7 | 4.8 | 90-100 |
| TraP5 v2::dgt-14 (pDAB105525) | | | | | | |
| 0 g ae/ha glyphosate | 4 | 0 | 0 | 0.0 | 0.0 | 0 |
| 420 g ae/ha glyphosate | 0 | 0 | 4 | 93.3 | 3.9 | 90-98 |
| 840 g ae/ha glyphosate | 0 | 0 | 4 | 97.5 | 3.8 | 92-100 |
| 1680 g ae/ha glyphosate | 0 | 0 | 4 | 93.0 | 2.5 | 90-95 |
| 3360 g ae/ha glyphosate | 0 | 0 | 4 | 91.7 | 2.4 | 90-95 |
| TraP8 v2::dgt-14 (pDAB105526) | | | | | | |
| 0 g ae/ha glyphosate | 4 | 0 | 0 | 0.0 | 0.0 | 0 |
| 420 g ae/ha glyphosate | 4 | 0 | 0 | 0.0 | 0.0 | 0 |
| 840 g ae/ha glyphosate | 4 | 0 | 0 | 1.3 | 2.5 | 0-5 |
| 1680 g ae/ha glyphosate | 4 | 0 | 0 | 0.0 | 0.0 | 0 |
| 3360 g ae/ha glyphosate | 4 | 0 | 0 | 4.0 | 4.0 | 2-10 |
| TraP9 v2::dgt-14 (pDAB105527) | | | | | | |
| 0 g ae/ha glyphosate | 4 | 0 | 0 | 0.0 | 0.0 | 0 |
| 420 g ae/ha glyphosate | 4 | 0 | 0 | 0.0 | 0.0 | 0 |
| 840 g ae/ha glyphosate | 4 | 0 | 0 | 0.0 | 0.0 | 0 |
| 1680 g ae/ha glyphosate | 4 | 0 | 0 | 0.0 | 0.0 | 0 |
| 3360 g ae/ha glyphosate | 4 | 0 | 0 | 4.3 | 1.5 | 2-5 |
| TraP12 v2::dgt-14 (pDAB105528) | | | | | | |
| 0 g ae/ha glyphosate | 4 | 0 | 0 | 0.0 | 0.0 | 0 |
| 420 g ae/ha glyphosate | 4 | 0 | 0 | 0.0 | 0.0 | 0 |
| 840 g ae/ha glyphosate | 4 | 0 | 0 | 0.0 | 0.0 | 0 |
| 1680 g ae/ha glyphosate | 4 | 0 | 0 | 2.5 | 5.0 | 0-10 |
| 3360 g ae/ha glyphosate | 4 | 0 | 0 | 4.8 | 2.1 | 2-7 |
| TraP13 v2::dgt-14 (pDAB105529) | | | | | | |
| 0 g ae/ha glyphosate | 4 | 0 | 0 | 0.0 | 0.0 | 0 |
| 420 g ae/ha glyphosate | 4 | 0 | 0 | 0.0 | 0.0 | 0 |
| 840 g ae/ha glyphosate | 4 | 0 | 0 | 0.0 | 0.0 | 0 |
| 1680 g ae/ha glyphosate | 4 | 0 | 0 | 0.0 | 0.0 | 0 |
| 3360 g ae/ha glyphosate | 4 | 0 | 0 | 1.8 | 2.4 | 0-5 |
| dgt-1 (pDAB3759) | | | | | | |
| 0 g ae/ha glyphosate | 4 | 0 | 0 | 0.0 | 0.0 | 0 |
| 420 g ae/ha glyphosate | 0 | 2 | 2 | 42.5 | 9.6 | 30-50 |
| 840 g ae/ha glyphosate | 0 | 4 | 0 | 40.0 | 0.0 | 40 |
| 1680 g ae/ha glyphosate | 0 | 3 | 1 | 47.5 | 15.0 | 40-70 |
| 3360 g ae/ha glyphosate | 0 | 0 | 4 | 77.5 | 17.1 | 60-100 |
| Non-transformed control | | | | | | |
| 0 g ae/ha glyphosate | 4 | 0 | 0 | 0.0 | 0.0 | 0 |
| 420 g ae/ha glyphosate | 0 | 0 | 4 | 100.0 | 0.0 | 100 |
| 840 g ae/ha glyphosate | 0 | 0 | 4 | 100.0 | 0.0 | 100 |
| 1680 g ae/ha glyphosate | 0 | 0 | 4 | 100.0 | 0.0 | 100 |
| 3360 g ae/ha glyphosate | 0 | 0 | 4 | 100.0 | 0.0 | 100 |

Dgt-14 as a Selectable Marker

The use of dgt-14 as a selectable marker for glyphosate selection agent is tested with the Arabidopsis transformed plants described above. Approximately 50 T$_4$ generation Arabidopsis seed (homozygous for dgt-14) are spiked into approximately 5,000 wildtype (sensitive to glyphosate) seed. The seeds are germinated and plantlets are sprayed with a selecting dose of glyphosate. Several treatments of glyphosate are compared; each tray of plants receives either one or two application timings of glyphosate in one of the following treatment schemes: 7 DAP (days after planting), 11 DAP, or 7 followed by 11 DAP. Since all plants also contain a glufosinate resistance gene in the same transformation vector, dgt-14 containing plants selected with glyphosate can be directly compared to DSM-2 or pat containing control plants selected with glufosinate.

Glyphosate treatments are applied with a DeVilbiss spray tip as previously described. Transgenic plants containing dgt-14 are identified as "resistant" or "sensitive" 17 DAP. Treatments of 26.25-1680 g ae/ha glyphosate applied 7 and 11 days after planting (DAP), show effective selection for transgenic Arabidopsis plants that contain dgt-14. Sensitive and resistant plants are counted and the number of glyphosate tolerant plants is found to correlate with the original number of transgenic seed containing the dgt-14 transgene which are planted. These results indicate that dgt-14 can be effectively used as an alternative selectable marker for a population of transformed Arabidopsis.

Heritability of Dgt-14

Confirmed transgenic T$_1$ Arabidopsis events were self-pollinated to produce T$_2$ seed. These seed were progeny tested by applying Ignite™ herbicide containing glufosinate (200 g ae/ha) to 100 random T$_2$ siblings. Each individual T$_2$ plant was transplanted to 7.5-cm square pots prior to spray application (track sprayer at 187 L/ha applications rate). The T$_1$ families (T$_2$ plants) segregated in the anticipated 3 Resistant: 1 Sensitive model for a dominantly inherited single locus with Mendelian inheritance as determined by Chi square analysis (P>0.05). The percentage of T$_1$ families that segregated with the expected Mendelian inheritance are illustrated in Table 9, and demonstrate that the dgt-14 trait is passed via Mendelian inheritance to the T$_2$ generation. Seed were collected from 5 to 15 T$_2$ individuals (T$_3$ seed). Twenty-five T$_3$ siblings from each of 3-4 randomly-selected T$_2$ families were progeny tested as previously described. Data showed no segregation and thus demonstrated that dgt-14 is stably integrated within the chromosome and inherited in a Mendelian fashion to at least three generations.

TABLE 9

Percentage of T$_1$ families (T$_2$ plants) segregating as single Mendelian inheritance for a progeny test of 100 plants.

| Gene of Interest | T$_1$ Families Tested Segregating at 1 Locus (%) |
|---|---|
| TraP4 v2 - dgt-14 | 80% |
| TraP5 v1 - dgt-14 | 80% |
| TraP5 v2 - dgt-14 | 75% |
| TraP8 v2 - dgt-14 | 100% |
| TraP9 v2 - dgt-14 | 100% |
| TraP12 v2 - dgt-14 | 100% |
| TraP13 v2 - dgt-14 | 50% |
| yfp Transgenic Control | 100% |

Example 8: Transformation of Additional Crop Species

Soybean may be transformed with dgt-14, dgt-11, dgt-12, dgt-18, dgt-29, or dgt-30 genes to provide high levels of resistance to the herbicide glyphosate by utilizing the same techniques previously described in Example #11 or Example #13 of WO 2007/053482.

Cotton may be transformed with dgt-14, dgt-11, dgt-12, dgt-18, dgt-29, or dgt-30 genes to provide high levels of resistance to the herbicide glyphosate by utilizing the same techniques previously described in Examples #14 of U.S. Pat. No. 7,838,733 or Example #12 of WO 2007/053482 (Wright et al.).

Canola may be transformed with dgt-14, dgt-11, dgt-12, dgt-18, dgt-29, or dgt-30 genes to provide high levels of resistance to the herbicide glyphosate by utilizing the same techniques previously described in Example #26 of U.S. Pat. No. 7,838,733 or Example #22 of WO 2007/053482 (Wright et al.).

Example 9: *Agrobacterium*-Mediated Transformation of Other Crops

In light of the subject disclosure, additional crops can be transformed according to embodiments of the subject disclosure using techniques that are known in the art. For *Agrobacterium*-mediated transformation of rye, see, e.g., Popelka J C, Xu J, Altpeter F., "Generation of rye with low transgene copy number after biolistic gene transfer and production of (*Secale cereale* L.) plants instantly marker-free transgenic rye," *Transgenic Res.* 2003 October; 12(5): 587-96.). For *Agrobacterium*-mediated transformation of sorghum, see, e.g., Zhao et al., "*Agrobacterium*-mediated sorghum transformation," *Plant Mol. Biol.* 2000 December; 44(6):789-98. For *Agrobacterium*-mediated transformation of barley, see, e.g., Tingay et al., "*Agrobacterium tumefaciens*-mediated barley transformation," *The Plant Journal*, (1997) 11: 1369-1376. For *Agrobacterium*-mediated transformation of wheat, see, e.g., Cheng et al., "Genetic Transformation of Wheat Mediated by *Agrobacterium tumefaciens*," *Plant Physiol.* 1997 November; 115 (3): 971-980. For *Agrobacterium*-mediated transformation of rice, see, e.g., Hiei et al., "Transformation of rice mediated by *Agrobacterium tumefaciens*," *Plant Mol. Biol.* 1997 September; 35 (1-2):205-18.

The latin names for these and other plants are given below. It should be clear that other (non-*Agrobacterium*) transformation techniques can be used to transform dgt-14, for example, into these and other plants. Examples include, but are not limited to; Maize (*Zea mays*), Wheat (*Triticum* spp.), Rice (*Oryza* spp. and *Zizania* spp.), Barley (*Hordeum* spp.), Cotton (*Abroma augusta* and *Gossypium* spp.), Soybean (*Glycine max*), Sugar and table beets (*Beta* spp.), Sugar cane (*Arenga pinnata*), Tomato (*Lycopersicon esculentum* and other spp., *Physalis ixocarpa, Solanum incanum* and other spp., and *Cyphomandra betacea*), Potato (*Solanum tuberosum*), Sweet potato (*Ipomoea batatas*), Rye (*Secale* spp.), Peppers (*Capsicum annuum, chinense*, and *frutescens*), Lettuce (*Lactuca sativa, perennis*, and *pulchella*), Cabbage (*Brassica* spp.), Celery (*Apium graveolens*), Eggplant (*Solanum melongena*), Peanut (*Arachis hypogea*), Sorghum (*Sorghum* spp.), Alfalfa (*Medicago sativa*), Carrot (*Daucus carota*), Beans (*Phaseolus* spp. and other genera), Oats (*Avena sativa* and *strigosa*), Peas (Pisum, *Vigna*, and *Tetragonolobus* spp.), Sunflower (*Helianthus annuus*), Squash (*Cucurbita* spp.), Cucumber (*Cucumis sativa*). Tobacco (*Nicotiana* spp.), *Arabidopsis* (*Arabidopsis thaliana*), Turfgrass (*Lolium, Agrostis, Poa, Cynodon*, and other genera), Clover (*Trifolium*), Vetch (*Vicia*). Transformation of such plants, with dgt-14, dgt-11, dgt-12, dgt-18, dgt-29, and dgt-30 genes, for example, is contemplated in embodiments of the subject disclosure.

Dgt-14, dgt-11, dgt-12, dgt-18, dgt-29, and dgt-30 genes have the potential to increase the applicability of key glyphosate herbicides for in-season use in many deciduous and evergreen timber cropping systems. Glyphosate herbicide resistant timber species would increase the flexibility of over-the-top use of these herbicides without injury concerns. These species include, but are not limited to; alder (*Alnus* spp.), ash (*Fraxinus* spp.), aspen and poplar species (*Populus* spp.), beech (*Fagus* spp.), birch (*Betula* spp.), cherry (*Prunus* spp.), eucalyptus (*Eucalyptus* spp.), hickory (*Carya* spp.), maple (*Acer* spp.), oak (*Quercus* spp.), and pine (*Pinus* spp.).

Use of glyphosate herbicide resistance for the selective weed control in ornamental and fruit-bearing species is also within the scope of embodiments of this disclosure. Examples include, but are not limited to; rose (*Rosa* spp.), burning bush (*Euonymus* spp.), petunia (*Petunia* spp.), begonia (*Begonia* spp.), rhododendron (*Rhododendron* spp.), crabapple or apple (*Malus* spp.), pear (*Pyrus* spp.), peach (*Prunus* spp.), and marigolds (*Tagetes* spp.).

Example 10: Maize Transformation

DNA Constructs for Maize Transformation

Standard cloning methods, as described above, are used in the construction of binary vectors for use in *Agrobacterium tumefaciens*-mediated transformation of maize. The following gene elements are used in the vectors which contain dgt-14; the *Zea mays* Ubiquitin 1 promoter (ZmUbi1; U.S. Pat. No. 5,510,474) is used to drive the dgt-14 coding sequence which is flanked by a *Zea mays* Lipase 3' untranslated region (ZmLip 3'UTR; U.S. Pat. No. 7,179,902), the selectable marker cassette consists of the *Zea mays* Ubiquitin 1 promoter which is used to drive the aad-1 coding sequence (U.S. Pat. No. 7,838,733) which is flanked by a *Zea mays* Lipase 3' untranslated region. The aad-1 coding sequence confers tolerance to the phenoxy auxin herbicides, such as, 2,4-dichlorophenoxyacetic acid (2,4-D) and to aryloxyphenoxypropionate (AOPP) herbicides. The dgt-14 constructs are built as standard binary vectors and *Agrobacterium* superbinary system vectors (Japan Tobacco, Tokyo, JP).

Ear Sterilization and Embryo Isolation

To obtain maize immature embryos, plants of the *Zea mays* inbred line B104 are grown in the greenhouse and are self or sib-pollinated to produce ears. The ears are harvested approximately 9-12 days post-pollination. On the experimental day, ears are surface-sterilized by immersion in a 20% solution of sodium hypochlorite (5%) and shaken for 20-30 minutes, followed by three rinses in sterile water. After sterilization, immature zygotic embryos (1.5-2.4 mm) are aseptically dissected from each ear and randomly distributed into micro-centrifuge tubes containing liquid infection media (LS Basal Medium, 4.43 gm/L; N6 Vitamin Solution [1000×], 1.00 mL/L; L-proline, 700.0 mg/L; Sucrose, 68.5 gm/L; D(+) Glucose, 36.0 gm/L; 10 mg/ml of 2,4-D, 150 µL/L). For a given set of experiments, pooled embryos from three ears are used for each transformation.

*Agrobacterium* Culture Initiation:

Glycerol stocks of *Agrobacterium* containing the binary transformation vectors described above are streaked on AB minimal medium plates containing appropriate antibiotics and are grown at 20° C. for 3-4 days. A single colony is picked and streaked onto YEP plates containing the same antibiotics and is incubated at 28° C. for 1-2 days.

Agrobacterium Culture and Co-Cultivation:

Agrobacterium colonies are taken from the YEP plate, suspended in 10 mL of infection medium in a 50 mL disposable tube, and the cell density is adjusted to O.D.600 nm of 0.2-0.4 using a spectrophotometer. The *Agrobacterium* cultures are placed on a rotary shaker at 125 rpm, room temperature, while embryo dissection is performed. Immature zygotic embryos between 1.5-2.4 mm in size are isolated from the sterilized maize kernels and placed in 1 mL of the infection medium) and washed once in the same medium. The *Agrobacterium* suspension (2 mL) is added to each tube and the tubes are placed on a shaker platform for 10-15 minutes. The embryos are transferred onto co-cultivation media (MS Salts, 4.33 gm/L; L-proline, 700.0 mg/L; Myo-inositol, 100.0 mg/L; Casein enzymatic hydrolysate 100.0 mg/L; 30 mM Dicamba-KOH, 3.3 mg/L; Sucrose, 30.0 gm/L; Gelzan™, 3.00 gm/L; Modified MS-Vitamin [1000×], 1.00 ml/L; 8.5 mg/ml AgNo$_3$, 15.0 mg/L; DMSO, 100 µM), oriented with the scutellum facing up and incubated at 25° C., under 24-hour light at 50 mmole m$^{-2}$ sec$^{-1}$ light intensity for 3 days.

Callus Selection and Regeneration of Putative Events

Following the co-cultivation period, embryos are transferred to resting media (MS Salts, 4.33 gm/L; L-proline, 700.0 mg/L; 1,2,3,5/4,6-Hexahydroxycyclohexane, 100 mg/L; MES [(2-(n-morpholino)-ethanesulfonic acid), free acid] 0.500 gm/L; Casein enzymatic hydrolysate 100.0 mg/L; 30 mM Dicamba-KOH, 3.3 mg/L; Sucrose, 30.0 gm/L; Gelzan 2.30 gm/L; Modified MS-Vitamin [1000×], 1.00 ml/L; 8.5 mg/ml AgNo3, 15.0 mg/L; Carbenicillin, 250.0 mg/L) without selective agent and incubated under 24-hour light at 50 µmole m-2 sec-1 light intensity and at 25° C. for 3 days. Growth inhibition dosage response experiments suggested that glyphosate concentrations of 0.25 mM and higher are sufficient to inhibit cell growth in the untransformed B104 maize line. Embryos are transferred onto Selection 1 media containing 0.5 mM glyphosate (MS Salts, 4.33 gm/L; L-proline, 700.0 mg/L; Myo-inositol, 100.0 mg/L; MES [(2-(n-morpholino)-ethanesulfonic acid), free acid] 0.500 gm/L; Casein enzymatic hydrolysate 100.0 mg/L; 30 mM Dicamba-KOH, 3.3 mg/L; Sucrose, 30.0 gm/L; Gelzan™ 2.30 gm/L; Modified MS-Vitamin [1000×], 1.00 ml/L; 8.5 mg/ml AgNo3, 15.0 mg/L; Carbenicillin, 250.0 mg/L) and incubated in either dark and/or under 24-hour light at 50 µmole m-2 sec-1 light intensity for 7-14 days at 28° C. Proliferating embryogenic calli are transferred onto Selection 2 media containing 1.0 mM glyphosate (MS Salts, 4.33 gm/L; 1,2,3,5/4,6-Hexahydroxycyclohexane, 100 mg/L; L-proline, 700.0 mg/L; MES [(2-(n-morpholino)-ethanesulfonic acid, free acid] 0.500 gm/L; Casein enzymatic hydrolysate 100.0 mg/L; 30 mM Dicamba-KOH, 3.3 mg/L; Sucrose, 30.0 gm/L; Gelzan™ 2.30 gm/L; Modified MS-Vitamin [1000×], 1.00 ml/L; 8.5 mg/ml AgNo3, 15.0 mg/L; Carbenicillin, 250.0 mg/L; R-Haloxyfop acid 0.1810 mg/L), and are incubated in either dark and/or under 24-hour light at 50 µmole m-2 sec-1 light intensity for 14 days at 28° C. This selection step allowed transgenic callus to further proliferate and differentiate. The callus selection period lasts for three to four weeks. Proliferating, embryogenic calli are transferred onto PreReg media containing 0.5 mM glyphosate (MS Salts, 4.33 gm/L; 1,2,3,5/4,6-Hexahydroxycyclohexane, 100 mg/L; L-proline, 350.0 mg/L; MES [(2-(n-morpholino)-ethanesulfonic acid), free acid] 0.250 gm/L; Casein enzymatic hydrolysate 50.0 mg/L; NAA-NaOH 0.500 mg/L; ABA-EtOH 2.50 mg/L; BA 1.00 mg/L; Sucrose, 45.0 gm/L; Gelzan™ 2.50 gm/L; Modified MS-Vitamin [1000×], 1.00 ml/L; 8.5 mg/ml AgNo3, 1.00 mg/L; Carbenicillin, 250.0 mg/L) and cultured under 24-hour light at 50 µmole m-2 sec-1 light intensity for 7 days at 28° C. Embryogenic calli with shoot-like buds are transferred onto Regeneration media containing 0.5 mM glyphosate (MS Salts, 4.33 gm/L; 1,2,3,5/4,6-Hexahydroxycyclohexane, 100.0 mg/L; Sucrose, 60.0 gm/L; Gellan Gum G434™ 3.00 gm/L; Modified MS-Vitamin [1000×], 1.00 ml/L; Carbenicillin, 125.0 mg/L) and cultured under 24-hour light at 50 µmole m-2 sec-1 light intensity for 7 days. Small shoots with primary roots are transferred to rooting media (MS Salts, 4.33 gm/L; Modified MS-Vitamin [1000×], 1.00 ml/L; 1,2,3,5/4,6-Hexahydroxycyclohexane, 100 mg/L; Sucrose, 60.0 gm/L; Gellan Gum G434™ 3.00 gm/L; Carbenicillin, 250.0 mg/L) in phytotrays and are incubated under 16/8 hr. light/dark at 140-190 µmole m-2 sec-1 light intensity for 7 days at 27° C. Putative transgenic plantlets are analyzed for transgene copy number using the protocols described above and transferred to soil.

Molecular Confirmation of the Presence of the Dgt-14 and Aad-1 Transgenes within Maize Plants The presence of the dgt-14 and aad-1 polynucleotide sequences are confirmed via hydrolysis probe assays. Isolated $T_0$ maize plants are initially screened via a hydrolysis probe assay, analogous to TAQMAN™, to confirm the presence of a aad-1 and dgt-14 transgenes. The data generated from these studies are used to determine the transgene copy number and used to select transgenic maize events for back crossing and advancement to the $T_1$ generation.

Tissue samples are collected in 96-well plates, tissue maceration is performed with a KLECO™ tissue pulverizer and stainless steel beads (Hoover Precision Products, Cumming, Ga.), in QIAGEN™ RLT buffer. Following tissue maceration, the genomic DNA is isolated in high-throughput format using the BIOSPRINT 96™ Plant kit (Qiagen, Germantown, Md.) according to the manufacturer's suggested protocol. Genomic DNA is quantified by QUANT IT PICO GREEN DNA ASSAY KIT™ (Molecular Probes, Invitrogen, Carlsbad, Calif.). Quantified genomic DNA is adjusted to around 2 ng/µL for the hydrolysis probe assay using a BIOROBOT3000™ automated liquid handler (Qiagen, Germantown, Md.). Transgene copy number determination by hydrolysis probe assay, analogous to TAQMAN® assay, is performed by real-time PCR using the LIGHTCYCLER®480 system (Roche Applied Science, Indianapolis, Ind.). Assays are designed for aad-1, dgt-14 and an internal reference gene Invertase (Genbank Accession No: U16123.1) using the LIGHTCYCLER® Probe Design Software 2.0. For amplification, LIGHTCYCLER®480 Probes Master mix (Roche Applied Science, Indianapolis, Ind.) is prepared at 1× final concentration in a 10 µL volume multiplex reaction containing 0.4 µM of each primer for aad-1 and dgt-14 and 0.2 µM of each probe. A two-step amplification reaction is performed with an extension at 60° C. for 40 seconds with fluorescence acquisition. All samples are run and the averaged Cycle threshold (Ct) values are used for analysis of each sample. Analysis of real time PCR data is performed using LightCycler® software release 1.5 using the relative quant module and is based on the ΔΔCt method. Controls included a sample of genomic DNA from a single copy calibrator and known two copy check that are included in each run.

Postemergence Herbicide Tolerance in Dgt-14 Transformed $T_0$ Corn $T_0$ events are allowed to acclimate in the greenhouse and are grown until two to four new, normal looking leaves emerge from the whorl (i.e., plants that transition from tissue culture to greenhouse growing conditions). Plants are grown at 27° C. under 16 hour light:8 hour dark conditions in the greenhouse. The plants are then treated with commercial formulations of Durango DMA™ (containing the herbicide glyphosate) with the addition of 2% w/v ammonium-sulfate. Herbicide applications are made with a track sprayer at a spray volume of 187 L/ha, 50-cm spray height. $T_0$ plants are sprayed with a range of glyphosate from 280-4480 g ae/ha glyphosate, which is capable of significant injury to untransformed corn lines. A lethal dose is defined as the rate that causes >95% injury to the B104 inbred.

The results of the $T_0$ dgt-14 corn plants demonstrates that tolerance to glyphosate is achieved at rates up to 4480 g ae/ha. Selected $T_0$ plants are selfed or backcrossed for further characterization in the next generation. Additional experiments include a 100 plant progeny test which is conducted on chosen dgt-14 lines containing the $T_1$ plants. All plants are sprayed with 140-1120 g ae/ha glufosinate or 105-1680 g ae/ha glyphosate as previously described. Both the selectable marker and glyphosate resistant gene are constructed on the same plasmid. Therefore, if one herbicide tolerant gene is selected for by spraying with an herbicide, both genes are believed to be present. At fourteen DAT, resistant and sensitive plants are counted to determine the percentage of lines that segregated as a single locus, dominant Mendelian trait (3R:1S) as determined by Chi square analysis. These data demonstrate that dgt-14 is inheritable as a robust glyphosate resistance gene in a monocot species. Increased rates of glyphosate are applied to the $T_1$ or $F_1$ survivors to further characterize the tolerance and protection which is provided by the dgt-14 gene.

Postemergence Herbicide Tolerance Use of Glyphosate as a Selectable Marker

As previously described, $T_0$ transformed plants are moved from tissue culture and acclimated in the greenhouse. The events tested contain dgt-14 linked to several different chloroplast transit peptides. It is demonstrated that these $T_0$ plants provide robust tolerance up to 4480 g ae/ha glyphosate, and non-transformed plants are controlled with glyphosate at concentrations as low as 280 g ae/ha. These data demonstrate that dgt-14 can be utilized as a selectable marker using a concentration of glyphosate ranging from 280-4480 g ae/ha.

Another embodiment includes spiking a set number of seed from fixed lines of corn which contain the dgt-14 transgene into a set number of non-transformed corn seed. The seed are planted and allowed to grow to the V1-V3 developmental stage at which time the plantlets are sprayed with a selecting dose of glyphosate in the range of 280-4480 g ae/ha. Following 7-10 days, sensitive and resistant plants are counted and the amount of glyphosate tolerant plants is found to correlate with the original number of transgenic seed containing the dgt-14 transgene which are planted.

Example 11: Stacking with Other Traits

Transgenic crops containing insect resistance (IR) traits are prevalent in corn, soybean, and cotton plants throughout North America, and usage of these traits is expanding worldwide. Commercial transgenic crops combining insect resistant and herbicide tolerant (HT) traits have been developed by multiple seed companies. These include *Bacillus thuringiensis* traits (e.g. Bt toxins listed at the website lifesci.sussex.ac.uk, 2006), non-Bt insect resistance traits, and any or all of the HT traits mentioned above. The ability to control multiple pest problems through IR traits is a valuable commercial product concept. However, the convenience of this product concept will be restricted if weed control and insect control are independent of one another. Dgt-14, alone or stacked with one or more additional HT traits, can be stacked with one or more additional input traits (e.g., insect resistance, fungal resistance, or stress tolerance, et al) (see www.isb. vt.edu) either through conventional breeding or jointly as a novel transformation event. Exemplary IR traits can be stacked with dgt-14. Upon obtaining a coding sequence of an IR trait, one skilled in the art would add expression elements (e.g. promoter, intron, 3'UTR, etc.) and molecularly stack the IR trait with dgt-14 via recombinant DNA methodologies. Exemplary IR trait candidates include; Cry1F (U.S. Pat. Nos. 5,126,133; 5,188,960; 5,691,308; 6,096,708; 6,573,240; and 6,737,273), Cry1A(c) (U.S. Pat. Nos. 6,114,138; 5,710,020; 6,251,656; and 6,229,004), Cry1F and Cry1A(c) as a triple stack with either dgt-14, Cry34Ab(1) (U.S. Pat. Nos. 7,323,556; 7,897,342; 7,888,495; 7,875,430; 7,932,033; 7,956,246; 6,340,593), Cry35 Ab(1) (U.S. Pat. Nos. 6,340,593; 7,323,556; 7,897,342; 7,888,495; 7,875,430; 7,932,033; 7,956,246), or Cry35Ab (1) and Cry 34Ab(1) as a triple stack with either dgt-14. Benefits include the improved weed control offered by dgt-14 and described in previous examples linked with the ability to manage insect pests and/or other agronomic stresses. Thus, embodiments of the subject disclosure can be used to provide a complete agronomic package of improved crop quality with the ability to flexibly and cost effectively control any number of agronomic issues.

Combined IR and HT traits have application in most agronomic and horticultural/ornamental crops and forestry. The combination of dgt-14 and its commensurate herbicide tolerance and insect resistance afforded by any of the number of Bt or non-Bt IR genes can be applied to the crop species listed (but not limited to) in Examples 8 and 9. One skilled in the art of weed control will recognize that use of any of various commercial herbicides described is enabled by dgt-14 transformation and stacking with the corresponding HT trait or IR trait either by conventional breeding or genetic engineering. Specific rates of herbicides representative of these chemistries can be determined by the herbicide labels compiled in the CPR (Crop Protection Reference) book or similar compilation, labels compiled online (e.g., cdms.net/manuf/manuf.asp), or any commercial or academic crop protection guides such as the Crop Protection Guide from Agriliance (2005). Each alternative herbicide enabled for use in HTCs by dgt-14 whether used alone, tank mixed, or sequentially, is considered within the scope of embodiments of this disclosure.

Example 12: DGT-14 Trait Stacked with an AAD Trait in any Crop

By stacking a dgt-14 trait with an aad trait (e.g. aad-1 described in U.S. Pat. No. 7,838,733; or aad-12 described in WO 2007/053482 A2) either through conventional breeding or jointly as a novel transformation event, weed control efficacy, flexibility, and the ability to manage weed shifts and herbicide resistance development can be improved.

Transforming crops with aad-1 allows a grower to selectively apply aryloxyalkanoate herbicides in monocot crops. Such monocot crops will have a higher margin of phenoxy auxin safety. In addition, phenoxy auxins can be selectively applied in dicot crops transformed with aad-1. Transforming crops with aad-12, allows a grower to selectively apply pyridyloxy auxin and aryloxyalkanoate herbicides in dicot crops to control weed species. By stacking dgt-14 with the aad-1 or aad-12 traits, growers are provided a broader spectrum of herbicides for the management of weeds. Moreover, the use of herbicide combinations will result in more flexibility for managing herbicide resistance within weed species.

Several scenarios for improved weed control options can be envisioned where a dgt-14 trait and an aad trait are stacked in any monocot or dicot crop species:

a) Glyphosate can be applied at a standard postemergent application rate (420 to 2160 g ae/ha, preferably 560 to 1120 g ae/ha) for the control of most grass and broadleaf weed species. The dgt-14 trait can provide tolerance at these application rates of glyphosate. For the control of glyphosate resistant broadleaf weeds like *Conyza canadensis* or weeds inherently difficult to control with glyphosate (e.g., *Commelina* spp), 280-2240 g ae/ha (preferably 560-1120 g ae/ha) of 2,4-D can be applied sequentially, tank mixed, or as a premix with glyphosate to provide additional control. Both aad-1 and aad-12 provide tolerance to 2,4-D.

In addition, aad-12 provides tolerance to pyridyloxy auxin herbicides such as triclopyr and fluoroxypyr. The pyridyloxy auxin herbicides can be applied to control glyphosate resistant broadleaf weeds like *Conyza canadensis* and *Commelina* spp. For triclopyr, application rates would typically range from 70-1120 g ae/ha, more typically 140-420 g ae/ha. For fluoroxypyr, application rates would typically range from 35-560 g ae/ha, more typically 70-280 ae/ha.

b) Glyphosate can be applied at a standard postemergent application rate (420 to 2160 g ae/ha, preferably 560 to 1120 g ae/ha) for the control of most grass and broadleaf weed species. For the control of glyphosate resistant grass species like *Lolium rigidum* or *Eleusine indica*, 10-200 g ae/ha (preferably 20-100 g ae/ha) quizalofop can be applied sequentially, tank mixed, or as a premix with glyphosate to provide effective control. Aad-1 provides tolerance to quizalofop. Stacking aad-1 in combination with dgt-14 in crop species would result in crops which are tolerant to the herbicides described above.

c) Glyphosate is efficacious in controlling grass species other than broadleaf weed species. Aad-1 and dgt-14 stacked traits will allow for the application of grass-effective rates of glyphosate (105-840 g ae/ha, more preferably 210-420 g ae/ha). 2,4-D (at 280-2240 g ae/ha, more preferably 560-1120 g ae/ha) can then be applied sequentially, tank mixed, or as a premix with grass-effective rates of glyphosate to provide necessary broadleaf weed control. An AOPP herbicide like quizalofop at 10-200 g ae/ha (preferably 20-100 g ae/ha and more preferably 20-35 g ae/ha), can be used for more robust grass weed control and/or for delaying the development of glyphosate resistant grasses. The low rate of glyphosate will also provide some benefit to the broadleaf weed control; however, primary control will be from the 2,4-D.

d) Likewise, aad-12 and dgt-14 stacked traits will allow for the application of grass-effective rates of glyphosate (105-840 g ae/ha, more preferably 210-420 g ae/ha). 2,4-D (at 280-2240 g ae/ha, more preferably 560-1120 g ae/ha) can then be applied sequentially, tank mixed, or as a premix with grass-effective rates of glyphosate to provide necessary broadleaf weed control. Triclopyr and fluoroxypyr used at rates mentioned above will also be acceptable components in the treatment regimen. The low rate of glyphosate will also provide some benefit to the broadleaf weed control; however, primary control will be from the 2,4-D, triclopyr, or fluoroxypyr.

One skilled in the art of weed control will recognize that use of one or more commercial aryloxy auxin herbicides alone or in combination (sequentially or independently) is enabled by aad-12 transformation into crops. Likewise the use of one or more commercial phenoxy auxin herbicides alone or in combination (sequentially or independently) with one or more commercial AOPP herbicides is enabled by aad-1. Stacking either of these traits with dgt-14 allows for more robust management of weed species. The specific rates of other herbicides representative of these chemistries can be determined by the herbicide labels compiled in the CPR (Crop Protection Reference) book or similar compilation, labels compiled online (e.g., cdms.net/manuf/manuf.asp), or any commercial or academic crop protection guides such as the Crop Protection Guide from Agriliance (2005). Each alternative herbicide enabled for use in HTCs by aad-12, aad-1, or dgt-14 whether used alone, tank mixed, or sequentially, is considered within the scope of embodiments of this disclosure.

Example 13: DGT-14 Stacked with AHAS Trait in any Crop

Traits encoding imidazolinone herbicide tolerance (AHAS) are currently present in a number of crops planted in North America including, but not limited to, corn, rice, sunflower, and wheat. Additional imidazolinone tolerant crops (e.g., cotton and sugar beet) have been under development but have not been commercially released to date. Many imidazolinone herbicides (e.g., imazamox, imazethapyr, imazaquin, and imazapic) are currently used selectively in various conventional crops. The use of imazethapyr, imazamox, and the non-selective imazapyr has been enabled through imidazolinone tolerance traits like AHAS. Imidazolinone tolerant HTCs to date have the advantage of being non-transgenic. This chemistry class also has significant soil residual activity, thus being able to provide weed control that extends beyond the application timing, unlike glyphosate or glufosinate-based systems. However, the spectrum of weeds controlled by imidazolinone herbicides is not as broad as glyphosate (Agriliance, 2003). Additionally, imidazolinone herbicides have a mode of action (inhibition of acetolactate synthase, ALS) to which many weeds have developed resistance (Heap I (2004). The international survey of herbicide resistant weeds, available at www.weedscience.com). By stacking dgt-14 with an imidazolinone tolerance trait, either through conventional breeding or jointly as a novel transformation event, weed control efficacy, flexibility, and ability to manage weed shifts and herbicide resistance development could be improved. As mentioned in previous examples, by transforming crops with dgt-14, one can selectively apply glyphosate herbicides in monocot and dicot crops. Several scenarios for improved weed control options can be envisioned where dgt-14 and an imidazolinone tolerance trait are stacked in any monocot or dicot crop species.

a) Imazethapyr can be applied at a standard postemergent application rate (35 to 280 g ae/ha, preferably 70-140 g ae/ha) for the control of many grass and broadleaf weed species.
   i) ALS-inhibitor resistant broadleaf weeds like *Amaranthus rudis, Ambrosia trifida, Chenopodium album* (among others, Heap, 2004) can be controlled by tank mixing glyphosate at 420 to 2160 g ae/ha, preferably 560 to 1120 g ae/ha.
   ii) Inherently more tolerant broadleaf species to imidazolinone herbicides like *Ipomoea* spp. can also be controlled by tank mixing glyphosate at 420 to 2160 g ae/ha, preferably 560 to 1120 g ae/ha.
  iii) ALS-inhibitor resistant grass weeds like *Sorghum halepense* and *Lolium* spp. can be controlled by tank mixing glyphosate at 420 to 2160 g ae/ha, preferably 560 to 1120 g ae/ha.
  iv) Inherently tolerant grass weed species (e.g., *Agropyron repens*) can also be controlled by tank mixing glyphosate at 420 to 2160 g ae/ha, preferably 560 to 1120 g ae/ha.

One skilled in the art of weed control will recognize that use of any of various commercial imidazolinone herbicides or glyphosate herbicide, alone or in multiple combinations, is enabled by dgt-14 transformation and stacking with any imidazolinone tolerance trait either by conventional breeding or genetic engineering. Specific rates of other herbicides representative of these chemistries can be determined by the herbicide labels compiled in the CPR (Crop Protection Reference) book or similar compilation, labels compiled online (e.g., cdms.net/manuf/manuf.asp), or any commercial or academic crop protection guides such as the Crop Protection Guide from Agriliance (2005). Each alternative herbicide enabled for use in HTCs by dgt-14 and ALS-tolerant trait whether used alone, tank mixed, or sequentially, is within the scope of this disclosure.

Example 14: Soybean Transformation

Transgenic soybean (*Glycine max*) containing a stably integrated dgt-14 transgene is generated through *Agrobacterium*-mediated transformation of soybean cotyledonary node explants. A disarmed *Agrobacterium* strain carrying a binary vector containing a functional dgt-14 is used to initiate transformation.

*Agrobacterium*-mediated transformation is carried out using a modified half-cotyledonary node procedure of Zeng et al. (Zeng P., Vadnais D. A., Zhang Z., Polacco J. C., (2004), *Plant Cell Rep.*, 22(7): 478-482). Briefly, soybean seeds (cv. Maverick) are germinated on basal media and cotyledonary nodes are isolated and infected with *Agrobacterium*. Shoot initiation, shoot elongation, and rooting media are supplemented with cefotaxime, timentin and vancomycin for removal of *Agrobacterium*. Selection via a herbicide is employed to inhibit the growth of non-transformed shoots. Selected shoots are transferred to rooting medium for root development and then transferred to soil mix for acclimatization of plantlets.

Terminal leaflets of selected plantlets are treated topically (leaf paint technique) with a herbicide to screen for putative transformants. The screened plantlets are transferred to the greenhouse, allowed to acclimate and then leaf-painted with a herbicide to reconfirm tolerance. These putative transformed $T_0$ plants are sampled and molecular analyses is used to confirm the presence of the herbicidal selectable marker, and the dgt-14 transgene. $T_0$ plants are allowed to self fertilize in the greenhouse to produce $T_1$ seed.

A second soybean transformation method can be used to produce additional transgenic soybean plants. A disarmed *Agrobacterium* strain carrying a binary vector containing a functional dgt-14 is used to initiate transformation.

*Agrobacterium*-mediated transformation is carried out using a modified half-seed procedure of Paz et al., (Paz M., Martinez J., Kalvig A., Fonger T., and Wang K., (2005) *Plant Cell Rep.*, 25: 206-213). Briefly, mature soybean seeds are sterilized overnight with chlorine gas and imbibed with sterile $H_2O$ twenty hours before *Agrobacterium*-mediated plant transformation. Seeds are cut in half by a longitudinal cut along the hilum to separate the seed and remove the seed coat. The embryonic axis is excised and any axial shoots/buds are removed from the cotyledonary node. The resulting half seed explants are infected with *Agrobacterium*. Shoot initiation, shoot elongation, and rooting media are supplemented with cefotaxime, timentin and vancomycin for removal of *Agrobacterium*. Herbicidal selection is employed to inhibit the growth of non-transformed shoots. Selected shoots are transferred to rooting medium for root development and then transferred to soil mix for acclimatization of plantlets.

Terminal leaflets of selected plantlets are treated topically (leaf paint technique) with a herbicide to screen for putative transformants. The screened plantlets are transferred to the greenhouse, allowed to acclimate and then leaf-painted with a herbicide to reconfirm tolerance. These putative transformed $T_0$ plants are sampled and molecular analyses is used to confirm the presence of the selectable marker and the dgt-14 transgene. Several events are identified as containing the transgenes. These $T_0$ plants are advanced for further analysis and allowed to self fertilize in the greenhouse to give rise to $T_1$ seed. Soybean plants containing the dgt-14 transgene are obtained. The dgt-14 soybean plants are sprayed with varying concentrations of glyphosate and shown to provide tolerance to glyphosate at concentrations up to 3360 g ae/ha.

Example 15: Transformation of the DGT-14 Gene in Rice

Transgenic rice (*Oryza sativa*) containing a stably integrated dgt-14 transgene is generated through *Agrobacterium*-mediated transformation of soybean cotyledonary node explants. A disarmed *Agrobacterium* strain carrying a binary vector containing a functional dgt-14 is used to initiate transformation.

Culture media are adjusted to pH 5.8 with 1 M KOH and solidified with 2.5 g/l Phytagel (Sigma-Aldrich, St. Louis, Mo.). Embryogenic calli are cultured in 100×20 mm petri dishes containing 40 ml semi-solid medium. Rice plantlets are grown on 50 ml medium in MAGENTA boxes. Cell suspensions are maintained in 125 ml conical flasks containing 35 ml liquid medium and rotated at 125 rpm. Induction and maintenance of embryogenic cultures occur in the dark at 25-26° C., and plant regeneration and whole-plant culture occur in illuminated room with a 16-h photoperiod (Zhang et al. 1996).

Induction and maintenance of embryogenic callus is performed on a modified NB basal medium as described previously (Li et al. 1993), wherein the media is adapted to contain 500 mg/l glutamine. Suspension cultures are initiated and maintained in SZ liquid medium (Zhang et al. 1998) with the inclusion of 30 g/l sucrose in place of maltose. Osmotic medium (NBO) consisting of NB medium with the addition of 0.256 M each of mannitol and sorbitol. Herbicide resistant callus is selected on NB medium supplemented with the appropriate herbicide selective agent for 3-4 weeks. Pre-regeneration is performed on medium (PRH50) consisting of NB medium with 2,4-dichlorophenoxyacetic acid (2,4-D), 1 mg/l α-naphthaleneacetic acid (NAA), 5 mg/l abscisic acid (ABA) and selective herbicide for 1 week. Regeneration of plantlets follow the culturing on regeneration medium (RNH50) comprising NB medium containing 2,4-D, 0.5 mg/l NAA, and selective herbicide until putatively transgenic shoots are regenerated. Shoots are transferred to rooting medium with half-strength Murashige and Skoog basal salts and Gamborg's B5 vitamins, supplemented with 1% sucrose and selective herbicide.

Mature desiccated seeds of *Oryza sativa* L. *japonica* cv. Taipei 309 are sterilized as described in Zhang et al. 1996. Embryogenic tissues are induced by culturing sterile mature rice seeds on NB medium in the dark. The primary callus approximately 1 mm in diameter, is removed from the scutellum and used to initiate cell suspension in SZ liquid medium. Suspensions are then maintained as described in Zhang 1996. Suspension-derived embryogenic tissues are removed from liquid culture 3-5 days after the previous subculture and placed on NBO osmotic medium to form a circle about 2.5 cm across in a petri dish and cultured for 4 h prior to bombardment. Sixteen to twenty hours after bombardment, tissues are transferred from NBO medium onto NBH50 selection medium, ensuring that the bombarded surface is facing upward, and incubated in the dark for 14-17 days. Newly formed callus is then separated from the original bombarded explants and placed nearby on the same medium. Following an additional 8-12 days, relatively compact, opaque callus is visually identified, and transferred to PRH50 pre-regeneration medium for 7 days in the dark. Growing callus, which become more compact and opaque is then subcultured onto RNH50 regeneration medium for a period of 14-21 days under a 16-h photoperiod. Regenerating shoots are transferred to MAGENTA boxes containing ½ MSH50 medium. Multiple plants regenerated from a single explant are considered siblings and are treated as one independent plant line. A plant is scored as positive for the dgt-14 gene if it produces thick, white roots and grows vigorously on ½ MSH50 medium. Once plantlets reach the top of the MAGENTA boxes, they are transferred to soil in a 6-cm pot under 100% humidity for a week, and then are moved to a growth chamber with a 14-h light period at 30° C. and in the dark at 21° C. for 2-3 weeks before transplanting into 13-cm pots in the greenhouse. Seeds are collected and dried at 37° C. for one week prior to storage at 4° C.

Putatively transgenic rice plantlets at the 3-5 leaf stage are sprayed with a solution of glyphosate. Once sprayed, plantlets are allowed to dry for one hour before being moved out of the fume hood. Rating for sensitivity or resistance to glyphosate is completed from 10-14 days after treatment (DAT). Glyphosate resistant rice plantlets which contain a fully integrated copy of the dgt-14 plant are identified. Rice plants containing the dgt-14 transgene are obtained. The dgt-14 rice plants are sprayed with varying concentrations of glyphosate and shown to provide tolerance to glyphosate at concentrations up to 3360 g ae/ha.

Example 16: Turf Grass Transformation Procedures

*Agrobacterium tumefaciens*-mediated genetic transformation of the dgt-14 transgene in creeping bentgrass is achieved through embryogenic callus initiated from seeds (cv. Penn-A-4). See "Efficiency of *Agrobacterium tumefaciens*-mediated turfgrass (*Agrostis stolonifera* L) transformation" (Luo et. al., 2004).

Callus cells are infected with an *A. tumefaciens* strain harboring a super-binary vector that contains an herbicide-resistant transgene driven (e.g. dgt-14) by a monocot specific promoter. The overall stable transformation efficiency ranges from 18% to 45%. Southern blot and genetic analysis confirm transgene integration within the creeping bentgrass genome and normal transmission and stable expression of the transgene in the $T_1$ generation. All independent transformation events carry one to three copies of the transgene, and a majority (60-65%) contain only a single copy of the transgene with no apparent rearrangements.

Mature seeds are dehusked with sand paper and surface sterilized in 10% (v/v) Clorox™ bleach (6% sodium hypochlorite) plus 0.2% (v/v) Tween 20 (Polysorbate 20) with vigorous shaking for 90 min. Following rinsing five times in sterile distilled water, the seeds are placed onto callus-induction medium (MS basal salts and vitamins, 30 g/l sucrose, 500 mg/l casein hydrolysate, 6.6 mg/l 3,6-dichloro-o-anisic acid (dicamba), 0.5 mg/l 6-benzylaminopurine (BAP) and 2 g/l Phytagel. The pH of the medium is adjusted to 5.7 before autoclaving at 120° C. for 20 min).

The culture plates containing prepared seed explants are kept in the dark at room temperature for 6 weeks. Embryogenic calli are visually selected and subcultured on fresh callus-induction medium in the dark at room temperature for 1 week before co-cultivation.

One day before *Agrobacterium* mediated-infection, the embryogenic callus is divided into 1- to 2-mm pieces and placed on callus-induction medium containing 100 µM acetosyringone. A 10-µl aliquot of *Agrobacterium* suspension (OD=1.0 at 660 nm) which harbors the dgt-14 transgene is then applied to each piece of callus, followed by 3 days of co-cultivation in the dark at 25° C. The callus is then transferred and cultured for 2 weeks on callus-induction medium plus 125 mg/l cefotaxime and 250 mg/l carbenicillin to suppress bacterial growth.

Selection of transgenic plants occurs when the callus is moved to callus-induction medium containing 250 mg/l cefotaxime and an herbicide. The callus material is maintained on this medium for 8 weeks with a selection subculture interval of 3 weeks. The selection process is performed at room temperature in the dark.

For plant regeneration, the herbicide-resistant proliferating callus events are first moved to regeneration medium (MS basal medium, 30 g/l sucrose, 100 mg/l myo-inositol, 1 mg/l BAP and 2 g/l Phytagel) supplemented with cefotaxime, and a herbicide for selection. These calli are kept in the dark at room temperature for 1 week and then moved into the light for 2-3 weeks to develop shoots.

Developed shoots are separated and transferred to hormone-free regeneration medium containing a herbicide and cefotaxime to promote root growth while maintaining selection pressure and suppressing any remaining *Agrobacterium* cells. Plantlets with well-developed roots (3-5 weeks) are then transferred to soil and grown either in the greenhouse or in the field.

Transgenic plants are maintained out of doors in a containment nursery (3-6 months) until the winter solstice in December. The vernalized plants are then transferred to the greenhouse and kept at 25° C. under a 16/8 h photoperiod and surrounded by non-transgenic control plants that physically isolate the transgenic plants from other pollen sources. The transgenic plants begin flowering 3-4 weeks after being moved back into the greenhouse. These plants are outcrossed with the pollen from the surrounding control plants. The seeds collected from each individual transgenic plant are germinated in soil at 25° C., and $T_1$ plants are grown in the greenhouse for further analysis.

Other grasses that are contemplated for dgt-14 transformation according to the described protocol include Annual meadowgrass (*Poa annua*), Bahiagrass, Bentgrass, Bermudagrass, Bluegrass, Bluestems, *Brachiaria*, Bromegrass, Browntop bent (*Agrostis capillaries*), Buffalograss, Canary Grass, Carpetgrass, Centipedegrass, Chewings fescue (*Festuca rubra commutate*), Crabgrass, Creeping bent (*Agrostis stolonifera*), Crested hairgrass (*Koeleria macrantha*), Dallisgrass, Fescue, Festolium, Hard/sheeps fescue (*Festuca ovina*), Gramagrass, Indiangrass, Johnsongrass, Lovegrass, mixes (Equine, Pasture, etc.), Native Grasses, Orchardgrass, Perennial ryegrass (*Lolium perenne*), Redtop, Rescuegrass, annual and perennial Ryegrass, Slender creeping red fescue (*Festuca rubra trichophylla*), Smooth-stalked meadowgrass (*Poa pratensis*), St. Augustine, Strong creeping red fescue (*Festuca rubra rubra*), Sudangrass, Switchgrass, Tall fescue (*Festuca arundinacea*), Tufted hairgrass (*Deschampsia caespitosa*), Turfgrasses, Wheatgrass, and Zoysiagrass.

Example 17: DGT-14 in Rapeseed (*Brassica napus*)

The dgt-14 gene conferring resistance to glyphosate is used to transform *Brassica napus* var. Nexera™ 710 with *Agrobacterium*-mediated transformation.

*Brassica napus* seeds are surface-sterilized with 10% commercial bleach for 10 minutes and rinsed 3 times with sterile distilled water. The seeds are then placed on one half concentration of MS basal medium (Murashige and Skoog, 1962) and maintained under growth regime set at 25° C., and a photoperiod of 16 hrs light/8 hrs dark.

Hypocotyl segments (3-5 mm) are excised from 5-7 day old seedlings and placed on callus induction medium K1D1 (MS medium with 1 mg/l kinetin and 1 mg/l 2,4-D) for 3 days as pre-treatment. The segments are then transferred into a petri plate and treated with an *Agrobacterium tumefaciens* strain containing a construct comprised of dgt-14. The *Agrobacterium tumefaciens* is grown overnight at 28° C. in the dark on a shaker at 150 rpm and subsequently re-suspended in the culture medium.

After a 30 min treatment of the hypocotyl segments with *Agrobacterium*, these segments are placed back on the callus induction medium for 3 days. Following co-cultivation, the segments are placed in K1D1TC (callus induction medium containing 250 mg/l Carbenicillin and 300 mg/l Timentin) for one week of recovery. Alternately, the segments are placed directly on selection medium K1D1H1 (above medium with a herbicide). Carbenicillin and Timentin are the antibiotics used to kill the *Agrobacterium*. The selection agent allows for the growth of the transformed cells.

Callus samples from isolated independent events are tested by PCR. Samples that test positive for the presence of dgt-14 are confirmed and advanced to media for regeneration. The callused hypocotyl segments are then placed on B3Z1H1 (MS medium, 3 mg/l benzylamino purine, 1 mg/l Zeatin, 0.5 gm/l MES [2-(N-morpholino) ethane sulfonic acid], 5 mg/l silver nitrate, selective herbicide, Carbenicillin and Timentin) shoot regeneration medium. After 3 weeks shoots begin regeneration. Hypocotyl segments along with the shoots are transferred to B3Z1H3 medium (MS medium, 3 mg/l benzylamino purine, 1 mg/l Zeatin, 0.5 gm/l MES [2-(N-morpholino) ethane sulfonic acid], 5 mg/l silver nitrate, selective herbicide, Carbenicillin and Timentin) for another 3 weeks.

Shoots are excised from the hypocotyl segments and transferred to shoot elongation medium MESH10 (MS, 0.5 gm/l MES, selective herbicide, Carbenicillin, Timentin) for 2-4 weeks. The elongated shoots are cultured for root induction on MSI.1 (MS with 0.1 mg/l Indolebutyric acid). Once the plants establish a root system, the plants are transplanted into soil. The plants are acclimated under controlled environmental conditions in a Conviron™ for 1-2 weeks before transfer to the greenhouse.

The transformed $T_0$ plants are self-pollinated in the greenhouse to obtain $T_1$ seed. The $T_0$ plants and $T_1$ progeny are sprayed with a range of glyphosate herbicide concentrations to establish the level of protection by the dgt-14 gene.

Example 18: Tobacco Transformation

Tobacco (cv. Petit Havana) leaf pieces are transformed using *Agrobacterium tumefaciens* containing the dgt-14 transgene. Single colonies containing the plasmid which contains the dgt-14 transgene are inoculated into 4 mL of YEP medium containing antibiotics for selection of the vector containing dgt-14 and incubated overnight at 28° C. on a shaker at 190 rpm. The 4 mL seed culture is subsequently used to inoculate a 25 mL culture of the same medium in a 125 mL baffled Erlenmeyer flask. This culture is incubated at 28° C. shaking at 190 rpm until it reaches an $OD_{600}$ of ~1.2. Ten mL of *Agrobacterium* suspension are then placed into sterile 60×20 mm Petri™ dishes. Freshly cut leaf pieces (0.5 cm$^2$) from plants aseptically grown on MS medium (Phytotechnology Labs, Shawnee Mission, Kans.,) with 30 g/L sucrose in PhytaTrays (Sigma, St. Louis, Mo.) are soaked in 10 mL of overnight culture of *Agrobacterium* for a few minutes, blotted dry on sterile filter paper and then placed onto the same medium with the addition of 1 mg/L indoleacetic acid and 1 mg/L 6-benzylamino purine. Three days later, leaf pieces co-cultivated with *Agrobacterium* harboring the dgt-14 transgene are transferred to the same medium with 5 mg/L Basta™ and 250 mg/L cephotaxime. After 3 weeks, individual $T_0$ plantlets are transferred to MS medium with 10 mg/L Basta™ and 250 mg/L cephotaxime an additional 3 weeks prior to transplanting to soil and transfer to the greenhouse. Selected $T_0$ plants (as identified using molecular analysis protocols described above) are allowed to self-pollinate and seed is collected from capsules when they are completely dried down. $T_1$ seedlings are screened for zygosity and reporter gene expression (as described below) and selected plants containing the dgt-14 transgene are identified.

While aspects of this disclosure have been described in certain embodiments, they can be further modified within the spirit and scope of this disclosure. This application is therefore intended to cover any variations, uses, or adaptations of embodiments of the disclosure using its general principles. Further, this application is intended to cover such departures from the present disclosure as come within known or customary practice in the art to which these embodiments pertain and which fall within the limits of the appended claims.

What is claimed is:

1. An isolated nucleic acid molecule comprising a polynucleotide having at least 90% sequence identity to SEQ ID NO:2 or SEQ ID NO:3,
wherein the polynucleotide encodes the polypeptide of SEQ ID NO:1, wherein the polypeptide has glyphosate-resistant 5-enolpyruvylshikimate-3-phosphate synthase (EPSPS) activity, and
wherein the polynucleotide is operably linked to a heterologous promoter.

2. The nucleic acid molecule of claim 1, wherein the polynucleotide is a synthetic sequence that has been designed for expression in a plant.

3. The nucleic acid molecule of claim 1, wherein the nucleic acid molecule is a vector.

4. The nucleic acid molecule of claim 3, comprising a further polynucleotide encoding a heterologous polypeptide.

5. A host cell comprising the nucleic acid molecule of claim 1.

6. The nucleic acid molecule of claim 1, wherein the heterologous promoter is an AtUbi10 promoter.

7. The host cell of claim 5, wherein the host cell is a plant cell.

8. A transgenic plant part, plant organ, or plant cell, that comprises the nucleic acid molecule of claim 1.

9. The transgenic plant part, plant organ, or plant cell of claim 8, wherein the plant part, plant organ, or plant cell is tolerant to glyphosate, when compared to a wild-type plant part, plant organ, or plant cell of the same species.

10. A tissue culture of regenerable plant cells that comprise the nucleic acid molecule of claim 1.

11. A protoplast comprising the nucleic acid molecule of claim 1.

12. The tissue culture of claim 10, wherein the regenerable cells are selected from the group consisting of leaf cells, pollen cells, embryo cells, cotyledon cells, hypocotyl cells, meristematic cells, root cells, root tip cells, anther cells, flower cells, stem cells, and pod cells.

13. A plant or seed that comprises the nucleic acid molecule of claim 1, wherein the plant or seed comprises the polypeptide of SEQ ID NO:1, and wherein the plant or seed is resistant to glyphosate.

14. The plant part, plant organ, or plant cell of claim 8, wherein the polynucleotide has at least 95% sequence identity to SEQ ID NO:2 or SEQ ID NO:3, and wherein the polynucleotide and heterologous promoter are integrated in the genome of the plant part, plant organ, or plant cell.

15. A method of generating a transgenic plant part, plant organ, or plant cell, the method comprising:
transforming the plant part, plant organ, or plant cell with the nucleic acid molecule of claim 1, so as to express the polypeptide of SEQ ID NO:1, thereby generating the transgenic plant part, plant organ, or plant cell.

16. The method according to claim 15, wherein the plant part, plant organ, or plant cell is resistant to glyphosate.

17. The method according to claim 15, wherein the polynucleotide has at least 95% sequence identity to SEQ ID NO:2 or SEQ ID NO:3.

18. The method according to claim 15, wherein the polynucleotide is SEQ ID NO:2 or SEQ ID NO:3.

19. A method for controlling weeds in an area under cultivation containing the glyphosate resistant plant or seed of claim 13, the method comprising:
applying to the area under cultivation an amount of glyphosate that controls weeds in the area under cultivation without causing more than 40% injury to the glyphosate resistant plant or seed.

20. The method according to claim 19, wherein the glyphosate resistant plant or seed comprises a second polynucleotide encoding a heterologous polypeptide.

21. The method according to claim 20, wherein the second polynucleotide comprises α-ketoglutarate-dependent dioxygenase-1 (aad-1) or α-ketoglutarate-dependent dioxygenase-12 (aad-12).

22. A method for conferring resistance to glyphosate in a plant, the method comprising:
transforming a plant cell with the nucleic acid molecule of claim 1, so as to express the polypeptide of SEQ ID NO:1 in the plant; and
regenerating a transformed plant, thereby conferring resistance to glyphosate in the plant.

23. The method according to claim 22, further comprising transforming the plant cell with a second polynucleotide encoding a heterologous polypeptide expressible in the plant.

24. The method according to claim 23, wherein the heterologous polypeptide is α-ketoglutarate-dependent dioxygenase-1 (AAD-1) or α-ketoglutarate-dependent dioxygenase-12 (AAD-12).

25. A plant comprising the nucleic acid molecule of claim 1 in its genome, wherein the heterologous promoter is functional in the plant.

26. The plant of claim 25, wherein the plant is a soybean plant.

27. The plant of claim 25, wherein the plant is a corn plant.

28. The plant of claim 25, wherein the plant is selected from the group consisting of wheat, corn, soybean, tobacco, *Brachiaria*, rice, millet, barley, tomato, apple, pear, strawberry, orange, alfalfa, cotton, carrot, potato, sugar beets, yam, lettuce, spinach, petunia, rose, chrysanthemum, turf grass, pine, fir, spruce, heavy metal accumulating plants, sunflower, safflower, rapeseed, and *Arabidopsis*.

29. The plant of claim 25, wherein the plant is a species selected from the group consisting of genera Asparagus, *Avena, Brachiaria, Brassica, Citrus, Citrullus, Capsicum, Cucurbita, Daucus, Erigeron, Glycine, Gossypium, Hordeum, Helianthus, Lactuca, Lolium, Lycopersicon, Malta, Manihot, Nicotiana, Orychophragmus, Oryza, Persea, Phaseolus, Pisum, Pyrus, Prunus, Raphanus, Secale, Solanum, Sorghum, Triticum, Vitis, Vigna,* and *Zea*.

30. The method according to claim 16, further comprising regenerating a plant that is resistant to glyphosate.

31. The method according to claim 19, wherein the glyphosate is applied to the area under cultivation in an amount of between 420 g ae/ha and 3360 g ae/ha.

32. The glyphosate-resistant plant or seed of claim 13, wherein the plant or seed is a plant.

* * * * *